(12) United States Patent
Orth et al.

(10) Patent No.: US 9,140,698 B2
(45) Date of Patent: Sep. 22, 2015

(54) MODULATING BACTERIAL MAM POLYPEPTIDES IN PATHOGENIC DISEASE

(75) Inventors: Kim Orth, Dallas, TX (US); Hyeilin Ham, Dallas, TX (US); Anne-Marie Krachler, Malvern (GB)

(73) Assignee: The Board of Regents of the University of Texas System, Austin, TX (US)

(*) Notice: Subject to any disclaimer, the term of this patent is extended or adjusted under 35 U.S.C. 154(b) by 0 days.

(21) Appl. No.: 14/009,724

(22) PCT Filed: Mar. 30, 2012

(86) PCT No.: PCT/US2012/031552
§ 371 (c)(1),
(2), (4) Date: Dec. 17, 2013

(87) PCT Pub. No.: WO2012/138570
PCT Pub. Date: Oct. 11, 2012

(65) Prior Publication Data
US 2014/0093477 A1 Apr. 3, 2014

Related U.S. Application Data

(60) Provisional application No. 61/472,440, filed on Apr. 6, 2011.

(51) Int. Cl.
*A61K 38/16* (2006.01)
*G01N 33/554* (2006.01)
*G01N 33/569* (2006.01)
*A61K 35/74* (2015.01)
*A61K 35/741* (2015.01)
*A23L 1/30* (2006.01)

(52) U.S. Cl.
CPC ............ *G01N 33/554* (2013.01); *A23L 1/3014* (2013.01); *A61K 35/74* (2013.01); *A61K 35/741* (2013.01); *A61K 38/164* (2013.01); *G01N 33/56911* (2013.01); *G01N 2333/195* (2013.01)

(58) Field of Classification Search
None
See application file for complete search history.

(56) References Cited

U.S. PATENT DOCUMENTS

| | | |
|---|---|---|
| 2008/0213286 A1 | 9/2008 | Fitzgerald et al. |
| 2009/0048160 A1 | 2/2009 | Bannerman et al. |
| 2009/0088385 A1 | 4/2009 | Wu et al. |
| 2009/0214476 A1 | 8/2009 | Pretzer et al. |
| 2010/0105078 A1 | 4/2010 | Benning et al. |

OTHER PUBLICATIONS

Hawley et al. (PLOS One, 8:e81216, 1-9, 2013).*
Alouf, "Bacterial Protein Toxins: An Overview," *Methods Mol. Biol.*, 145:1-26, 2000.
Awai, et al., "A phosphatidic acid-binding protein of the chloroplast inner envelope membrane involved in lipid trafficking," *Proc. Natl. Acad. Sci., USA*, 103(28):10817-10822, 2006.
Cismasiu, et al., "The MAM (Meprin/A5-protein/PTPmu) domain is a hemophilic binding site promoting the lateral dimerization of receptor-like protein-tyrosince phosphatase," *J. Biol. Chem.*, 279(26):26922-31, 2004.
Daniels et al., "*Vibrio parahaemolyticus* Infections in the United States, 1973-1998," *J. Infect. Dis.*, 181:1661-1666, 2000.
Galan, "Common Themes in the Design and Function of Bacterial Effectors," *Cell Host Microbe.*, 5:571-579, 2009.
Krachler, et al., "Outer membrane adhesion factor multivalent adhesion molecule 7 initiates host cell binding during infection by Gram-negative pathogens," *Proc. Natl. Acad. Sci., USA*, 108(28):11614-11619, 2011.
PCT International Search Report and Written Opinion issued in International Application No. PCT/US2012/031552, mailed Sep. 28, 2012.
Extended Search Report and Opinion issued in European Application No. 12767481.1, mailed Mar. 17, 2015.
Krachler and Orth, "Functional characterization of the interaction between bacterial adhesion multivalent adhesion molecule 7 (MAM7) protein and its host cell ligands," *J Biol. Chem.*, 286:38939-38947, 2011.
Krachler et al., "Turnabout is fair play—Use of the bacterial multivalent adhesion molecule 7 as an antimicrobial agent," *Virulence*, 3(1):68-71, 2012.

* cited by examiner

*Primary Examiner* — Brian J Gangle
(74) *Attorney, Agent, or Firm* — Parker Highlander PLLC

(57) ABSTRACT

The disclosure relates to methods and compositions for preventing or inhibiting pathogenic bacterial infections in a subject caused by pathogenic bacteria expressing a multivalent adhesion molecule (MAM) polypeptide by administering to a subject a composition comprising a MAM polypeptide or a non-pathogenic bacterium expressing a MAM polypeptide, or a combination thereof.

26 Claims, 25 Drawing Sheets

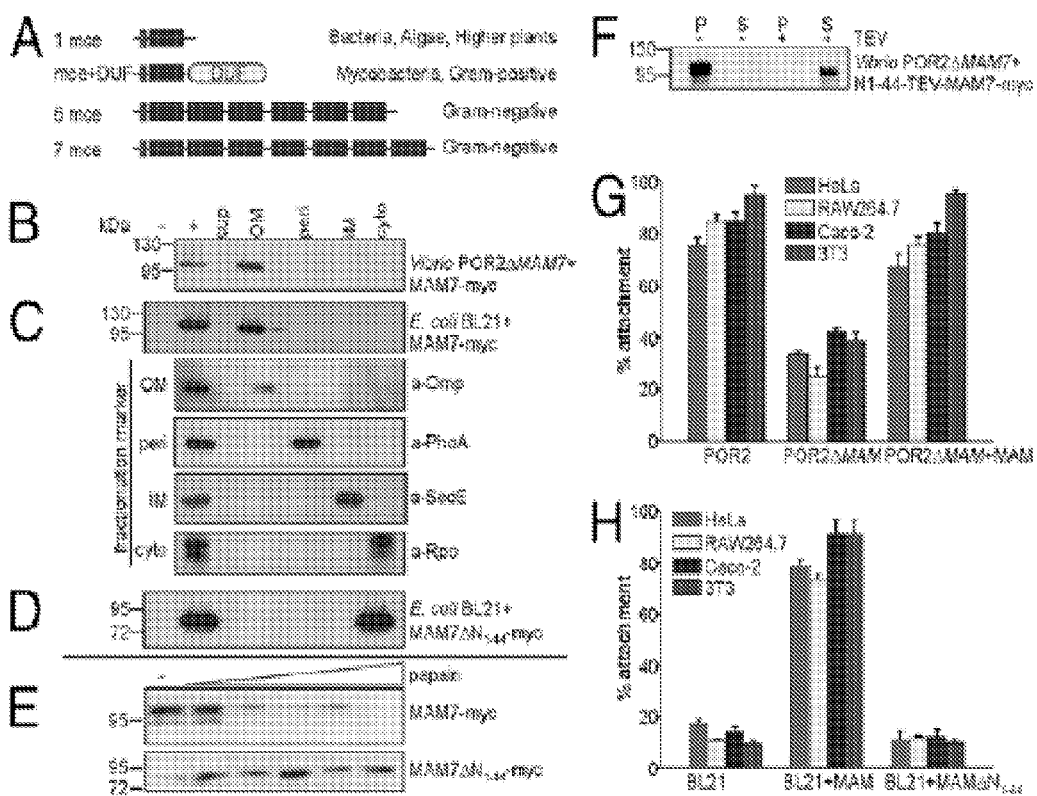
FIG. 1A-H

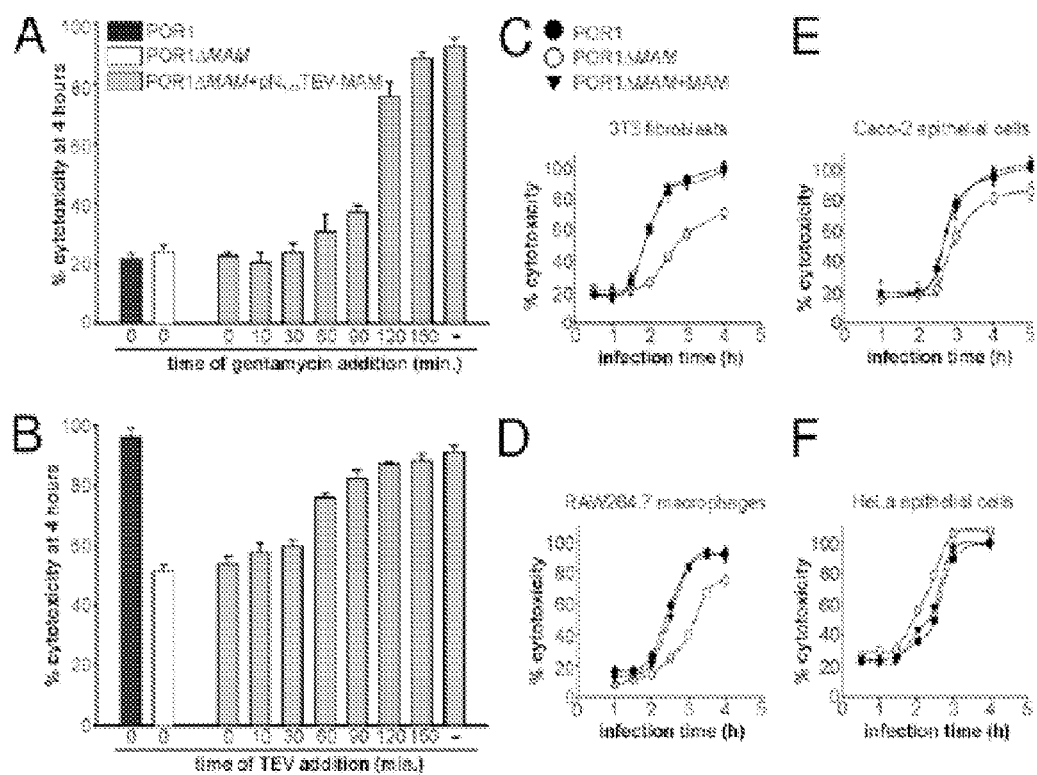
FIG. 2A-F

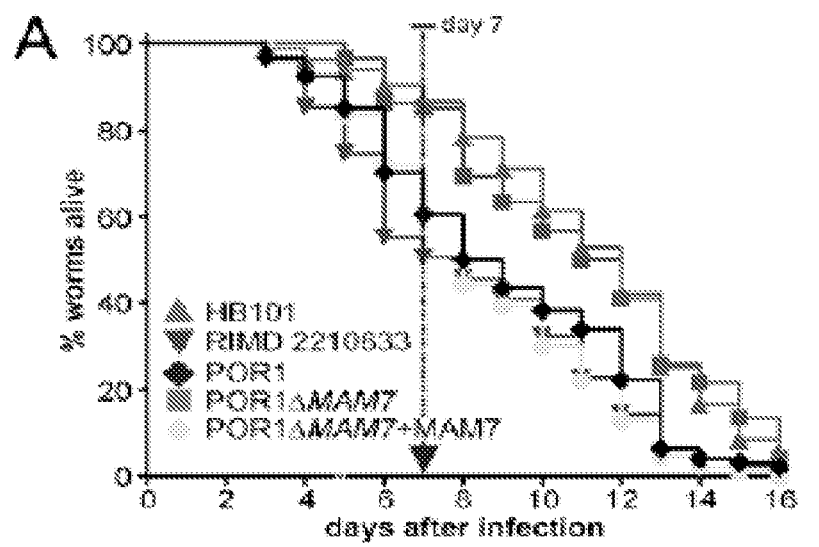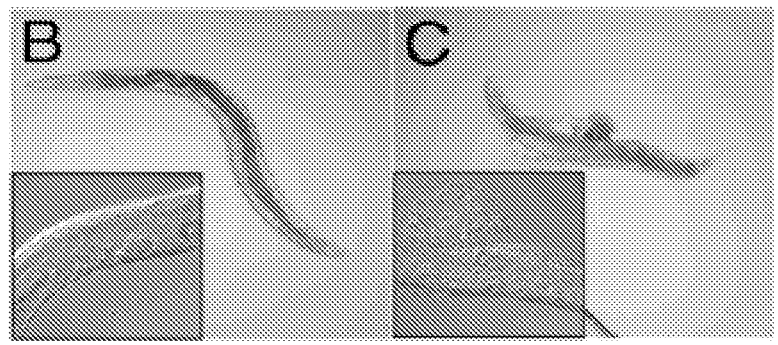
FIG. 3A-C

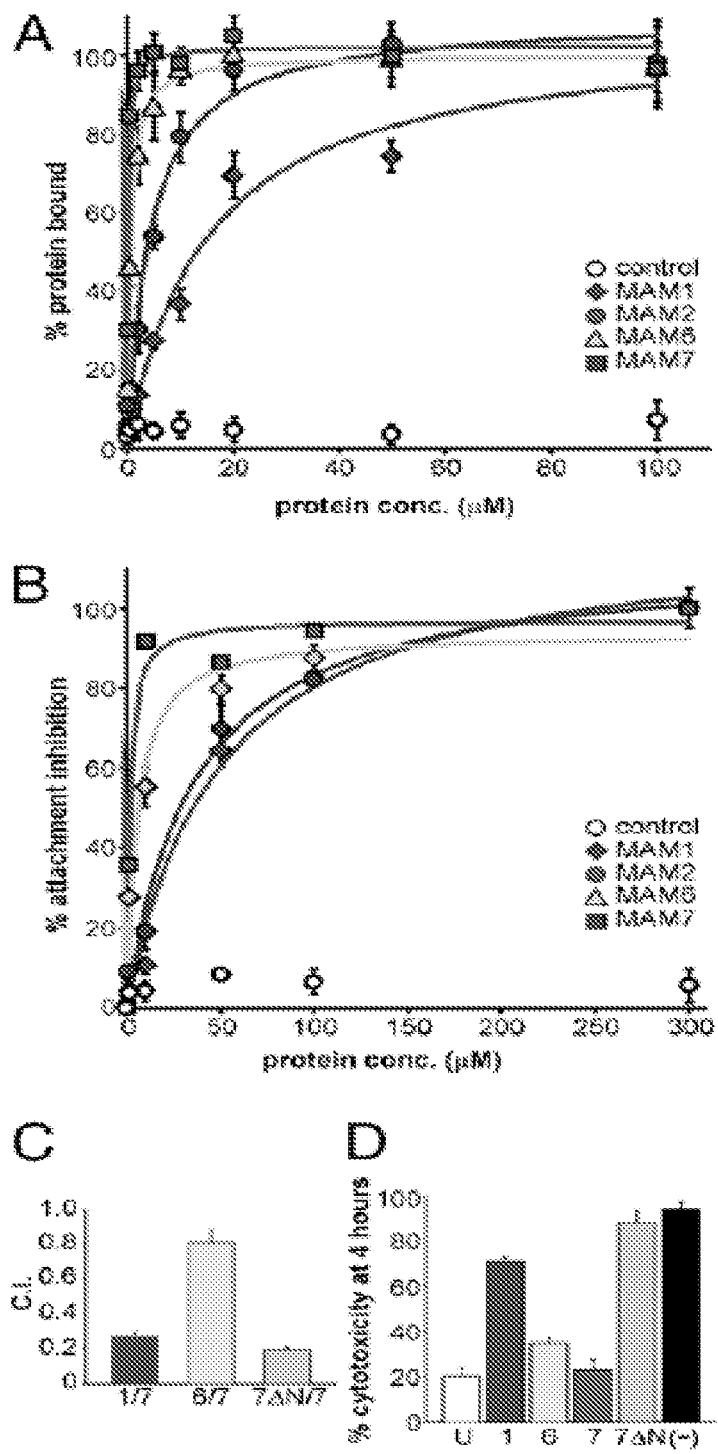
FIG. 4A-D

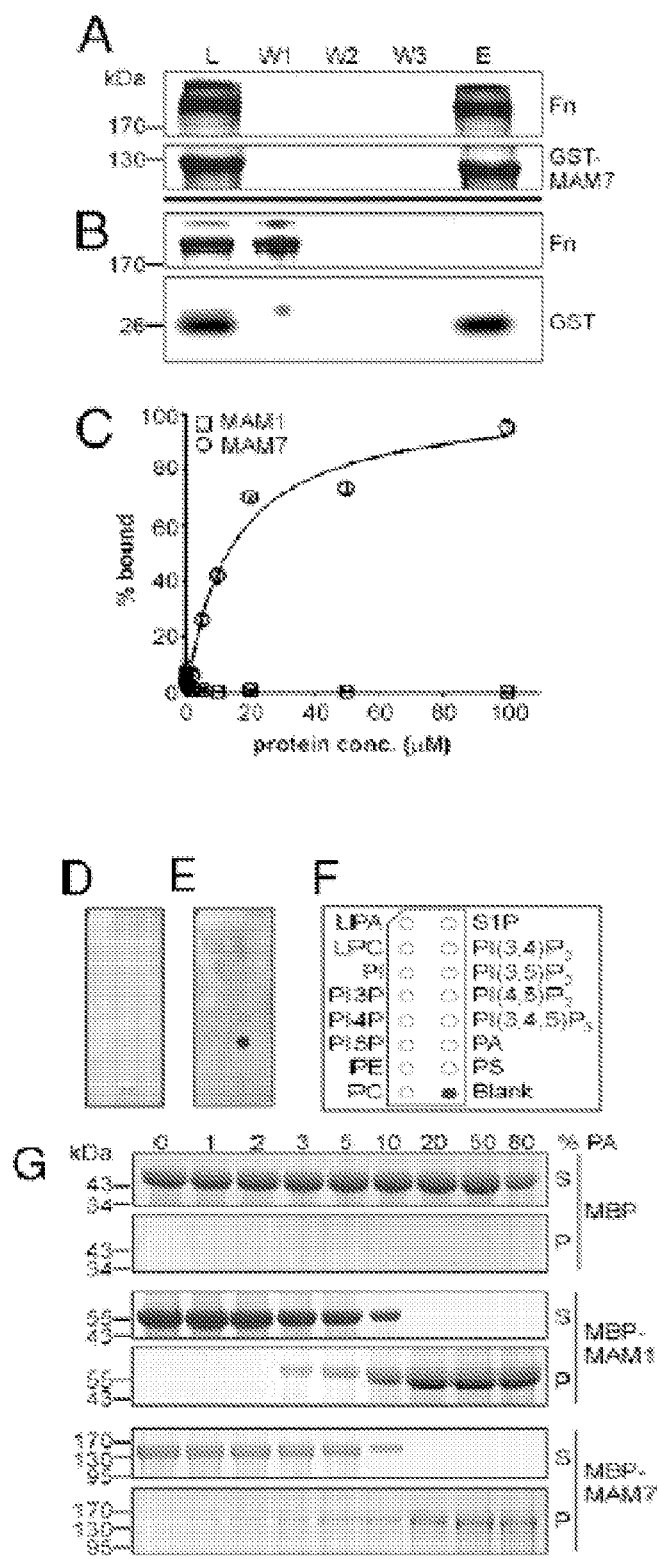
FIG. 5A-G

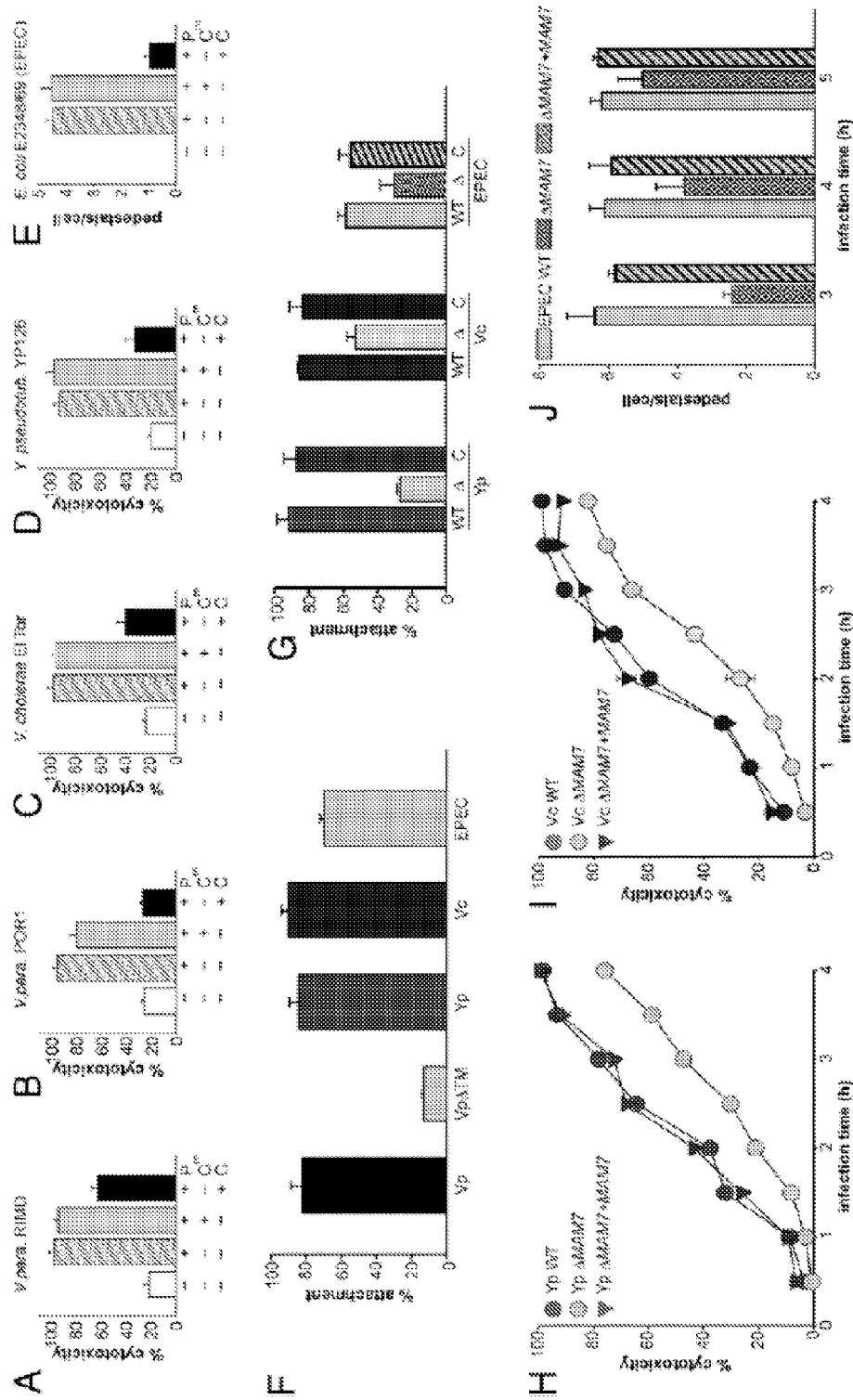
FIG. 6A-J

```
                    10         20         30         40         50         60
                    |          |          |          |          |          |
V.para      MSDQNNSQTSYVFIVFRSKGISPLWLLPILPMVLAGWLVVKSISDAQRVQHYFSDAASL
V.cholerae  MSQENTTQTSYTPEIRKPFGISPLWILFIVTMILAGWLVFKAVRDAGVRIQIRFENAQSL
Y.pseudot   -MQQETPSTPTEAHVRHKPRFSPFWLLFFIALLITGWLIYNNWQERGTEITIDFQSTAGI
EPEC        -MSQETPASTTEAQIENKPRISPFWLLPFIALXIAGWLIWDSYQDRGNTVTHDFMSADSI
            :.:...:.  ..:*. : :**:*:**:::::::***:.  :: *  : *  *  .: *:

70         80         90        100        110        120
                    |          |          |          |          |          |
V.para      VAGPTTIPYQGLEVGMVRDINLSEIDLGSIYVEADIYPEATKLLNDKIFFWLVKPTAGLTG
V.cholerae  IAGPTTIPYQGLEVGMVRDIKLSPGLDSIYVEADIYPEATKLLSNQIFFWMVKPTAGLSG
Y.pseudot   VAGPTPIPYQGVEVGLVQSIRLDDNLRNIKVTASIKNLMEDSLRSGTQFWLVTPKASLAG
EPEC        VPGPTPVPYQGVEVGTVQDISLSDDLRKIEVRVSIKSLMKDALRGETQFWLVTPKASLAG
            :.***.:*****:***  *:.*  *:.:*  *  ..*  :  . *  :  *:**:*.*.***:*

130        140        150        160        170        180
                    |          |          |          |          |          |
V.para      VSSLDALVSGNYISIQFG---DGQEFETTFHALDSAFTDLVS
V.cholerae  VSSLDALVSGNYIAIQPGSTHQEDYPTQYQALDSAFSDLLAQ
Y.pseudot   VSSLDALVSGNYISMMPG---EGKPQSHFTALDTQPKFRLNI
EPEC        VSSLDALVSGNYISMMPG---KGNEQDHFVALDTQFKYPLDN
            ********.****.:  **    .  : ***; *.       * * *.: ***.:.  *

190        200        210        220        230        240
                    |          |          |          |          |          |
V.para       
V.cholerae   
Y.pseudot    
EPEC         
            *  :  :*:***:*  *:.*  :  :.: *:. *,..: ,:::  *******, *,..:.*.
```

```
            670        680        690        700        710        720
             |          |          |          |          |          |
V.para     KGMPIEYQGVKVGEVTLVVENFRRILVEVTAPILFEYVENIAVEGTHEWLTEPEIGLGEN
V.cholerae VGTPVQKQGVQIGEVFEIIPDFESDIVKLAAPIEPQYAPKIAEQREQFWISQATIGLGEI
Y.pseudot  ACMPIRYLGIDIGQVESLKLAPERNEVLAKVLIFEYVQNITRAIHFSIVSIPISAAGV
EPEC       VGMPIRYLGIDIGQIQTLDLITARNEVQAKAVLIFEIVQTPARGSIRFSVVIPQISAAGV
            * *;,*  *;,;*;;  ;       ;  *     * ; *;*,  ,;;   ,;;*  ;  ,*;

730        740        750        760        770        780
             |          |          |          |          |          |
V.para     KNLGAIVSKSISVEPGNGKAKFDFQLEKGFDR----V
V.cholerae ENVQNLLGQSIEVQPGNGESRFEFELHREARHG---Q
Y.pseudot  NNLETLFQPYINVEPGKGSPLRNFELQTATITDSRYL
EPEC       ENLETILQPYINVEPGPGNFPRDFELQEATITDSRYL
            ;;;    ;.    *,*;**;*,   ,;*;*,          *     ;;;  ;  **;  ;****;*;

790        800        810        820        830        840
             |          |          |          |          |          |
V.para
V.cholerae
Y.pseudot
EPEC
            *;;***  *  ,,  **  ;;****   ;;;*    ,;  ;*;;*;*;***  ,**  ,,,;*;  *,   ;*;*

850        860        870        880        890
             |          |          |          |          |
V.para          GIAFSTPEQSQIFPAAKRGHSFYLYPRADESWVQWRTPIPPP  (SEQ ID NO: 1)
V.cholerae      GITFATPEQKQLTPAAPEGHTFYLYPQAQEEWTHWRTPIPPP  (SEQ ID NO: 18)
Y.pseudot       GIAFRTPPTIPLAPRANVQHFLLAPEEPKDWRKWGTAIPPS   (SEQ ID NO: 26)
EPEC            GIAFRTPPGTPLAPKAQEGHFLLQESEPKEWREWGTALPY-   (SEQ ID NO: 4)
                *;;,;***** ;*;**    ;,*  *   ,;  * *    ;,* ;* *,;*;
```

FIG. 7B (cont.)

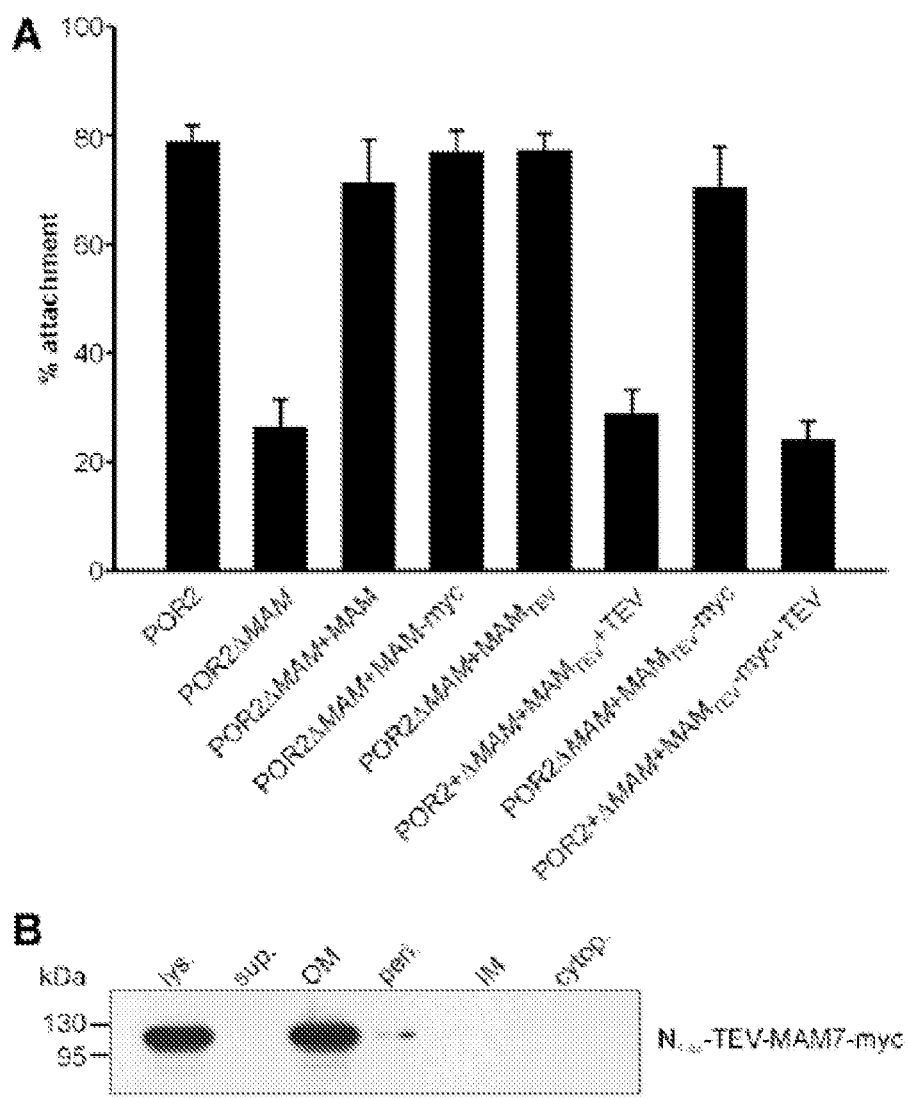
FIG. 10A-B

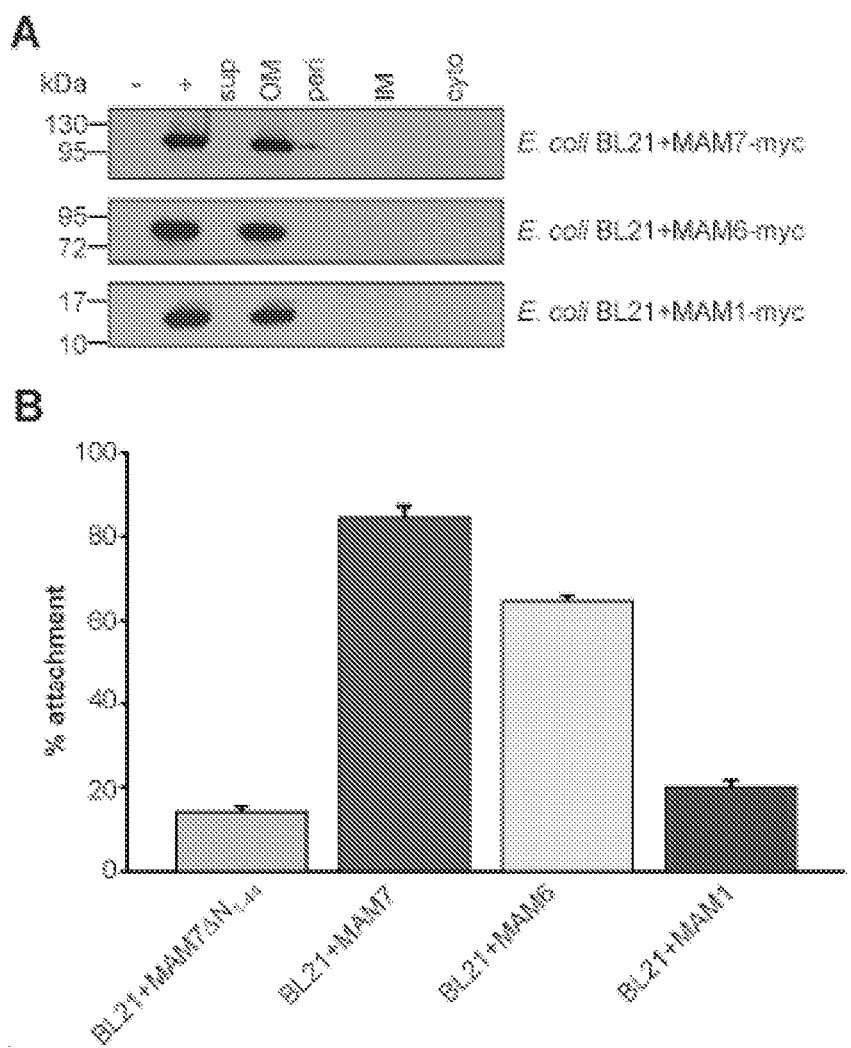
FIG. 11A-B

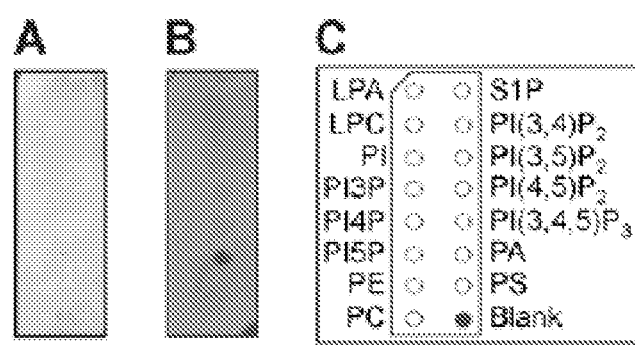
FIG. 12A-C

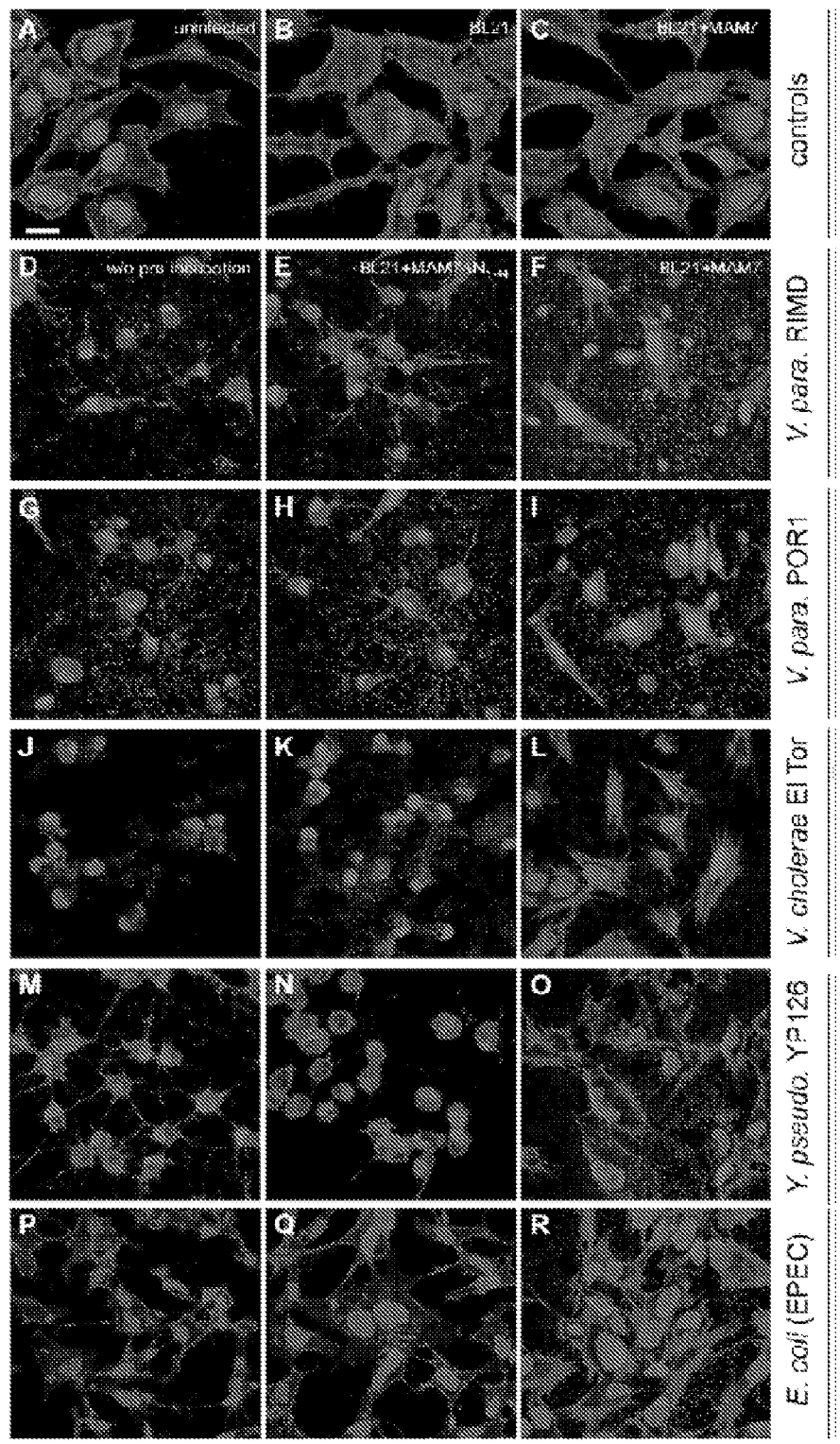
FIG. 13A-R

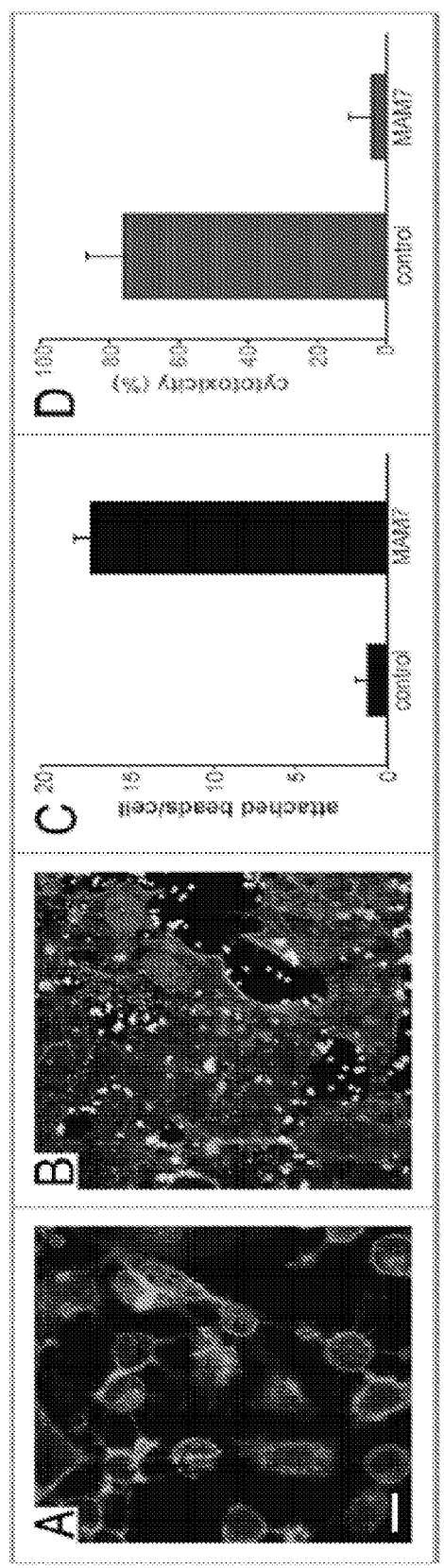
FIG. 14A-D

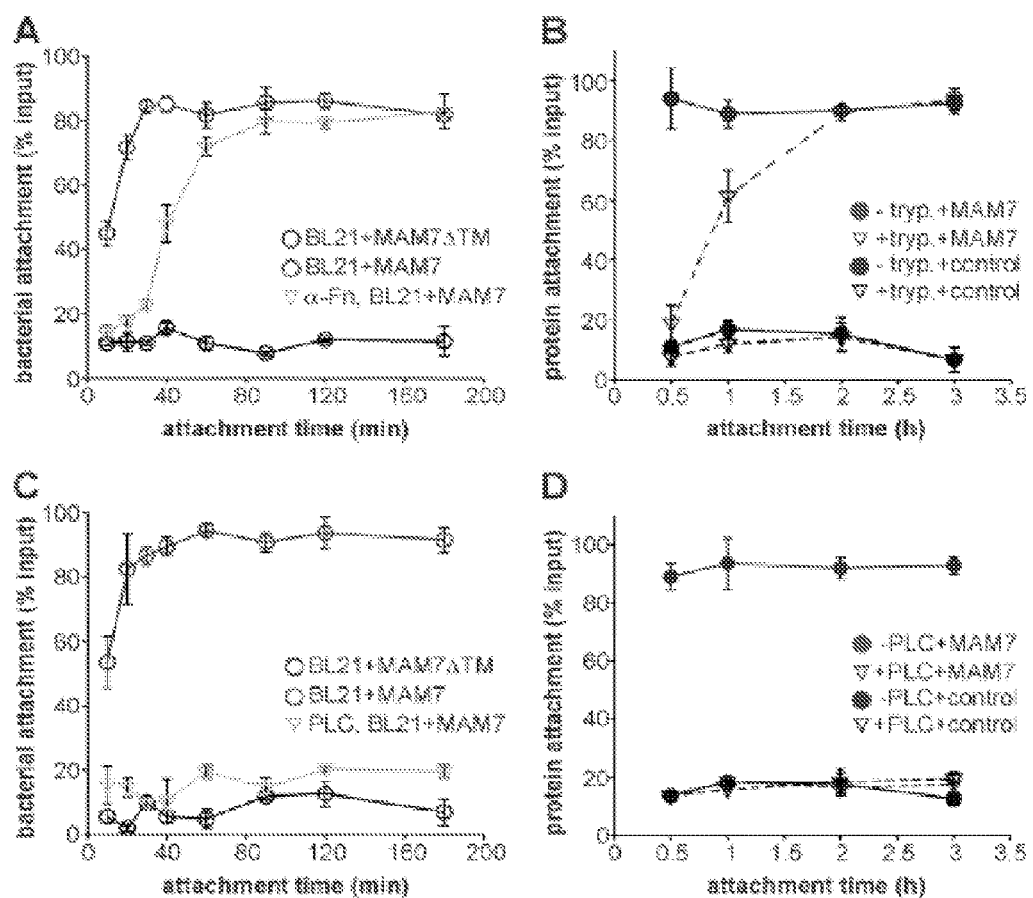
FIG. 15A-D

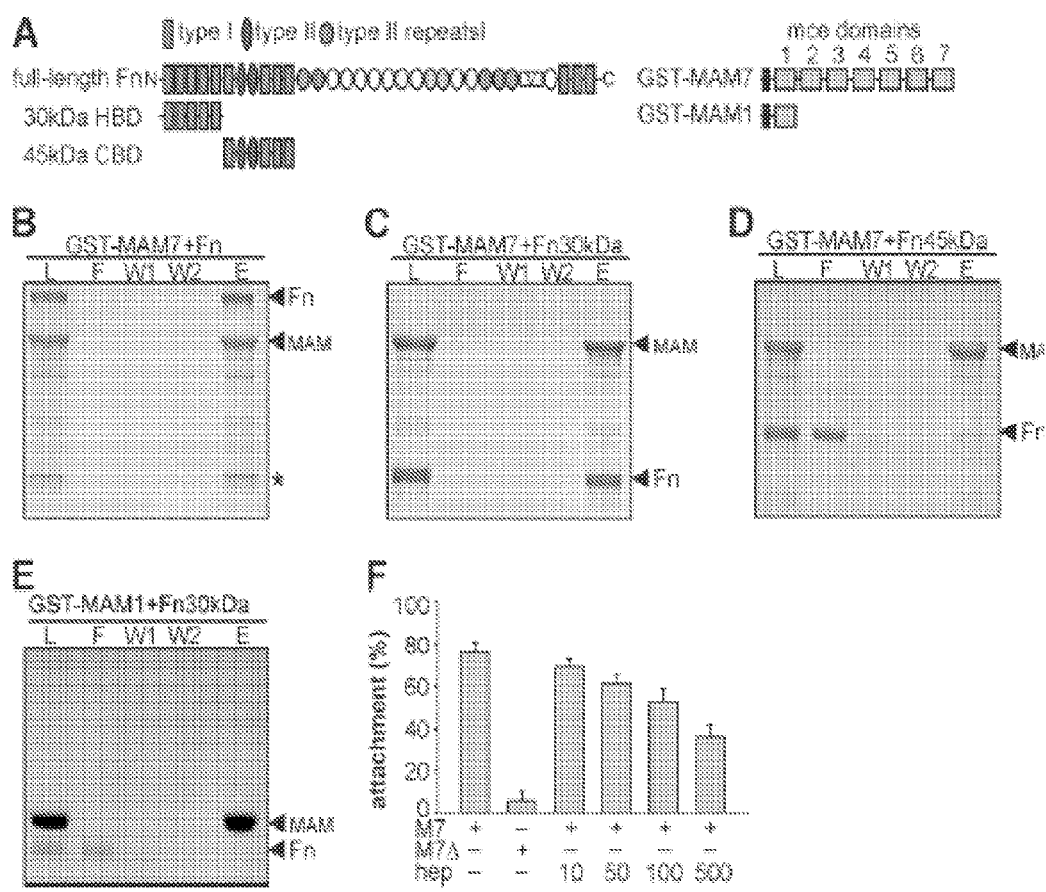
FIG. 16A-F

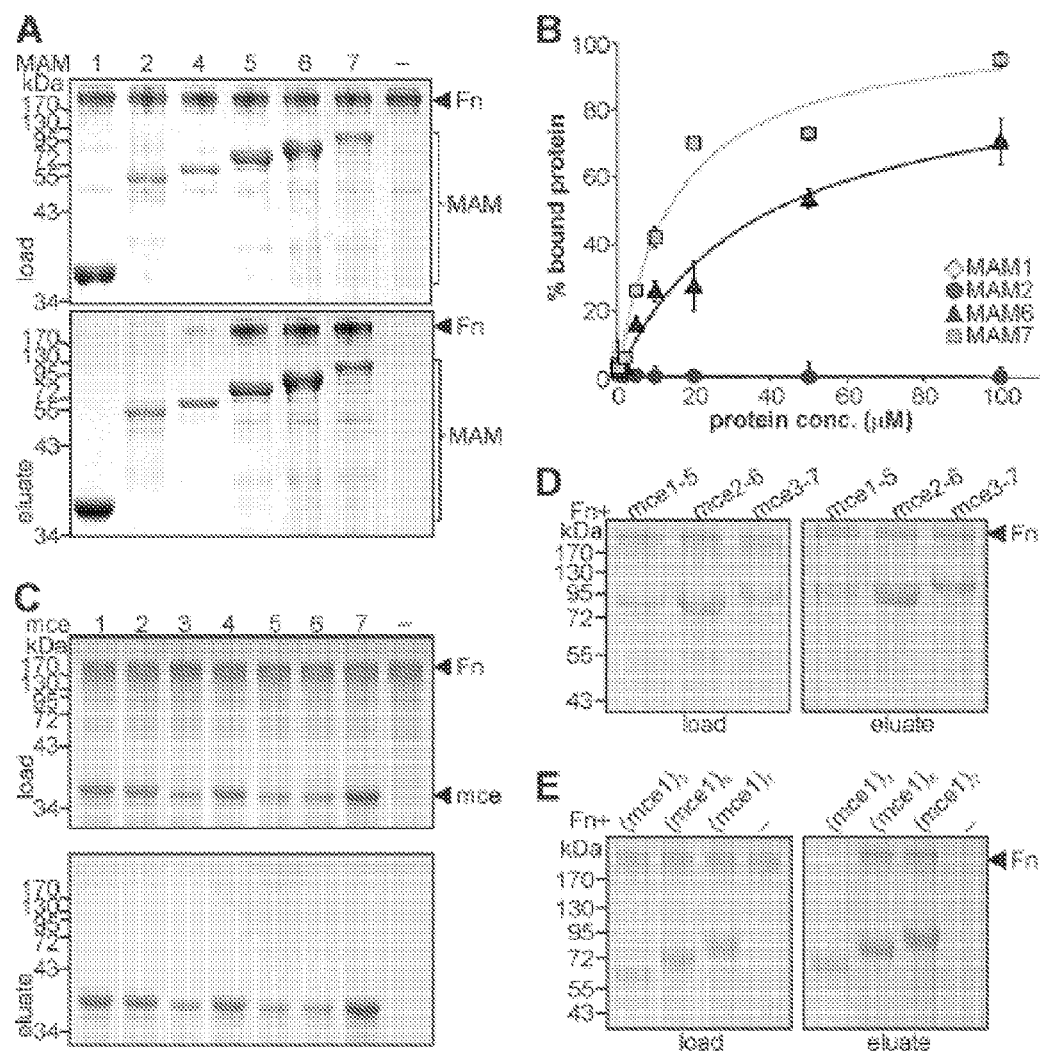
FIG. 17A-E

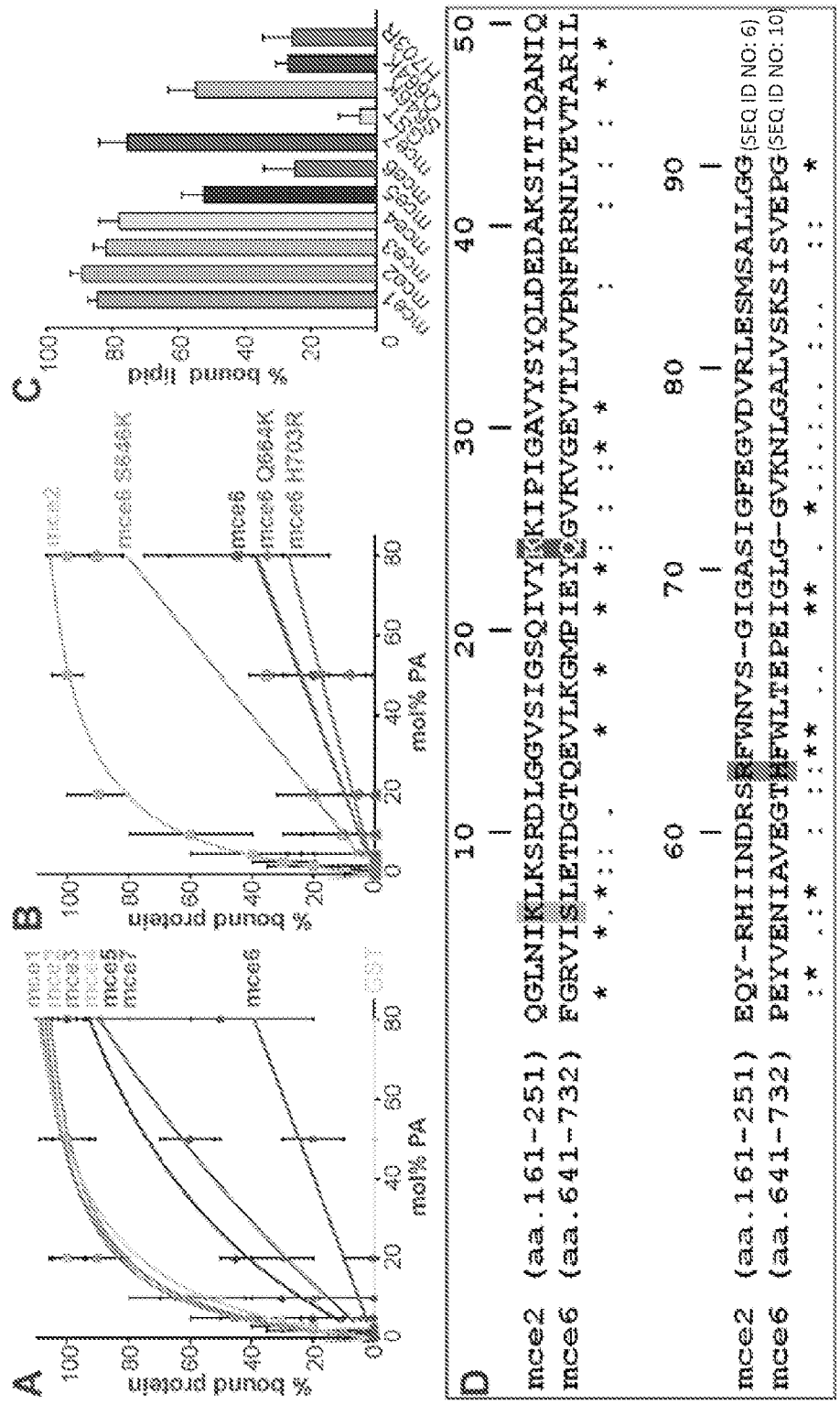
FIGS. 18A-D

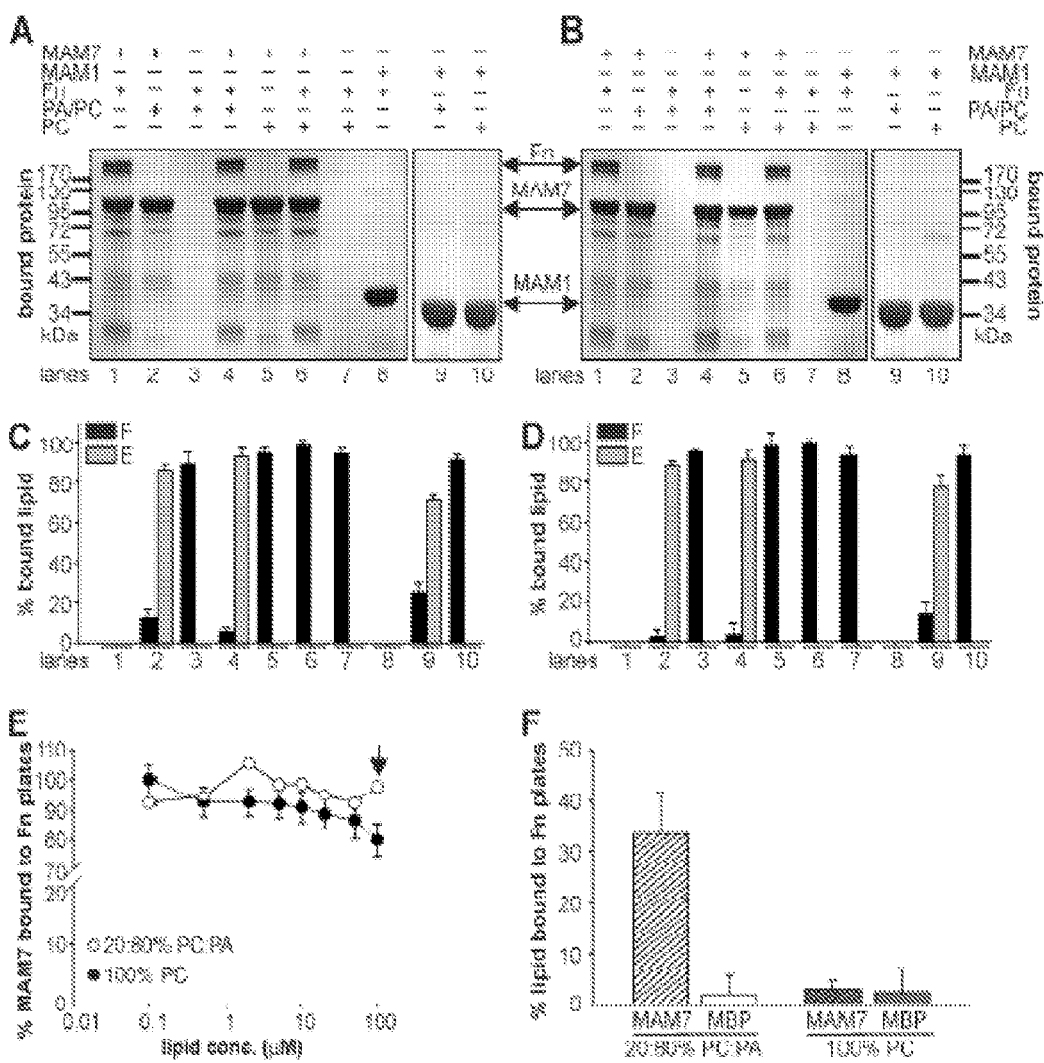
FIG. 19A-F

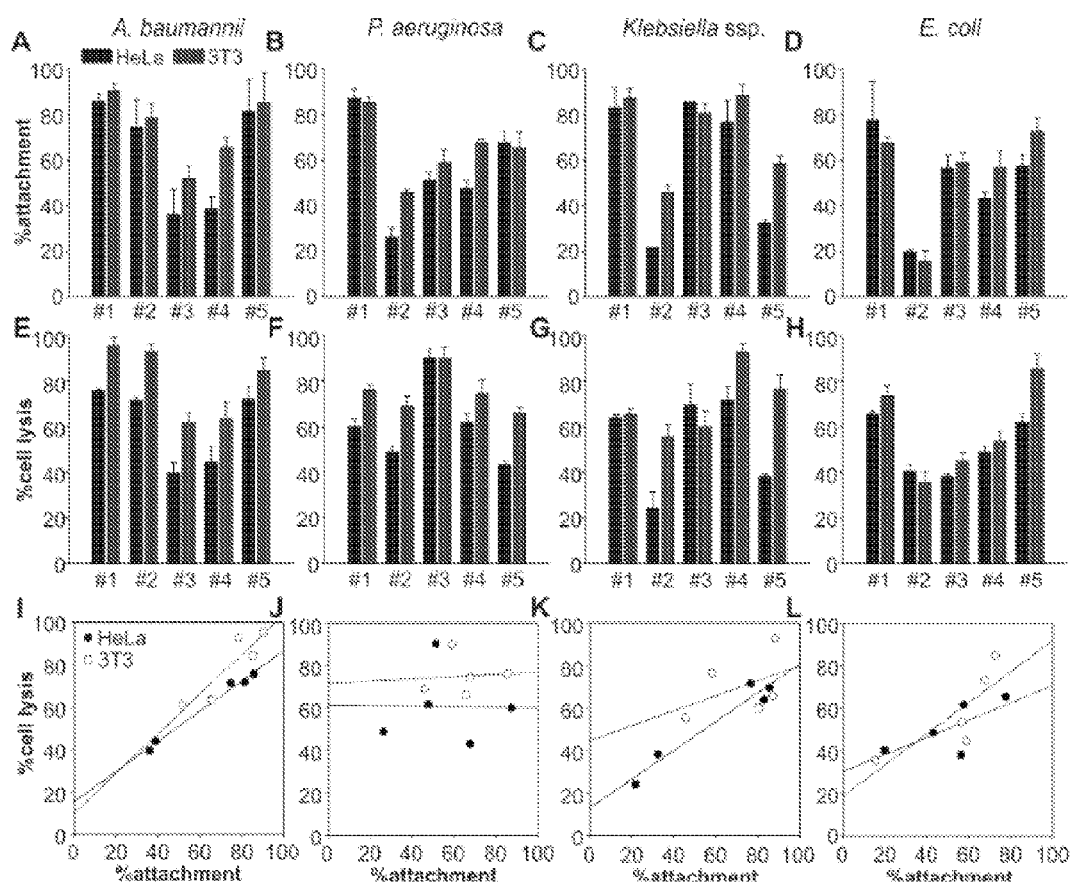
FIG. 20A-L

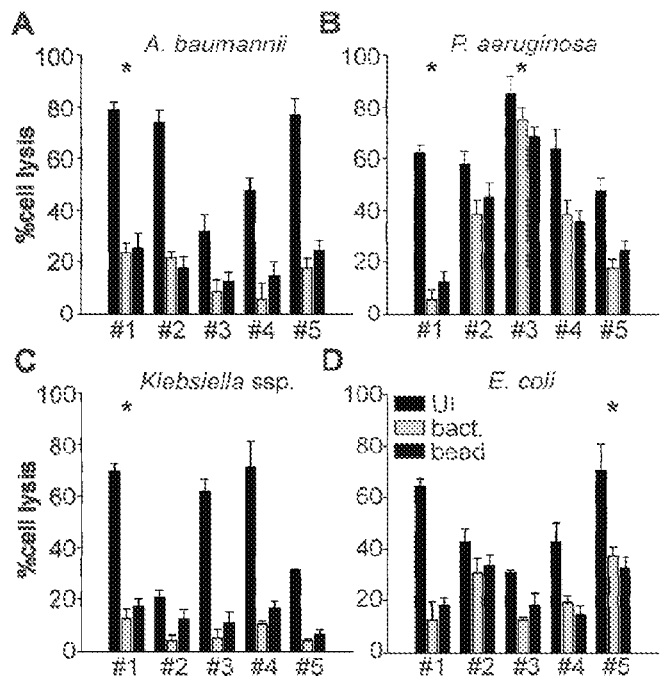
FIG. 21A-D
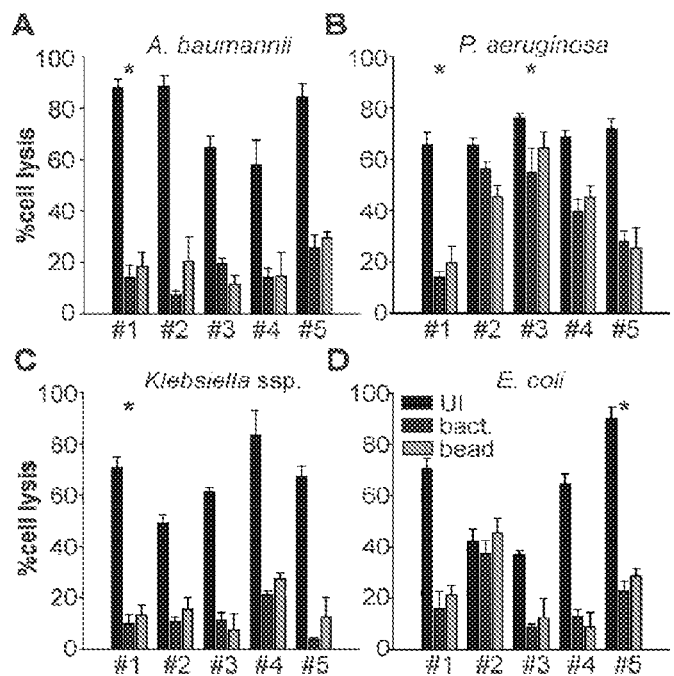
FIG. 22A-D

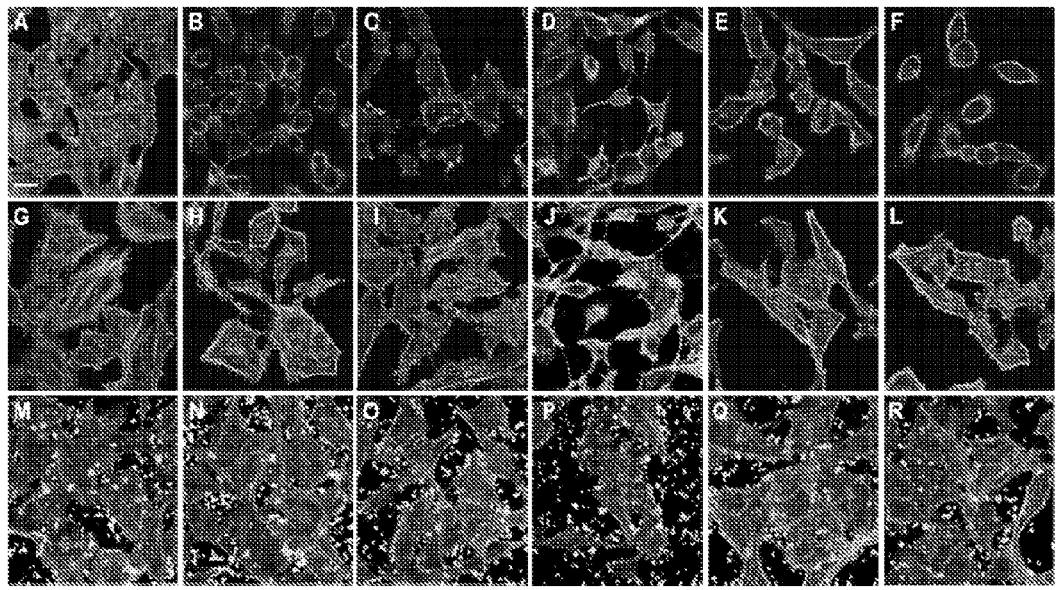
FIG. 23A-R
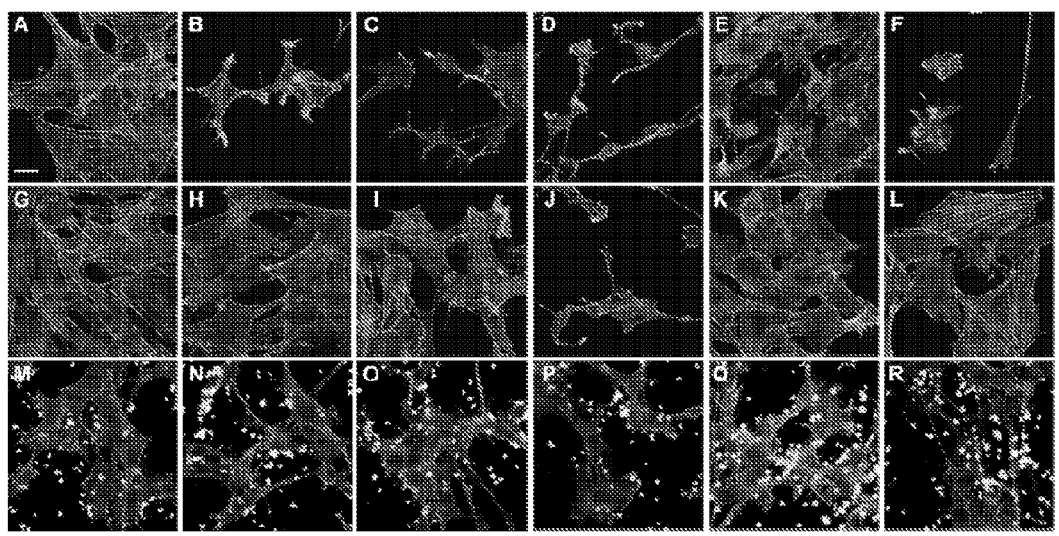
FIG. 24A-R

MODULATING BACTERIAL MAM POLYPEPTIDES IN PATHOGENIC DISEASE

The invention was made with government support under grant numbers R01-AI056404 and R01-AI087808 awarded by the National Institutes of Health. The government has certain rights in the invention.

This application is a national phase application under 35 U.S.C. §371 of International Application No. PCT/US2012/031552, filed Mar. 30, 2012, which claims benefit of priority to U.S. Provisional Application Ser. No. 61/472,440, filed Apr. 6, 2011, the entire contents of each of which are hereby incorporated by reference.

BACKGROUND OF THE INVENTION

1. Field of the Invention

The present invention relates to fields of microbiology and medicine. More particularly, the present invention relates to a bacterial protein designated as MAM and methods and compositions for exploiting its use in treating pathogenic bacterial infections.

2. Description of Related Art

Bacterial pathogens possess a large repertoire of virulence factors that target and manipulate the host cellular machinery to enable infection. Delivery of effector proteins to the host cytosol by type III, type IV and type VI secretion systems as well as delivery of extracellular toxins is a common strategy used by bacterial pathogens to abrogate the host immune response and alter cellular pathways to the pathogen's advantage (Alouf, 2000; Galan, 2009). Since the secretion of effector and toxin proteins is contact-dependent, the bacteria need to establish tight binding to the host to successfully start an infection. If one could establish the existence of a common virulence factor across species that enables a wide range of pathogen to establish strong initial host binding, which is required for the activation and secretion of other virulence factors, it would be possible to design a broadly effective therapeutic strategy that focuses on inhibition of this factor.

SUMMARY OF THE INVENTION

Thus, in accordance with the present invention, there is provided a method of preventing or inhibiting a pathogenic bacterial infection in a subject caused by a pathogenic bacterium expressing a MAM polypeptide, comprising administering to said subject a composition comprising a non-pathogenic bacterium expressing a MAM polypeptide comprising at least 5 mce repeat regions. The subject may be a mammal, such as a human or a non-human mammal. The pathogenic bacterium may be a Gram-negative, such as selected from the group consisting of *Vibrio parahaemolyticus, Vibrio cholera, Yersinia pseutotuberculosis*, and enteropathogenic *Escherichia coli*. The composition may be administered more than once.

The non-pathogenic bacterium may express a native MAM polypeptide, or a MAM polypeptide heterologous to the bacterium. The non-pathogenic bacterium may be *E. coli* strain BL21 or *E. coli* strain HS. The non-pathogenic bacterium may comprise a gene encoding a MAM polypeptide in an extrachromosomal self-replicating vector. The non-pathogenic bacterium may comprise a gene encoding a MAM polypeptide integrated into a chromosome of said non-pathogenic bacterium. The MAM polypeptide of said non-pathogenic bacterium may comprise 5, 6 or 7 mce repeat regions, or more than 7 mce repeat regions.

The composition may further comprise a probiotic, and/or may be administered orally, and/or may be selected from the group consisting of milk, yogurt, curd, cheese, fermented milks, milk based fermented products, ice-creams, fermented cereal based products, milk based powders, infant formulae, pet food, a tablet, a liquid bacterial suspension, dried oral supplement and wet oral supplement. The composition may also be administered topically, such as in the case where a subject has suffered a burn injury. The topical composition may be formulated as a cream, a gel, a salve, an ointment or a powder. The topical composition may be comprised in or disposed on a wound dressing. The composition may be comprised in or disposed on a surgical mesh or implantable device.

In another embodiment, there is provided a method of preventing or inhibiting a pathogenic bacterial infection in a subject caused by a pathogenic bacterium expressing a MAM polypeptide, comprising administering to said subject a composition comprising a MAM peptide or protein comprising at least 5 mce repeat regions. The subject may be a mammal, such as a a human or non-human mammal. The pathogenic bacterium may be Gram-negative, such as selected from the group consisting of *Vibrio parahaemolyticus, Vibrio cholera, Yersinia pseutotuberculosis*, and enteropathogenic *Escherichia coli*.

The composition may be delivered orally. The composition may be administered more than once. The composition may be administered topically, such as to a subject that has suffered a burn injury. The topical composition may be formulated as a cream, a gel, a salve, an ointment or a powder. The composition may be comprised in or disposed on a wound dressing, surgical mesh or implantable device.

The MAM peptide or protein may comprise 5, 6 or 7 mce repeat regions, or more than 7 mce repeat regions. The MAM protein or peptide may be coupled to a particle or bead, such as a particle or bead comprised of a polymer, a metal, or a lipid. The particle or bead may in particular be made of polystyrene, latex, a metal oxide, or polylactic-coglycolic acid (PLGA). The particle or bead may be a microsphere, a liposome, an nanoparticle, or a quantum dot.

Also provided is a method for identifying or quantifying phosphatidic acid on a membrane comprising contacting a membrane with a peptide or polypeptide comprising MAM mce repeat region. The peptide may comprise 1, 2, 3, 4 or 5 mce repeat regions. The peptide or polypeptide may be labeled, such as with a fluorescent label, a chemilluminscent label, and enzyme label, a dye, a colorimetric label, a quantum dot, or a ligand. The membrane may be part of an intact cell, such as a fixed cell or a living cell. The living cell may have been treated with an agent, and may further have, prior to treatment with said agent, been contacted with a MAM peptide or polypeptide to identify or quantify phosphatidic acid on said cell's membrane.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-H. MAM7 is an outer membrane protein involved in host cell adhesion. (FIG. 1A) Classification of mce-containing proteins using PFAM (Finn et al., 2009). Western Blotting of subcellular fractions of (FIG. 1B) *V. parahaemolyticus* POR2, (FIG. 1C) *E. coli* B1121 expressing MAM7-myc and (FIG. 1D) *E. coli* BL21 expressing MAM7ΔN1-44-myc. (−) total lysate before induction, (+) total lysate after induction, sup: culture supernatant, OM: outer membrane, peri: periplasm, IM: inner membrane, cyto: cytoplasm. (FIG. 1E) Detection profile of MAM7 and MAM7ΔN1-44 after papain degradation (FIG. 1F) Detection profile of N1-44-TEV-MAM7myc after TEV treatment. P: cell pellet, S: supernatant. (FIG. 1G) Attachment of *V. parahaemolyticus* POR2, POR2ΔMAM7 and POR2ΔMAM7 complemented with plasmid-borne MAM7 (pMAM7) to HeLa, RAW264.7, Caco-2 and 3T3 fibroblast cells. (FIG. 1H) Attachment of *E. coli* BL21 expressing MAM7 or MAM7ΔN1-44.

FIGS. 2A-F. Impact of MAM7-mediated adhesion on the outcome of *V. parahaemolyticus* infection. Lysis of (FIG. 2A) 3T3 fibroblasts, (FIG. 2B) Caco-2 epithelial cells, (FIG. 2C) RAW264.7 macrophages or (FIG. 2D) HeLa epithelial cells with POR1 (●), POR1ΔMAM7 (○) or POR1ΔMAM7+pMAM7 (V). Cytotoxicity of 3T3 fibroblasts after infection with POR1 (black bar), POR1ΔMAM7 (white bar) or POR1ΔMAM7+pMAM7 (gray bar) and treatment with (FIG. 2E) gentamycin or (FIG. 2F) TEV protease.

FIGS. 3A-C. MAM7 adhesin is an important virulence factor for *V. parahaemolyticus* pathogenicity in the nematode *C. elegans*. (FIG. 3A) Lethality assays were performed using the germline deficient *C. elegans* strain SS104 glp-4(bn2) fed on RIMD 2210633, POR1, POR1ΔMAM7 or a POR1ΔMAM7 complemented strain. Dead worms were scored and data were analyzed using the Kaplan-Meier method. Morphology of worms fed on (FIG. 3B) HB101 or (FIG. 3C) POR1 for 48 hours and pictured using Nomarski optics.

FIGS. 4A-D. Relationship between mce domain number, strength of binding and competitiveness. (FIG. 4A) Saturation binding experiments with cultivated HeLa cells and purified, ALEXAFLUOR®-labeled (fluorescent dye) MBP-MAM1, -MAM2, -MAM6 and -MAM7 proteins. Equilibrium dissociation constants (KD values) were determined as 14.9±3.3, 4.4±0.8, 0.6±0.1 and 0.2±0.1 μM for MAM1, MAM2, MAM6 and MAM7, respectively. (FIG. 4B) Indirect determination of binding affinities using MAM proteins to block the cell surface prior to attachment of *E. coli* BL21 expressing MAM7. KD values were 49.4±12.2, 36.0±7.3, 5.4±2.2 and 1.5±0.5 μM for MAM1, MAM2, MAM6 and MAM7, respectively. (FIG. 4C) HeLa cell attachment of BL21+MAM1, BL21+MAM6 and BL21+MAM7ΔN1-44 compared to BL21+MAM7 are determined as competitive indices (C.I.). (FIG. 4D) *E. coli* BL21 expressing either MAM1, MAM6, MAM7 or MAM7ΔN1-44 were analyzed for their ability to block POR1 attachment to host cells and thus POR1-mediated cytotoxicity.

FIGS. 5A-G. MAM7 attaches to host cells via fibronectin- and phospholipid-interactions. Pulldown of fibronectin from human plasma with (FIG. 5A) GST-tagged MAM7 or (FIG. 5B) GST-tag only. (FIG. 5C) Saturation binding experiment with fluorescently labeled MBP-MAM1 and MBP-MAM7 on immobilized fibronectin. MBP-MAM7 binds to fibronectin with an affinity of 15±4 μM, while no binding was detected with MAM1. Lipid overlay assays with (FIG. 5D) MBP and (FIG. 5E) MBP-MAM7. (FIG. 5F) Key for lipid strip. (FIG. 5G) Liposome association assays with MBP-tag, MBP-MAM1 and MBPMAM7. Proteins were incubated with liposomes containing only phosphatidylcholine (lane 1) or containing mixtures of PC and increasing mol % of phosphatidic acid (PA), lanes 2-9). Supernatant (S) and pellet (P) fractions were analyzed by SDS-PAGE.

FIGS. 6A-J. Importance of MAM7 in *V. parahaemolyticus, Y. pseudotuberculosis, V. cholerae* and EPEC infection. HeLa cells were infected with (FIG. 6A) *V. parahaemolyticus* RIMD, (FIG. 6B) *V. parahaemolyticus* POR1, (FIG. 6C) *V. cholerae*, (FIG. 6D) *Y. pseudotuberculosis* or (FIG. 6E) EPEC. P: addition of pathogen, C: competition of pathogen with BL21-MAM7, $C^m$: competition of pathogen with BL21-MAM7ΔN$_{1-44}$. (FIG. 6F) Attachment of BL21-MAM7 (left), *V. parahaemolyticus* MAM7ΔTM, and MAM7 homologs from *Y. pseudotuberculosis* (Yp), *V. cholerae* (Vc) or EPEC to 3T3 fibroblasts. (FIG. 6G) Attachment of wild-type (WT), ΔMAM7 (Δ) and complemented ΔMAM7 (C) strains of Yp, Vc an EPEC to 3T3 fibroblasts. (FIG. 6H) Cytotoxicity (LDH release) of Yp wild-type (WT), ΔMAM7 (Δ) and complemented ΔMAM7 (C) strains towards 3T3 fibroblasts over time. (FIG. 6I) Cytotoxicity of Vc wild-type (Vc WT), ΔMAM7 (vc ΔMAM7) and complemented ΔMAM7 (Vc ΔMAM7+MAM7) strains towards 3T3 cells. (FIG. 6J) Pedestal formation of EPEC wild-type, ΔMAM7 (checkered) and complemented ΔMAM7 (striped) strains on 3T3 cells over time.

FIGS. 7A-B. (FIG. 7A) Mce-domain boundaries as predicted for *V. parahaemolyticus* MAM7 are indicated in very light grey (mce1, SEQ ID NO: 5), light grey (mce2, SEQ ID NO: 6), dark grey (mce3, SEQ ID NO: 7), very dark grey (mce4, SEQ ID NO: 8), grey (mce5, SEQ ID NO: 9), very light grey (mce6, SEQ ID NO: 10) and light grey (mce7, SEQ ID NO: 11), respectively. (FIG. 7B) Alignments of MAM7 mce domains from *V. parahaemolyticus* MAM7 and MAM7 homologs from *Vibrio parahaemolyticus* (GI: 28898385, SEQ ID NO: 1), *Vibrio cholerae* (GI:15641510, SEQ ID NO: 18), *Yersinia pseudotuberculosis* (GI:170024018, SEQ ID NO: 26) and EPEC (*Escherichia coli* O127:H6, GI:215487047, SEQ ID NO: 4) were created using ClustalW.

FIGS. 10A-B. Analysis of attachment and TEV-induced cleavage of bacteria expressing N$_{1-44}$-TEV-MAM7. (FIG.

10A) Attachment of POR2 and derivative strains to 3T3 fibroblasts in the presence or absence of TEV protease. (FIG. 10B) Subcellular fractionation of POR2ΔMAM7 expressing $N_{1-44}$-TEV-MAM7-myc from a plasmid. Lys: total lysate, sup: culture supernatant, OM: outer membrane, peri: periplasm, IM: inner membrane, cytop: cytoplasm.

FIGS. 11A-B. Subcellular localization and adhesive properties of MAM mutants. (FIG. 11A) Myc-tagged MAM7, MAM6 and MAM1 were expressed in E. coli BL21 and bacteria were subjected to subcellular fractionation. All three constructs were exclusively detected in the outer membrane fraction after Western Blotting with myc-specific antibody. (−): uninduced lysate, (+): induced lysate, sup: culture supernatant, OM: outer membrane, peri: periplasm, IM: inner membrane, cyto: cytoplasm. (FIG. 11B) Bacterial attachment to HeLa cells was determined for E. coli BL21 expressing either MAM7ΔN$_{1-44}$, MAM7, MAM6 or MAM1.

FIGS. 12A-C. Lipid-binding properties of MAM1. Lipid overlay assays were carried out with (FIG. 12A) MBP only or (FIG. 12B) MBP-MAM1. Mce1, but not the tag alone binds phosphatidic acid (PA). (FIG. 12C) Key for lipid strip.

FIGS. 13A-R. E. coli B21 expressing MAM7 protects against V. parahaemolyticus, Y. pseudotuberculosis, V. cholerae. Phenotypes of (FIG. 13A) uninfected HeLa cells, (FIG. 13B) HeLa cells treated with BL21 or (FIG. 13C) BL21 expressing MAM7 as used for competition experiments shown in FIGS. 13D-R. (FIGS. 13D-R) HeLa cells with either no-preincubation (left panels), preincubation with BL21 expressing MAM7ΔN$_{1-44}$ (middle) or MAM7 (right panels) were infected with (FIGS. 13D-F) V. parahaemolyticus RIMD 2210633, (FIGS. 13G-I) V. parahaemolyticus POR1, (FIGS. 13J-L) V. cholerae El Tor N16961, (FIGS. 13M-O) Y. pseudotuberculosis YP126 or (FIGS. 13P-R) EPEC O127:H6 E2348/69. Cells were stained with Hoechst DNA stain (blue) and rhodamine-phalloidin actin stain (red). Scalebar, 20 μm.

FIGS. 14A-D. Inhibition of Pseudomonas aeruginosa-mediated cytotoxicity using bead-immobilized MAM7. Hela epithelial cells (80% confluency) were pre-incubated with bead-immobilized GST (FIG. 14A) or GST-MAM7 (FIG. 14B) for 30 minutes prior to infection with P. aeruginosa strain PAO1 at a multiplicity of infection of 20 for four hours. Cells were fixed and stained for DNA (dark grey) and actin (grey). Attached beads, light grey. Scale bar, 20 μm. Attached beads per cell were determined by counting (FIG. 14C, black) and cytotoxicity was determined by measuring LDH released into the culture medium (FIG. 14D, dark grey). Error bars indicate s.e.m. (n≥9). Cloning of expression constructs for GST and GST-MAM7 fusion protein as well as protein purifications have been described above. Purified proteins were immobilized on 1 μm fluorescent orange latex beads (Sigma) as described by El Shazly et al. 2007). For inhibition experiments, a total amount of 7.5 μg protein/$10^6$ beads/well in PBS were used.

FIGS. 15A-D. MAM7 binding to fibronectin is required for rapid attachment to host cells. Attachment of bacteria expressing MAM7 (BL21-MAM7, FIGS. 15A and 15C) or ALEXAFLUOR® 488-labeled (fluorescent dye) MAM7 protein or labeled MBP control (FIGS. 15B and 15D) to host cells treated with α-fibronectin antibody (FIG. 15A), trypsin (FIG. 15B) or phospholipase C (FIGS. 15C and 15D).

FIGS. 16A-F. The N-terminal 30 kDa fragment of fibronectin is sufficient for MAM7 binding. (FIG. 16A) Fibronectin subunit (220 kDa) consisting of type I, type II and type III repeats. Each subunit contains an N-terminal region ($I_{1-5}$, 30 kDa fragment) required for fibrin- and heparin binding (HBD), followed by a 45 kDa collagen binding domain (CBD, $I_6$, $II_{1-2}$, $I_{7-9}$). MAM7 contains an N-terminal transmembrane region, which was excluded from recombinant proteins, followed by 7 consecutive mce domains. GST-MAM7 and MAM1 constructs used for pull-downs are depicted. Pull-down assays with GST-MAM7 and intact Fn (FIG. 16B), Fn30 kDa (FIG. 16C) or Fn45 kDa (FIG. 16D) or GST-MAM1 and Fn30 kDa (FIG. 16E). Heparin inhibits attachment of BL21-MAM7 to host cells (FIG. 16F). M7: BL21-MAM7, M7Δ: BL21-MAM7ΔTM.

FIGS. 17A-E. A minimum of five mce domains is required for stable binding of fibronectin to MAM. Pull-down experiments were performed using intact fibronectin and GST-MAM1, -MAM2, -MAM4, -MAM5, -MAM6 or -MAM7. Load and eluate fractions were analyzed by SDS-PAGE and visualized by Coomassie Staining (FIG. 17A). Binding of labeled MBP-MAM1, -MAM2, -MAM6 and -MAM7 to Fn-coated plates was determined using fluorescence saturation binding assays (FIG. 17B). Pull-down assays with GST-tagged individual mce domains (mce1 to mce7) and fibronectin. Load and eluate fractions were analyzed by SDS-PAGE and visualized by Coomassie Staining (FIG. 17C). Pull-down assays with GST-tagged mce1-5, 2-6 and 3-7 proteins and fibronectin (FIG. 17D), or GST-tagged (mce1)$_3$, (mce1)$_5$ and (mce1)$_7$ concatemers and fibronectin (FIG. 17E).

FIGS. 18A-D. Analysis of phosphatidic acid binding by MAM7 mce domains. Liposome association assays with individual mce domains and liposomes prepared from PC and PA and containing increasing concentrations of PA as indicated (0-80 mol %). Supernatant and pellet fractions were analyzed by SDS-PAGE and visualized by Coomassie staining (data not shown). % bound protein were determined by densitometry of gels and used to compare the affinities of mce1-7 constructs (FIG. 18A). Densitometry of mce6 (weakest binding to PA) compared to mce2 (tightest binding) and three mce6 point mutants (FIG. 18B). Pull-down assay of liposomes containing 50 mol % PA and 50 mol % PC on immobilized GST-mce domains (FIG. 18C). Sequence alignment of mce2 (SEQ ID NO: 6) and mce6 (SEQ ID NO: 10) (FIG. 18D). Positions of point mutations in mce6 are shown in blue (S646K), dark purple (Q664K) and pink (H703R), respectively.

FIGS. 19A-F. MAM7, fibronectin and phosphatidic acid form a tripartite complex. Pull-down assays using GST-MAM7 or -MAM1, fibronectin and liposomes (with or without PA). GST-MAM proteins were incubated with fibronectin followed by liposomes (FIGS. 19A, 19C) or liposomes followed by fibronectin (FIGS. 19B, 19D). Bound proteins were analyzed by SDS-PAGE and Coomassie staining (FIGS. 9A, 19B). Liposomes in flowthrough and eluate fractions were quantitated using a molybdophosphoric acid assay and expressed as fractions of loaded lipid (FIG. 19C, FIG. 19D). ALEXAFLUOR® 488-labeled (fluorescent dye) MAM7 was tested for binding to Fn-coated plates in the presence of increasing concentrations of liposomes prepared from PC(●) or a mixture containing 20:80 mol % PC:PA (○) (FIG. 19E). Samples incubated with the highest concentration of liposomes (arrow) were analyzed for bound liposomes using the molybdophosphoric acid assay and compared to plate assays carried out with MBP control (FIG. 19F).

FIGS. 20A-L. Host cell attachment and lysis by bacterial isolates. Attachment (top) and cell lysis (LDH release), (middle) caused by five different isolates each of A. baumannii (FIGS. 20A, 20E), P. aeruginosa (FIGS. 20B, 20F), K. pneumoniae (FIGS. 20C, 20G) and E. coli (FIGS. 20D, 20H) tested on HeLa (blue) and 3T3 (red) cells. Values given are means±standard error (n=3) from a representative experiment performed in triplicate. Correlation between attachment and cytotoxicity on HeLa (●) and 3T3 (○) cells across different isolates (FIGS. 20I-L).

FIGS. 21A-D. Anti-adhesion treatment of HeLa cells infected with bacterial isolates. Cytotoxocity of *A. baumannii* (FIG. 21A), *P. aeruginosa* (FIG. 21B), *K. pneumoniae* (FIG. 21C) and *E. coli* (FIG. 21D) isolates was measured following infection of HeLa cells left untreated (black), BL21-MAM7 treated (light grey) or treated with bead-immobilized MAM7 (dark grey). Values given are means±standard error (n=3) from a representative experiment performed in triplicate. Data points marked by an asterix were chosen for visualization using confocal microscopy (FIGS. 23A-R).

FIGS. 22A-D. Anti-adhesion treatment of 3T3 cells infected with bacterial isolates. Cytotoxocity of *A. baumannii* (FIG. 22A), *P. aeruginosa* (FIG. 22B), *K. pneumoniae* (FIG. 22C) and *E. coli* (FIG. 22D) isolates was measured following infection of 3T3 cells left untreated (black), BL21-MAM7 treated (light grey) or treated with bead-immobilized MAM7 (dark grey). Values given are means±standard error (n=3) from a representative experiment performed in triplicate. Data points marked by an asterix were chosen for visualization using confocal microscopy (FIGS. 24A-R).

FIGS. 23A-R. Visualization of anti-adhesion treatment of HeLa cells for representative examples from each group of bacterial isolate. HeLa cells were either left untreated (row 1), pre-incubated with BL21-MAM7 (row 2) or pre-treated with bead-immobilized MAM7 (row 3). Cells were then left uninfected (controls, FIGS. 23A, 23G, 23M) or infected with *A. baumannii* isolate #1 (FIGS. 23B, 23H, 23N), *P. aeruginosa* isolate #1 (FIGS. 23C, 23I, 23O), *P. aeruginosa* isolate #3 (FIGS. 23D, 23J, 23P), *K. pneumoniae* isolate #1 (FIGS. 23E, 23K, 23Q) or *E. coli* isolate #5 (FIGS. 23F, 23L, 23R) for four hours. Cells were stained for actin (phalloidin-ALEX-AFLUOR® 488 (, light grey) and DNA (Hoechst stain). Fluorescent latex beads are shown in yellow. Scalebar, 20 μm.

FIGS. 24A-R. Visualization of anti-adhesion treatment of 3T3 cells for representative examples from each group of bacterial isolate. 3T3 cells were either left untreated (row 1), pre-incubated with BL21-MAM7 (row 2) or pre-treated with bead-immobilized MAM7 (row 3). Cells were then left uninfected (controls, FIGS. 24A, 24G, 24M) or infected with *A. baumannii* isolate #1 (FIGS. 24B, 24H, 24N), *P. aeruginosa* isolate #1 (FIGS. 24C, 24I, 24O), *P. aeruginosa* isolate #3 (FIGS. 24D, 24J, 24P), *K. pneumoniae* isolate #1 (FIGS. 24E, 24K, 24Q) or *E. coli* isolate #5 (FIGS. 24F, 24L, 24R) for four hours. Cells were stained for actin (phalloidin-ALEX-AFLUOR® 488, fluorescent dye, green) and DNA (Hoechst stain). Fluorescent latex beads are shown in yellow. Scalebar, 20 μm.

DESCRIPTION OF ILLUSTRATIVE EMBODIMENTS

Figure 8:
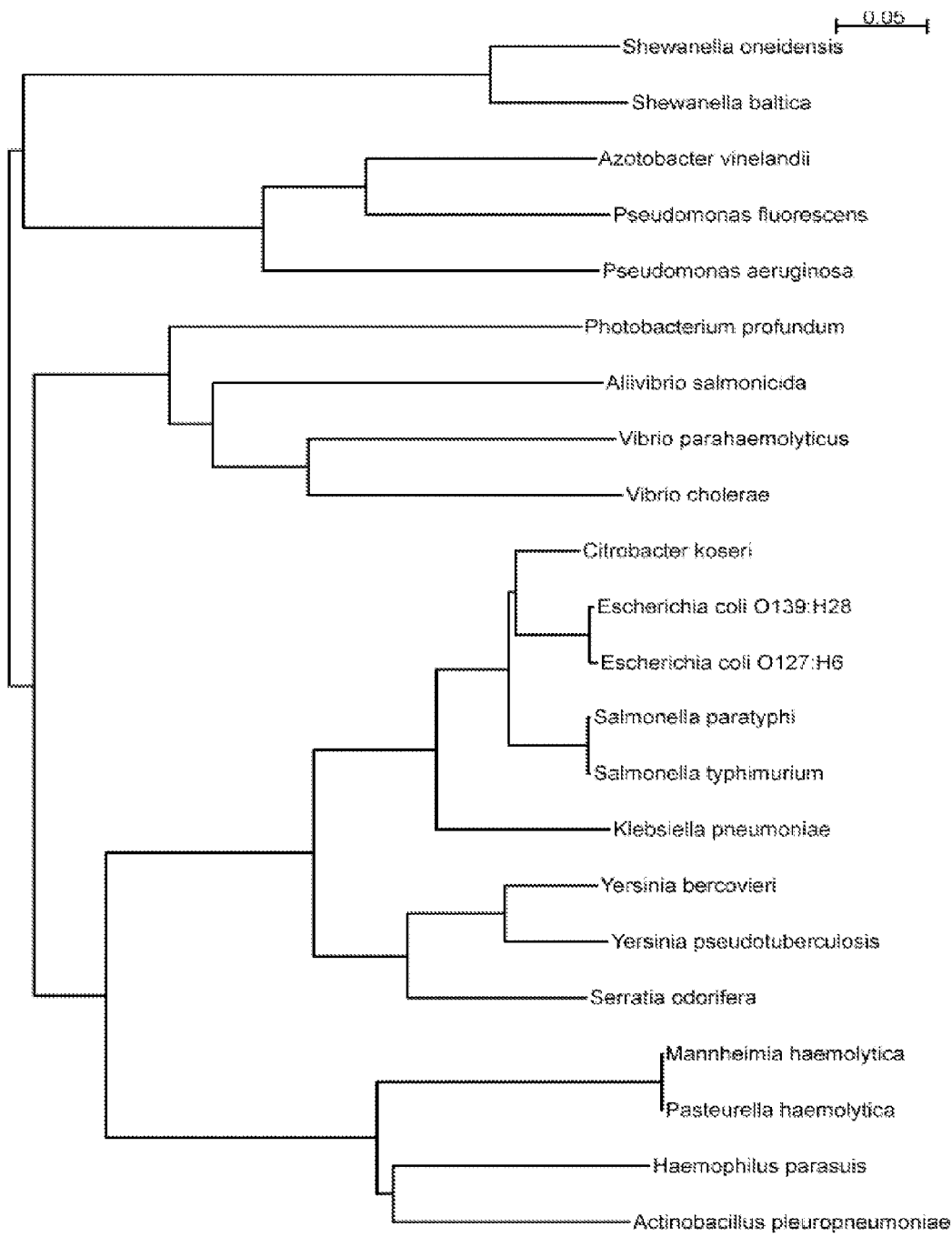
FIG. 8. Phylogenetic relationship among MAM7 adhesins in selected Gram-negative species. Evolutionary distances were calculated using the neighbor joining method. Branch lengths are proportional to the evolutionary distance.

Using bioinformatics, the inventors discovered a predicted outer membrane molecule that the have designated multivalent adhesion molecule (MAM) that encodes a putative transmembrane motif followed by six (MAM6) or seven (MAM7) mammalian cell entry (mce) domains. Unexpectedly, they found that MAM6 or MAM7 is encoded in a wide range of Gram-negative animal pathogens, but not Gram-positive or plant pathogenic bacteria. In contrast, proteins containing a single mce domain are wide-spread. In *Mycobacterium* ssp. and some Gram-positive bacteria, such as *Rhodococcus* ssp. or *Streptomyces* ssp., the mce domain occurs in conjunction with a second domain of unknown function (DUF3407) (Arruda et al., 1993; Chitale et al., 2001). Proteins containing one mce domain and a C-terminal low complexity region are thought to represent an accessory component of ABC transporters occurring in algae, higher plants and bacteria.

The inventors have tested whether MAMs, which constitute a new class of predicted outer membrane proteins from Gram-negative bacteria, are involved in cellular attachment. *V. parahaemolyticus*, a Gram-negative bacterium that occurs in marine and estuarine environments and can cause shellfish-borne food-poisoning, was used as the representative Gram-negative bacterium for analysis of MAM7s (Daniels et al., 2000). As discussed below, MAM enables a wide range of Gram-negative pathogens to establish high affinity binding to host cells during the early stage of infection by engaging both protein-protein and protein-lipid interactions with the host cell membrane. Exploiting this interaction, the inventors have demonstrated that non-pathogenic bacteria expressing MAM can protect host cells from pathogen-mediated cytotoxicity by preventing the binding of a range of Gram-negative pathogens to host cells. This work has been extended to the use of isolated recombinant MAM proteins with positive results. These and other aspects of the invention are discussed further below.

1. MAM

The present invention relates to peptides and polypeptides of MAM. An exemplary sequence for *V. parahaemolyticus* MAM7 is presented in SEQ ID NO:1.

A. Polypeptides and Peptides

MAM polypeptides/peptides will comprise molecules of 90 to about 830 residues in length having the sequence of SEQ ID NO:1, SEQ ID NO: 18, SEQ ID NO: 20, SEQ ID NO: 21, or SEQ ID NO: 26. A particular preferred length may be less than 850 residues, less than 800 residues, less than 750 residues, less than 700 residues, less than 650 residues, less than 600 residues, less than 550 residues, less than 500 residues, less than 450 residues, less than 400 residues, less than 350 residues, less than 300 residues, 250 residues, less than 200 residues, less than 150 residues, less than 100 residues, less than 75 residues, or less than 50, including all intervals in-between.

MAM polypeptides/peptides may also be defined by the number of mce domains. For example, MAM polypeptides/peptides may have more than 7 mce domains, such as 8, 9, 10, 11, 12, 13, 14, 15, 16 or 20 mce domains, including ranges of 8-10, 8-12, 8-14, 8-16, and 8-20 domains. Alternatively, the number of domains may be 7 or fewer, including no more than 6, 5, 4, 3 or 2 mce domains.

The peptides may be generated synthetically or by recombinant techniques, and are purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

The peptides may be labeled using various molecules, such as fluorescent, chromogenic or colorimetric agents. The peptides may also be linked to other molecules. The links may be direct or through distinct linker molecules. The linker molecules in turn may be subject, in vivo, to cleavage, thereby releasing the agent from the peptide. Peptides may also be rendered multimeric by linking to larger, and possibly inert, carrier molecules.

B. Variants or Analogs of MAM i) Substitutional Variants

It also is contemplated in the present invention that variants or analogs of MAM peptides may also inhibit bacterial infection. Polypeptide sequence variants of MAM, primarily making conservative amino acid substitutions to SEQ ID NO:1, SEQ ID NO: 18, SEQ ID NO: 20, SEQ ID NO: 21, or SEQ ID NO: 26 may provide improved compositions. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a peptide that defines that peptide's biological functional activity, certain amino acid substitutions can be made in a protein sequence, and its underlying DNA coding sequence, and nevertheless obtain a peptide with like properties. It is thus contemplated by the inventors that various changes may be made in the DNA sequences coding the peptide without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of MAM, but with altered and even improved characteristics.

ii) Altered Amino Acids

The present invention may employ peptides that comprise modified, non-natural and/or unusual amino acids. A table of exemplary, but not limiting, modified, non-natural and/or unusual amino acids is provided herein below. Chemical synthesis may be employed to incorporated such amino acids into the peptides of interest.

TABLE 1

Modified, Non-Natural and Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | | iii) Mimetics

In addition to the variants discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

iv) Modifications

A useful modification for delivery of peptides and peptidomimetics is PEG-ylation. PEG-ylation is the process of covalent attachment of polyethylene glycol polymer chains to another molecule, normally a drug or therapeutic protein. PEG-ylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. PEG-ylation can also provide water solubility to hydrophobic drugs and proteins. Exemplary PEG-ylation technologies are described in U.S. Pat. Nos. 7,666,400, 7,610,156, 7,587,286, 6,552,170 and 6,420,339.

C. Fusion Proteins

Another variant is a fusion protein. This molecule generally has all or a substantial portion of the original molecule, in this case a peptide comprising 2, 3, 4, 5, 6, 7, 8, 9, 10, 11, 12, 13, 14, 15, 16 or more MCE sequences, linked at the N- or C-terminus, to all or a portion of a second peptide or polypeptide, for example, linked at the N-terminal to glutathione 5-transferase (GST), or linked at the C terminal to a myc tag.

D. Purification of Peptides Proteins

It may be desirable to purify MAMs, variants, peptidemimics or analogs thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Peptide Synthesis

MAM-related peptides may be generated synthetically for use in various embodiments of the present invention. Because of their relatively small size, the peptides of the invention can be synthesized in solution or on a solid support in accordance with conventional techniques. Various automatic synthesizers are commercially available and can be used in accordance with known protocols. See, for example, Stewart & Young, (1984); Tam et al., (1983); Merrifield, (1986); Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

2. MAM NUCLEIC ACIDS

Important aspects of the present invention concern isolated DNA segments and recombinant vectors encoding MAM and portions thereof, the creation and use of recombinant host cells through the application of DNA technology, that express MAM or peptides thereof, and biologically functional equivalents thereof. Sequences for MAM nucleic acids include SEQ ID NO:1 and fragments thereof.

The present invention concerns DNA segments, isolatable from bacterial cells that are free from total genomic DNA and that encode a MAM polypeptide or peptide. As used herein, the term "DNA segment" refers to a DNA molecule that has been isolated free of total genomic DNA of a particular species. Therefore, a DNA segment encoding MAM refers to a DNA segment that contains wild-type, polymorphic or mutant MAM coding sequences yet is isolated away from, or purified free from, total mammalian genomic DNA. Included within the term "DNA segment" including DNA segments such recombinant vectors, including, for example, plasmids, cosmids, phage, viruses, and the like.

A. Homlogs

Certain aspects of the present invention concern isolated DNA segments and recombinant vectors incorporating DNA sequences that are homologous to a nucleic acid sequence encoding MAM and the portions thereof SEQ ID NO:1, which illustrates the MAM7 protein of *Vibrio parahaemolyticus* (GI:28898385). As used herein, the term "homologous" is defined as being substantially identical, sufficiently complementary, similar, or having a common ancestry or evolutionary origin to a MAM nucleic acid encoded by SEQ ID NO:1, SEQ ID NO: 18, SEQ ID NO: 20, SEQ ID NO: 21, or SEQ ID NO: 26 or a fragment thereof. Homologs may be defined by percentage homology at either the protein or nucleic level. Alternatively, homologs are identified operationally by hybridization under various conditions.

MAM homologs were identified in *Shewanella oneidensis* (GI:24374148; SEQ ID NO:12), *Shewanella baltica* (GI:126174666; SEQ ID NO:13), *Azotobacter vinelandii* (GI:226946271; SEQ ID NO:14), *Pseudomonas aeruginosa* (GI:12698379; SEQ ID NO:15), *Photobacterium profundum* (GI:54309112; SEQ ID NO:16), *Aliivibrio salmonicida* (GI:209695044; SEQ ID NO:17), *Vibrio cholerae* (GI:15641510; SEQ ID NO:18), *Citrobacter koseri* (GI:157145397; SEQ ID NO:19), *Escherichia coli* O139:H28 (non-pathogenic) (GI:157157260; SEQ ID NO:20), *Escherichia coli* O127:H6 (pathogenic) (GI:215487047; SEQ ID NO:21), *Salmonella paratyphi* (GI:56413233; SEQ ID NO:22), *Salmonella typhimurium* (GI:16765190; SEQ ID NO:23), *Klebsiella pneumonia* (GI:152970897; SEQ ID NO:24), *Yersinia bercovieri* (GI:238783417; SEQ ID NO:25), *Yersinia pseudotuberculosis* (GI:170024018; SEQ ID NO:26), *Serratia odorifera* (GI:270261529; SEQ ID NO:27), *Mannheimia haemolytica* (GI:254363206; SEQ ID NO:28), *Pasteurella (multocida) haemolytica* (GI:15602131; SEQ ID NO:29), *Haemophilus parasuis* (GI:167854634; SEQ ID NO:30), and *Actinobacillus pleuropneumoniae* (GI:53729097; SEQ ID NO:31). The MAM homologs listed above are exemplary and are not limiting.

B. Variants

In particular embodiments, the invention concerns isolated DNA segments and recombinant vectors incorporating DNA sequences that encode a MAM, a peptide, peptide-mimic or a biologically functional equivalent of an entire MAM or an mce domain thereof. The term "biologically functional equivalent" is well understood in the art and is further defined in detail herein. Accordingly, protein or nucleic acid sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more particularly about 81% and about 90% or about 85% to about 99%; or even more particularly, between about 91% and about 99%; of amino acids that are identical or functionally equivalent to the amino acids of, for example, SEQ ID NO:1, SEQ ID NO: 18, SEQ ID NO: 20, SEQ ID NO: 21, or SEQ ID NO: 26. In particular embodiments, the biological activity of a MAM peptide, or a biologically functional equivalent, comprises binding to the MAM host cell receptor.

Another way of defining homology for nucleic acids is by hybridization conditions. For example, a nucleic acid will hybridize to sequences of greater or less homology based on the stringency of the hybridization conditions. For example, high stringency conditions may be exemplified by those including approximately 10 mM Tris-HCl (pH 8.3), 50 mM KCl, 1.5 µM MgCl$_2$, at temperatures ranging from approximately 40° C. to about 72° C.

It will also be understood that nucleic acid sequences may include those that encode additional residues, such as 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

3. BACTERIAL SPECIES

A. Pathogens i. *Acetinobacter baumannii*

*Acetinobacter baumannii* is a Gram-negative bacterial pathogen that has rapidly emerged as a leading cause of infection world-wide. In fact, *A. baumannii* is now responsible for up to 20% of all intensive care unit infections in some regions of the world. This organism causes a range of diseases, with pneumonia being the most prevalent. As a result of its resistance to drug treatment, some estimates state the disease is killing tens of thousands of U.S. hospital patients each year.

*A. baumannii* forms opportunistic infections. There have been many reports of *A. baumannii* infections among American soldiers wounded in Iraq, earning it the nickname "Iraqibacter." Multi-drug resistant *Acinetobacter baumannii* is abbreviated as MDRAB. Multidrug-resistant *Acinetobacter* is not a new phenomenon; it has always been inherently resistant to multiple antibiotics.

*Acinetobacter baumannii* is the most relevant human pathogen within the *Acinetobacter* genus. Most *A. baumannii* isolates are multiresistant, containing in their genome small, isolated islands of alien (meaning transmitted genetically from other organisms) DNA and other cytological and genetic material; this has led to more virulence. *Acinetobacter* have no flagellum; the name is Greek for "motionless."

*Acinetobacter* enters into the body through open wounds, catheters, and breathing tubes. It usually infects those with compromised immune systems, such as the wounded, the elderly, children or those with immune diseases. Colonization poses no threat to people who aren't already ill, but colonized health care workers and hospital visitors can carry the bacteria into neighboring wards and other medical facilities. The number of nosocomial infections (hospital-acquired infections) caused by *A. baumannii* has increased in recent years; as have most other nosocomial pathogens (MRSA, VRSA, VRE, etc.).

The first military outbreaks of severe *A. baumannii* infections occurred in April, 2003 in American soldiers returning from Iraq. Early reports attributed the infections to the Iraqi soil. Later testing demonstrated widespread contamination of field hospitals, via transportation of personnel and equipment from previously contaminated European hospitals, as the most plausible vector.

Nosocomial *A. baumannii* bacteremia may cause severe clinical disease that is associated with an elevated mortality rate. This opportunistic pathogen expresses a myriad of factors that could play a role in human pathogenesis. Among these factors are the attachment to and persistence on solid surfaces, the acquisition of essential nutrients such as iron, the adhesion to epithelial cells and their subsequent killing by apoptosis, and the production and/or secretion of enzymes and toxic products that damage host tissues. However, very little is known about the molecular nature of most of these processes and factors and almost nothing has been shown with regard to their role in bacterial virulence and the pathogenesis of serious infectious diseases. Fortunately, some of these gaps can now be filled by testing appropriate isogenic derivatives in relevant animal models that mimic the infections in humans, particularly the outcome of deadly pneumonia. Such an approach should provide new and relevant information on the virulence traits of this normally underestimated bacterial human pathogen.

Multidrug-resistant *A. baumannii* is a common problem in many hospitals in the U.S. and Europe. First line treatment is with a carbapenem antibiotic such as imipenem, but carbapenem resistance is increasingly common. Other treatment options include polymyxins, tigecycline and aminoglycosides. The institution of strict infection-control measures, such as monitored hand washing, can lower hospital infection rates. MDRAB infections are difficult and costly to treat. A study at a public teaching hospital found that the mean total hospital cost of patients who acquired MDRAB was $98,575 higher than that of control patients who had identical burn severity of illness indices.

ii. *Staphylococcus aureus*

*Staphylococcus aureus* is a major human pathogen, causing a wide variety of illnesses ranging from mild skin and soft tissue infections and food poisoning to life-threatening illnesses such as deep post-surgical infections, septicaemia, endocarditis, necrotizing pneumonia, and toxic shock syndrome. These organisms have a remarkable ability to accumulate additional antibiotic resistance determinants, resulting in the formation of multiply-drug-resistant strains. Methicillin, being the first semi-synthetic penicillin to be developed, was introduced in 1959 to overcome the problem of penicillin-resistant *S. aureus* due to β-lactamase (penicillinase) production (Livermore, 2000). However, methicillin-resistant *S. aureus* (MRSA) strains were identified soon after the introduction of methicillin (Barber, 1961; Jevons, 1961).

Since their first identification, strains of MRSA have spread and become established as major nosocomial (hospital-acquired (HA)-MRSA) pathogens worldwide (Ayliffe, 1997; Crossley et al., 1979; Panlilio et al., 1992; Voss et al., 1994). Recently, these organisms have evolved and emerged as a major cause of community-acquired infections (CA-MRSA) in healthy individuals lacking traditional risk factors for infection, and are causing community-outbreaks, which pose a significant threat to public health (Begier et al., 2004; Beilman et al., 2005; Conly et al., 2005; Gilbert et al., 2006; Gilbert et al., 2005; Harbarth et al., 2005; Holmes et al., 2005; Issartel et al., 2005; Mulvey et al., 2005; Robert et al., 2005; Said-Salim et al., 2005; Vandenesch et al., 2003; Vourli et al., 2005; Wannet et al., 2005; Wannet et al., 2004; Witte et al., 2005; Wylie & Nowicki, 2005).

iii. *Acinetobacter* spp.

*Acinetobacter* spp. other than *A. baumannii* include *A. calcoaceficus, A. lwoffii, A. junii, A. anitratus, A. baumannii-calcoacificus* complex. *Acinetobacter* is a Gram-negative genus of bacteria belonging to the Gammaproteobacteria. Non-motile, *Acinetobacter* species are oxidase-negative, and occur in pairs under magnification. They are important soil organisms where they contribute to the mineralisation of, for example, aromatic compounds. *Acinetobacter* are a key source of infection in debilitated patients in the hospital. Different species of bacteria in this genus can be identified using Fluorescence-Lactose-Denitrification medium (FLN) to find the amount of acid produced by metabolism of glucose.

Species of the genus *Acinetobacter* are strictly aerobic, nonfermentative, Gram-negative bacilli. They show preponderantly a coccobacillary morphology on nonselective agar. Rods predominate in fluid media, especially during early growth. The morphology of *Acinetobacter* spp. can be quite variable in Gram stained human clinical specimens, and cannot be used to differentiate *Acinetobacter* from other common causes of infection.

Most strains of *Acinetobacter*, except some of the *A. lwoffii* strains, grow well on MacConkey agar (without salt). Although officially classified as non-lactose fermenting, they are often partially lactose fermenting when grown on MacConkey agar. They are oxidase negative, nonmotile and usually nitrate negative.

*Acinetobacter* species are generally considered nonpathogenic to healthy individuals. However, several species persist in hospital environments and cause severe, life-threatening infections in compromised patients. The spectrum of antibiotic resistances of these organisms together with their survival capabilities make them a threat to hospitals as documented by recurring outbreaks both in highly developed countries and elsewhere. An important factor for their pathogenic potential is probably an efficient means of horizontal gene transfer even though such a mechanism has so far only been observed and analyzed in *Acinetobacter baylyi*, a species that lives in the soil and has never been associated with infections. *Acinetobacter* is frequently isolated in nosocomial infections and is especially prevalent in intensive care units, where both sporadic cases as well as epidemic and endemic occurrence is common. *A. lwoffi* is responsible for most cases of *Acinetobacter* meningitis.

*Acinetobacter* species are innately resistant to many classes of antibiotics, including penicillin, chloramphenicol, and often aminoglycosides. Resistance to fluoroquinolones has been reported during therapy and this has also resulted in increased resistance to other drug classes mediated through active drug efflux. A dramatic increase in antibiotic resistance in *Acinetobacter* strains has been reported by the CDC and the carbapenems are recognized as the gold-standard and treatment of last resort. *Acinetobacter* species are unusual in that they are sensitive to sulbactam; sulbactam is most commonly used to inhibit bacterial beta-lactamase, but this is an example of the antibacterial property of sulbactam itself.

iv. *Pseudomonas aeruginosa*

*Pseudomonas aeruginosa* is a common bacterium which can cause disease in animals and humans. It is found in soil, water, skin flora and most man-made environments throughout the world. It thrives not only in normal atmospheres, but also with little oxygen, and has thus colonised many natural and artificial environments. It uses a wide range of organic material for food; in animals, the versatility enables the organism to infect damaged tissues or people with reduced immunity. The symptoms of such infections are generalised inflammation and sepsis. If such colonisations occur in critical body organs such as the lungs, the urinary tract, and kidneys, the results can be fatal. Because it thrives on most surfaces, this bacterium is also found on and in medical equipment including catheters, causing cross infections in hospitals and clinics. It is implicated in hot-tub rash.

It is a Gram-negative, aerobic, rod-shaped bacterium with unipolar motility. An opportunistic human pathogen, *P. aeruginosa* is also an opportunistic pathogen of plants. *P. aeruginosa* is the type species of the genus *Pseudomonas* (Migula).

*P. aeruginosa* secretes a variety of pigments, including pyocyanin (blue-green), fluorescein (yellow-green and fluorescent, now also known as pyoverdin), and pyorubin (redbrown). King, Ward, and Raney developed *Pseudomonas* Agar P (aka King A media) for enhancing pyocyanin and pyorubin production and *Pseudomonas* Agar F (aka King B media) for enhancing fluorescein production.

*P. aeruginosa* is often preliminarily identified by its pearlescent appearance and grape-like or tortilla-like odor in vitro. Definitive clinical identification of *P. aeruginosa* often includes identifying the production of both pyocyanin and fluorescein, as well as its ability to grow at 42° C. *P. aeruginosa* is capable of growth in diesel and jet fuel, where it is known as a hydrocarbon-utilizing microorganism, causing microbial corrosion. It creates dark gellish mats sometimes improperly called "algae" because of their appearance.

Although classified as an aerobic organism, *P. aeruginosa* is considered by many as a facultative anaerobe, as it is well adapted to proliferate in conditions of partial or total oxygen depletion. This organism can achieve anaerobic growth with nitrate as a terminal electron acceptor, and, in its absence, it is also able to ferment arginine by substrate-level phosphorylation. Adaptation to microaerobic or anaerobic environments is essential for certain lifestyles of *P. aeruginosa*, for example, during lung infection in cystic fibrosis patients, where thick layers of alginate surrounding bacterial mucoid cells can limit the diffusion of oxygen.

The G+C-rich *Pseudomonas aeruginosa* chromosome consists of a conserved core and a variable accessory part. The core genomes of *P. aeruginosa* strains are largely collinear, exhibit a low rate of sequence polymorphism, and contain few loci of high sequence diversity, notably the pyoverdine locus, the flagellar regulon, pilA, and the O-antigen biosynthesis locus. Variable segments are scattered throughout the genome, of which about one-third are immediately adjacent to tRNA or tmRNA genes. The three known hot spots of genomic diversity are caused by the integration of genomic islands of the pKLC102/PAGI-2 family into tRNA$^{Lys}$ or tRNA$^{Gly}$ genes. The individual islands differ in their repertoire of metabolic genes, but share a set of syntenic genes which confer their horizontal spread to other clones and species. Colonization of atypical disease habitats predisposes to deletions, genome rearrangements, and accumulation of loss-of-function mutations in the *P. aeruginosa* chromosome. The *P. aeruginosa* population is characterized by a few dominant clones widespread in disease and environmental habitats. The genome is made up of clone-typical segments in core and accessory genome and of blocks in the core genome with unrestricted gene flow in the population.

Cell-surface polysaccharides play diverse roles in the bacterial lifestyle. They serve as a barrier between the cell wall and the environment, mediate host-pathogen interactions, and form structural components of biofilms. These polysaccharides are synthesized from nucleotide-activated precursors, and, in most cases, all the enzymes necessary for biosynthesis, assembly, and transport of the completed polymer are encoded by genes organized in dedicated clusters within the genome of the organism. Lipopolysaccharide is one of the most important cell-surface polysaccharides, as it plays a key structural role in outer membrane integrity, as well as being an important mediator of host-pathogen interactions. The genetics for the biosynthesis of the so-called A-band (homopolymeric) and B-band (heteropolymeric) O antigens have been clearly defined, and much progress has been made toward understanding the biochemical pathways of their biosynthesis. The exopolysaccharide alginate is a linear copolymer of β-1,4-linked D-mannuronic acid and L-glucuronic acid residues, and is responsible for the mucoid phenotype of late-stage cystic fibrosis disease. The pel and psl loci are two recently-discovered gene clusters which also encode exopolysaccharides found to be important for biofilm formation. Rhamnolipid is a biosurfactant whose production is tightly regulated at the transcriptional level, but the precise role that it plays in disease is not well understood at present. Protein glycosylation, particularly of pilin and flagellin, is a recent focus of research by several groups, and it has been shown to be important for adhesion and invasion during bacterial infection.

An opportunistic, nosocomial pathogen of immunocompromised individuals, *P. aeruginosa* typically infects the pulmonary tract, urinary tract, burns, wounds, and also causes other blood infections.

It is the most common cause of infections of burn injuries and of the external ear (otitis externa), and is the most frequent colonizer of medical devices (e.g., catheters). *Pseudomonas* can, in rare circumstances, cause community-acquired pneumonias, as well as ventilator-associated pneumonias, being one of the most common agents isolated in several studies. Pyocyanin is a virulence factor of the bacteria and has been known to cause death in *C. elegans* by oxidative stress. However, research indicates that salicylic acid can inhibit pyocyanin production. One in ten hospital-acquired infections are from *Pseudomonas*. Cystic fibrosis patients are also predisposed to *P. aeruginosa* infection of the lungs. *P. aeruginosa* may also be a common cause of "hot-tub rash" (dermatitis), caused by lack of proper, periodic attention to water quality. The most common cause of burn infections is *P. aeruginosa*. *Pseudomonas* is also a common cause of post-operative infection in radial keratotomy surgery patients. The organism is also associated with the skin lesion ecthyma gangrenosum. *Pseudomonas aeruginosa* is frequently associated with osteomyelitis involving puncture wounds of the foot, believed to result from direct inoculation with *P. aeruginosa* via the foam padding found in tennis shoes.

Depending on the nature of infection, an appropriate specimen is collected and sent to a bacteriology laboratory for identification. First, a Gram stain is performed, which should show Gram negative rods with no particular arrangement. Then, if the specimen is pure, the organism is grown on MacConkey agar plate to produce colorless colonies (as it does not ferment lactose); but, if the specimen is not pure, then the use of a selective plate is essential. Cetrimide agar has been traditionally used for this purpose. When grown on it, *P. aeruginosa* may express the exopigment pyocyanin, which is blue-green in color, and the colonies will appear flat, large, and oval. It also has a characteristic fruity smell. *P. aeruginosa* is catalase+, oxidase+, nitrase+, and lipase+. When grown on TSI medium, it has a K/K/g−/H$_2$S-profile, meaning that the medium will not change color. Finally, serology could help, which is based on H & O antigens.

*P. aeruginosa* is frequently isolated from non-sterile sites (mouth swabs, sputum, and so forth), and, under these circumstances, it often represents colonisation and not infection. The isolation of *P. aeruginosa* from non-sterile specimens should, therefore, be interpreted cautiously, and the advice of a microbiologist or infectious diseases physician/pharmacist should be sought prior to starting treatment. Often no treatment is needed.

When *P. aeruginosa* is isolated from a sterile site (blood, bone, deep collections), it should be taken seriously, and almost always requires treatment.

*P. aeruginosa* is naturally resistant to a large range of antibiotics and may demonstrate additional resistance after unsuccessful treatment, particularly through modification of a porin. It should usually be possible to guide treatment according to laboratory sensitivities, rather than choosing an antibiotic empirically. If antibiotics are started empirically, then every effort should be made to obtain cultures, and the choice of antibiotic used should be reviewed when the culture results are available.

Antibiotics that have activity against *P. aeruginosa* include: aminoglycosides (gentamicin, amikacin, tobramycin); quinolones (ciprofloxacin, levofloxacin, and moxifloxacin); cephalosporins (ceftazidime, cefepime, cefoperazone, cefpirome, but not cefuroxime, ceftriaxone, cefotaxime); ureidopenicillins and carboxypenicillins (piperacillin, ticarcillin: *P. aeruginosa* is intrinsically resistant to all other penicillins); carbapenems (meropenem, imipenem, doripenem, but not ertapenem); polymyxins (polymyxin B and colistin); and monobactams (aztreonam). These antibiotics must all be given by injection, with the exception of fluoroquinolones and of aerosolized tobramycin. For this reason, in some hospitals, fluoroquinolone use is severely restricted in order to avoid the development of resistant strains of *P. aeruginosa*. In the rare occasions where infection is superficial and limited (for example, ear infections or nail infections), topical gentamicin or colistin may be used. Phage therapy against ear infections caused by *Pseudomonas aeruginosa* was reported in the journal Clinical Otolaryngology in August 2009.

*Pseudomonas aeruginosa* is a highly relevant opportunistic pathogen. One of the most worrisome characteristics of *P. aeruginosa* is its low antibiotic susceptibility. This low susceptibility is attributable to a concerted action of multidrug efflux pumps with chromosomally-encoded antibiotic resistance genes (e.g., mexAB, mexXY, etc.) and the low permeability of the bacterial cellular envelopes. In addition to this intrinsic resistance, *P. aeruginosa* easily develops acquired resistance either by mutation in chromosomally-encoded genes or by the horizontal gene transfer of antibiotic resistance determinants. Development of multidrug resistance by *P. aeruginosa* isolates requires several different genetic events including acquisition of different mutations and/or horizontal transfer of antibiotic resistance genes. Hypermutation favors the selection of mutation-driven antibiotic resistance in *P. aeruginosa* strains producing chronic infections, whereas the clustering of several different antibiotic resistance genes in integrons favors the concerted acquisition of antibiotic resistance determinants. Some recent studies have shown that phenotypic resistance associated to biofilm formation or to the emergence of small-colony variants may be important in the response of *P. aeruginosa* populations to antibiotics treatment.

v. *Burkholderia* spp.

*Burkholderia* spp. (*B. cepacia, B. cenocepacia, B. cepacia* complex) are members of a genus of proteobacteria probably best-known for its pathogenic members *Burkholderia mallei* (responsible for glanders, a disease that occurs mostly in horses and related animals), *Burkholderia pseudomallei* (causative agent of melioidosis), and *Burkholderia cepacia* (an important pathogen of pulmonary infections in people with cystic fibrosis).

The *Burkholderia* (previously part of *Pseudomonas*) genus name refers to a group of virtually ubiquitous gram-negative, motile, obligately aerobic rod-shaped bacteria including both animal/human and plant pathogens as well as some environmentally-important species. In particular, *B. xenovorans* (previously named *Pseudomonas cepacia* then *B. cepacia* and *B. fungorum*) is renowned for its ability to degrade chlororganic pesticides and polychlorinated biphenyls (PCBs). Due to their antibiotic resistance and the high mortality rate from their associated diseases, *Burkholderia mallei* and *Burkholderia* pseudomallei are considered to be potential biological warfare agents, targeting livestock and humans.

vi. *Klebsiella pneumoniae*

*Klebsiella pneumoniae* is a Gram-negative, non-motile, encapsulated, lactose fermenting, facultative anaerobic, rod shaped bacterium found in the normal flora of the mouth, skin, and intestines. It is clinically the most important member of the *Klebsiella* genus of Enterobacteriaceae; it is closely related to *K. oxytoca* from which it is distinguished by being indole-negative and by its ability to grow on both melezitose and 3-hydroxybutyrate. It naturally occurs in the soil and about 30% of strains can fix nitrogen in anaerobic conditions. As a free-living diazotroph, its nitrogen fixation system has been much studied.

Members of the *Klebsiella* genus typically express 2 types of antigens on their cell surface. The first, O antigen, is a lipopolysaccharide of which 9 varieties exist. The second is K antigen, a capsular polysaccharide with more than 80 varieties. Both contribute to pathogenicity and form the basis for subtyping.

Research has implicated molecular mimicry between HLA-B27 and two molecules in *Klebsiella* microbes as the cause of ankylosing spondylitis. As a general rule, *Klebsiella* infections tend to occur in people with a weakened immune system from improper diet (alcoholics and diabetics). Many of these infections are obtained when a person is in the hospital for some other reason (a nosocomial infection). The most common infection caused by *Klebsiella* bacteria outside the hospital is pneumonia.

New antibiotic resistant strains of *K. pneumoniae* are appearing, and it is increasingly found as a nosocomial infection. *Klebsiella* ranks second to *E. coli* for urinary tract infections in older persons. It is also an opportunistic pathogen for patients with chronic pulmonary disease, enteric pathogenicity, nasal mucosa atrophy, and rhinoscleroma. Feces are the most significant source of patient infection, followed by contact with contaminated instruments.

Multiply-resistant *Klebsiella pneumoniae* have been killed in vivo via intraperitoneal, intravenous or intranasal administration of phages in laboratory tests.

vii. *Stenotrophomonas maltophilia*

*Stenotrophomonas maltophilia* is an aerobic, nonfermentative, Gram-negative bacterium. It is an uncommon bacteria and it is difficult to treat infections in humans. Initially classified as *Pseudomonas maltophilia, S. maltophilia* was also grouped in the genus *Xanthomonas* before eventually becoming the type species of the genus *Stenotrophomonas* in 1993.

*S. maltophilia* are slightly smaller (0.7–1.8×0.4-0.7 micrometers) than other members of the genus. They are motile due to polar flagella and grow well on MacConkey agar producing pigmented colonies. *S. maltophilia* are catalase-positive, oxidase-negative (which distinguishes them from most other members of the genus) and have a positive reaction for extracellular DNase.

*S. maltophilia* is ubiquitous in aqueous environments, soil and plants, including water, urine, or respiratory secretions; it has also been used in biotechnology applications. In immunocompromised patients, *S. maltophilia* can lead to nosocomial infections.

*S. maltophilia* frequently colonizes breathing tubes such as endotracheal or tracheostomy tubes, the respiratory tract and indwelling urinary catheters. Infection is usually facilitated by the presence of prosthetic material (plastic or metal), and the most effective treatment is removal of the prosthetic material (usually a central venous catheter or similar device). The growth of *S. maltophilia* in microbiological cultures of respiratory or urinary specimens is therefore sometimes difficult to interpret and not a proof of infection. If, however, it is grown from sites which would be normally sterile (e.g., blood), then it usually represents true infection.

In immunocompetent individuals, S. maltophilia is a relatively unusual cause of pneumonia, urinary tract infection, or blood stream infection; in immunocompromised patients, however, S. maltophilia is a growing source of latent pulmonary infections. S. maltophilia colonization rates in individuals with cystic fibrosis have been increasing.

S. maltophilia is naturally resistant to many broad-spectrum antibiotics (including all carbapenems) and is thus often difficult to eradicate. Many strains of S. maltophilia are sensitive to co-trimoxazole and ticarcillin, though resistance has been increasing. It is not usually sensitive to piperacillin, and sensitivity to ceftazidime is variable.

viii. Haemophilus influenzae

Haemophilus influenzae, formerly called Pfeiffer's bacillus or Bacillus influenzae, is a non-motile Gram-negative rod-shaped bacterium first described in 1892 during an influenza pandemic. A member of the Pasteurellaceae family, it is generally aerobic, but can grow as a facultative anaerobe. H. influenzae was mistakenly considered to be the cause of influenza until 1933, when the viral etiology of the flu became apparent. Still, H. influenzae is responsible for a wide range of clinical diseases.

In 1930, 2 major categories of H. influenzae were defined: the unencapsulated strains and the encapsulated strains. Encapsulated strains were classified on the basis of their distinct capsular antigens. There are six generally recognized types of encapsulated H. influenzae: a, b, c, d, e, and f. Genetic diversity among unencapsulated strains is greater than within the encapsulated group. Unencapsulated strains are termed nontypable (NTHi) because they lack capsular serotypes, however they can be classified by multi-locus sequence typing. The pathogenesis of H. influenzae infections is not completely understood, although the presence of the capsule in encapsulated type b (Hib), a serotype causing conditions such as epiglottitis, is known to be a major factor in virulence. Their capsule allows them to resist phagocytosis and complement-mediated lysis in the non-immune host. The unencapsulated strains are almost always less invasive, however they can produce an inflammatory response in humans which can lead to many symptoms. Vaccination with Hib conjugate vaccine is effective in preventing Hib infection. Several vaccines are now available for routine use against Hib, however vaccines are not yet available against NTHi.

Most strains of H. influenzae are opportunistic pathogens—that is, they usually live in their host without causing disease, but cause problems only when other factors (such as a viral infection or reduced immune function) create an opportunity.

Naturally-acquired disease caused by H. influenzae seems to occur in humans only. In infants and young children, H. influenzae type b (Hib) causes bacteremia, pneumonia, and acute bacterial meningitis. Occasionally, it causes cellulitis, osteomyelitis, epiglottitis, and infectious arthritis. Due to routine use of the Hib conjugate vaccine in the U.S. since 1990, the incidence of invasive Hib disease has decreased to 1.3/100,000 in children. However, Hib remains a major cause of lower respiratory tract infections in infants and children in developing countries where vaccine is not widely used. Unencapsulated H. influenzae causes ear infections (otitis media), eye infections (conjunctivitis), and sinusitis in children and is associated with pneumonia.

Clinical diagnosis of H. influenzae is typically performed by bacterial culture or latex particle agglutination. Diagnosis is considered confirmed when the organism is isolated from a sterile body site. In this respect, H. influenzae cultured from the nasopharyngeal cavity or sputum would not indicate H. influenzae disease because these sites are colonized in disease free individuals. However, H. influenzae isolated from cerebrospinal fluid or blood would indicate a H. influenzae infection.

Bacterial culture of H. influenzae is performed on agar plates, preferably Chocolate agar, plate with added X (Hemin) & V (NAD) factors at 37° C. in an enriched CO2 incubator. Blood agar growth is only achieved as a satellite phenomenon around other bacteria. Colonies of H. influenzae appear as convex, smooth, pale, grey or transparent colonies. Gram-stained and microscopic observation of a specimen of H. influenzae will show Gram-negative, coccobacilli, with no specific arrangement. The cultured organism can be further characterized using catalase and oxidase tests, both of which should be positive. Further serological is necessary to distinguish the capsular polysaccharide and differentiate between H. influenzae b and non-encapsulated species.

Although highly specific, bacterial culture of H. influenzae lacks in sensitivity. Use of antibiotics prior to sample collection greatly reduces the isolation rate by killing the bacteria before identification is possible. Beyond this, H. influenzae is a finicky bacterium to culture, and any modification of culture procedures can greatly reduce isolation rates. Poor quality of laboratories in developing countries has resulted in poor isolation rates of H. influenzae.

H. influenzae will grow in the hemolytic zone of Staphylococcus aureus on Blood Agar plates. The hemolysis of cells by S. aureus releases nutrients vital to the growth of H. influenzae. H. influenzae will not grow outside the hemolytic zone of S. aureus due to the lack of nutrients in these areas.

Haemophilus influenzae produces beta lactamases, and it is also able to modify its penicillin binding protein, so it has gained resistance to the penicillin family of antibiotics. In severe cases cefotaxime and ceftriaxone are the elected antibiotics, delivered directly into the bloodstream, and for the less severe cases an association of ampicillin and sulbactam, cephalosporins of the second and third generation, or fluoroquinolones.

ix. Streptococcus pneumoniae

Streptococcus pneumoniae is a gram-positive, alpha-hemolytic, bile soluble aerotolerant anaerobe and a member of the genus Streptococcus. A significant human pathogenic bacterium, S. pneumoniae was recognized as a major cause of pneumonia in the late 19th century and is the subject of many humoral immunity studies.

Despite the name, the organism causes many types of pneumococcal infection other than pneumonia, including acute sinusitis, otitis media, meningitis, bacteremia, sepsis, osteomyelitis, septic arthritis, endocarditis, peritonitis, pericarditis, cellulitis, and brain abscess. S. pneumoniae is the most common cause of bacterial meningitis in adults and children, and is one of the top two isolates found in ear infection, otitis media. Pneumococcal pneumonia is more common in the very young and the very old.

S. pneumoniae can be differentiated from S. viridans, some of which are also alpha hemolytic, using an optochin test, as S. pneumoniae is optochin sensitive. S. pneumoniae can also be distinguished based on its sensitivity to lysis by bile. The encapsulated, gram-positive coccoid bacteria have a distinctive morphology on gram stain, the so-called, "lancet shape." It has a polysaccharide capsule that acts as a virulence factor for the organism; more than 90 different serotypes are known, and these types differ in virulence, prevalence, and extent of drug resistance.

S. pneumoniae is part of the normal upper respiratory tract flora but as with many natural flora, it can become pathogenic under the right conditions (e.g., if the immune system of the host is suppressed). Invasins such as Pneumolysin, an antiphagocytic capsule, various adhesins and immunogenic cell wall components are all major virulence factors.

Both *H. influenzae* and *S. pneumoniae* can be found in the human upper respiratory system. A study of competition in a laboratory revealed that, in a petri dish, *S. pneumoniae* always overpowered *H. influenzae* by attacking it with hydrogen peroxide. When both bacteria are placed together into a nasal cavity, within 2 weeks, only *S. pneumoniae* survives. When both are placed separately into a nasal cavity, each one survives. Upon examining the upper respiratory tissue from mice exposed to both bacteria, an extraordinarily large number of neutrophil immune cells were found. In mice exposed to only one bacteria, the cells were not present. Lab tests show that neutrophils that were exposed to already dead *H. influenzae* were more aggressive in attacking *S. pneumoniae* than unexposed neutrophils. Exposure to killed *H. influenzae* had no effect on live *H. influenzae*.

x. *Escherichia coli*

*Escherichia coli*, commonly abbreviated as *E. coli*, is a Gram-negative, rod-shaped, facultative anaerobic and non-sporulating bacterium that is commonly found in the lower intestine of warm-blooded organisms (endotherms). Most *E. coli* strains are harmless, but some, such as serotype O157:H7, can cause serious food poisoning in humans, and are occasionally responsible for product recalls.

Virulent strains of *E. coli* can cause gastroenteritis, urinary tract infections, and neonatal meningitis. In rarer cases, virulent strains are also responsible for haemolytic-uremic syndrome, peritonitis, mastitis, septicaemia and Gram-negative pneumonia.

Certain strains of *E. coli*, such as O157:H7, O121 and O104:H21, produce potentially lethal toxins. Food poisoning caused by *E. coli* is usually caused by eating unwashed vegetables or undercooked meat. *E. coli* infection outbreaks in the United States have also occurred even when eating shelled nuts, including Hazelnuts. O157:H7 is also notorious for causing serious and even life-threatening complications such as Hemolytic-uremic syndrome. This particular strain is linked to the 2006 United States *E. coli* outbreak due to fresh spinach. Severity of the illness varies considerably; it can be fatal, particularly to young children, the elderly or the immunocompromised, but is more often mild. Earlier, poor hygienic methods of preparing meat in Scotland killed seven people in 1996 due to *E. coli* poisoning, and left hundreds more infected.

If *E. coli* bacteria escape the intestinal tract through a perforation (for example from an ulcer, a ruptured appendix, or due to a surgical error) and enter the abdomen, they usually cause peritonitis that can be fatal without prompt treatment. However, *E. coli* are extremely sensitive to such antibiotics as streptomycin or gentamicin. Unfortunately, it has been suggested that *E. coli* quickly acquires drug resistance and the treatment with antibiotics does not improve the outcome of the disease, but may in fact significantly increase the chance of developing haemolytic-uremic syndrome.

Intestinal mucosa-associated *E. coli* are observed in increased numbers in the inflammatory bowel diseases, Crohn's disease and ulcerative colitis. Invasive strains of *E. coli* exist in high numbers in the inflamed tissue, and the number of bacteria in the inflamed regions correlates to the severity of the bowel inflammation Enteric *E. coli* are classified on the basis of serological characteristics and virulence properties. Virotypes include: Enterotoxigenic *E. coli* (ETEC), Enteropathogenic *E. coli* (EPEC), Enteroinvasive *E. coli* (EIEC), Enterohemorrhagic *E. coli* (EHEC), and Enteroaggregative *E. coli* (EAEC).

Among these virotypes, EPEC causes diarrhea in humans, rabbits, dogs, cats and horses. EPEC cells utilize an adhesin known as intimin to bind host intestinal cells. Adherence to the intestinal mucosa causes a rearrangement of actin in the host cell, causing significant deformation. EPEC cells are moderately invasive and elicit an inflammatory response. Changes in intestinal cell ultrastructure due to "attachment and effacement" is likely the prime cause of diarrhoea in those afflicted with EPEC.

Transmission of pathogenic *E. coli* often occurs via faecal-oral transmission. Common routes of transmission include: unhygienic food preparation, farm contamination due to manure fertilization, irrigation of crops with contaminated greywater or raw sewage, feral pigs on cropland, or direct consumption of sewage-contaminated water. Dairy and beef cattle are primary reservoirs of *E. coli* O157:H7, and they can carry it asymptomatically and shed it in their faeces. Food products associated with *E. coli* outbreaks include raw ground beef, raw seed sprouts or spinach, raw milk, unpasteurized juice, unpasteurized cheese and foods contaminated by infected food workers via faecal-oral route.

Certain strains of *E. coli*, specifically serotype O157:H7, have also been transmitted by flies, as well as direct contact with farm animals, petting zoo animals, and airborne particles found in animal-rearing environments.

xi. *Vibrio cholerae*

*Vibrio cholera*, also known as Kommabacillus, is a gram negative comma-shaped bacterium with a polar flagellum that causes cholera in humans. There are two major biotypes of *Vibrio cholerae* identified by hemaggluttination testing, classical and El Tor, and numerous serogroups. The classical biotype is found only in Bangladesh, whereas the El Tor is found throughout the world.

*Vibrio cholerae* pathogenicity genes code for proteins directly or indirectly involved in the virulence of the bacteria. Because of their same transcriptional regulation and their implication in the same pathway, pathogenicity genes are generally organized in operons and/or gene clusters. In *Vibrio cholerae*, most of virulence genes are located in two pathogenicity plasmids, which are organized as prophages: CTX (Cholera ToXins) plasmid and TCP (Toxin-Coregulated Pilus) plasmid, also named as *Vibrio cholerae* Pathogenicity Island (VPI). Virulent and epidemic strains of *Vibrio cholerae* require these two genetic elements to cause infections.

xii. *Vibrio parahaemolyticus*

*Vibrio parahaemolyticus* is a curved, rod-shaped, Gram-negative bacterium found in brackish saltwater that causes gastrointestinal illness in humans, when ingested. *V. parahaemolyticus* is oxidase positive, facultatively aerobic, and does not form spores. Like other members of the genus *Vibrio*, this species is motile, with a single, polar flagellum.

While infection of *Vibrio parahaemolyticus* can occur via the fecal-oral route, the predominant cause of the acute gastroenteritis caused by *Vibrio parahaemolyticus* is through ingestion of bacteria in raw or undercooked seafood, usually oysters. Wound infections also occur, but are less common than seafood-borne disease. The disease mechanism of *Vibrio parahaemolyticus* infections has not been fully elucidated.

Outbreaks tend to be concentrated along coastal regions during the summer and early fall when higher water temperatures favor higher levels of bacteria. Seafood most often implicated includes squid, mackerel, tuna, sardines, crab, shrimp, and bivalves like oysters and clams. The incubation period of ~24 hours is followed by explosive, watery diarrhea accompanied by nausea, vomiting, abdominal cramps, and sometimes fever. *Vibrio parahaemolyticus* symptoms typically resolve with-in 72 hours, but can persist for up to 10 days in immunocompromised individuals. As the vast majority of cases of *Vibrio parahaemolyticus* food infection are self-limiting, treatment is not typically necessary. In severe cases, fluid and electrolyte replacement is indicated.

Additionally, swimming or working in affected areas can lead to infections of the eyes or ears and open cuts and wounds. Following Hurricane Katrina, there were 3 wound infections caused by *Vibrio parahaemolyticus* and 2 of these led to death.

xiii. *Yersinia pseudotuberculosis*

*Yersinia pseudotuberculosis* is a Gram-negative bacterium which primarily causes Pseudotuberculosis (*Yersinia*) disease in animals; humans occasionally get infected zoonotically, most often through the food-borne route.

In animals, *Yersinia pseudotuberculosis* can cause tuberculosis-like symptoms, including localized tissue necrosis and granulomas in the spleen, liver, and lymph node.

In humans, symptoms of Pseudotuberculosis (*Yersinia*) include fever and right-sided abdominal pain, but the diarrheal component is often absent, which sometimes makes the resulting condition difficult to diagnose. *Yersinia pseudotuberculosis* infections can mimic appendicitis, especially in children and younger adults, and, in rare cases the disease may cause skin complaints (erythema nodosum), joint stiffness and pain (reactive arthritis), or spread of bacteria to the blood (bacteremia).

Pseudotuberculosis (*Yersinia*) usually becomes apparent 5-10 days after exposure and typically lasts 1-3 weeks without treatment. In complex cases or those involving immunocompromised patients, antibiotics may be necessary for treatment; ampicillin, aminoglycosides, tetracycline, chloramphenicol, or a cephalosporin may all be effective.

The recently described syndrome Izumi-fever has also been linked to infection with *Y. pseudotuberculosis*.

This bacterium possesses many virulence factors to facilitate attachment, invasion, and colonization of its host. Superantigens, bacterial adhesions, and the actions of Yops (which are bacterial proteins once thought to be "*Yersinia* outer membrane proteins") that are encoded on the "[plasmid] for *Yersinia* virulence"—commonly known as the pYV—cause host pathogenesis and allow the bacteria to live parasitically.

*Yersinia pseudotuberculosis* adheres strongly to intestinal cells via chromosomally encoded proteins so that Yop secretion may occur, to avoid being removed by peristalsis, and to invade target host cells.

Certain strains of *Yersinia pseudotuberculosis* express a superantigenic exotoxin, YPM, or the *Yersinia pseudotuberculosis*-derived mitogen, from the chromosomal ypm gene. Strains which carry the exotoxin gene are rare in Western countries where the disease, when at all apparent, manifests itself largely with minor symptoms, whereas more than 95% of strains from Far Eastern countries contain ypm and are correlated with Izumi fever and Kawasaki disease.

Although the superantigen poses the greatest threat to host health, all virulence factors contribute to *Yersinia pseudotuberculosis* viability in vivo and define the bacterium's pathogenic characteristics. *Yersinia pseudotuberculosis* can live extracellularly due to its formidable mechanisms of phagocytosis and opsonisation resistance; yet, by limited pYV action, it can populate host cells, especially macrophages, intracellularly to further evade immune responses and be disseminated throughout the body.

xiv. *Salmonella*

*Salmonella* is a genus of rod-shaped, Gram-negative, non-spore-forming, predominantly motile enterobacteria with flagella which grade in all directions (i.e. peritrichous). They are chemoorganotrophs, obtaining their energy from oxidation and reduction reactions using organic sources, and are facultative anaerobes. Most species produce hydrogen sulfide, which can readily be detected by growing them on media containing ferrous sulfate, such as TSI. Most isolates exist in two phases: a motile phase I and a nonmotile phase II.

*Salmonella* is closely related to the *Escherichia* genus and are found worldwide in cold- and warm-blooded animals, including humans, and in the environment. They cause illnesses like typhoid fever, paratyphoid fever, and the food-borne illness. *Salmonella* infections are zoonotic and can be transferred between humans and nonhuman animals. Many infections are due to ingestion of contaminated food. Typhoid/paratyphoid *Salmonella* is distinguished from enteritis *Salmonella* because of the possession of a special virulence factor and a capsule protein (virulence antigen), which can cause serious illness, such as *Salmonella enterica* subsp. *enterica* serovar *Typhi*. *Salmonella typhi*. is adapted to humans and does not occur in animals.

Enteritis Salmonelliosis or Food Poisoning *Salmonella* is a group consisting of potentially all other serotypes (over a thousand) of the *Salmonella* bacterium, most of which have never been found in humans. These are encountered in various *Salmonella* species, most having never been linked to a specific host, and can also infect humans. The organism enters through the digestive tract and must be ingested in large numbers to cause disease in healthy adults. Gastric acidity is responsible for the destruction of the majority of ingested bacteria. The infection usually occurs as a result of massive ingestion of foods in which the bacteria are highly concentrated similarly to a culture medium. However, infants and young children are much more susceptible to infection, easily achieved by ingesting a small number of bacteria. It has been shown that, in infants, the contamination could be through inhalation of bacteria-laden dust.

After a short incubation period of a few hours to one day, the germ multiplies in the intestinal lumen causing an intestinal inflammation with diarrhoea that is often muco-purulent and bloody. In infants, dehydration can cause a state of severe toxicosis. The symptoms are usually mild. There is normally no sepsis, but it can occur exceptionally as a complication in weakened elderly patients (Hodgkin's disease, for example). Extraintestinal localizations are possible, especially *Salmonella* meningitis in children, osteitis, etc. Enteritis *Salmonella*, e.g., *Salmonella enterica* subsp. *enterica* serovar enteritidis, can cause diarrhoea, which usually does not require antibiotic treatment. However, in people at risk such as infants, small children, the elderly, *Salmonella* infections can become very serious, leading to complications. If these are not treated, HIV patients and those with suppressed immunity can become seriously ill. Children with sickle cell anaemia who are infected with *Salmonella* may develop osteomyelitis.

In Germany, *Salmonella* infections must be reported. Between 1990 and 2005, the number of officially recorded cases decreased from approximately 200,000 cases to approximately 50,000. It is estimated that every fifth person in Germany is a carrier of *Salmonella*. In the USA, there are approximately 40,000 cases of *Salmonella* infection reported each year. According to the World Health Organization, over 16 million people worldwide are infected with typhoid fever each year, with 500,000 to 600,000 fatal cases.

*Salmonella* can survive for weeks outside a living body. They have been found in dried excrement after more than 2.5 years. *Salmonella* are not destroyed by freezing. Ultraviolet radiation and heat accelerate their demise; they perish after being heated to 55° C. (131° F.) for one hour, or to 60° C. (140° F.) for half an hour. To protect against *Salmonella* infection, it is recommended that food be heated for at least ten minutes at 75° C. (167° F.) so that the centre of the food reaches this temperature.

B. Non-Pathogenic Bacteria

In accordance with the present invention, it will be useful to provide non-pathogenic bacteria into which recombinant mce-containing constructs can be introduced. Such non-pathogenic bacteria are defined simply as those that do not produce overt disease and/or those that produce acceptable/clinically manageable side effects.

i. *Escherichia coli*

As described supra, *Escherichia coli*, commonly abbreviated as *E. coli*, is a Gram-negative rod-shaped bacterium. While some strains of *E. coli* are pathogenic, most and can benefit their hosts by producing vitamin K2, and by preventing the establishment of pathogenic bacteria within the intestine.

*E. coli* and related bacteria possess the ability to transfer DNA via bacterial conjugation, transduction or transformation, which allows genetic material to spread horizontally through an existing population.

*E. coli* normally colonizes an infant's gastrointestinal tract within 40 hours of birth, arriving with food or water or with the individuals handling the child. In the bowel, it adheres to the mucus of the large intestine. It is the primary facultative anaerobe of the human gastrointestinal tract. Facultative anaerobes are organisms that can grow in either the presence or absence of oxygen. As long as these bacteria do not acquire genetic elements encoding for virulence factors, they remain benign commensals.

Nonpathogenic *Escherichia coli* strain Nissle 1917 also known as Mutaflor is used as a probiotic agent in medicine, mainly for the treatment of various gastroenterological diseases, including inflammatory bowel disease Because of its long history of laboratory culture and ease of manipulation, *E. coli* also plays an important role in modern biological engineering and industrial microbiology.

Considered a very versatile host for the production of heterologous proteins, researchers can introduce genes into the microbes using plasmids, allowing for the mass production of proteins in industrial fermentation processes. Genetic systems have also been developed which allow the production of recombinant proteins using *E. coli*. Modified *E. coli* have been used in vaccine development, bioremediation, and production of immobilised enzymes. *E. coli* cannot, however, be used to produce some of the more large, complex proteins which contain multiple disulfide bonds and, in particular, unpaired thiols, or proteins that also require post-translational modification for activity.

*E. coli* is frequently used as a model organism in microbiology studies. Cultivated strains (e.g., *E. coli* K12) are well-adapted to the laboratory environment, and, unlike wild-type strains, have lost their ability to thrive in the intestine.

BL21 strain of *E. coli* has been widely used as a host for the expression of recombinant proteins. As an *E. coli* B strain, it lacks the major protease, encoded by the lon gene, catalyzing the endoproteolytic cleavage of damaged and recombinant proteins in the cell. (GE Healthcare life sciences).

*E. coli* HS strain is a human commensal isolate that was originally isolated from a laboratory scientist at the Walter Reed Army Institute of Research. In human challenge experiments, strain HS colonized the human gastrointestinal tract with no overt signs of disease. The genome sequence of strain HS represents the genomic baseline for colonization of the human gastrointestinal tract. This isolate is serotype O9, phylogroup A, motile, competent and amenable to genetic manipulation.

4. ENGINEERING CELLS TO EXPRESS MAM PROTEINS

In certain embodiments, the present invention involves either the production of MAM peptides or the transfer of a MAM nucleic acid to a host cell. Such methods both rely upon expression constructs containing a MAM coding region and the means for its expression, plus elements that permit replication of the constructs. Within certain embodiments, expression vectors are employed to express the MAM polypeptide product or variants thereof. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

5. METHODS OF TREATING BACTERIAL INFECTIONS

The present invention contemplates, in one embodiment, the treatment of subjects suffering from bacterial infections or at risk of the same due to various medical or environmental conditions. A variety of medical situations lend themselves to risk of infections. For example, patients on chronic antibiotic therapy, immunosuppressed patients, patients having had surgery, and patients with traumatic wounds including burns all are at risk of developing bacterial infections.

Administration of compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions. Upon formulation, solutions will be administered in a manner compatible with the dosage formulation and in such amount as is therapeutically effective.

A. Cell-Based Therapies

Specifically, the present inventors intend to provide a non-pathogenic bacterial cell that expresses a MAM peptide or polypeptide. The lengthy discussion of expression vectors and the genetic elements employed therein is incorporated into this section by reference.

Non-pathogenic bacterial cells provided herein include bacteria that are harmless to the host, as well as probiotic bacteria that are beneficial to the host. Throughout the application, the term "probiotic" refers to a live microorganism beneficial to the host organism. These probiotic microorganisms provide a variety of benefits, including immune system support, cancer prevention and irritable bowel syndrome relief. Probiotics are commonly consumed as part of fermented foods with specially added active live cultures; such as in yogurt, soy yogurt, or as dietary supplements. Probiotic microorganisms include, but not limited to, certain bacteria, yeasts and bacilli. The most common types of probiotic bacteria are lactic acid bacteria and bifidobacteria.

In certain embodiments, nonpathogenic bacterial cells used for treatment of pathogenic bacterial infection express a native MAM polypeptide. The MAM peptide expressed therein has one or more mce repeat regions, preferably 6 or more mce repeat regions, more preferably, 6 or 7 mce repeat regions. Non-pathogenic bacterial cells expressing a native MAM polypeptide. The extensive discussion of polypeptides, nucleic acids and non-pathogenic bacterial species is incorporated here.

In further embodiments, non-pathogenic bacterial cells used for treatment of pathogenic bacterial infection do not express a native MAM polypeptide and are engineered to express a MAM polypeptide heterologous to that bacterium. The heterologous MAM peptide expressed therein has one or more mce repeat regions, preferably 5 or more, or 6 or more mce repeat regions, more preferably, 6 or 7 mce repeat regions. Non-pathogenic bacterial cells used for expressing a heterologous MAM peptide include, but not limited to, certain harmless *E. coli* strains, such as BL21 or HS. The methods of engineering cells to express a MAM polypeptide has been extensively discussed supra, and are incorporated into this section by its entirety.

In still further embodiments, non-pathogenic bacterial cells used for treatment of pathogenic bacterial infection express a native MAM polypeptide and are further engineered to express a heterologous MAM polypeptide. The native MAM polypeptide and the heterologous MAM polypeptide expressed therein may contain the same number of mce repeat regions or different number of mce repeat regions. The native MAM polypeptide and the heterologous MAM polypeptide expressed therein may originate from the same bacterial stain or different bacterial stains.

The present invention contemplates the use of nonpathogenic bacterial cells provided herein, as well as compositions that include such cells, to treat pathogenic bacterial infection in a subject. Such compositions may further comprise other probiotic microorganisms, including, but not limited to, certain strains of bacteria, such as lactic acid bacteria and bifidobacteria, yeasts and bacilli.

In another aspect of the present invention, the nonpathogenic bacterial cells and the compositions provided herein are administered to a subject, preferably a mammal, such as a human, a horse, a cow, a dog, a cat, more preferably, a human.

The present invention contemplates the treatment of subjects suffering from diseases caused by pathogenic bacterial infections or at risk of the same due to various medical or environmental conditions. Such diseases and conditions include, for example, pneumonia, deep post-surgical infections, septicaemia, endocarditis, necrotizing pneumonia, toxic shock syndrome, inflammation and sepsis pneumonia, urinary tract infections, blood stream infection bacteremia, acute bacterial meningitis, pneumococcal infections, including acute sinusitis, otitis media, meningitis, bacteremia, sepsis, osteomyelitis, septic arthritis, endocarditis, peritonitis, pericarditis, cellulitis, and brain abscess astroenteritis, neonatal meningitis haemolytic-uremic syndrome, peritonitis, mastitis, septicaemia, Gram-negative pneumonia, cholera, gastrointestinal illness, tuberculosis-like symptoms, including localized tissue necrosis and granulomas in the spleen, liver, and lymph node, typhoid fever, paratyphoid fever, diarrhea, ear infections, inflammatory bowel diseases, Crohn's disease, ulcerative colitis, and foodborne illnesses.

It is also contemplated that the non-pathogenic bacterial cells administered to a subject to prevent or inhibit a pathogenic bacterial infection may selectively or preferably localize or accumulate in the host's organism infected by said pathogenic bacteria. For example, certain virulent *E. coli* strains may mainly infect urinary tract and gastrointestinal tract. The nonpathogenic bacteria which is prone to reside or proliferate in those locations are optionally engineered and administered to said subject. The administered non-pathogenic bacteria can survive, replicate, proliferate and accumulate at those locations. The selective accumulation mainly attributes to the proliferative properties of administered non-pathogenic bacteria and the condition or the environment of the infection site. In some embodiments, the selective accumulation of the non-pathogenic bacterial cells at a target site may be enhanced through the incorporation of a targeting moiety into the cells. The administered non-pathogenic bacteria normally do not cause any harmful effects to the body of the subject and are usually cleared from the body by the subject's immune system.

B. Peptide/Protein Therapy

Another therapy approach is the provision, to a subject, of MAM peptides, synthetic or recombinant, or variants, mimetics or analogs thereof. Formulations would be selected based on the route of administration and purpose including, but not limited to, parenteral formulations, topical formulations, liposomal formulations and classic pharmaceutical preparations for oral administration.

In another aspect of delivery, the peptides and polypeptides of the present invention can be delivered by encapsulating or embedding in a delivery vehicle. For example, liposomes, which are artificially prepared vesicles made of lipid bilayers have been used to delivery a variety of drugs. Liposomes can be composed of naturally-derived phospholipids with mixed lipid chains (like egg phosphatidylethanolamine) or other surfactants. In particular, liposomes containing cationic or neutral lipids have been used in the formulation of drugs. Liposomes should not be confused with micelles and reverse micelles composed of monolayers, which also can be used for delivery.

Nanoparticles are generally considered to be particulate substances having a diameter of 100 nm or less. Microparticles may be large, such as those in the micrometer range. In contrast to liposomes, which are hollow, nanoparticles tend to be solid. Thus, the drug will be less entrapped and more either embedded in or coated on the nanoparticle. Nanoparticles can be made of metals including oxides, silica, polymers such as polymethyl methacrylate, and ceramics. Similarly, nanoshells are somewhat larger and encase the delivered substances with these same materials. Either nanoparticles or nanoshells permit sustained or controlled release of the peptide or polypeptide, and can stabilize it to the effects of in vivo environment.

The present invention contemplates that all types of materials and structures, including inorganic and organic materials, can be used for the nanoparticles of the present invention. Non-limiting examples of these materials and structures include polymersomes, liposomes, polyplexes and conjugates described infra. Additional non-limiting materials include poly(orthoesters), poly(anhydrides), poly(phosphoesters), poly(phosphazenes) and others. Preferably, the material is the biodegradable polymer poly(lactic-co-glycolic acid) (PLGA). PLGA is a well-studied polymer for drug delivery and is FDA-approved for a number of in vivo applications. Other non-limiting materials include, for example, polyesters (such as poly(lactic acid), poly(L-lysine), poly (glycolic acid) and poly(lactic-co-glycolic acid)), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly (carboxyphenoxy hexane), copolymers of these monomers and the like), poly(anhydride-co-imides), poly(amides), poly (ortho esters), poly(iminocarbonates), poly(urethanes), poly (organophasphazenes), poly(phosphates), poly(ethylene vinyl acetate) and other acyl substituted cellulose acetates and derivatives thereof, poly(caprolactone), poly(carbonates), poly(amino acids), poly(acrylates), polyacetals, poly(cyanoacrylates), poly(styrenes), poly(vinyl chloride), poly(vinyl fluoride), poly(vinyl imidazole), chlorosulfonated polyolefins, polyethylene oxide, copolymers, polystyrene, and blends or co-polymers thereof. In another aspects, the nanoparticles include hydroxypropyl cellulose (HPC), N-isopropylacrylamide (NIPA), polyethylene glycol, polyvinyl alcohol (PVA), polyethylenimine, chitosan, chitin, dextran sulfate, heparin, chondroitin sulfate, gelatin, etc. and their derivatives, co-polymers, and mixtures thereof. In particular, one type of nanoparticles is semiconductor quantum dots with a size smaller than 10 nm. Quantum dots are inorganic nanocrystals possessing fluorescent properties. Peptides can be coated onto quantum dots using a thiol-exchange reaction. The quantum dots can be further coupled with a substance, such as polyethylene glycol (PEG), that reduces aggregation of the quantum dots, minimize non-specific binding and maintains solubility in aqueous solvents (Kerman et al., 2002). A non-limiting method for making nano-particles is described in U.S. Patent Publication 2003/0138490, which is incorporated by reference.

In a further aspect of the present invention, the peptides and polypeptides of the present invention can be delivered by nanoparticles or nanoclusters comprising a plurality of nanoparticles.

Nanoparticles/nanoclusters can associate or conjugate with nucleic acids, proteins, peptides, polypeptides, drugs, vaccine and virus vectors, and other therapeutic agents, diagnostic agents, and a combination thereof. These conjugates may be entangled, embedded, incorporated, encapsulated, bound to the surface through covalent and/or non-covalent bonds, with nanoparticles. Nanoparticles may associate with multiple conjugates. For example, nanoparticles may contain a first conjugate on its surface, a second conjugate encapsulated within nanoparticles, and a third conjugate incorporated into the material of nanoparticles.

It is contemplated that nanoparticles or nanoclusters release conjugates in a given environment in an immediate release or a sustained release manner, or after a given period of time in a controlled matter. It is further contemplated that nanoparticles or nanoclusters associated with multiple conjugates may release different conjugates at the same time, or at different time in a controlled manner or in response to a specific trigger event. Non-limiting examples of trigger events include a selected pH range, a selected temperature range, an electric current, a selected ion strength, pressure, the presence of certain liquid, the presence of a specific enzyme, protein, chemical.

In certain embodiments of the present invention, nanoparticles/nanoclusters conjugate with MAM peptides, synthetic or recombinant, or variants, mimetics or analogs thereof. The MAM peptide has one or more mce repeat regions, preferably 6 or more mce repeat regions, more particularly, 6 or 7 mce repeat regions. Nanoparticles/nanoclusters may conjugate with several different MAM peptides comprising different number of mce repeat regions, or MAM peptides of different species.

In further embodiments of the present invention, nanoparticles/nanoclusters further comprise a moiety or an ingredient which directs or assists conjugated nanoparticles/nanoclusters to a target site in a body, for example, gastrointestinal tract.

It is contemplated that after conjugated nanoparticles/nanoclusters are administered into the body of a subject, the conjugated MAM peptides are released in an immediate and/or sustained release manner, preferably at the target site.

The present invention contemplates the treatment of subjects suffering from diseases caused by pathogenic bacterial infections or at risk of the same due to various medical or environmental conditions by administering a composition comprising MAM peptides. Such diseases and conditions include, for example, pneumonia, deep post-surgical infections, septicaemia, endocarditis, necrotizing pneumonia, toxic shock syndrome, inflammation and sepsis pneumonia, urinary tract infections, blood stream infection bacteremia, acute bacterial meningitis, pneumococcal infections, including acute sinusitis, otitis media, meningitis, bacteremia, sepsis, osteomyelitis, septic arthritis, endocarditis, peritonitis, pericarditis, cellulitis, and brain abscess astroenteritis, neonatal meningitis haemolytic-uremic syndrome, peritonitis, mastitis, septicaemia, Gram-negative pneumonia, cholera, gastrointestinal illness, tuberculosis-like symptoms, including localized tissue necrosis and granulomas in the spleen, liver, and lymph node, typhoid fever, paratyphoid fever, diarrhea, ear infections, inflammatory bowel diseases, Crohn's disease, ulcerative colitis, and foodborne illness.

In another aspect of the present invention, a composition comprising both MAM peptides and non-pathogenic bacteria expressing MAM peptides is administered to a subject to prevent or inhibit a pathogenic bacterial infection.

C. Combined Therapy

In order to increase the effectiveness of an MAM-expressing non-pathogenic bacterium, protein or peptide therapy, it may be desirable to combine these compositions with another agent effective in the treatment of bacterial infections. The terms "contacted" and "exposed," when applied to a cell, tissue or organism, are used herein to describe the process by which an MAM-expressing non-pathogenic bacterium, protein or peptide and another anti-bacterial agent are delivered to a target cell, tissue or organism or are placed in direct juxtaposition with the target cell, tissue or organism.

The MAM-expressing non-pathogenic bacterium, protein or peptide may precede, be co-current with and/or follow the other agent(s) by intervals ranging from minutes to weeks. In embodiments where the MAM-expressing non-pathogenic bacterium, protein or peptide and other agent(s) are applied separately to a cell, tissue or organism, one would generally ensure that a significant period of time did not expire between the time of each delivery, such that the MAM-expressing non-pathogenic bacterium, protein or peptide and other agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the MAM-expressing non-pathogenic bacterium, protein or peptide. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 18 hours, about 24 hours, about 36 hours, about 48 hours, about 3 days, about 4 days, about 5 days, about 6 days, about 7 days, about 8 days, about 9 days, about 10 days, about 11 days, about 12 days, about 13 days, about 14 days, about 21 days, about 4 weeks, about 5 weeks, about 6 weeks, about 7 week or about 8 weeks or more, and any range derivable therein, prior to and/or after administering the MAM-expressing non-pathogenic bacterium, protein or peptide.

Various combination regimens of the MAM-expressing non-pathogenic bacterium, protein or peptide treatment and one or more other anti-bacterial agents may be employed. Non-limiting examples of such combinations are shown below, wherein an MAM-expressing non-pathogenic bacterium, protein or peptide composition is "A" and the other anti-bacterial agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the MAM-expressing non-pathogenic bacterium, protein or peptide to a cell, tissue or organism may follow general protocols for the administration of pharmaceuticals, taking into account the toxicity, if any. It is expected that the treatment cycles would be repeated as necessary. In particular embodiments, it is contemplated that various additional agents may be applied in any combination with the present invention.

Antibiotics that may be employed include the aminoglycosides (Amikacin (IV), Gentamycin (IV), Kanamycin, Neomycin, Netilmicin, Paromomycin, Streptomycin (IM), Tobramycin (IV)), the carbapenems (Ertapenem (IV/IM), Imipenem (IV), Meropenem (IV)), Chloramphenicol (IV/PO), the fluoroquinolones (Ciprofloxacin (IV/PO), Gatifloxacin (IV/PO), Gemifloxacin (PO), Grepafloxacin (PO), Levofloxacin (IV/PO), Lomefloxacin, Moxifloxacin (IV/PO), Norfloxacin, Ofloxacin (IV/PO), Sparfloxacin (PO), Trovafloxacin (IV/PO)), the glycopeptides (Vancomycin (IV), the lincosamides (Clindamycin (IV/PO), macrolides/ketolides (Azithromycin (IV/PO), Clarithromycin (PO), Dirithromycin, Erythromycin (IV/PO), Telithromycin), the cephalosporins (Cefadroxil (PO), Cefazolin (IV), Cephalexin (PO), Cephalothin, Cephapirin, Cephradine, Cefaclor (PO), Cefamandole (IV), Cefonicid, Cefotetan (IV), Cefoxitin (IV), Cefprozil (PO), Cefuroxime (IV/PO), Loracarbef (PO), Cefdinir (PO), Cefditoren (PO), Cefixime (PO), Cefoperazone (IV), Cefotaxime (IV), Cefpodoxime (PO), Ceftazidime (IV), Ceftibuten (PO), Ceftizoxime (IV), Ceftriaxone (IV), Cefepime (IV)), monobactams (Aztreonam (IV)), nitroimidazoles (Metronidazole (IV/PO)), oxazolidinones (Linezolid (IV/PO)), penicillins (Amoxicillin (PO), Amoxicillin/Clavulanate (PO), Ampicillin (IV/PO), Ampicillin/Sulbactam (IV), Bacampicillin (PO), Carbenicillin (PO), Cloxacillin, Dicloxacillin, Methicillin, Mezlocillin (IV), Nafcillin (IV), Oxacillin (IV), Penicillin G (IV), Penicillin V (PO), Piperacillin (IV), Piperacillin/Tazobactam (IV), Ticarcillin (IV), Ticarcillin/Clavulanate (IV)), streptogramins (Quinupristin/Dalfopristin (IV), sulfonamide/folate antagonists (Sulfamethoxazole/Trimethoprim (IV/PO)), tetracyclines (Demeclocycline, Doxycycline (IV/PO), Minocycline (IV/PO), Tetracycline (PO)), azole antifungals (Clotrimazole, Fluconazole (IV/PO), Itraconazole (IV/PO), Ketoconazole (PO), Miconazole, Voriconazole (IV/PO)), polyene antifungals (Amphotericin B (IV), Nystatin), echinocandin antifungals (Caspofungin (IV), Micafungin), and other antifungals (Ciclopirox, Flucytosine (PO), Griseofulvin (PO), Terbinafine (PO)).

D. Pharmaceutical Formulations

Pharmaceutical formulations of the present invention comprise an effective amount of an MAM-expressing non-pathogenic bacterium, protein or peptide dissolved or dispersed in a pharmaceutically acceptable carrier. The phrases "pharmaceutical or pharmacologically acceptable" refer to compositions that do not produce an adverse, allergic or other untoward reaction when administered to an animal, such as, for example, a human, as appropriate. The preparation of such pharmaceutical compositions are known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

The pharmaceuticals of the present invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, topically, locally, inhalation (e.g., aerosol), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The pharmaceuticals may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The present invention also provides kits, such as therapeutic kits, as well as kits for preparing expression constructs encoding MAM polypeptide. For example, a kit may comprise one or more pharmaceutical composition as described herein and optionally instructions for their use. Kits may also comprise one or more devices for accomplishing administration of such compositions. For example, a subject kit may comprise a pharmaceutical composition and device for accomplishing intramuscular injection of the pharmaceutical composition comprising the expression constructs encoding MAM peptide into a human subject, and bacterial cells carrying the same.

Kits may comprise a container with a label. Suitable containers include, for example, bottles, vials, and test tubes. The containers may be formed from a variety of materials such as glass or plastic. The container may hold a composition which includes an expression constructs that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

6. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Bioinformatic Analysis.

Classification of mce domain-containing proteins was supported by analysis of domain architecture using PFAM (Protein Families Database, world-wide-web at pfam.sanger-.ac.uk/) and manual identification of mce domains using multiple sequence alignments generated with ClustalW (world-wide-web at ebi.ac.uk/clustalw/) (Finn et al., 200). PSORTb v3.0.2 (world-wide-web at psort.org/psortb/, (Yu et al., 2010) and the TMHMM server v2.0 (world-wide-web at cbs.dtu.dk/services/TMHMM/) were used to predict subcellular localization and transmembrane regions within MAM7. A neighbor-joining tree of MAM7 proteins was based on a multiple sequence alignment from ClustalW and generated using the programs quicktree and newicktops from the mobyle portal (mobyle.pasteurfecgi-bin/portal.py, (Neron et al., 2009; Howe et al., 2002).

Recombinant DNA.

MAM7-(myc) constructs for expression in $V.$ $parahaemolyticus$ were generated by amplification of MAM7 including the endogenous promoter region from POR1 genomic DNA and cloning of the resulting fragment into NcoI/EcoRI sites of plasmid pBAD/Myc-His (Invitrogen) in which the ampicillin resistance gene was replaced by a kanamycin resistance gene to allow selection in $V.$ $parahaemolyticus$. The same method was used to generate complementation vectors for EPEC, $Y.$ $pseudotuberculosis$ and $V.$ $cholerae$ MAM7 knockout strains, except that the $V.$ $cholerae$ MAM7 construct was cloned into SacI/KpnI sites. MAM7-(myc), MAM7ΔN$_{1-44}$(myc), MAM1-(myc) and MAM6-(myc) for expression in $E.$ $coli$ were also amplified from POR1 genomic DNA and cloned into NcoI/EcoRI sites of pBAD/Myc-His Kn$^R$ but excluded the promoter region and their expression was driven by the araBAD promoter. N$_{1-44}$-TEV-MAM7-

(myc) constructs for expression in *V. parahaemolyticus* or *E. coli* were generated by introducing a TEV (tobacco etch virus protease)-cleavage site into existing MAM7-(myc) constructs through site directed mutagenesis. MBP (maltose binding protein)-Cys-mce constructs containing zero (control), one, two, six or seven mce domains were amplified from POR1 genomic DNA and cloned into BamHI and NotI sites of pET28b-MBP (6×His-tag, MBP-tag). GST (glutathione S-transferase-tag)-MAM7 construct was produced by cloning the MAM7 into BamHI/NotI sites of pGEX-4T-1 (GE Healthcare).

Construction of EPEC, *V. Parahaemolyticus, V. Cholerae* and *Y. pseudotuberculosis* ΔMAM7 Deletion Strains.

An EPEC ΔMAM7 strain was generated using Gene doctoring as previously described (Lee et al., 2009). Deletion strains of *V. parahaemolyticus, Y. pseudotuberculosis* and *V. cholerae* were generated essentially as described (Milton et al., 1996; Garbom et al., 2004). Briefly, regions 1 kb upstream and downstream of VP1611 (MAM7) were cloned into the suicide vector pDM4 using BglII, SpeI and SalI sites. The construct was transferred into *E. coli* SM10 cells by electroporation and SM10 cells were used as donor strain for triparental mating with *V. parahaemolyticus* POR1 and POR2. After mating, positive clones were selected by replating on MMM (marine minimal medium) containing 25 μg/ml chloramphenicol. Individual colonies were streaked on MMM plates containing 15% sucrose to cure the plasmid. Individual colonies were screened for loss of the plasmid and deletion of VP1611 was confirmed by transcriptional analysis and sequencing. For transcriptional analysis, RNA was isolated from POR strains, deletion strains and complemented strains using the RNeasy kit (QIAGEN). RNA was treated with DNAse I (QIAGEN) and used as template for reverse transcription (M-MLT reverse transcriptase, Promega). Both cDNA and original RNA (control) were used as template for PCR with both VP1611-specific and ribosomal protein 14-specific (control) primers.

Subcellular Fractionation.

Cells expressing myc-tagged MAM proteins were pelleted and resuspended in 10 mM Tris-HCl pH 7.5, 5 mM EDTA, 20% w/v sucrose and 0.1 mg/ml lysozyme to give an $OD_{600}$ of 6.0. Samples were left at 22° C. for 30 minutes and subsequently pelleted again (5 min, 10000×g, 4° C.). The supernatant (periplasmic and outer membrane fractions) was transferred to a fresh tube and centrifuged at 100000×g, 4° C. for one hour to separate periplasmic (soluble) and outer membrane (pellet) fractions. To recover the cytoplasmic and inner membrane fractions the residual pellet after the first incubation and centrifugation step was resuspended to an $OD_{600}$ of 6.0 in 10 mM Tris-HCl pH 7.5, 5 mM EDTA and left at 22° C. for 10 minutes. Lysed spheroblasts were separated in inner membrane (pellet) and cytoplasmic (soluble) fractions by centrifugation (100000×g, 4° C. for one hour). Pellet fractions were resuspended to a volume equal to the supernatant and equal volumes of samples were separated by SDS-PAGE. Myc-tagged proteins were detected using Western Blotting.

Western Blotting.

Proteins were separated by SDS-PAGE and transferred onto nitrocellulose membrane. Membranes were blocked with 5% skim milk powder in TBS-T (Tris-buffered saline containing 0.05% TWEEN 20® (non-ionic surfactant)) for one hour at 22° C. Membranes were probed with anti-myc antibody 9E10 (Santa Cruz) diluted 1:1000 into blocking buffer for 1 hour at 22° C. After three washes with TBS-T, membranes were incubated with anti-mouse HRP (horseradish peroxidase)-conjugated secondary antibody (GE Healthcare) diluted 1:5000 into blocking buffer for 1 hour at 22° C. Membranes were washed three more times with TBS-T and proteins were detected using the ECL plus detection system (GE Healthcare). To ensure successful fractionation, the inventors probed with antibodies specific to the outer membrane protein OmpA (a gift from the Silhavy lab, 1:300,000, 1 h at 22° C.), the periplasmic protein PhoA (Acris, 1:1000, 1 h at 22° C.), the inner membrane protein SecE (a gift from the Collinson group, 1:10000, 1 h at 22° C.) or the cytoplasmic protein RNA-polymerase (Acris, 1:1000, 1 h at 22° C.).

Protease Protection Experiments.

Cells expressing myc-tagged MAM constructs were resuspended in PBS to give an $OD_{600}$ of 1. Papain was added to final concentrations of 0, 0.1, 1, 10, 100 and 500 μg/ml and cells were incubated at 22° C. for 10 minutes. Reactions were stopped by adding Complete Protease Inhibitor Cocktail (Roche), 5×SDS loading buffer and then boiled for 10 minutes. Samples were separated by SDS-PAGE and myc-tagged proteins were detected by Western Blotting.

Attachment Assays.

Tissue culture cells were washed with PBS (phosphate-buffered saline) prior to the addition of bacteria in tissue culture medium without antibiotics. Bacteria were added to give a multiplicity of infection (MOI) of 10. To determine the exact amount of input, bacteria were added to empty wells. Plates were centrifuged (1000×g, 22° C., 5 minutes) prior to incubation at 37° C. for 30 minutes to 1 hour. Cells were washed three times with PBS and lysed by adding 0.5% Triton X-100 in PBS. Input samples and lysates were serially diluted, plated on either MLB (*V. parahaemolyticus*) or LB (*E. coli, Y. pseudotuberculosis, V. cholerae*) plates and enumerated by colony counting. For competition experiments, tissue culture cells were incubated with anti-Fn or anti-mouse IgG antibodies (50 μg/ml in PBS) for 30 minutes prior to attachment experiments. For experiments with phospholipase C (PLC), tissue culture cells were treated with either 10 or 50 μg/ml phospholipase C (Sigma) in PBS for 15 minutes prior to infection. In other cases, bacterial cells were pre-incubated with fibronectin from human plasma (200 μg/ml in PBS) or PBS-buffered liposomes prepared from 1,2-Dioleoyl-sn-glycero-3-phosphocholine (PC) or a mixture containing 20 mol % of PC and 80 mol % of 1,2-dioleoyl-sn-glycero-3-phosphate (PA) (both Avanti Polar Lipids Inc.) as described below.

Cytotoxicity Assays.

Tissue culture cells were washed with PBS prior to the addition of bacteria in tissue culture medium without antibiotics at an MOI of 10 (Vibrio) or an MOI of 100 (*Yersinia*, EPEC). Infections were started by centrifugation of plates (1000×g, 22° C., 5 minutes) prior to incubation at 37° C. 200 μl of supernatant was removed in triplicate from each well at timepoints as indicated, centrifuged (1000×g, 22° C., 5 minutes), and 100 μl of the supernatant transferred to a fresh 96 well plate for assays. To quantitate cell lysis, the inventors measured the amount of lactate dehydrogenase (LDH) released into the culture medium using the LDH cytotoxicity detection kit (Takara) according to the manufacturer's protocol.

Gentamycin-Protection and TEV-Cleavage Assays.

Tissue culture cells washed with PBS were incubated with bacteria diluted into DMEM to give an MOI of 10. For gentamycin protection experiments, gentamycin was added to a final concentration of 150 μg/ml at indicated time points. For TEV-cleavage assays, TEV protease was added to a final concentration of 8 μg/ml at time points as indicated. For 0 minutes time points, gentamycin or TEV protease were added prior to the centrifugation step. Cytotoxicity was determined 4 hours after infection using LDH release assays.

Expression and Purification of Recombinant MAM Proteins.

*E. coli* BL21 cells transformed with the appropriate expression construct were grown in LB containing appropriate antibiotics for 16 hours. Fresh LB containing antibiotics as indicated were inoculated with pre-culture at a ratio of 1:100 and grown at 37° C. shaking at 120 rpm until the culture reached an $OD_{600}$ of 0.6. Protein production was induced by adding IPTG to a final concentration of 0.4 mM and cells were grown for a further four hours at 37° C. Cells were harvested by centrifugation and the pellet resuspended in 5 volumes of binding buffer (20 mM Tris-HCl pH 7.5, 250 mM NaCl, 5 mM imidazole for MBP-MAM constructs or 20 mM Tris-HCl pH 7.5, 150 mM NaCl for GST-MAM7). PMSF (phenylmethylsulfonyl fluoride), lysozyme and $MgCl_2$ were added to concentrations of 1 mM, 2 mg/ml and 5 mM, respectively, and after 30 minutes of incubation on ice the suspension was sonicated on ice for a total time of 2 minutes (3 sec. on, 7 sec. off, 70% output) using a Sonicator3000 (Misonix) and centrifuged (30 min., 8000×g, 4° C.). For MBP-MAM constructs, the supernatant was loaded onto a 5 ml HIS-TRAP® HP affinity column (GE Healthcare) charged with 3 column volumes (c.v.) of 50 mM $NiSO_4$ and equilibrated with 3 c.v. of binding buffer. The column was washed with binding buffer at a flow rate of 1.5 ml/min until the absorbance of the eluate went back to background levels before bound protein was eluted using a linear gradient of 5-500 mM imidazole over 10 c.v. Fractions were analyzed by SDS-PAGE and those containing the protein of interest were pooled and dialyzed against gel-filtration buffer (50 mM Tris-HCl pH 7.5, 250 mM NaCl). Dialyzed fractions were further purified by gel-filtration on a SUPERDEX® S75 HL 16/60 column (GE Healthcare) equilibrated with 2 c.v. of gel-filtration buffer using a flow rate of 1 ml/min. Fractions containing pure protein of interest were pooled, concentrated to 100 µM and buffer-exchanged against 20 mM Hepes pH 7.0.

Fluorescent Labeling of Recombinant MAM Proteins.

MBP-MAM proteins were labeled on a single cysteine residue introduced between the MBP tag and MAM protein sequence using ALEXAFLUOR® 488 $C_5$ maleimide (fluorescent dye; Invitrogen). For labeling, proteins were incubated in 20 mM Hepes pH 7.0 with a 10-fold molar excess of TCEP (tris(2-carboxyethyl)phosphine) at 4° C. for 2 hours, followed by a 5-fold molar excess of ALEXAFLUOR® 488 $C_5$ maleimide (fluorescent dye) at 37° C. for one hour. The reaction was quenched by adding an excess of beta-mercaptoethanol. Excess dye was removed and protein was buffer-exchanged into PBS using centrifugal filters (Millipore). Protein labeling was determined to be more than 95% efficient using mass spectrometry.

GST-MAM7 lysate was prepared as described above, but using 20 mM Tris-HCl pH 7.5, 150 mM NaCl as resuspension buffer. The cleared lysate was purified using 1 ml glutathione-sepharose beads (GE Healthcare) equilibrated in binding buffer. Bound protein was washed with 40 c.v. of binding buffer and eluted with 5 c.v. of 20 mM Tris-HCl pH 7.5, 10 mM NaCl, 0.1% beta-mercaptoethanol, 0.3% glutathione. After buffer exchanging, the protein was further purified by gel-filtration as described for MBP-MAM proteins.

Fluorescence Attachment Assays.

HeLa cells were cultured in sterilized Corning costar 96 well plates (15 000 cells/well) for 16 hours prior to experiments. ALEXAFLUOR®-labeled (fluorescent dye) proteins were diluted into PBS to give final concentrations of 0.1-100 µM and incubated with cells washed with PBS for 1 hour at 37° C. Initial fluorescence and fluorescence output were measured on a plate reader ($\lambda_{excitation}$ 485 nm, $\lambda_{emission}$ 520 nm) prior to and following three washes with PBS, respectively. Data was expressed as % bound fluorescence and corrected for values determined for MBP alone. Levels of bound protein were blotted as a function of protein concentration and data were fit to a single-site binding model using Sigma Plot. For fluorescence attachment assays on trypsinized cells, cells were detached from the culture dish by trypsinization, which was stopped by adding DMEM after 5 minutes. Cells were adjusted to 600,000/ml in PBS and incubated with 100 µM labeled MBP-MAM7 or MBP in PBS for 30 minutes at 37° C. Fluorescence of the cell suspension was measured before and after extensive washing with PBS as described above.

Competitive Binding Experiments.

MBP-MAM proteins were prepared in DMEM at concentrations between 0 and 300 µM, added to HeLa cells cultured at a density of 150,000 cells/ml. After incubation at 37° C. for one hour, *E. coli* BL21 cells expressing MAM7 were added to an MOI of 1, centrifuged to enable attachment and incubated a further hour at 37° C. Cells were washed three times with PBS and lysed by adding PBS containing 0.5% Triton X-100. Lysates were serially diluted and the number of attached bacteria was determined by plating and counting. The number of attached bacteria was expressed as percentage of input (also quantified by dilution plating).

Determination of Competitive Index.

Bacterial cultures of *E. coli* BL21 expressing MAM7ΔN1-44, MAM6 and MAM1 were mixed with a strain expressing MAM7 and empty pGEX plasmid, which was used as an additional ampicillin resistance marker, and incubated with cultured 3T3 fibroblasts at an MOI of 10 for each strain at 37° C. for one hour. Cells were washed three times with PBS, lysed and bacteria were quantitated by dilution plating. Lysates were double plated on both LB containing kanamycin and LB containing kanamycin and ampicillin. Competitive indices were calculated as follows:

$$C.I.=\text{cfu of mutant/cfu of wild-type bacteria}=[(\text{cfu on kan})-(\text{cfu on kan+amp})]/(\text{cfu on kan+amp})$$

Competition Experiments with BL21 and Pathogenic Bacteria.

HeLa cells were cultured on cover slips at 150,000 cells/ml and incubated with *E. coli* BL21 expressing MAM7 or MAM7ΔN$_{1-44}$ (MOI 100) for one hour at 37° C. Cells were washed three times with PBS and infected with pathogenic bacteria for four hours. After four hours, replicate wells of cells were either lysed or washed with PBS and fixed with 3.2% paraformaldehyde in PBS for 15 minutes. The culture supernatants from lysed cells were used to determine cytotoxicity using LDH-release assays. Fixed cells were permeabilized with 0.1% Triton X-100 in PBS for 3 minutes and treated with Hoechst (Sigma) and rhodamine-phalloidin (Molecular Probes) for 10 minutes to stain for DNA and actin, respectively. Cover slips were mounted onto 10% (w/v) glycerol and 0.7% (w/v) propyl gallate in PBS, sealed with nail polish and viewed using a Zeiss LSM510 META Laser Scanning Confocal Microscope. Images were processed using ImageJ and Photoshop software.

Pull-Down and Plate Assays with Fibronectin.

For pull-down experiments, equimolar mixtures of purified fibronectin derived from human plasma (Fisher Scientific) and either GST-MAM7 or GST (control) were incubated in 10 mM phosphate buffer pH 7.5 containing 150 mM NaCl at 22° C. for 30 minutes. 10% of the sample volume were retained as loading control, while the residual sample was incubated with 0.2 volumes of glutathione-sepharose beads equilibrated in assay buffer at 22° C. for one hour. Beads were washed three times with 0.9 volumes of assay buffer prior to boiling in 0.9 volumes of SDS loading buffer. Equal volumes of loading control, washes and eluate were analyzed by SDS-PAGE and Coomassie staining. For plate assays, ALEXA FLUOR® 488-labeled (fluorescent dye) MBP-MAM proteins were diluted into PBS to give final concentrations between 0.1 and 100 µM. Proteins were incubated in human fibronectin coated 96-well plates (R&D systems) at 22° C. for one hour. Fluorescence levels were measured prior and after washing plates three times with PBS. Data were analyzed as described for fluorescence attachment assays.

Lipid Overlay Assays.

Pre-spotted PIPstrips™ (Echelon Biosciences Inc.) were incubated in T-TBS containing 5% dry milk powder for one hour at 22° C. MBP-MAM proteins were diluted into blocking buffer to give a final concentration of 10 µM and incubated with the PIP strip for one hour at 22° C. Strips were washed with T-TBS three times for 10 minutes each and incubated with His antibody (QIAGEN) diluted 1:1000 into blocking buffer at 22° C. for one hour. Strips were washed three times with T-TBS and incubated with anti-mouse HRP-conjugated secondary antibody (GE Healthcare) diluted 1:5000 into blocking buffer for 1 hour at 22° C. After three more washes, bound proteins were detected using the ECL plus detection system (GE Healthcare).

Liposome Association Experiments.

PBS-buffered liposomes were prepared from 1,2-Dioleoyl-sn-glycero-3-phosphocholine (PC) or mixtures of PC and 1,2-dioleoyl-sn-glycero-3-phosphate (PA) (both Avanti Polar Lipids Inc.) as described previously (Selyunin et al., 2011), but using PBS as buffer. 300 µg liposomes were incubated with 100 µg MBP-MAM protein in PBS for one hour at 22° C. Mixtures were centrifuged at 100 000×g, 4° C. for one hour and both pellet and supernatant fractions were separated by SDS-PAGE and proteins were detected by Coomassie staining.

Nematode Lethality Assays.

150 µl bacterial culture were spotted on NGM (nematode growth medium) plates and incubated at 30° C. for 16 hours prior to transfer of 20 to 30 synchronized L4 stage worms onto the bacterial lawn. *C. elegans* germline deficient mutant SS104 glp-4(bn2) strain was used for all experiments. Prior to seeding, worms were maintained at 15° C. on nematode growth medium (NGM) agar plates and fed on *E. coli* HB101. The worms were washed with M9 buffer twice to remove surface-bound bacteria prior to plating. Plates containing worms were maintained at 25° C. to inhibit egg laying during the experiment and scored for dead worms every 24 hours. Worms were considered dead when they no longer responded to touch. For complementation experiments, kanamycin was added to plates prior to spotting bacterial cultures to maintain the plasmid. Data was analyzed using the Kaplan-Meier method and survival curves were compared using the log rank test. For microscopy, worms were fed on test strains for 48 hours, mounted on 2% agarose pads and observed under Nomarski optics using a Zeiss Axioplan microscope.

Statistical Analysis.

Statistical significance was analyzed using the unpaired two-tailed t-test. All experiments were done at least three times in triplicate, except for attachment experiment, which were done three times in duplicate and attachment experiment with recombinant proteins, which were done twice in duplicate. All values are given as means±standard deviation, unless otherwise indicated. For nematode lethality assays, data were plotted according to the Kaplan-Meier method and survival curves were compared using the log rank test. Statistical significance was set at P<0.005. RIMD (P<0.0001), POR1 (P<0.0001), POR1ΔMAM7 (P=0.99), POR1ΔMAM7+pMAM7 (P=0.0002) were compared with HB101.

Results

Figure 7A:
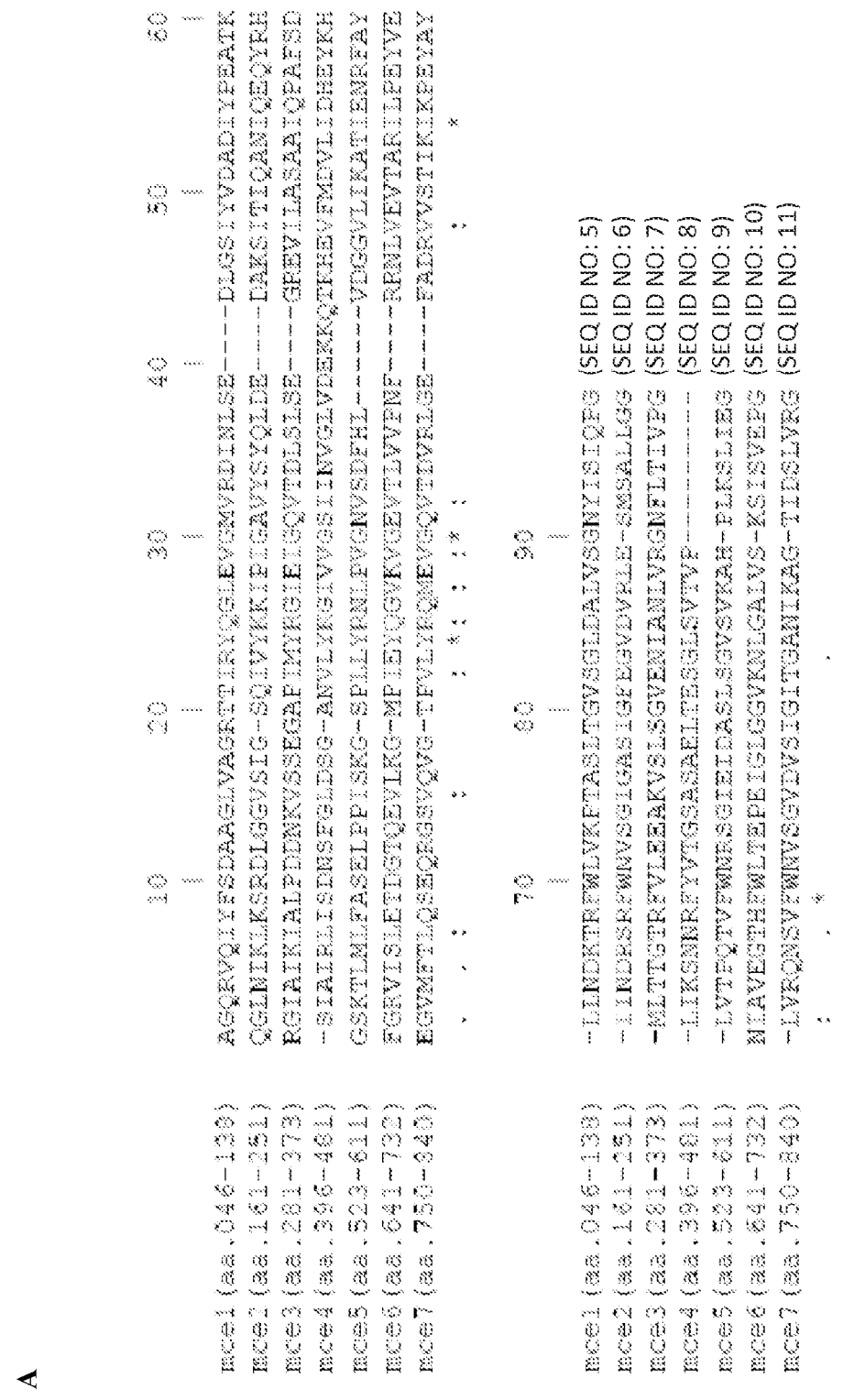
Figure 7B:
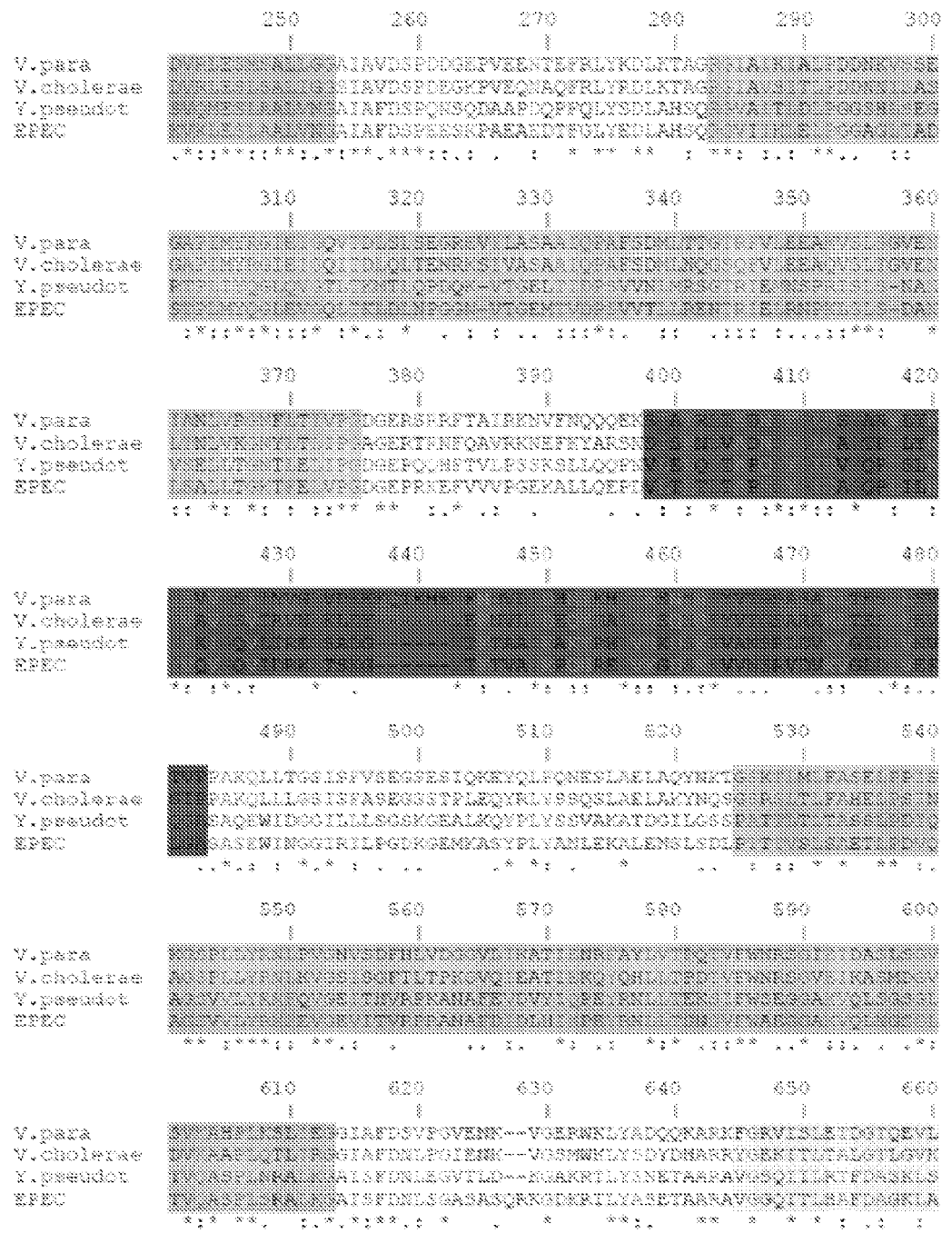

Using bioinformatics, the inventors searched the genome of *Vibrio* parahaemolyticus, a Gram-negative bacterium that occurs in marine and estuarine environments and can cause shellfish-borne food-poisoning, for a constitutively expressed protein that might be involved in the initial binding of bacteria to a host cell (Daniels et al., 2000). The inventors discovered a predicted outer membrane molecule that the inventors have called multivalent adhesion molecule (MAM) that includes a putative transmembrane motif followed by six (MAM6) or seven (MAM7) mammalian cell entry (mce) domains (FIG. 1A, FIG. 7A). Unexpectedly, the inventors found that MAM6 or MAM7 is encoded in a wide range of Gram-negative animal pathogens but not Gram-positive or plant pathogenic bacteria (FIG. 1A, FIG. 7B, FIG. 8). In contrast, proteins containing a single mce domain are wide-spread (FIG. 1A). In *Mycobacterium* ssp. and some Gram-positive bacteria, such as *Rhodococcus* ssp. or *Streptomyces* ssp., the mce domain occurs in conjunction with a second domain of unknown function (DUF3407) (Arruda et al., 1993; Chitale et al., 2001). Proteins containing one mce domain and a C-terminal low complexity region are thought to represent an accessory component of ABC transporters occurring in algae, higher plants and bacteria (Awai et al., 2005). Herein, the inventors tested whether MAMs, which constitute a novel class of predicted outer membrane proteins from Gram-negative bacteria, are involved in cellular attachment. Initially, the inventors used *V. parahaemolyticus* as the representative Gram-negative bacterium for analysis of MAM7s and followed these studies with analyses on the role of MAMs in attachment for other Gram-negative pathogens (Daniels et al., 2000).

MAM7 is a Novel Outer Membrane Protein Mediating Host Cell Attachment.

Figure 9:
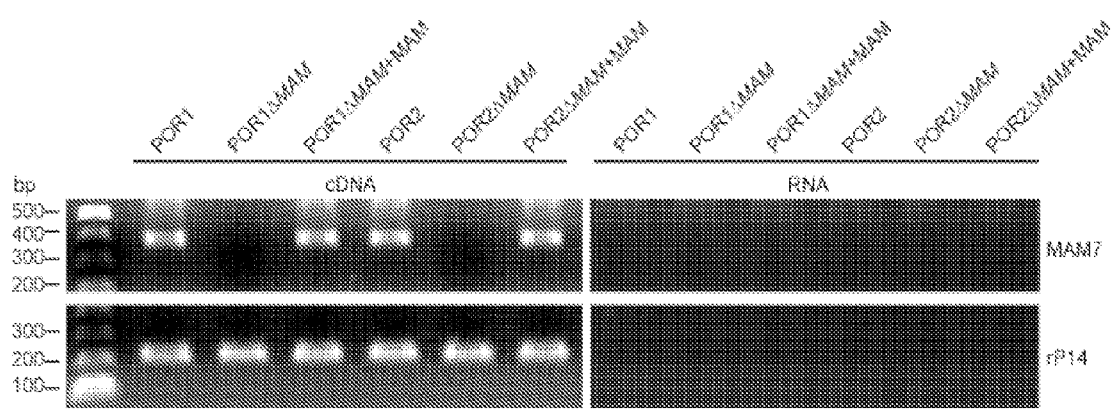
FIG. 9. Expression of MAM7 in *V. parahaemolyticus* strains used in this study. RNA was extracted from POR1, POR2 and derivative strains and either reverse-transcribed into cDNA (left) prior to PCR or directly used for PCR (right) with MAM7-(upper panels) or ribosomal protein 14-specific primers (rP14, positive control, lower panels). POR1, POR2 and complemented ΔMAM7 strains show expression of MAM7. No products were observed with RNA only controls.

The inventors analyzed the intracellular localization of *V. parahaemolyticus* MAM7 (VP1611) by replacing the endogenous gene with a plasmid-borne, C-terminally myc-tagged version of MAM7 under the control of its endogenous promoter using a non-cytotoxic strain of *V. parahaemolyticus* [POR2 (Park et al., 2004)], (FIG. 9). MAM7-myc was constitutively transcribed when the strain was grown in marine LB (MLB, FIG. 9) and, based on subcellular fractionation, localizes exclusively to the outer membrane (FIG. 1B). Outer membrane localization was also observed after arabinose-induced, heterologous expression of *V. parahaemolyticus* MAM7-myc in *E. coli* strain BL21 (FIG. 1C), which does not contain a MAM7 ortholog. The first 44 N-terminal amino acids of MAM7 contain a stretch of hydrophobic residues (aa. 21-40) predicted to form a transmembrane helix. Deletion of the N-terminal 44 amino acids (MAM7ΔN$_{1-44}$-myc) lead to cytoplasmic retention of the protein (FIG. 1D). To assess whether MAM7 was on the surface of the bacteria, BL21-MAM7 and BL21-MAM7ΔN$_{1-44}$-myc were tested for protease sensitivity. Treatment of these strains with increasing concentrations of papain lead to a gradual loss of the epitope tag on cells expressing MAM7-myc, but not MAM7ΔN$_{1-44}$-myc, further supporting the localization of the C-terminal epitope to the extracellular space (FIG. 1E). To explore if the N-terminal sequence is embedded in the outer membrane, the inventors introduced a TEV protease-cleavable peptide between the hydrophobic N-terminal sequence (res. 1-44) and the mce domains (N$_{1-44}$-TEV-MAM7-myc). The protein expressed from this construct was correctly localized and successfully cleaved by TEV protease incubated with intact bacteria (FIG. 1F), demonstrating that the N-terminal peptide contains the information necessary for outer membrane targeting and membrane anchored of MAM7, while the rest of the protein is exposed extracellularly.

Having established that MAM7 is an outer membrane protein, the inventors next tested whether MAM7 is important for early attachment of *V. parahaemolyticus* to host cells. Using *V. parahaemolyticus* POR2 (Park et al., 2004) and the POR2ΔMAM7 derivative, the inventors observed that in the absence of MAM7, attachment of *V. parahaemolyticus* was decreased from approximately 80% to ~35-40% for all tested host cell lines, including HeLa and Caco-2 epithelial cells, RAW264.7 macrophages and 3T3 fibroblasts. The attachment of POR2 MAM7 was recovered by a plasmid expressing MAM7 with or without a TEV cleavage site or myc tag (FIG. 1G, FIGS. 10A-B). The non-adherent BL21 strain was converted to an adherent strain by inducing expression of *V. parahaemolyticus* MAM7, but not by the mutant MAM7ΔN$_{1-44}$ (FIG. 1H). The inventors conclude that MAM7 contributes to the attachment of *V. parahaemolyticus* to a broad range of mammalian cells and is sufficient to mediate efficient cellular attachment of a Gram-negative strain in the absence of other adhesion proteins.

MAM7-Mediated Attachment Augments Type-III-Mediated Cell Death.

The translocation of effector proteins to manipulate host signaling pathways is a key step in the pathogenesis of many Gram-negative organisms. *V. parahaemolyticus* features two type III secretion systems (T3SS) that translocate at least eight different effector proteins into the host cytosol with the aim to alter the cellular response to infection to the pathogen's advantage (Burdette et al., 2008; Broberg et al., 2010). The inventors hypothesized that intimate association that can be mediated through a variety of adhesion mechanisms between pathogen and host is a prerequisite for successful T3SS-effector translocation during infection. POR1, a *V. parahaemolyticus* strain containing both T3SSs but lacking the thermostable direct hemolysins tdhA and tdhS, causes T3SS-dependent cell lysis within 2-3 hours after infection (Park et al., 2004; Burdette et al., 2008). To test the contribution of MAM7 in POR1-mediated cell lysis, the inventors created a POR1 strain deleted for MAM7 (POR1ΔMAM7, FIG. 9) and a POR1ΔMAM7 strain complemented with MAM7 containing a TEV-cleavable sequence inserted between residues 44 and 45 and a C-terminal myc tag (N$_{1-44}$-TEV-MAM7-myc). The N$_{1-44}$-TEV-MAM7-myc protein was confirmed to localize to the outer membrane (FIG. 10B). In addition, treatment of the POR2ΔMAM7+N$_{1-44}$-TEV-MAM7-myc strain with TEV-protease for five minutes resulted in a strain that displayed a decrease in attachment comparable to that observed for POR2ΔMAM7 (FIG. 10A). The inventors next used the POR1 strains to assess the contribution of MAM7 attachment to host cell cytotoxicity during *V. parahaemolyticus* infections.

Gentamycin protection assays were used to assess how long bacteria must remain attached to induce 100% lysis. *V. parahaemolyticus* strains were used to infect 3T3 cells and at various time points during the infection gentamycin was added. After four hours of infection, the cells were tested for cell lysis using an LDH release assay. When gentamycin was added at the start of the infection (0 minutes) minimal lysis was observed after 4 hours, whereas if no gentamycin was added almost 100% lysis was observed after the same time. When infected cells were treated at 10, 30, 60 or 90 minutes after infection with gentamycin, minimal lysis was observed.

These results support the hypothesis that *V. parahaemolyticus* has to remain associated with 3T3 fibroblasts for at least 90 minutes to efficiently mediate T3SS-induced cell lysis (FIG. 2A). To test if MAM7-mediated attachment contributes to host cell binding through this initial phase of infection, the inventors performed infections using the POR1ΔMAM7+N$_{1-44}$-TEV-MAM7 strain and treated cells with TEV protease at various time points during the infection. Cell lysis was measured at four hours after infection. As predicted, cells infected with either POR1 strain or the POR1ΔMAM7+N$_{1-44}$-TEV-MAM7 strain, but not the POR1ΔMAM7 strain, displayed 100% cell lysis. However, POR1ΔMAM7+N$_{1-44}$-TEV-MAM7 infected cells treated with TEV protease immediately, 10 or 30 minutes after the start of infection showed a decrease of ~40% cytotoxicity (FIG. 2B). This level of toxicity is comparable to that observed with the POR1ΔMAM7 strain, supporting the hypothesis that MAM7 is playing an important role in attachment during the early stages of infection.

To further investigate the role of MAM7 in adhesion and cytotoxicity, the inventors performed time course infection studies on a range of mammalian cell lines using POR1, POR1ΔMAM7 and POR1ΔMAM7 complemented strains. The POR1ΔMAM7 strain lysed 3T3 fibroblasts and RAW264.7 macrophages less efficiently than either POR1 or POR1ΔMAM7+ MAM7 (FIGS. 2C-D). In addition, the onset of lysis induced by the POR1ΔMAM7 strain was delayed by 30-40 minutes (FIGS. 2C-D). In contrast, no significant difference was observed between POR1 and POR1ΔMAM7 in either Caco-2 or HeLa epithelial cells (FIGS. 2E-F). In total these results support the hypothesis that, with some cell lines, MAM7 mediated attachment plays an important role in mediating the initial attachment of bacteria to host cells during the early stages of infection. It also supports the hypothesis that other molecules, some of which might be host cell type dependent, are playing a role in attachment during later stages of infection with *V. parahaemolyticus*.

MAM7 is Required for *V. Parahaemolyticus*-Induced Pathogenicity in *C. Elegans*.

The nematode *C. elegans* has been used as a model host for a variety of bacterial pathogens, including *Vibrio cholerae* and *Vibrio vulnificus* (Vaitkevicius et al., 2006; Dhakal et al., 2006). In the absence of a relevant animal model for *V. parahaemolyticus*, the inventors tested whether MAM7 mediated adhesion plays a role during infection of nematodes. Synchronized germline-deficient L4 stage worms were fed with either RIMD 2210633, POR1, POR1ΔMAM7 or POR1ΔMAM7+ MAM7 strains. Worms fed either non-pathogenic *E. coli* HB101 or POR1ΔMAM7 exhibited a normal life expectancy profile (FIG. 3A). RIMD 2210633 and POR1-infected worms displayed severe phenotypic changes by day 2 of feeding including growth retardation, and increased frequency in distention of the intestinal tract leading to abdominal rupture, and died at a much faster rate than worms fed either HB101 or POR1ΔMAM7 (FIGS. 3A-C). Both RIMD 2210633 and POR1 killed the worms within 13 days, supporting the hypothesis that most of the lethality is mediated by T3SS effectors rather than the thermostable hemolysins (Park et al., 2004). Full virulence was reconstituted in the POR1ΔMAM7 by reconstituting the strain with plasmid-encoded MAM7 (FIG. 3A). Analysis of worms for abdominal rupture at day seven revealed a significant increase in injury of the RIMD 2210633 and POR1 fed worms (FIG. 3D). Overall, the results support the hypothesis that MAM7 adhesion plays an important role during pathogenicity in the nemotode infection model.

Multiple Mce-Domains are Required to Mediate Stable Attachment of MAM to Host Cells.

The number of tandem mce domains in pathogenic Gram-negative bacteria is strikingly constant (always 6-7 domains). The inventors therefore hypothesized that 6-7 mce domains are the minimum number of domains required for stable host cell attachment and thus explored the relation between domain number and host cell affinity. The inventors produced recombinant proteins containing one, two, six or seven mce domains in tandem with a maltose binding protein (MBP)-tag and a single cysteine residue between mce-domains and MBP-tag to allow labeling of the proteins with a single fluorophore. The amount of protein bound to host cells was measured using fluorescence spectroscopy and the affinities of individual constructs was determined using saturation binding experiments. The affinity increased non-linearly with the number of mce-domains, with equilibrium dissociation constants ranging from 15±3 µM for one mce domain to 0.2±0.1 µM for seven domains in tandem (FIG. 4A). The affinities of MAM proteins for host cells were also determined indirectly, using unlabeled MAM proteins to block the host cell surface prior to measuring residual binding of $E.$ $coli$ BL21 expressing MAM7. Affinities determined by this method were consistent with those determined by fluorescence assays (FIG. 4B).

Having established the binding affinities for proteins containing varying numbers of mce domains, the inventors analyzed whether strains expressing one mce domain were able to compete for host adhesion with strains expressing six or seven domains in tandem. All MAM constructs used were correctly localized to the outer membrane, as shown by subcellular fractionation and attachment experiments (FIGS. 11A-B). $E.$ $coli$ BL21 strains expressing MAM1, MAM6 or MAM7$\Delta N_{1-44}$ were mixed with a strain expressing MAM7 and the ratio of attachment to host cells was determined as competitive index between the strains. While MAM6 and MAM7 were similarly effective in conferring adhesive properties on $E.$ $coli$ BL21 (C.I. of 0.8), MAM1 and MAM7$\Delta N1$-44 were far less competitive (C.I. of 0.27 and 0.19, respectively) (FIG. 4C). Next, the inventors investigated the ability of $E.$ $coli$ BL21 expressing MAM1, MAM6 or MAM7 to inhibit attachment of and cytolysis by $V.$ $parahaemolyticus$ POR1. When POR1 infections were performed in the presence of $E.$ $coli$ BL21 expressing MAM7 or MAM6 at an identical multiplicity of infection, the attachment of POR1 and thus pathogen-mediated cytotoxicity was significantly decreased. Addition of BL21 expressing MAM1 or MAM7$\Delta N_{1-44}$, however, had little or no effect on the outcome of a POR1 infection (FIG. 4D). These data demonstrate how the requirement for high affinity attachment to host cells necessitates the presence of a high number of mce domains. While the inventors observed low affinity binding with one or two mce domains, the expression of six or seven domains in tandem results in a steep increase in affinity enabling the bacterial strain expressing these constructs to successfully compete for host binding. Due to problems with misfolding and insolubility, the inventors could not study constructs containing between three to five mce repeats, and hypothesize that such proteins might not occur in nature for similar reasons.

MAM7 Establishes Both Protein-Protein and Protein-Lipid Interactions with Host Cells.

The secondary structure of MAM7 is predicted to be rich in beta-strands connected by flexible loop regions, a composition similar to that of fibronectin-binding proteins from Gram-positive bacteria (Schwarz-Linek et al., 2003). The inventors therefore tested if MAM7 could also bind fibronectin. Immobilized GST-MAM7 but not GST alone was able to pull-down purified fibronectin from human plasma (FIGS. 5A-B). Titrations of fluorophore-labeled MBP-MAM7 against immobilized Fn showed the interaction between hFn and MAM7 to be of moderate affinity ($K_D$ of 15±4 µM), while no measurable interaction was detected between fibronectin and MAM1 (FIG. 5C). To further explore the possibility that MAM7 binds fibronectin on cells, the inventors treated the cells with trypsin to degrade extracellular proteins and then assessed whether MAM7 could bind to cells. Cells treated with trypsin reduced the number of MAM7 molecules on cells by over 100-fold (FIG. 5D). Furthermore, the specificity of binding by MAM7 to fibronectin on cells was shown by either blocking MAM7 binding to cells with an anti-fibronectin antibody or by competing with soluble fibronectin (FIG. 5E).

$Arabidopsis$ Tgd2 is the substrate-binding component of a chloroplast lipid transporter which is involved in phosphatidic acid (PA) trafficking and necessary for biogenesis of thylakoid membrane lipids (Awai et al., 2006). Tgd2 contains a single mce domain which was shown to display weak binding to phosphatidic acid (Lu and Benning, 2009). Using lipid overlay assays, the inventors showed that both MAM1 and MAM7 bound to PA, while no binding was observed with the MBP-tag alone (FIGS. 5F-H, FIGS. 12A-C). The inventors compared the binding affinities for MAM1 and MAM7 to PA using liposome association assays (FIG. 5I). While MAM7 showed stoichiometric binding to PA when present in the liposomes at concentrations as low as 1 mol %, MAM1 only bound to liposomes containing at least 3 mol % PA. To assess whether MAM7 binding to PA occurs in vivo, the inventors analyzed binding of MAM7 to 3T3 cells incubated without and with prior phospholipase C (PLC) treatment. In the presence of PLC, PA is converted to diacylglycerol and the inventors observed that binding of BL21 expressing MAM7 to cells is compromised (FIG. 5J). To further assess whether MAM7 is binding to PA on cells, the inventors pre-incubated BL21-MAM7 with phospholipids and assessed attachment of the bacteria to 3T3 cells. BL21-MAM7 could bind to cells after incubation with liposomes containing 1,2-Dioleoyl-sn-glycero-3-phosphocholine (PC) but not after incubation with liposomes containing 20 mol % of PC and 80 mol % PA (FIG. 5K). These observations further support the model that MAM7 binds PA on the surface of cells.

Non-Pathogenic $E.$ $Coli$ Heterologously Expressing MAM7 Ameliorates the Effects of Infection by Gram-Negative Pathogens.

Since the inventors successfully used non-pathogenic $E.$ $coli$ BL21 expressing MAM7 to inhibit infection by $V.$ $parahaemolyticus$ POR1 (FIG. 4D and FIG. 6B, FIGS. 13G-I), the inventors hypothesized that pre-incubation of host cells with BL21 expressing MAM7 would ameliorate infections caused by a broad range of pathogenic Gram-negative strains that are predicted to encode MAM7. The inventors investigated the protective effect of $E.$ $coli$ BL21+MAM7 upon infection with $V.$ $parahaemolyticus$ RIMD 2210633 strain that is equivalent to POR1 but features two thermostable direct hemolysins that are thought to contribute to cell lysis (Nishibuchi et al., 1992) (FIG. 6A, FIGS. 13D-F), $V.$ $cholerae$ El Tor N16961 (FIG. 6C, FIGS. 13J-L), $Y.$ $pseudotuberculosis$ YP126 (FIG. 6D, FIGS. 13M-O) and the enteropathogenic $E.$ $coli$ (EPEC) strain O127:H6 E2348/69 (FIG. 6E, FIGS. 23P-R). For all infections the inventors performed, the inventors observed a drastic decrease in pathogenicity as manifested either by decreased cytotoxicity ($V.$ $parahaemolyticus$, $V.$ $cholerae$ and $Y.$ $pseudotuberculosis$) or decreased actin pedestal formation (EPEC). Pre-incubation with $E.$ $coli$ BL21-MAM7 alone did not induce any phenotypic changes in host cells (FIGS. 13A-C), and therefore, residual cytotoxicity was presumably due to soluble toxins being secreted into the extracellular medium. Based on these results the inventors propose that MAM7 expressed on the non-pathogenic E. coli strain is masking sites needed by the pathogenic bacteria to initiate binding with the host cells.

We hypothesized that MAM7 from the various species are functionally redundant in that all mediate binding to host cells. To test this, the inventors cloned and expressed the MAM7 from Y. pseudotuberculosis, V. cholerae or EPEC into non-adhesive E. coli BL21. Each of these MAM7 homologues enabled BL21 cells to attach to 3T3 cells at a level similar to that observed for BL21 expressing V. parahaemolyticus MAM7 (FIG. 6F). To assess whether MAM7 from Y. pseudotuberculosis, V. cholerae or EPEC plays a role in host cell adhesion during infection, the inventors created MAM7 deletion strains for each of these pathogens (YpΔ-MAM7, VcΔMAM7, EPECΔMAM7) and then reconstituted the MAM7 deletion strains with a wild-type copy of MAM7 (YpΔMAM7+MAM7, VcΔMAM7+MAM7, EPECΔ-MAM7+MAM7). After incubating these various strains with 3T3 cells, the inventors observed that attachment is compromised for the MAM7 deletion strains, but not for the wild-type or reconstituted deletion strains (FIG. 6G). The inventors next tested whether the absence of MAM7 might attenuate cell culture cytotoxicity induced by Y. pseudotuberculosis and V. cholerae or reduce pedestal formation by EPEC. 3T3 cells infected with either YpΔMAM7 or VcΔMAM7 displayed reduced cytotoxicity over time when compared to wild-type or reconstituted Y. pseudotuberculosis and V. cholerae strains (FIGS. 6H, 6I). When 3T3 cells were infected with EPECΔMAM7, a reduced number of pedestals was observed over time when compared to wild-type or reconstituted EPEC. Interestingly, the phenotype induced by the pathogen appears only to be attenuated during the early time points in the infection (FIG. 6J). In agreement with findings from others, the attachment at the later times of infection is mediated by adherence molecules induced during infection, such as Yersinia invasin, Enterococcus ace, or type IV pili (Lebreton et al., 2009; Heroven and Dersch, 2006; Boekema et al., 2004).

One of the pathogens the inventors focus on is Pseudomonas aeruginosa. P. aeruginosa thrives in most environments, including water, soil and on human skin. In immunocompromised patients, it can cause catheter-associated lung and urinary tract infections, but it is also a major burden for cystic fibrosis patients and can cause persistent wound infections, for example in burn patients (Hoiby, 2011; Branski et al., 2009). Due to its clinical importance, the inventors studied if P. aeruginosa-mediated cytotoxicity could be attenuated by MAM7 in a tissue culture model of infection (FIGS. 14A-D). The second focus of the inventors' current studies in MAM7-based inhibitors is dedicated to finding alternative modes of delivery. While non-pathogenic bacteria expressing surface-bound MAM7 may be a suitable vehicle for gastrointestinal delivery of MAM7 to prevent or combat enteric pathogens, their use on an open wound would most likely exacerbate inflammatory responses and could therefore have adverse effects on wound healing. The inventors are therefore studying alternative modes of delivery for MAM7 to the site of infection. One such approach is to immobilize recombinant MAM7 on the surface of inert polymer beads, which are similar in size to the bacteria the inventors have previously used (1 µm). The inventors tested the efficacy of bead-immobilized MAM7 against P. aeruginosa infection of epithelial cells and compared it to control beads displaying GST, which do not bind to host cells (FIGS. 1A-D). In each case, the inventors counted the number of bound beads per cell (fluorescent beads were used for ease of visualization) and determined the cytotoxic effect of P. aeruginosa using lactate dehydrogenase (LDH) release assays. Upon infection, host cells lyse and release LDH into the culture medium, which can be detected colorimetrically and compared to a standard of detergent-lysed cells (100% lysis). GST-beads did not show any significant attachment to host cells and failed to inhibit infection (FIGS. 1A, 1C). In contrast, MAM7 beads bound to host cells (17.1±0.9 beads/cell) and, as a consequence, attenuated P. aeruginosa-mediated cell killing (cytotoxicity decreased from 76% to 4%).

These studies demonstrate that MAM7-based inhibition may potentially be developed as a tool to attenuate not only enteric pathogens but also hospital-acquired and wound-associated infections, such as those caused by P. aeruginosa. The adhesin can be expressed at the surface of non-pathogenic bacteria but may also be delivered by alternative routes, such as immobilized on beads, which may aid in future applications in decreasing risks associated with the introduction of live bacteria into a living organism. In the future, the inventors hope to be able to extend the application of MAM7 to include other clinically relevant Gram-negative pathogens and develop tools for its efficient delivery to the site of potential infection.

Discussion

Although many bacterial adhesins are known, they are usually species-specific and many are induced during infection (Boland et al., 2000; Kline et al., 2009). Herein, the inventors have described a novel adherence factor, MAM7, used by a wide range of Gram-negative bacterial pathogens to mediate an initial, high-affinity interaction with host cells. While the N-terminal hydrophobic sequence of MAM7 is necessary for outer membrane localization and anchoring of the protein, no dedicated system is necessary for protein transport or membrane insertion, since MAM7 can be heterologously expressed and correctly localized by E. coli BL21. MAM7 is used for bacterial adhesion to a variety of mammalian cells and is a crucial factor contributing to host cell infection, as was observed in a tissue culture model for Gram-negative pathogens, including V. parahaemolyticus, Y. pseudotuberculosis, V. cholerae or EPEC. By means of multivalent interactions with the host cell surface, MAM7 contributes to the adherence of bacterial pathogens during the early stages of infection thereby facilitating injection of T3SS effectors into the host cytoplasm. However, specificity of a pathogen for a certain cell type must be mediated by other, strain-specific adhesion molecules, which are most likely strengthened by the initial MAM7 interaction with host cells. The other adhesion factors are likely to dominate attachment during later phases of infection, where MAM7 binding becomes dispensable (FIGS. 2A-F).

The binding of the outer membrane adhesion factor MAM7 to host cells is mediated by a multivalent protein-protein interaction between the adhesin and the extracellular matrix component fibronectin. By contrast, the protein-lipid interaction between MAM7 and membrane-bound phosphatidic acid can be mediated by a single mce domain, albeit at a lower apparent affinity. Therefore, while mce domains have been integrated into a diverse range of proteins, the number of mce domains plays an important role in determining ligand binding affinities and thus the functionality of mce containing proteins: Mce-proteins involved in lipid transport require a low affinity transient interaction with their ligand and contain only one mce domain (e.g., Tgd2). In contrast, constitutively expressed proteins with multiple mce domains appear to mediate an early, high affinity interaction with the host cell surface. The inventors show that this not only increased lipid-binding affinity but also gives rise to a new functionality (fibronectin-binding) which further strengthens the interaction between MAM7 and host cells. While interactions with extracellular matrix components such as fibronectin are a common strategy employed by both Gram-positive (FnBPs of *Staphylococcus* ssp.) and Gram-negative (e.g., *Yersinia* invasin YadA, *Salmonella* MisL or *Campylobacter* CadF) pathogens to achieve host cell adhesion, the direct binding of an adhesin to membrane phosphatidic acid is, to the inventors' knowledge, a novel mechanism for host-pathogen interaction (Froman et al., 1987; Tertti et al., 1992; Dorsey et al., 2005; Konkel et al., 1997; Henderson et al., 2011). Although at 2-3 mol % phosphatidic acid is only a minor component of eukaryotic membranes, the inventors showed that these concentrations are sufficient to mediate stable attachment of MAM7. The strategies for protein and lipid interactions are combined in MAM7-mediated adhesion to achieve efficient binding of Gram-negative pathogens to their host.

The inventors show that non-pathogenic BL21 expressing MAM7 can be used to prevent binding of a range of Gram-negative pathogens to host cells, thus offering protection against pathogen-mediated cytotoxicity. Based on bioinformatic analysis, it appears that a large number of Gram-negative pathogens contain a MAM7 (or MAM6) and are predicted to use this protein to mediate the initial, high affinity attachment to host cells. The inventors' studies show that MAM7 molecules from several Gram-negative pathogens, including *V. parahaemolyticus, Y. pseudotuberculosis, V. cholerae* or EPEC, mediate early attachment of the pathogen to host cells. Based on these studies with aforementioned pathogens, the inventors propose that MAM7 could play an important role during the initial phase of infection for many Gram-negative pathogens that express this adhesion molecule.

The identification and initial characterization of this broadly expressed adhesion factor is important for understanding molecular interactions between Gram-negative pathogens and their target host cells. The adhesion factor MAM7 appears to be constitutively expressed, allowing the bacteria to be primed for immediate attachment when encountering a host cell. The MAM7-mediated attachment appears to be important during the initial phases of infection to allow for the production or presentation of other factors that might be involved in later stages of infection (FIGS. 2A-F, FIGS. 6A-J). These initial studies demonstrate how bacteria expressing MAM7 have an advantage over other bacteria that do not have MAM7 on their cell surface (FIGS. 4A-D). In addition, the multivalent interaction of the mce repeats in MAM7 allows for binding of substrates not recognized by a single repeat. Finally, future microbial and biochemical studies will address the possibility of countering Gram-negative pathogens with their own outer membrane adhesion factor, MAM7, to attenuate infection.

Example 2

Materials & Methods

Construction of Plasmids.

Cloning of MAM7 for expression in BL21, MBP-MAM7 for fluorophore labeling and GST-MAM7 has been described elsewhere (Krachler et al., 2011). Constructs for GST-MAM6, -mce1-5, -mce2-6, -mce3-7 as well as GST-mce1 to -mce7 were all amplified from *V. parahaemolyticus* POR1 genomic DNA and cloned into the plasmid pGEX-rTEV using BamHI and NotI sites. GST-mce2 point mutants were generated by whole plasmid mutagenesis using GST-mce2 as template. GST-mce1 concatemers containing 3, 5 or 7 mce1 domains were generated by amplifying mce 1 fragments containing the following restriction sites: BamHI/XbaI, XbaI/HindIII, HindIII/XhoI, XhoI/EcoRI, EcoRI/PstI, PstI/NcoI and NcoI/NotI for mce 1 fragments 1-7, respectively, and cloning into plasmid pGEX-rTEV.

Protein Purification.

MBP-His-tagged and GST-tagged proteins were purified using Ni-NTA and glutathione agarose beads, respectively, followed by gel filtration as described previously (Krachler et al., 2011).

Attachment Assays.

Attachment assays with live bacteria or purified labeled protein were carried out as described (Krachler et al., 2011). To determine if attachment was fibronectin- and phosphatidic acid-dependent, tissue culture cells were incubated with anti-Fn antibody (50 µg/ml in PBS, Sigma) or treated with 50 µg/ml phospholipase C (Sigma) in PBS for 15 minutes prior to infection. For attachment of labeled protein in the absence of fibronectin, the inventors used trypsinized cells as described previously (Krachler et al., 2011). To test if bacterial attachment could be abolished using heparin, cells were pre-incubated with heparin at concentrations between 10-500 µM in DMEM for 30 minutes prior to attachment assays.

Fn Pull-Down Assays.

A detailed protocol for pull-down assays with GST-MAM constructs and fibronectin can be found elsewhere (Krachler et al., 2011). Variations of this protocol included the use of proteolytic fibronectin fragments (30 kDa N-terminal heparin binding domain and 45 ka gelatin binding domain, both from Sigma) or an additional incubation step with an equimolar amount of liposomes (30 min at 22° C.). PBS-buffered liposomes were prepared from 1,2-Dioleoyl-sn-glycero-3-phosphocholine (PC) or mixtures of PC and 1,2-dioleoyl-sn-glycero-3-phosphate (PA), (both Avanti Polar Lipids Inc.) as described previously (Selyunin et al., 2011).

Quantitation of Phospholipids.

Liposomes in load, flowthrough and eluate fractions were quantified using the method of Worth an Wright (1977). Briefly, samples were extracted with a mixture of chloroform and methanol, centrifuged and molybdophosphoric acid (Sigma) was added to the organic phase. Samples were centrifuged and the aqueous phase removed. Metol and sodium bisulfate were added to reduce the organic phase and the aqueous phase was removed again following centrifugation. The amount of phospholipid was determined by measuring absorbance at 680 nm and expressed as fraction of the amount detected in loaded fractions.

Fn Plate Assay with Labeled Protein.

96-well plates coated with 1 µg fibronectin per well were incubated with MAM constructs prepared in PBS at concentrations between 0.1 and 100 µM at 22° C. for one hour. Initial fluorescence and fluorescence output were measured on a plate reader ($\lambda_{excitation}$ 485 nm, $\lambda_{emission}$ 520 nm) prior to and following three washes with PBS, respectively. Data was expressed as % bound fluorescence and corrected for values determined for MBP alone. Levels of bound protein were blotted as a function of protein concentration and data were fit to a single-site binding model using Sigma Plot.

Liposome Association Assays.

Binding of GST and GST-mce constructs to liposomes were carried out as described in the literature (Krachler et al., 2011). 300 µg liposomes containing PC alone or 1-80 mol % PA were incubated with 100 µg GST and GST-mce proteins in PBS for one hour at 22° C. Mixtures were centrifuged at 100,000×g, 4° C. for one hour and both pellet and supernatant fractions were separated by SDS-PAGE and proteins detected by Coomassie staining Band intensities were determined using the gel analysis software UN-SCAN-IT (Silk Scientific Inc.) and intensities of pellet samples (% bound) were expressed as fraction of total intensities (supernatant and pellet samples combined).

Results

Phosphatidic Acid is Essential for MAM7 Attachment to Host Cells, while Fibronectin Reduces the Time Required for Binding.

The inventors' previous studies showed that two different types of host receptors, the extracellular matrix protein fibronectin and the membrane phospholipid phosphatidic acid, recognize MAM7 adhesin in vitro and contribute to attachment in vivo (Krachler et al., 2011). When studying MAM7 binding to cells independent of fibronectin, the inventors observed that although no binding was detected without fibronectin after 30 minutes, attachment to cells would gradually take place if the incubation time was extended. The inventors therefore performed a 3 hour time course experiment looking at binding of E. coli BL21 expressing V. parahaemolyticus MAM7 on their surface (BL21-MAM7) to Hela cells in the presence and absence of fibronectin (FIG. 15A). Attachment was compared to a negative control of BL21 expressing MAM7ΔTM, a version of MAM7 missing the N-terminal 44 amino acids containing the translocation and membrane anchoring signal (Krachler et al., 2011).

In the presence of both host receptors, binding of BL21-MAM7 to host cells was highly efficient, with more that 40% of bacteria binding within the first 10 minutes of incubation (FIG. 15A). Full binding capacity was reached after 30 minutes. When binding to fibronectin was blocked with anti-fibronectin antibodies so that binding could be studied independent of the contribution of fibronectin, no bacterial attachment was observed within the first 30 minutes of the experiment and the binding was the same as the negative control (FIG. 15A). However, gradual binding was observed from 40 minutes onwards, and close to full binding capacity was reached after 60 minutes. Overall, binding in the absence of fibronectin was delayed by approximately 30 minutes. When the inventors repeated the time course experiment using host cells that were treated with trypsin to degrade fibronectin and purified, fluorophore-labeled MAM7, they obtained similar results showing a delay in host cell binding of approximately one hour (FIG. 15B).

Next, the inventors studied the contribution of phosphatidic acid on host cells to MAM7 attachment. They performed similar time course experiments as described for fibronectin, but instead phosphatidic acid was eliminated from the host surface by treatment with phospholipase C (PLC). In the absence of phosphatidic acid, binding of both BL21-MAM7 (FIG. 15C) and labeled MAM7 protein (FIG. 15D) was reduced to background binding for the duration of the experiment (3 hours), similar to that observed with of BL21-MAM7ΔTM and MBP controls, respectively. The inventors conclude that although both fibronectin and phosphatidic acid act as host receptor for MAM7 attachment, the contribution of fibronectin to overall binding is dispensable when more time is allowed for attachment. While phosphatidic acid is essential for MAM7-mediated binding, fibronectin contributes by accelerating bacterial attachment.

A 30 kDa N-Terminal Fragment of Fibronectin is Sufficient for Binding to MAM7.

Fibronectin is a dimeric 440 kDa glycoprotein involved in many vital processes including cell adhesion, migration, differentiation and wound healing (Grinnell, 1984; Pankov and Yamada, 2002). Each fibronectin molecule is composed of three types of domains denoted type I, type II and type III repeats, which vary in terms of structural and functional properties (Pankov and Yamada, 2002) (FIG. 16A). To analyze which region of fibronectin is involved in MAM7 binding, the inventors performed pull-down experiments with GST-MAM7 and either full-length soluble fibronectin, a 30 kDa proteolytic fragment containing the N-terminal 5 type I repeats ($I_{1-5}$, heparin binding region I) or a 45 kDa fragment containing repeat $I_6$, $II_{1-2}$ and $I_{7-9}$ (gelatin and collagen binding region, FIG. 16A). Both full-length fibronectin and the 30 kDa fragment, but not the 45 kDa fragment, were pulled-down by GST-MAM7 (FIG. 16B-D). As negative control, the inventors used MAM1, which does not bind fibronectin (Krachler et al., 2011) and no interaction with the 30 kDa fragment was observed (FIG. 16E). Since the 30 kDa fragment has been shown to bind heparin (Ingham et al., 1990), the inventors tested whether attachment of BL21-MAM7 to Hela cells would be inhibited by adding heparin to the attachment assay. While in the absence of heparin ~80% of bacteria attached to the host cells within 30 minutes, the addition of increasing concentrations (10-500 µM) of heparin from intestinal mucosa gradually blocked attachment, with only ~40% of BL21-MAM7 remaining attached at 500 µM heparin (FIG. 16F). This demonstrates that the N-terminal region of fibronectin encompassing repeats $I_{1-5}$ mediates MAM7 attachment and that early binding of bacteria could be blocked by adding the competing fibronectin ligand heparin.

At Least 5 Tandem Mce Domains are Required for Stable Binding to Fibronectin.

As previously described, full-length MAM7 can stably bind to fibronectin, while no binding was detected with a construct containing only the first N-terminal mce domain of MAM7 (MAM1) (Krachler et al., 2011). To further delineate the region of MAM7 required for fibronectin binding, the inventors performed pull-down experiments of fibronectin with GST-tagged proteins containing all seven mce domains (MAM7) or successive truncations of mce domains from the C-terminus (designated MAM6 to MAM1). Both load and eluates were analyzed by SDS-PAGE and Coomassie staining Fibronectin was only pulled down by GST-MAM7, GST-MAM6 and GST-MAM5, while no appreciable interaction was observed with GST-MAM1 to -MAM4 (FIG. 17A). Affinity measurements using immobilized fibronectin and fluorophore-labeled MAM constructs showed that MBP-MAM7 bound fibronectin with a $K_D$ of 15±3 µM, while the affinity was decreased for MBP-MAM6 ($K_D$=36±9 µM). No interaction could be detected with either MBP-MAM1 or MBP-MAM2 (FIG. 17B). The inventors could not determine affinities for MAM3-MAM5, as MBP-tagged constructs were unstable and selective thiol-labeling is unfeasible with GST-tagged proteins (GST itself contains cysteins). To determine if one mce domain specifically was responsible for mediating the interaction with fibronectin, the inventors used GST-constructs of all seven individual mce domains for pull-down experiments. Individual mce domains were autonomously folded into a mixed α/β structure, as determined by NMR (unpublished observation). This approach showed that none of the single mce domains was bound by fibronectin (FIG. 3C). However, several constructs containing stretches of five mce domains (mce 1-5, mce 3-6 and mce 2-7) efficiently interacted with fibronectin in pull-down assays (FIG.

17D). These data support the idea that all mce domains contributed to binding, but at least five domains in tandem were required to achieve detectable binding affinity. To further test this, the inventors constructed concatemers containing 3, 5 or 7 identical mce 1 domains and analyzed their interaction with fibronectin using pull-downs. Concatemers containing 5 or 7 mce 1 domains, but not the concatemer containing 3 mce 1 domains, were able to pull-down fibronectin (FIG. 17E). Taken together, these findings are consistent with the hypothesis that, in principle, all mce domains can contribute to fibronectin binding, but at least five domains together are required to achieve a high affinity interaction.

Key Basic Residues Modulate Binding Affinity of Mce Domains to Phosphatidic Acid.

As described above, phosphatidic acid is essential for stable binding of MAM7 to host cells. Although the inventors had previously shown that MAM1 is sufficient to bind to phosphatidic acid, it was unclear how the other mce domains contributed to phosphatidic acid binding in the absence of fibronectin. The inventors tested all seven individual mce domains (mce1-mce7) for phosphatidic acid binding using liposome association assays. Proteins were incubated with liposomes containing a mixture of PC and increasing amounts (1-80 mol %) of PA, followed by separation of liposome-bound and un-bound fractions by ultracentrifugation. All fractions were analyzed by SDS-PAGE (data not shown) followed by densitometry (FIG. 18A). In contrast to GST alone, which did not bind liposomes and was only found in supernatants (data not shown), all seven mce domains were bound by PA-containing liposomes. However, the inventors observed significant differences in their apparent affinities: While mce 1, 2, 3 and 4 bound equally well, binding was decreased ~6-fold for mce 5, ~20-fold for mce 7 and more than 100-fold for mce 6 (FIG. 18A). Although so far only few phosphatidic acid binding proteins have been characterized in detail, it has been demonstrated that basic residues are often key determinants of binding affinity (Stace and Ktistakis, 2006; Lu and Benning, 2009). When the inventors analyzed the mce domains of MAM7 for overall charge, they found only minor differences between individual domains. When they looked at charge distribution, however, the inventors observed that several basic residues that are otherwise well conserved between individual domains are mutated in mce 6. These include two residues which are lysines in mce 2, the strongest binding mce domain, but a serine and glutamine in mce 6, respectively, and a well conserved arginine which is replaced by a histidine in mce 6 (FIG. 18D). To test if these residues contributed to phosphatidic acid binding, the inventors mutated the respective positions in mce 6 to the amino acids of the corresponding position in mce 2 (mce 6 S646K, Q664K and H703R) and tested the resulting proteins for PA binding in liposome association assays. The mce 6 S664K mutant, but not the Q664K or H703R mutants, showed a significant increase in association with liposomes, changing the binding affinity of mce 6 relative to high binding mce domains from 100 fold less to approximately 10 fold less. (FIG. 18B and data not shown). The inventors also used liposomes containing 50 mol % PA and 50 mol % PC to perform pull-down experiments, a composition of liposomes where some degree of binding was observed with all mce constructs. GST-mce proteins were immobilized and incubated with liposomes. Bound liposomes were quantified using a molybdophosphoric acid assay. In agreement with liposome assays, these experiments also showed strong binding of liposomes to mce 1, 2, 3, 4 and 7 while mce 5 and 6 showed weaker binding (FIG. 18C). Mce 6 S646K displayed enhanced affinity compared to wild-type mce 6, while the other mutants had equally low affinities as mce 6.

MAM7 Forms a Tripartite Complex with Fibronectin and Phosphatidic Acid.

Although the inventors have dissected the individual interactions between MAM7 and fibronectin and PA, it remains unclear if MAM7 binds to both types of receptors simultaneously or binding is mutually exclusive. To analyze whether MAM7, fibronectin and phosphatidic acid is competitive, the inventors performed pull-down assays with equimolar amounts of MAM7, Fn and PA (in the form of liposomes consisting of a 1:1 mixture of PC and PA or, as negative control, PC only). First, the inventors pre-incubated GST-MAM7 with liposomes, followed by incubation with fibronectin (FIGS. 19A, 19C). Next, they pre-incubated GST-MAM7 with fibronectin first and competed with liposomes (FIGS. 19B, 19D). For both experiments, the inventors analyzed eluate and flow-through fractions after adding the competing molecule by SDS-PAGE to detect protein (FIGS. 19A, 19B and data not shown) and with a molybdophosphoric acid assay to detect liposome-containing fractions (FIGS. 19C-D). Both fibronectin and PA-containing liposomes were pulled down individually by MAM7 (FIGS. 19A-D, lane 1 and 2, respectively). Addition of an equimolar mix of both ligands also resulted in efficient pull down of both ligands by MAM7 (FIGS. 19A-D, lane 4). As a control, the inventors performed binding assays with liposomes containing only PC and the inventors did not observe binding of MAM7 to liposomes but did observe binding to fibronectin (FIGS. 19A-D, lanes 5-7). Furthermore, no binding to MAM1 was observed with fibronectin or liposomes containing PC alone, but was observed with liposomes containing a 1:1 mixture of PC:PA (FIGS. 19A-D, lanes 8-10). To test for competition between fibronectin and PA binding, the inventors also performed plate assays using fibronectin-coated plates and fluorophore-labeled MBP-MAM7. MAM7-fluorescence was measured before and after incubation with liposomes containing either PC or a mixture of PC and 80 mol % PA. Incubation with increasing concentrations of liposomes did not replace fibronectin as MAM7 ligand, so that MAM7 remained bound to the plate and fluorescence levels did not decrease significantly (FIG. 19E). The inventors also analyzed samples from the plate assay after incubation with liposomes containing 100 μM PA or PC only (FIG. 19E, arrow). Using the molybdophosphoric acid assay, they found that PA-containing liposomes remained associated with Fn-bound MAM7 after washing steps, while liposomes prepared from PC alone did not (FIG. 19F). In addition, the inventors did not detect any associated liposomes when Fn-coated plates were pre-incubated with MBP-tag alone (FIG. 19F). These results support the hypothesis that MAM7 can interact with both fibronectin and phosphatidic acid ligands simultaneously, forming a tripartite complex.

Discussion

The inventors' previous work has identified MAM7 as a factor involved in the initial attachment of bacterial pathogens to host cells. They have also demonstrated that MAM7 expressed on the surface of non-pathogenic bacteria may be utilized as a potent inhibitor of pathogen infection in tissue culture. MAM7 is capable of binding both fibronectin and phosphatidic acid on the host cell surface and both interactions are required for bacterial adhesion to host cells (Krachler et al., 2011). Upon further dissection of host cell binding into discrete binding events, either by masking fibronectin with an anti-Fn antibody or by degrading phosphatidic acid, the inventors found that in the absence of fibronectin, MAM7 is still able to attach to host cells but establishment of a stable interaction takes significantly longer than in the presence of fibronectin (FIGS. 15A-D). Since fibronectin is an abundant protein in the extracellular matrix surrounding cells in vivo as well as in tissue culture, they speculate that it facilitates rapid initial attachment of bacteria in the vicinity of the host cell membrane, thereby increasing the likelyhood for the pathogen to establish a high affinity interaction with the host cell membrane via the second MAM7 ligand, phosphatidic acid.

The inventors found that the MAM7 binding site in fibronectin is located to the 30 kDa N-terminal region (FIGS. 16A-F). The same region is also exploited as receptor by other bacterial adhesins, including fibronectin-binding proteins (FnBPs) from the Gram-positive pathogens *Staphylococcus aureus* and *Streptococcus pyogenes* (Schwarz-Linek et al., 2006). Thus, future experiments will be carried out to address whether MAM7 binding to host cells might be able to diminish adhesion and invasion of these pathogens. In contrast to FnBP-expressing pathogens utilizing the 30 kDa fragment for attachment, most of the MAM7-containing pathogens the inventors studied, such as *V. parahaemolyticus, V. cholerae, Y. pseudotuberculosis* and EPEC, remain extracellular during infection and are not internalized by host cells (Burdette et al., 2009; Simonet et al., 1990; Rosqvist et al., 1988; Celli et al., 2001). Equally, non-pathogenic BL21-MAM7 did not get internalized by host cells. Many factors could account for this difference in bacterial fate following fibronectin binding (Cossart and Sansonetti, 2004). FnBPs such as *S. pyogenes* F1 bind to fibronectin in a way that leaves the RGD motif required for integrin recruitment, which is necessary for internalization, exposed (Ensenberger et al., 2004). It is possible that MAM7 binding renders fibronectin in a different conformation, which does not allow for integrin recruitment. It is also possible that fibronectin does not get recruited by MAM7 at a density sufficient to induce clustering of integrin receptors and thus activation of downstream pathways necessary for cellular uptake (Tran Van Nhieu and isberg, 1993). Indeed, recent work analyzing the link between repeats within *S. aureus* FnBPA and cellular invasion has shown that only very high (subnanomolar) affinity interactions between FnBP repeats and fibronectin can lead to sufficient clustering of integrin receptors to promote cellular invasion (Edwards et al., 2010). It is thus possible that the interaction between MAM7 and fibronectin is not of high enough affinity to promote cellular uptake.

The 30 kDa fragment of fibronectin also contains features required for fibronectin cross-linking and fibrin binding (Hormann et al., 1987; Vakonakis et al., 2007). Thus, it is possible that binding of MAM7 interferes with these processes, as has been described for other adhesins interacting with the same region (Tomasini-Johansson et al., 2001; Matsuka et al., 2003). The inventors are currently conducting experiments to study the consequences of MAM7 binding on integrin signaling, fibrin-fibronectin cross-linking and fibrillogenesis. They detected no discernible binding with MAM constructs containing one to three mce domains, possibly due to very low affinity, and only weak binding with 4 mce domains. The inventors found that at least 5 mce domains are required for stable binding of MAM to fibronectin. The sharp increase in binding affinity between four and five mce domains (FIG. 17A) as well as the non-linear increase in affinity between six and seven mce domains observed in fluorescent saturation binding experiments (FIG. 17B) is in better agreement with a cooperative rather than a linear binding model. However, a clear distinction between the two would require fibronectin binding analyses with MBP-proteins containing three to five mce domains, which the inventors currently are unable to produce and purify. Since the 30 kDa region required for MAM binding contains five consecutive type I repeats, it is tempting to speculate that each of these repeats binds to one mce domain. However, determination of the exact stoichiometry of binding will be subject to further studies but might be difficult to determine in the context of lipid binding, which could modulate the affinity and stoichiometry of binding between MAM7 and fibronectin.

In contrast to fibronectin, which seems to contribute to fast binding but is dispensable for high affinity binding, phosphatidic acid is indispensable to establish stable binding of MAM7 to the host surface (FIGS. 15C, 15D). This underlines earlier findings showing that the relative binding affinity of MAM7 for fibronectin is relatively minor compared to its affinity for intact host cells (apparent $K_D$ of 15 μM and 200 nM for fibronectin and intact cells, respectively). No common motif mediating interactions between proteins and phosphatidic acid has been identified to date. However, many PA-binding motifs contain a high number of basic residues which are thought to establish electrostatic interactions with the phosphate headgroup (Lu and Benning, 2009). Based on alignments of individual mce domains within MAM7 and their differences in affinity for PA, the inventors determined at least one basic residue (mce 2 Lys166) which is crucial for PA-binding. The position is well conserved between different mce domains in MAM7 with the exception of mce 6 and mce 5, both of which bound PA with lower affinity than other mce domains. Mutation of this position to a lysine in mce 6 lead to at least 20-fold increased affinity for PA. Mutation of other candidate residues (which were conserved as basic residues in the other mce domains) within mce 6 that were mutated to basic residues did not seem to have any effect on PA binding. Ultimately, structural studies on mce domains in their free and ligand-bound forms will be required to shed more light on the detailed mechanisms behind host cell binding.

In this study, the inventors dissected the interaction of the adhesin MAM7 with host cells into discrete binding events and analyzed their contribution to overall host cell binding. They analyzed MAM7 for features defining its ability to interact with fibronectin and phosphatidic acid, respectively, and defined the region of fibronectin required for its interaction with MAM7. They also studied whether MAM7 is capable of binding to fibronectin and phosphatidic acid simultaneously and found that the three molecules likely form a tripartite complex. These studies form an important basis for current and future efforts to develop MAM7-derived tools for the attenuation of Gram-negative bacterial infections.

Example 3

Materials & Methods

Bacterial Strains-Isolation and Growth Conditions.

Bacterial isolates were acquired from patients treated at the San Antonio Military Medical Center within the period from 2006 to 2010. Cultures were obtained from sites as indicated in Table 1. All isolates were grown in LB or LB agar or in DMEM at 37° C. for attachment and infection experiments, unless otherwise indicated.

Attachment Assays.

Bacterial attachment to host cells was essentially tested for as previously described above. Briefly, mammalian cells were cultured in DMEM (Invitrogen) supplemented with 10% heat-inactivated fetal bovine serum (HeLa cells) or 10% bovine calf serum (3T3 fibroblasts), (SAFC Biosciences), 5 mM sodium pyruvate and penicillin/steptomycin mix at 37° C. with 5% $CO_2$. Cells were washed with PBS (phosphate-buffered saline) prior to the addition of bacteria in DMEM without antibiotics. Bacteria were added to give a multiplicity of infection (MOI) of 10. To determine the exact amount of input, bacteria were added to empty wells. Plates were centrifuged (1000×g, 22° C., 5 minutes) prior to incubation at 37° C. for 1 hour. Cells were washed three times with PBS and lysed by adding 0.5% Triton X-100 in PBS. Input samples and Triton lysates were serially diluted, plated on LB agar and enumerated by colony counting.

Lactate Dehydrogenase (LDH) Release Assays.

To measure cytotoxicity, tissue culture cells were washed with PBS prior to the addition of bacteria in DMEM without antibiotics at an MOI of 10. Infections were started by centrifugation of plates (1000×g, 22° C., 5 minutes) prior to incubation at 37° C. 200 µL1 of supernatant was removed in triplicate from each well four hours after infection, centrifuged (1000×g, 22° C., 5 minutes), and 100 µl of the supernatant transferred to a fresh 96 well plate for assays. To quantitate cell lysis, the amount of lactate dehydrogenase (LDH) released into the culture medium was measured using the LDH cytotoxicity detection kit (Takara) according to the manufacturer's protocol.

MAM7-Inhibition Experiments.

For inhibition experiments, tissue culture cells were pre-incubated with either *E. coli* BL21 expressing *V. parahaemolyticus* MAM7 or recombinant, bead-immobilized MAM7 for 30 minutes as described previously. Generation of BL21-MAM7, cloning of expression constructs for GST and GST-MAM7 fusion protein and protein purifications have been described elsewhere. Purified proteins were immobilized on 1 µm fluorescent orange latex beads (Sigma) as described by El Shazly et al. (2007). For inhibition experiments, a total of 7.5 µg protein/$10^6$ beads/well in PBS was used. After removing excess bacteria or beads by three PBS washes, cultured cells were infected with clinical isolates for four hours and cytotoxicity measured as described above for LDH release assays.

Fluorescence Microscopy.

Cells were seeded onto cover slips at 150,000 cells/ml and subjected to infection experiments the next day. Following infection experiments, cells were washed with PBS and fixed with 3.2% paraformaldehyde in PBS for 15 minutes. Fixed cells were permeabilized with 0.1% Triton X-100 in PBS for 5 minutes and treated with Hoechst (Sigma) and ALEX-AFLUOR® 488-phalloidin (fluorescent dye; Molecular Probes) for 10 minutes to stain for DNA and F-actin, respectively. Cover slips were mounted onto 10% (w/v) glycerol and 0.7% (w/v) propyl gallate in PBS, sealed with nail polish and viewed using a Zeiss LSM510 META Laser Scanning Confocal Microscope. Images were processed using ImageJ and Photoshop software.

Results

Isolation and PFGE Typing of Bacterial Pathogens Associated with Patient Wounds.

Bacterial pathogens were cultured after isolation from infected patients treated at the Military Medical Center at San Antonio, Tex., following their evacuation from Afghanistan and Iraq. The characterized a total of twenty different isolates obtained either by superficial or deep wound culture, blood culture (two cases) or urine culture (one case), each of which belonged to one of the four most predominant species of Gram-negative bacteria leading to wound infections, *Acinetobacter baumannii-calcoaceticus* complex, *Pseudomonas aeruginosa* and ESBL-producing *Klebsiella* ssp. and *Escherichia coli* (each represented by five isolates, respectively). Pulsed field gel electrophoresis was used to determine the genotype of all isolates and revealed a high degree of genotypic diversity within each of the four groups. Each of the five isolates within each group represented a distinct genotype (Table 2).

Clinical Isolates from Patient Wounds Vary in their Ability to Form Biofilms, Attach to Host Cells and Cause Cytotoxicity.

Next, the inventors studied the bacterial isolates for their ability to form biofilms (Table 2) and attach to cultured HeLa epithelial cells and 3T3 fibroblasts using serial dilution plating assays (FIGS. 20A-D). *P. aeruginosa* and *Klebsiella* ssp. isolates showed the greatest tendency to form biofilms (four out of five isolates tested positive for biofilm formation), followed by *A. baumannii* (two out of five) and *E. coli* (one out of five isolates), (Table 2). In contrast, *A. baumannii* isolates had the greatest ability to attach to host cells, followed by *Klebsiella* ssp., *P. aeruginosa* and *E. coli*. However, the inventors observed a large variability in attachment properties within each group, with *E. coli* isolates showing the most variability (attachment ranged from 15% for isolate #2 to 73% for isolate #5). In addition, the inventors tested all twenty isolates for their ability to cause cytotoxicity in host cells within a four hour infection experiment using lactate dehydrogenase (LDH) release assays (FIGS. 20E-H). *A. baumannii* isolates caused the highest overall cytotoxicity, followed by *P. aeruginosa*, *Klebsiella* ssp. and *E. coli*. The variability was largest amongst *Klebsiella* ssp., with cell lysis ranging from 24% for isolate #2 to 69% for isolate #3. Moreover, the inventors noted two interesting features when comparing attachment and cytotoxicity profiles of the tested isolates. First, in most cases the strains showed a slightly higher attachment and cytotoxic effect on 3T3 fibroblasts. Second, in the case of all groups of pathogens except *P. aeruginosa* the inventors observed positive correlation between host cell attachment and pathogen-induced cytotoxicity (FIGS. 20I-L).

Isolates Display a High Degree of Resistance Against a Wide Range of Commonly Used Antimicrobials.

One of the greatest problems faced in treatment of Gram-negative wound infections is the increasing number of multidrug resistant (MDR) bacteria found in patient isolates. The inventors performed antimicrobial susceptibility testing (AST) by determining the minimal inhibiting concentration (MIC) of a panel of antimicrobials on all twenty bacterial isolates using the BD Phoenix Automated Microbiology System (Table 3). Antimicrobial panels included several drugs from each of the four most commonly used classes of anti-microbials, aminoglycosides, β-lactams, carbapenems and fluoroquinolones. The panels also included antimicrobials from other classes, such as trimethoprim/sulfamethoxazole, but resistance to these was not considered in the classification of isolates as multidrug-resistant. According to the definition of multidrug resistance according to the Center for Disease Control and Prevention (where MDR is defined as resistant to all drugs tested in all or all but one antimicrobial drug classes commonly prescribed to treat Gram-negative infections), (Hospenthal et al., 2011) all tested *A. baumannii* and *P. aeruginosa* strains were found to be MDR. All isolates of ESBL-producing *Klebsiella* ssp. and *E. coli*, even though not conforming to the definition of MDR, displayed a high degree of resistance, being non-susceptible to most aminoglycosides, β-lactams and fluoroquinolones tested (Table 3). All

*Klebsiella* ssp. and *E. coli* isolates were susceptible to the tested carbapenems (imipenem, meropenem and ertapenem).

Anti-Adhesion Treatment Decreases Pathogen-Mediated Cytotoxicity for a Large Number of Clinical Isolates.

The inventors have previously demonstrated that a widely conserved adhesin found in Gram-negative bacteria, termed Multivalent Adhesion Molecule (MAM) 7 can be used to block bacterial attachment sites on host cells, thus diminishing infection by gastrointestinal pathogens such as *Vibrio parahaemolyticus, Vibrio cholerae, Yersinia pseudotuberculosis* and EPEC in tissue culture models of infection as described above. Herein, the inventors investigated if such treatment could be successfully extended to include relevant wound-associated pathogens and tested if MAM7-based anti-adhesion treatment would affect the cytotoxicity mediated by the clinical isolates on HeLa or 3T3 cells using LDH release assays. The inventors used MAM7 either expressed on the surface of non-pathogenic *E. coli* (BL21-MAM7) or recombinant, purified MAM7 protein immobilized on 1 μm latex beads to mimic surface display on bacteria (bead-MAM7). Cultured cells were pre-incubated with MAM7-inhibitors at a multiplicity of infection (MOI) of 100 for 30 minutes. Excess inhibitor was subsequently removed by washing and cells were infected with each of the twenty isolates at an MOI of 10. Cytotoxicity towards HeLa and 3T3 cells, either without pre-incubation or following anti-adhesion treatment with BL21-MAM7 or MAM7-beads, was assessed following four hours of infection (FIGS. 21A-D and FIGS. 22A-D, respectively). Overall, the inventors observed a large decrease in cytotoxicity when cells were pre-incubated with MAM7-based inhibitors, with the extent of inhibition mediated by either BL21-MAM7 or MAM7-beads being very similar. The highest protective effect towards HeLa cells was observed with treatment against *A. baumannii* (mean inhibition of 76±8% with BL21-MAM7 and 68±6% with MAM7-beads) and *Klebsiella* ssp. isolates (mean inhibition of 85±4% and 71±18% with BL21 and beads, respectively), (FIGS. 21A, 21C). In contrast, the inhibitory effect against *P. aeruginosa* (48±30% and 43±24% for bacteria and beads, respectively) and *E. coli* (54±19%/51±20%) was less pronounced for most strains, but the variability of treatment responses between different isolates within these groups was generally high (FIGS. 21B, 21D). For example in the case of *P. aeruginosa*, cytotoxicity inhibition ranged from >91% for isolate #1 to 12% for isolate #3. The inhibitory profiles were very similar between HeLa cells and 3T3 cells (FIG. 22A-D).

Visualization of MAM7 Inhibitory Potential on Bacterial Infections Using Confocal Microscopy.

To visualize the detrimental effects of individual pathogens as well as the protective potential of MAM7 inhibitors, the inventors chose representative strains from each of the four groups (marked with asterisks in FIGS. 21A-D and FIGS. 22A-D) and analyzed infections of both HeLa and 3T3 cells as well as inhibition experiments using confocal microscopy (FIGS. 23A-24R). This allowed us to further test and correlate results found in LDH release assays with cellular phenotypes. For this purpose, cells were infected with either *A. baumannii* #1, *P. aeruginosa* #1, *Klebsiella* ssp. #1 or *E. coli* #5 (all of which showed good responses to anti-adhesion treatment with MAM7). In addition, the inventors analyzed infections with *P. aeruginosa* #3, which showed the lowest response to inhibition. Comparative microscopic analyses of HeLa cells infected with either *P. aeruginosa* isolate #1 or #3 demonstrated a large difference between cellular phenotypes following infection with the two isolates, which is in agreement with the inventors' findings from LDH release experiments as well as PFGE analyses. While infection with *P. aeruginosa* #1 caused only limited cell rounding and lysis, even after several hours of infection, and was predominated by an actin phenotype characterized by induction of filopodia and microspikes, isolate #3 causes rapid cell rounding and cell lysis with seemingly no intermediate phenotype (FIGS. 23C-D). *A. baumannii* #1 and *E. coli* #5 both caused rapid cell rounding (FIGS. 23B, 23F), while *Klebsiella* ssp. #1 caused slower and limited rounding and lead to formation of actin protrusions which were distinct from those observed with *P. aeruginosa* isolate #1 (FIG. 23E). With 3T3 cells, it was harder to discern distinct phenotypes of infection, since upon infection with most bacterial isolates the 3T3 cells underwent rapid deterioration characterized by formation of actin stress fibers and microspikes, followed by cell lysis (FIGS. 245A-R). However, with both HeLa and 3T3 cells, pre-incubation with BL21-MAM7 and MAM7-beads markedly slowed down the progress of infection, with only limited cell rounding and lysis visible after infection with either *A. baumannii* #1, *P. aeruginosa* #1, *Klebsiella* ssp. #1 or *E. coli* #5. In all these cases, the remaining cellular phenotypes were limited to changes in actin phenotype, such as formation of stress fibers, filopodia or microspikes (FIGS. 23A-F and FIGS. 24H-R). In contrast, cellular phenotypes following infection with *P. aeruginosa* isolate #3 did not change upon pre-treatment with either BL21-MAM7 or MAM7-beads on either cell type (FIGS. 23A-F and FIGS. 24J, 24P), which is also in agreement with the inventors' results from LDH assays.

Discussion

Bacterial colonization and infection of wounds is a common cause of complication of treatment in military personnel treated in military medical facilities following evacuation from combat sites. Wound-associated infections with Gram-negative bacteria are predominantly caused by *A. baumannii, P. aeruginosa* and ESBL-producing *E. coli* and *Klebsiella* ssp. (Hospenthal et al., 2011). The increasing number of multidrug-resistant pathogens isolated from patients poses a serious concern and underpins the necessity for alternative measures in infection prophylaxis and treatment. Anti-adhesion therapy has been considered and tested as an alternative to small molecule antimicrobials. In most cases, this is based on administering molecular mimics of host cell receptor structures, such as sugars or sugar mimics (Salminen et al., 2007; Hansen et al., 1997; Pieters, 2006). Following the inventors' previous studies exploring the use of MAM7-based inhibitors in anti-adhesion treatment of bacterial infections with gastrointestinal pathogens, the inventors set out to explore the potential of these inhibitory molecules against infection with wound-associated Gram-negative pathogens.

The inventors utilized five representative patient isolates from each of the five above-mentioned Gram-negative bacterial species. PFGE typing showed that all isolates was genotypically distinct. A major problem in the treatment of wound-associated infections is the increasing number of multidrug-resistant organisms encountered. Admission-associated screening over the period of 2003-2009 has revealed that a wide range of patient isolates are resistant against most antimicrobials commonly used in the clinic and their ability to rapidly acquire additional resistance, such as described in the case of *Acinetobacter* baumannii isolates, which developed colistin resistance during the period of testing (Hospenthal et al., 2011, Jason et al., 2008). This tendency was also found with the isolates tested in the present study— all *Acinetobacter* baumannii isolates and most *Pseudomonas aeruginosa* isolates were multidrug-resistant. While all tested ESBL-producing *Klebsiella* ssp. and *E. coli* isolates are not multidrug-resistant according to the CDC's definition (Hospenthal et al., 2011), most of them displayed a very broad resistance profile, excluding most aminoglycosides, β-lactams and fluoroquinolones as treatment options.

The inventors further analyzed a range of parameters described to be important contributing factors for virulence, using in vitro and tissue culture assays. These included biofilm formation, attachment to host cells and cytotoxicity in tissue culture models of infection (Dallo and Weitao, 2010; Schierle et al., 2009; Davis et al., 2008; Vance et al., 2005). The majority of strains (64%) were found to form biofilms in vitro and all strains displayed an ability to attach to host cells and elucidate host cell killing. However, the degree of attachment and cytotoxicity varied widely across all tested isolates as well as between isolates within the same species, which is in agreement with the genotypic variance found during PFGE profiling of the isolates.

It is evident that for many pathogens, close contact has to be maintained with host cells in order to establish a successful infection. Many virulence factors are either soluble, secreted toxins, which directly bind and translocate across the host cell plasma membrane or form pores in the plasma membrane. Both these processes are concentration dependent and therefore require close contact with host cells to avoid loss by diffusion (Matsuda et al., 2010; Kim et al., 2008; Zrimi et al., 2011). Other important virulence factors are infected directly into the host cell's cytoplasm, either by type III, type IV or type VI secretion machinery, which also requires the bacterium to attach to host cells (Cambronne et al., 2006; Filloux et al., 2008; Winnen et al., 2008). For this reason, the inventors analyzed the correlation between host cell attachment and cytotoxicity across each group of pathogen. The inventors generally found a positive correlation between attachment and cytotoxicity for *A. baumannii*, *P. aeruginosa* and *E. coli* isolates. Interestingly, *P. aeruginosa* isolates showed no significant correlation between these two factors. One explanation for this would be a higher potency of virulence mechanisms in some *P. aeruginosa* strains compared to other pathogens or other strains within the same species (and thus only limited need for attachment to elucidate a high degree of cytotoxicity). In this light, it would be interesting to explore if some of the isolates are hypervirulent compared to others. Another explanation for the atypical behavior of some *P. aeruginosa* isolates would be that they use additional virulence mechanisms which do not strictly depend on direct contact between bacteria and host cells, such as bacterial outer membrane vesicles (OMVs) (Bomberger et al., 2009). OMVs are shedded by a wide variety of bacterial species and can be enriched in certain bacterial proteins (Haurat et al., 2011; Choi et al., 2011; Kulp et al., 2010). In some cases, this may be employed as a mechanism of translocating virulence factors across the host membrane, my means of vesicle/plasma membrane fusion and endocytosis of bacterial components (Jin and Lee, 2011; Parker et al., 2010).

Previously, the inventors have shown that pre-treatment of host cells with MAM7, either presented on the surface of non-pathogenic bacteria or immobilized on polymer beads, markedly decreased the effects of infection with gastro-intestinal pathogens, such as *V. cholera*, *V. parahaemolyticus*, *Y. pseudotuberculosis* and EPEC (see Example 1, above). The inventors further showed that the mechanism of MAM7-based attachment inhibition is likely to be competition for a limited number of host cell receptors (sites rich in both phosphatidic acid and fibronectin), rather than steric hindrance, since the number of attached bacteria or beads plateaus above a certain multiplicity of infection and the MAM7 dose required to achieve inhibition can be kept relatively low (see Example 2, above). Thus, the inventors hypothesized that other pathogens utilizing a MAM7 homolog for host cell attachment might also be responsive to the same mode of treatment and explored the potential of MAM7-based inhibitors in anti-adhesion treatment of infections with wound-associated Gram-negative pathogens. In general, the inventors observed a significant decrease of cytotoxic effects on cultured cells following pre-treatment with MAM7 across all five tested species. A few individual isolates of *P. aeruginosa* and one isolate of ESBL-producing *E. coli*, however, showed very limited responses to MAM7-treatment. Most prominently, the highly cytotoxic isolate *P. aeruginosa* #3 showed almost no response to MAM7 inhibition. In general, the inventors noticed that isolates with weak or no correlation between attachment and cytotoxicity were less responsive to treatment. Given that MAM7 inhibits the attachment of bacteria to host cells, it is conclusive that strains which display a high degree of cytotoxicity even at comparably low levels of attachment, such as *P. aeruginosa* #3, would be less susceptible to anti-adhesion therapy.

The inventors conclude that anti-adhesion prophylaxis or treatment with MAM7-based inhibitors shows promise in the fight against a number of important wound-associated pathogens which might be hard to treat with conventional small molecule antimicrobials. Thus, experiments presented here, investigating the efficacy of MAM7-based inhibition using tissue culture models of infection, should be extended to include relevant animal models of infection in the future, even though this is beyond the scope of the present study. Most importantly, the inventors demonstrate that the correlation between two important hallmarks of virulence which can easily be tested for in tissue culture, attachment and cytotoxicity, could serve as a useful predictor for the success of MAM7-based inhibition against bacterial infections, and potentially other molecules used in anti-adhesion therapy.

TABLE 2

Isolation and genotypic characterization of bacterial isolates

| Species | Isolate No. | Year of isolation | Source | PFGE type | Biofilm formation |
|---|---|---|---|---|---|
| *Acinetobacter baumannii* | 1 | 2006 | Blood | ABC PFT 4 | N |
| | 2 | 2006 | Blood | ABC PFT 3 | Y |
| | 3 | 2007 | Wound culture superficial | ABC PFT 1 | Y |
| | 4 | 2007 | Wound culture deep | ABC PFT 2 | N |
| | 5 | 2008 | Wound culture deep | ABC PFT 5 | N |
| *Pseudomonas aeruginosa* | 1 | 2008 | Wound culture deep | PA PFT 7 | N |
| | 2 | 2007 | Wound culture deep | PA PFT 2 | Y |
| | 3 | 2009 | Wound culture deep | PA PFT 1 | Y |
| | 4 | 2007 | Wound culture deep | PA PFT 4 | Y |
| | 5 | 2008 | Wound culture superficial | PA PFT 5 | Y |

TABLE 2-continued

Isolation and genotypic characterization of bacterial isolates

| Species | Isolate No. | Year of isolation | Source | PFGE type | Biofilm formation |
|---|---|---|---|---|---|
| Klebsiella ssp. | 1 | 2007 | Wound culture deep | KP PFT 1 | Y |
| | 2 | 2008 | Wound culture deep | KP PFT 2 | Y |
| | 3 | 2009 | Wound culture deep | KP PFT 7 | Y |
| | 4 | 2007 | Wound culture deep | KP PFT 3 | N |
| | 5 | 2008 | Wound culture deep | KP PFT 9 | Y |
| Escherichia coli | 1 | 2007 | Wound culture deep | EC PFT 3 | N |
| | 2 | 2007 | Wound culture superficial | EC PFT 4 | N |
| | 3 | 2009 | Wound culture deep | EC PFT 1 | N |
| | 4 | 2010 | Wound culture deep | EC PFT 7 | N |
| | 5 | 2008 | Urine culture | EC PFT 2 | Y |

TABLE 3

Strain susceptibility against commonly screened antibiotics

| Bacterial species | Isolate# | Amik. | AmoxC. | Amp. | Az. | Cefo. | Ceft. | Cefu. | Ceph. | Cipro. | Gati. | Gent. |
|---|---|---|---|---|---|---|---|---|---|---|---|---|
| Acinetobacter baumannii | 1 | >32 R | >16/8 R | >16 R | >16 R | >32 R | >16 R | >16 R | >16 R | >2 R | >4 R | >8 R |
| | 2 | >32 R | >16/8 R | >16 R | >16 R | >32 R | >16 R | >16 R | >16 R | >2 R | >4 R | >8 R |
| | 3 | 32 I | >16/8 R | >16 R | >16 R | >32 R | 8 S | >16 R | >16 R | >2 R | 4 I | >8 R |
| | 4 | >32 R | >16/8 R | >16 R | >16 R | >32 R | >16 R | >16 R | >16 R | >2 R | >4 R | >8 R |
| | 5 | >32 R | >16/8 R | >16 R | >16 R | >32 R | >16 R | >16 R | >16 R | >2 R | >4 R | >8 R |

| | Isolate# | Amik. | Amp. | AmpS. | Az. | Cefa. | Cefe. | Cx. | Cd. | Co. | Cefu. | Cipro. |
|---|---|---|---|---|---|---|---|---|---|---|---|---|
| Pseudomonas aeruginosa | 1 | ≤8 S | >16 R | >16/8 R | >16 R | >16 R | 16 I | >16 R | >16 R | >32 R | >16 R | >2 R |
| | 2 | 16 S | >16 R | >16/8 R | >16 R | >16 R | >16 R | >16 R | 8 S | >32 R | >16 R | >2 R |
| | 3 | 16 S | >16 R | >16/8 R | >16 R | >16 R | >16 R | >16 R | >16 R | >32 R | >16 R | >2 R |
| | 4 | 32 I | >16 R | >16/8 R | >16 R | >16 R | >16 R | >16 R | >16 R | >32 R | >16 R | >2 R |
| | 5 | 32 I | >16 R | >16/8 R | >16 R | >16 R | >16 R | >16 R | >16 R | >32 R | >16 R | >2 R |

| | Isolate# | Amik. | AmoxC. | Amp. | Az. | Cefa. | Cefe. | Cefo. | Cx. | Cd. | Co. | Cipro. |
|---|---|---|---|---|---|---|---|---|---|---|---|---|
| Klebsiella ssp. | 1 | ≤8 S | 16/8 R | >16 R | >16 R | NA | >16 R | >32 R | NA | >16 R | NA | >2 R |
| | 2 | ≤8 S | 16/8 R | >16 R | >16 R | >16 R | >16 R | >32 R | ≤4 S | >2 R* | >32 R | >2 R |
| | 3 | ≤8 S | 8/4 R | >16 R | >16 R | >16 R | 2 R* | ≤4 S | >16 R | >2 R* | 16 R | 1 S |
| | 4 | ≤8 S | >16/8 R | >16 R | >16 R | >16 R | >16 R | >32 R | 8 S | >2 R* | >32 R | ≤0.5 S |
| | 5 | >32 R | >16/8 R | >16 R | >16 R | NA | 2 R* | >32 R | NA | >16 R | NA | ≤0.5 S |

| | Isolate# | Amik. | Amp. | AmpS. | Az. | Cefa. | Cefe. | Cx. | Cd. | Co. | Cefu. | Cipro. |
|---|---|---|---|---|---|---|---|---|---|---|---|---|
| Escherichia coli | 1 | ≤8 S | >16 R | >16/8 R | >16 R | >16 R | >16 R | 8 S | >16 R | >32 R | >16 R | >2 R |
| | 2 | ≤8 S | >16 R | >16/8 R | >16 R | >16 R | >16 R | ≤4 S | >16 R | >32 R | >16 R | >2 R |
| | 3 | ≤8 S | >16 R | >16/8 R | >16 R | >16 R | >16 R | 8 S | >16 R | >32 R | >16 R | >2 R |
| | 4 | ≤8 S | >16 R | >16/8 R | >16 R | >16 R | >16 R | >16 R | >16 R | >32 R | >16 R | >2 R |
| | 5 | ≤8 S | >16 R | >16/8 R | 8 R* | >16 R | 8 R* | 8 S | 4 R* | >32 R | >16 R | >2 R |

| Bacterial species | Isolate# | Im. | Lev. | Mero. | Nf. | Pip. | Tet. | Tob. | TmSm. |
|---|---|---|---|---|---|---|---|---|---|
| Acinetobacter baumannii | 1 | 2 S | >4 R | 2 S | >64 R | >64 R | >8 R | 8 I | >2/38 R |
| | 2 | >8 R | >4 R | >8 R | >64 R | >64 R | 4 S | >8 R | >2/38 R |
| | 3 | >8 R | 4 I | >8 R | >64 R | >64 R | >8 R | >8 R | >2/38 R |
| | 4 | 2 S | >4 R | ≤1 S | >64 R | >64 R | >8 R | >8 R | >2/38 R |
| | 5 | >8 R | >4 R | >8 R | >64 R | >64 R | 8 I | 4 S | >2/38 R |

| | Isolate# | Gent. | Im. | Lev. | Mero. | Nf. | PipT. | Tet. | Tob. | TmSm |
|---|---|---|---|---|---|---|---|---|---|---|
| Pseudomonas aeruginosa | 1 | 4 S | >8 R | >4 R | 4 S | >64 R | >64/4 R | >8 R | ≤2 S | >2/38 R |
| | 2 | 4 S | >8 R | >4 R | >8 R | >64 R | >64/4 R | >8 R | >8 R | >2/38 R |
| | 3 | 8 I | >8 R | >4 R | >8 R | >64 R | >64/4 R | >8 R | ≤2 S | >2/38 R |
| | 4 | >8 R | >8 R | >4 R | >8 R | >64 R | 32/4 S | >8 R | >8 R | >2/38 R |
| | 5 | >8 R | 2 S | >4 R | 4 S | >64 R | >64/4 R | >8 R | >8 R | >2/38 R |

| | Isolate# | Ert. | Gent. | Im. | Lev. | Mero. | Nf. | PipT. | Tet. | Tob. | TmSm |
|---|---|---|---|---|---|---|---|---|---|---|---|
| Klebsiella ssp. | 1 | NA | >8 R | ≤1 S | >4 R | ≤1 S | >64 R | NA | >8 R | 8 I | >2/38 R |
| | 2 | ≤0.5 S | >8 R | ≤1 S | ≤1 S | ≤1 S | >64 R | 32/4 I | >8 R | >8 R | ≤0.5/9.5 S |
| | 3 | ≤0.5 S | 8 I | ≤1 S | ≤1 S | ≤1 S | >64 R | 16/4 S | >8 R | 8 I | ≤0.5/9.5 S |

TABLE 3-continued

Strain susceptibility against commonly screened antibiotics

|  |  |  |  |  |  |  |  |  |  |  |
|---|---|---|---|---|---|---|---|---|---|---|
|  | 4 | ≤0.5 S | >8 R | ≤1 S | ≤1 S | ≤1 S | >64 R | >64/4 R | >8 R | 8 I | ≤0.5/9.5 S |
|  | 5 | NA | >8 R | ≤1 S | ≤1 S | ≤1 S | >64 R | NA | >8 R | >8 R | >2/38 R |

|  |  | Gent. | Im. | Lev. | Mero. | Nf. | PipT. | Tet. | Tob. | TmSm |
|---|---|---|---|---|---|---|---|---|---|---|
| *Escherichia coli* | 1 | >8 R | ≤1 S | >4 R | ≤1 S | 32 S | 32/4 I | >8 R | >8 R | >2/38 R |
|  | 2 | >8 R | ≤1 S | >4 R | ≤1 S | ≤16 S | ≤2/4 S | ≤2 S | >8 R | >2/38 R |
|  | 3 | >8 R | ≤1 S | >4 R | ≤1 S | ≤16 S | 32/4 I | >8 R | >8 R | >2/38 R |
|  | 4 | ≤2 S | ≤1 S | >4 R | ≤1 S | ≤16 S | 16/4 I | >8 R | ≤2 S | >2/38 R |
|  | 5 | ≤2 S | ≤1 S | >4 R | ≤1 S | ≤16 S | 32/4 I | >8 R | >8 R | >2/38 R |

Table 3 Abbreviations:
Amik., Amikacin;
AmoxC., Amoxillin-Calvulanate;
Amp., Ampicillin;
AmpS., Ampicillin-Sulbactam;
Az., Aztreonam;
Cd., Ceftazidime;
Cefa., Cefazolin;
Cefe., Cefepime;
Cefo., Cefotaxime;
Ceft., Ceftazidime;
Cefu., Cefuroxime;
Ceph., Cephalotin;
Co., Ceftriaxone;
Cx., Cefoxitin;
Cipro., Ciprofloxacin;
Ert., Ertapenem;
Gati., Gatifloxacin;
Gent., Gentamicin;
Im., Imipenem;
Lev., Levofloxacin;
Mero., Meropenem;
Nf., Nitrofurantoin;
Pip., Piperacillin;
PipT., Piperacillin-Tazobactam;
Tet., Tetracycline;
Tob., Tobramycin;
TmSm., Trimethoprim-Sulfamethoxazole;
NA, data not available;
Values given are minimal inhibiting concentrations in μg/ml and interpretation of the result in terms of R, resistant; I, intermediate; S, susceptible;
*As a rule, when ESBL is detected, an interpretation of susceptible or intermediate for penicillins, cephalosporins and aztreonam is reported as resistant.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,683,202
U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,928,906
U.S. Pat. No. 5,929,237
U.S. Pat. No. 6,420,339
U.S. Pat. No. 6,552,170
U.S. Pat. No. 7,587,286
U.S. Pat. No. 7,610,156
U.S. Pat. No. 7,666,400
U.S. Patent Publn. 2003/0138490
Alouf, *Methods Mol. Biol.*, 145:1-26, 2000.
Arruda et al., *Science*, 261:1454-1457, 1993.
Ausubel et al., *Current Protocols in Molecular Biology*, Greene Publishing Associates and Wiley Interscience, N.Y., 1994.
Awai et al., *Proc. Natl. Acad. Sci. USA*, 103:10817-10822, 2006.
Ayliffe, *Clin. Infect. Dis.*, 24:S74-9, 1997.
Barany and Merrifield, In: *The Peptides*, Gross and Meienhofer (Eds.), Academic Press, NY, 1-284, 1979.
Barber, *J. Clin. Pathol.*, 14:385-393, 1961.
Begier et al., *Clin Infect Dis.*, 39(10):1446-1453, 2004.
Beilman et al., *Surg. Infect. (Larchmt).*, 6(1):87-92, 2005.

Boekema et al., *Infect. Immun.*, (72):691-700, 2004.
Boland and Cornelis, *Subcell Biochem.*, (33):343-382, 2000.
Bomberger et al., *PloS Pathogens*, 284(28):18778-18789, 2009.
Branski et al., *Surg. Infect. (Larchmt).*, 10:389-397, 2009.
Broberg et al., *Science*, 329:1660-1662, 2010.
Burdette et al., *Mol. Microbiol.*, 73:639-649, 2009.
Burdette et al., *Proc. Natl. Acad. Sci. USA*, 105:12497-12502, 2008.
Cambronne et al., *Traffic*, 7:929-939, 2006.
Capaldi et al., *Biochem. Biophys. Res. Comm.*, 74(2):425-433, 1977.
Celli et al., *EMBO J.* 20:1245-1258, 2001.
Chitale et al., *Cell Microbiol.*, 3:247-254, 2001.
Choi et al., *Proteomics*, 11(16):3438, 2011.
Conly et al., *Can. J. Infect. Dis. Med. Microbiol.*, 16:109, 2005.
Cossart and Sansonetti, *Science*, 304:242-248, 2004.
Crossley et al., *J. Infect. Dis.*, 139:273-279, 1979.
Dallo and Weitao, *Adv. Skin Wound Care*, 23(4):169-174, 2010.
Daniels et al., *J. Infect. Dis.*, 181:1661-1666, 2000.
Davis et al. *Wound Repair Regen.*, 16(1):23-29, 2008.
Dhakal et al., *Biochem. Biophys. Res. Commun.*, 346:751-757, 2006.
Dorsey et al., *Mol. Microbiol.*, (57):196-211, 2005.
Edwards, et al., *PLoS Pathog*, 6:e1000964, 2010.
El-Shazly et al., *J. Med. Microbiol.*, 56:1145-1151, 2007.
Ensenberger et al., *Biophys. Chem.*, 112:201-207, 2004.
Filloux et al., *Microbiology*, 154(Pt 6):1570-1583, 2008.
Finn et al., *Nucleic Acids Res.*, 38:D211-222, 2009.
Froman et al., *J. Biol. Chem.*, 262:6564-6571, 1987.
Galan, *Cell Host Microbe.*, 5:571-579, 2009.
Garbom et al., *Infect Immun.*, (72):1333-1340, 2004.
Gilbert et al., *Can. J. Infect. Dis. Med. Microbiol.*, 16:108, 2005.
Gilbert et al., *CMAJ*, 175(2):149-154, 2006.
Grinnell, *J. Cell Biochme.*, 26:107-116, 1984.
Hansen et al., *J. Am. Chem. Soc.*, 119(46):11277-11281, 1997.
Harbarth et al., *Emerg. Infect. Dis.*, 11(6):962-965, 2005.
Haurat et al., *J. Biol. Chem.*, 286(2):1269-1276, 2011.
Henderson et al., *FEMS Microbiol Rev* (35):147-200, 2011.
Heroven and Dersch, *Mol. Microbiol.*, (62):1469-1483, 2006.
Hoiby et al., *BMC Med.*, 9:32, 2011.
Holmes et al., *J. Clin. Microbiol.*, 43(5):2384-2390, 2005.
Hormann et al., *Biol. Chem. Hoppe Seyler*, 368:669-674, 1987.
Hospenthal et al., *J. Trauma*, 71(2 Suppl 2):S202-S209, 2011.
Howe et al., *Bioinformatics*, 18:1546-1547, 2002.
Ingham et al., *Biochem. J.*, 272:605-611, 1990.
Issartel et al., *Clin. Microbiol.*, 43(7):3203-3207, 2005.
Jason et al., *Clin. Orthop. Relat. Res.*, 466:1356-1362, 2008.
Jevons, *British Med. J.*, 1:124-125, 1961.
Jin and Lee et al., *PloS One*, 6(10):e26129, 2011.
Johannesson et al. *J. Med. Chem.*, 1999 Nov. 4; 42(22):4524-37, 1999.
Johnson et al., In: *Biotechnology And Pharmacy*, Pezzuto et al. (Eds.), Chapman and Hall, NY, 1993.
Kerman et al., *Proc. Natl. Acad. USA* 99:12617-12621, 2002
Kim et al., *Cell Microbiol.*, 12:372-385, 2008.
Kline et al., *Cell Host. Microbe.*, (5):580-592, 2009.
Konkel et al., *Mol. Microbiol.*, (24:953-963, 1997.
Krachler et al., *Proc. Natl. Acad. Sci. USA*, 108:11614-11619, 2011.
Kulp et al. *Annu. Rev. Microbiol.*, 64:163-184, 2010.
Kyte and Doolittle, *J. Mol. Biol.*, 157(1):105-132, 1982.
Lebreton et al., *Infect. Immun.*, (77):2832-2839, 2009.
Lee et al., *BMC Microbiol.*, (9):252, 2009.
Livermore, *Int. J. Antimicrob. Agents*, 16(1:)S3-10, 2000.
Lu and Benning, *J. Biol. Chem.*, 284:17420-17427, 2009.
Matsuda et al., *Infect. Immun.*, 78(2):603-610, 2010.
Matsuka et al., *Biochemistry*, 42:14643-14652, 2003.
Merrifield, *Science*, 232(4748):341-347, 1986.
Milton et al. *J. Bacteriol.*, 178:1310-1319, 1996.
Mulvey et al., *Emerg. Infect. Dis.*, 11(6):844-850, 2005.
Neron et al., *Bioinformatics*, 25:3005-3011, 2009.
Nishibuchi et al., *Infect. Immun.*, 60:3539-3545, 1992.
Pankov and Yamada, *J. Cell Sci.*, 115:3861-3863, 2002.
Panlilio et al., *Infect. Control Hosp. Epidemiol.*, 13:582-586, 1992.
Park et al., *Infect. Immun.*, 72:6659-6665, 2004.
Parker et al., *Infect. Immun.*, 78(7):3019-3026, 2010.
Pieters, *Med. Res. Rev.*, 27(6):796-816, 2007.
Remington's Pharmaceutical Sciences, 18th Ed. Mack Printing Company, 1990.
Robert et al., *Clin. Microbiol. Infect.*, 11(7):585-587, 2005.
Rosqvist et al., *Infect. Immun.*, 56:2139-2143, 1988.
Said-Salim et al., *J. Clin. Microbiol.*, 43(7):3373-3379, 2005.
Salminen et al., *J. Antimicrob. Chemother.*, 60(3):495-501, 2007.
Sambrook and Russell, Molecular Cloning: A Laboratory Manual, 3rd Edition, Cold Spring Harbor Laboratory, N.Y., 1989.
Schierle et al. *Wound Repair Regen.*, 17:354-359, 2009.
Schwarz-Linek et al., *Nature*, 423:177-181, 2003.
Selyunin et al., *Nature*, 469:107-111, 2011.
Simonet et al., *Infect. Immun.*, 58:841-845, 1990.
Stace and Ktistakis, *Biochim Biophys Acta*, 1761:913-926, 2006.
Stewart and Young, In: *Solid Phase Peptide Synthesis*, 2d. ed., Pierce Chemical Co., 1984.
Tam et al., *J. Am. Chem. Soc.*, 105:6442, 1983.
Tertti et al., *Infect. Immun.*, 60:3021-3024, 1992.
Tomasini-Johansson et al., *J. Biol. Chem.*, 276:23430-23439, 2001.
Tran Van Nhieu and Isberg, *EMBO J.*, 12:1887-1895, 1993.
Vaitkevicius et al., *Proc. Natl. Acad. Sci. USA*, 103:9280-9285, 2006.
Vakonakis et al., *EMBO J.*, 26:2575-2583, 2007.
Vance et al. *Infect. Immun.*, 73:1271-1274, 2005.
Vandenesch et al., *Emerg. Infect. Dis.*, 9(8):978-984, 2003.
Vita et al., *Biopolymers*, 47:93-100, 1998.
Voss et al., *Eur. J. Clin. Microbiol. Infect. Dis.*, 13:50-55, 1994.
Vourli et al., *Euro. Surveill.*, 10(5):78-79, 2005.
Wannet et al., *J. Clin. Microbiol.*, 42(7):3077-3082, 2004.
Wannet et al., *J. Clin. Microbiol.*, 43(7):3341-3345, 2005.
Weisshoff et al., *Eur. J. Biochem.*, 259(3):776-788, 1999.
Winnen et al., *Plos One*, 3(5):e2178, 2008.
Witte et al., *Eur. J. Clin. Microbiol. Infect. Dis.*, 24(1):1-5, 2005.
Worth and Wright, *Clin. Chem.*, 23:1995-1200, 1977.
Wylie and Nowicki, *J. Clin. Microbiol.*, 43(6):2830-2836, 2005.
Yu et al., *Bioinformatics*, 26:1608-1615, 2010.
Zrimi et al., *Plos One*, 5:e15347, 2011.

What is claimed is:

1. A method of preventing or inhibiting a pathogenic bacterial infection in a subject caused by a pathogenic bacterium expressing a multivalent adhesion molecule (MAM) polypeptide, comprising administering to said subject a composition comprising a non-pathogenic bacterium expressing a MAM polypeptide comprising at least 6 mce repeat regions.

2. The method of claim 1, wherein said pathogenic bacterium is Gram-negative.

3. The method of claim 2, wherein said pathogenic bacterium is selected from the group consisting of *Vibrio parahaemolyticus*, *Vibrio cholerae*, *Yersinia pseutotuberculosis*, and enteropathogenic *Escherichia coli*.

4. The method of claim 1, wherein said non-pathogenic bacterium expresses a native MAM polypeptide.

5. The method of claim 1, wherein said non-pathogenic bacterium expresses a heterologous MAM polypeptide.

6. The method of claim 5, wherein said non-pathogenic bacterium comprises a gene encoding a MAM polypeptide in an extrachromosomal self-replicating vector.

7. The method of claim 5, wherein said non-pathogenic bacterium comprises a gene encoding a MAM polypeptide integrated into a chromosome of said non-pathogenic bacterium.

8. The method of claim 1, wherein said composition further comprises a probiotic.

9. The method of claim 8, wherein said composition is administered orally.

10. The method of claim 8, wherein said composition is selected from the group consisting of milk, yogurt, curd, cheese, fermented milks, milk based fermented products, ice-creams, fermented cereal based products, milk based powders, infant formulae, pet food, a tablet, a liquid bacterial suspension, dried oral supplement and wet oral supplement.

11. The method of claim 1, wherein said composition is administered topically.

12. The method of claim 11, wherein said subject has suffered a burn injury.

13. The method of claim 11, wherein said composition is formulated as a cream, a gel, a salve, an ointment or a powder.

14. The method of claim 11, wherein said composition is comprised in or disposed on a wound dressing.

15. The method of claim 1, wherein said composition is comprises in or disposed on a surgical mesh or implantable device.

16. A method of preventing or inhibiting a pathogenic bacterial infection in a subject caused by a pathogenic bacterium expressing a multivalent adhesion molecule (MAM) polypeptide, comprising administering to said subject a composition comprising a MAM peptide or protein comprising at least 6 mce repeat regions coupled to a carrier.

17. The method of claim 16, wherein said pathogenic bacterium is Gram-negative.

18. The method of claim 17, wherein said pathogenic bacterium is selected from the group consisting of *Vibrio parahaemolyticus*, *Vibrio cholerae*, *Yersinia pseutotuberculosis*, and enteropathogenic *Escherichia coli*.

19. The method of claim 16, wherein said carrier is a particle or bead.

20. A method for identifying or quantifying phosphatidic acid on a membrane comprising contacting a membrane with a peptide or polypeptide comprising a multivalent adhesion molecule (MAM) mce repeat region.

21. The method of claim 20, wherein said membrane is part of an intact cell.

22. The method of claim 1, wherein the number of mce repeats is 6.

23. The method of claim 1, wherein the number of mce repeats is 7.

24. The method of claim 16, wherein the number of mce repeats is 6.

25. The method of claim 16, wherein the number of mce repeats is 7.

26. The method of claim 16, wherein said carrier is a liposome, a nanoparticle, a nanoshell, a nanocluster or a quantum dot.

\* \* \* \* \*

SEQUENCE LISTING

<160> NUMBER OF SEQ ID NOS: 31

<210> SEQ ID NO 1
<211> LENGTH: 882
<212> TYPE: PRT
<213> ORGANISM: Vibrio parahaemolyticus

<400> SEQUENCE: 1

Met Ser Asp Gln Asn Asn Ser Gln Thr Ser Tyr Val Pro Asp Val Lys
1               5                   10                  15

Arg Ser Lys Gly Ile Ser Pro Leu Trp Leu Pro Ile Leu Thr Met
            20                  25                  30

Val Leu Ala Gly Trp Leu Val Val Lys Ser Ile His Asp Ala Gly Gln
        35                  40                  45

Arg Val Gln Ile Tyr Phe Ser Asp Ala Ala Gly Leu Val Ala Gly Arg
    50                  55                  60

Thr Thr Ile Arg Tyr Gln Gly Leu Glu Val Gly Met Val Arg Asp Ile
65                  70                  75                  80

Asn Leu Ser Glu Asp Leu Gly Ser Ile Tyr Val Asp Ala Asp Ile Tyr
                85                  90                  95

Pro Glu Ala Thr Lys Leu Leu Asn Asp Lys Thr Arg Phe Trp Leu Val
            100                 105                 110

Lys Pro Thr Ala Ser Leu Thr Gly Val Ser Gly Leu Asp Ala Leu Val
            115                 120                 125

Ser Gly Asn Tyr Ile Ser Ile Gln Pro Gly Asp Gly Gln Glu Phe Glu
        130                 135                 140

Thr Thr Phe His Ala Leu Asp Ser Ala Pro Thr Asp Leu Arg Val Ser
145                 150                 155                 160

Gln Gly Leu Asn Ile Lys Leu Lys Ser Arg Asp Leu Gly Gly Val Ser
                165                 170                 175

Ile Gly Ser Gln Ile Val Tyr Lys Lys Ile Pro Ile Gly Ala Val Tyr
            180                 185                 190

Ser Tyr Gln Leu Asp Glu Asp Ala Lys Ser Ile Thr Ile Gln Ala Asn
    195                 200                 205

Ile Gln Glu Gln Tyr Arg His Ile Ile Asn Asp Arg Ser Arg Phe Trp
210                 215                 220

Asn Val Ser Gly Ile Gly Ala Ser Ile Gly Phe Glu Gly Val Asp Val
225                 230                 235                 240

Arg Leu Glu Ser Met Ser Ala Leu Leu Gly Gly Ala Ile Ala Val Asp
                245                 250                 255

Ser Pro Asp Asp Gly Glu Pro Val Glu Glu Asn Thr Glu Phe Arg Leu
            260                 265                 270

Tyr Lys Asp Leu Lys Thr Ala Gly Arg Gly Ile Ala Ile Lys Ile Ala
        275                 280                 285

Leu Pro Asp Asn Lys Val Ser Ser Glu Gly Ala Pro Ile Met Tyr
        290                 295                 300

Arg Gly Ile Glu Ile Gly Gln Val Thr Asp Leu Ser Leu Ser Glu Gly
305                 310                 315                 320

Arg Glu Val Ile Leu Ala Ser Ala Ile Gln Pro Ala Phe Ser Asp
                325                 330                 335

Met Leu Thr Thr Gly Thr Arg Phe Val Leu Glu Glu Ala Lys Val Ser
            340                 345                 350

Leu Ser Gly Val Glu Asn Ile Ala Asn Leu Val Arg Gly Asn Phe Leu
        355                 360                 365

```
Thr Ile Val Pro Gly Asp Gly Glu Arg Ser Arg Arg Phe Thr Ala Ile
    370                 375                 380

Arg Lys Asn Val Phe Asn Gln Gln Gln Glu Lys Ser Ile Ala Ile Arg
385                 390                 395                 400

Leu Ile Ser Asp Asn Ser Phe Gly Leu Asp Ser Gly Ala Asn Val Leu
                405                 410                 415

Tyr Lys Gly Ile Val Val Gly Ser Ile Ile Asn Val Gly Leu Val Asp
                420                 425                 430

Glu Lys Lys Gln Thr Lys His Glu Val Phe Met Asp Val Leu Ile Asp
        435                 440                 445

His Glu Tyr Lys His Leu Ile Lys Ser Asn Asn Arg Phe Tyr Val Thr
    450                 455                 460

Gly Ser Ala Ser Ala Glu Leu Thr Glu Ser Gly Leu Ser Val Thr Val
465                 470                 475                 480

Pro Pro Ala Lys Gln Leu Leu Thr Gly Ser Ile Ser Phe Val Ser Glu
                485                 490                 495

Gly Ser Glu Ser Ile Gln Lys Glu Tyr Gln Leu Phe Gln Asn Glu Ser
                500                 505                 510

Leu Ala Glu Leu Ala Gln Tyr Asn Lys Thr Gly Ser Lys Thr Leu Met
        515                 520                 525

Leu Phe Ala Ser Glu Leu Pro Pro Ile Ser Lys Gly Ser Pro Leu Leu
    530                 535                 540

Tyr Arg Asn Leu Pro Val Gly Asn Val Ser Asp Phe His Leu Val Asp
545                 550                 555                 560

Gly Gly Val Leu Ile Lys Ala Thr Ile Glu Asn Arg Phe Ala Tyr Leu
                565                 570                 575

Val Thr Pro Gln Thr Val Phe Trp Asn Arg Ser Gly Ile Glu Ile Asp
                580                 585                 590

Ala Ser Leu Ser Gly Val Ser Val Lys Ala His Pro Leu Lys Ser Leu
        595                 600                 605

Ile Glu Gly Gly Ile Ala Phe Asp Ser Val Pro Gly Val Glu Asn Lys
    610                 615                 620

Val Gly Glu Arg Trp Lys Leu Tyr Ala Asp Gln Gln Lys Ala Arg Lys
625                 630                 635                 640

Phe Gly Arg Val Ile Ser Leu Glu Thr Asp Gly Thr Gln Glu Val Leu
                645                 650                 655

Lys Gly Met Pro Ile Glu Tyr Gln Gly Val Lys Val Gly Glu Val Thr
                660                 665                 670

Leu Val Val Pro Asn Phe Arg Arg Asn Leu Val Glu Val Thr Ala Arg
        675                 680                 685

Ile Leu Pro Glu Tyr Val Glu Asn Ile Ala Val Glu Gly Thr His Phe
    690                 695                 700

Trp Leu Thr Glu Pro Glu Ile Gly Leu Gly Gly Val Lys Asn Leu Gly
705                 710                 715                 720

Ala Leu Val Ser Lys Ser Ile Ser Val Glu Pro Gly Asn Gly Lys Ala
                725                 730                 735

Lys Phe Asp Phe Gln Leu Glu Lys Gly Phe Asp Arg Val Glu Gly Val
                740                 745                 750

Met Phe Thr Leu Gln Ser Glu Gln Arg Gly Ser Val Gln Val Gly Thr
        755                 760                 765

Pro Val Leu Tyr Arg Gln Met Glu Val Gly Gln Val Thr Asp Val Arg
    770                 775                 780

Leu Gly Glu Phe Ala Asp Arg Val Val Ser Thr Ile Lys Ile Lys Pro
```

```
                785                 790                 795                 800
Glu Tyr Ala Tyr Leu Val Arg Gln Asn Ser Val Phe Trp Asn Val Ser
                    805                 810                 815
Gly Val Asp Val Ser Ile Gly Ile Thr Gly Ala Asn Ile Lys Ala Gly
                820                 825                 830
Thr Ile Asp Ser Leu Val Arg Gly Gly Ile Ala Phe Ser Thr Pro Glu
                835                 840                 845
Gln Ser Gln Ile Pro Pro Ala Ala Lys Arg Gly His Ser Phe Tyr Leu
            850                 855                 860
Tyr Pro Arg Ala Asp Glu Ser Trp Val Gln Trp Arg Thr Pro Ile Pro
865                 870                 875                 880
Lys Pro

<210> SEQ ID NO 2
<211> LENGTH: 879
<212> TYPE: PRT
<213> ORGANISM: Vibrio cholerae

<400> SEQUENCE: 2

Met Ser Gln Glu Asn Thr Thr Gln Thr Ser Tyr Thr Pro Glu Ile Arg
1               5                   10                  15
Lys Arg Arg Gly Ile Ser Pro Leu Trp Ile Leu Pro Ile Val Thr Met
                20                  25                  30
Ile Leu Ala Gly Trp Leu Val Phe Lys Ala Val His Asp Ala Gly Val
            35                  40                  45
Arg Ile Gln Ile His Phe Glu Asn Ala Gln Gly Leu Ile Ala Gly Arg
        50                  55                  60
Thr Thr Ile Arg Tyr Gln Gly Leu Glu Val Gly Met Val Arg Asp Ile
65                  70                  75                  80
Lys Leu Ser Glu Gly Leu Asp Ser Ile Tyr Val Glu Ala Asp Ile Tyr
                85                  90                  95
Pro Glu Ala Thr Lys Leu Leu Ser Asn Gln Thr Arg Phe Trp Met Val
                100                 105                 110
Lys Pro Thr Ala Ser Leu Ser Gly Val Ser Gly Leu Asp Ala Leu Val
            115                 120                 125
Ser Gly Asn Tyr Ile Ala Ile Gln Pro Gly Ser Thr His Gln Glu Asp
        130                 135                 140
Tyr Pro Thr Gln Tyr Gln Ala Leu Asp Ser Ala Pro Ser Asp Leu Leu
145                 150                 155                 160
Ala Gln Arg Gly Leu Thr Ile Ser Leu Lys Ala Arg Asp Leu Gly Gly
                165                 170                 175
Ile Ser Val Gly Ser Gln Ile Val Tyr Lys Lys Ile Pro Ile Gly Glu
            180                 185                 190
Val Phe Ser Tyr Gln Leu Asp Asp Asp Ala Gln Ser Val Ile Ile Gln
        195                 200                 205
Ala Ser Ile Lys Glu Glu Tyr Gln His Ile Ile Asn Thr Glu Ser Arg
            210                 215                 220
Phe Trp Asn Val Ser Gly Ile Gly Ala Ser Ile Gly Phe Glu Gly Val
225                 230                 235                 240
Asp Val Arg Leu Glu Ser Leu Ser Ala Leu Ile Gly Gly Ser Ile Ala
                245                 250                 255
Val Asp Ser Pro Asp Glu Gly Lys Pro Val Glu Gln Asn Ala Gln Phe
            260                 265                 270
Arg Leu Tyr Arg Asp Leu Lys Thr Ala Gly Arg Gly Ile Ala Val Ser
```

```
            275                 280                 285
Ile Thr Leu Pro Asp Asp Asn Asn Ile Ser Ala Ser Gly Ala Pro Ile
290                 295                 300
Met Tyr Arg Gly Ile Glu Ile Gly Gln Ile Thr Asp Leu Gln Leu Thr
305                 310                 315                 320
Glu Asn Arg Lys Ser Ile Val Ala Ser Ala Ile Gln Pro Ala Phe
                325                 330                 335
Ser Asp Met Leu Asn Gln Gly Ser Gln Phe Val Leu Glu Glu Ala Gln
                340                 345                 350
Val Ser Leu Thr Gly Val Glu Asn Leu Thr Asn Leu Val Lys Gly Asn
                355                 360                 365
Tyr Leu Thr Leu Ile Pro Gly Ala Gly Glu Arg Thr Arg Asn Phe Gln
370                 375                 380
Ala Val Arg Lys Asn Glu Phe Lys Tyr Ala Arg Ser Asn Ser Ile Ser
385                 390                 395                 400
Phe Asn Leu Val Ala Asp Asn Ser Phe Gly Leu Glu Ala Gly Thr Pro
                405                 410                 415
Ile Leu Tyr Arg Gly Val Ala Val Gly Ser Val Thr Ala Val Asn Leu
                420                 425                 430
Lys Leu Asp Tyr Val Glu Phe Asn Val Leu Ile Asp Glu Gln Tyr Gly
                435                 440                 445
Ala Leu Ile Arg Ser Gln Asn Arg Phe Tyr Val Thr Gly Ser Ala Ala
                450                 455                 460
Ala Glu Leu Thr Glu Ser Gly Leu Ser Val Ser Ile Pro Pro Ala Lys
465                 470                 475                 480
Gln Leu Leu Gly Ser Ile Ser Phe Ala Ser Glu Gly Ser Ser Thr
                485                 490                 495
Pro Leu Glu Gln Tyr Arg Leu Tyr Ser Ser Gln Ser Leu Ala Glu Leu
                500                 505                 510
Ala Lys Tyr Asn Gln Ser Gly Ser Arg Ser Leu Thr Leu Phe Ala His
                515                 520                 525
Glu Leu Pro Ser Ile Asn Ala Gly Ser Pro Leu Leu Tyr Arg Asn Leu
                530                 535                 540
Lys Val Gly Ser Ile Ser Gly Phe Thr Leu Thr Pro Lys Gly Val Gln
545                 550                 555                 560
Ile Glu Ala Thr Ile Glu Lys Gln Tyr Gln His Leu Leu Thr Pro Asp
                565                 570                 575
Thr Val Phe Trp Asn Arg Ser Gly Val Glu Ile Lys Ala Ser Met Asp
                580                 585                 590
Gly Val Asp Val Lys Ala Ala Pro Leu Gln Thr Leu Ile Arg Gly Gly
                595                 600                 605
Ile Ala Phe Asp Asn Leu Pro Gly Ile Glu Asn Lys Val Gly Ser Met
610                 615                 620
Trp Lys Leu Tyr Ser Asp Tyr Asp His Ala Arg Arg Tyr Gly Glu Lys
625                 630                 635                 640
Ile Thr Leu Thr Ala Leu Gly Thr Leu Gly Val Lys Val Gly Thr Pro
                645                 650                 655
Val Gln Tyr Gln Gly Val Gln Ile Gly Glu Val Phe Glu Ile Ile Pro
                660                 665                 670
Asp Phe Glu Ser Asp Phe Val Lys Leu Ala Ala Arg Ile Glu Pro Gln
                675                 680                 685
Tyr Ala Pro Lys Ile Ala Lys Gln Asn Ser Gln Phe Trp Leu Ser Gln
                690                 695                 700
```

```
Ala Lys Ile Gly Leu Ser Gly Ile Glu Asn Val Gln Asn Leu Leu Gly
705                 710                 715                 720

Gln Ser Ile Glu Val Gln Pro Gly Asn Gly Glu Ser Arg Phe Glu Phe
            725                 730                 735

Glu Leu His Lys Glu Ala Arg His Gly Gly Ala Gly Asn Thr Tyr Thr
            740                 745                 750

Leu Gln Ser Glu Lys Arg Gly Ser Val Ser Val Gly Thr Pro Ile Leu
        755                 760                 765

Tyr Arg Asp Ile Glu Val Gly Lys Val Ile Asp Val Arg Leu Gly Glu
    770                 775                 780

Phe Ala Asp Arg Val Ile Thr Thr Ile Arg Ile Ala Pro Gln Tyr Thr
785                 790                 795                 800

Tyr Leu Arg Gln Asn Ser Val Phe Trp Asn Val Ser Gly Leu Asp
            805                 810                 815

Met Ser Ile Gly Ile Thr Gly Ala Asn Val Lys Ala Gly Thr Phe Asp
            820                 825                 830

Ser Met Leu Arg Gly Gly Ile Thr Phe Ala Thr Pro Glu Gln Lys Gln
        835                 840                 845

Leu Thr Pro Ala Ala Pro Glu Gly His Thr Phe Tyr Leu Tyr Pro Gln
    850                 855                 860

Ala Gln Glu Glu Trp Thr Lys Trp Arg Thr Pro Ile Pro Lys Pro
865                 870                 875

<210> SEQ ID NO 3
<211> LENGTH: 876
<212> TYPE: PRT
<213> ORGANISM: Yersinia pseudotuberculosis

<400> SEQUENCE: 3

Met Gln Gln Glu Thr Pro Ser Thr Pro Thr Glu Ala His Val Lys His
1               5                   10                  15

Lys Arg Arg Phe Ser Pro Phe Trp Leu Leu Pro Phe Ile Ala Leu Leu
            20                  25                  30

Ile Thr Gly Trp Leu Ile Tyr Asn Asn Trp Gln Glu Arg Gly Thr Glu
        35                  40                  45

Ile Thr Ile Asp Phe Gln Ser Thr Ala Gly Ile Val Ala Gly Arg Thr
    50                  55                  60

Pro Ile Arg Tyr Gln Gly Val Asp Val Gly Leu Val Gln Ser Ile Arg
65                  70                  75                  80

Leu Asp Asp Asn Leu Arg Asn Ile Lys Val Thr Ala Ser Ile Lys Asn
                85                  90                  95

Asp Met Glu Asp Ser Leu Arg Glu Gly Thr Gln Phe Trp Leu Val Thr
            100                 105                 110

Pro Lys Ala Ser Leu Ala Gly Val Ser Gly Leu Asp Ala Leu Val Gly
        115                 120                 125

Gly Asn Tyr Ile Gly Met Met Pro Gly Glu Gly Lys Pro Gln Ser His
    130                 135                 140

Phe Thr Ala Leu Asp Thr Gln Pro Lys Phe Arg Leu Asn Thr Gly Glu
145                 150                 155                 160

Leu Met Ile His Leu Ser Ala Pro Asp Leu Gly Ser Leu Asn Asn Gly
                165                 170                 175

Ser Leu Val Tyr Tyr Arg Lys Ile Pro Val Gly Lys Val Tyr Asp Tyr
            180                 185                 190

Thr Ile Ala Pro Asp Asn Asn Gly Val Ile Ile Asp Val Leu Ile Asp
```

-continued

```
            195                 200                 205
Arg Arg Phe Ala Asn Leu Val Lys Lys Asp Ser Arg Phe Trp Asn Val
210                 215                 220
Ser Gly Phe Lys Ala Asp Phe Ser Leu Ser Gly Ala Ser Val Gln Met
225                 230                 235                 240
Glu Ser Leu Ala Ala Leu Val Asn Gly Ala Ile Ala Phe Asp Ser Pro
                    245                 250                 255
Gln Asn Ser Gln Asp Ala Ala Pro Asp Gln Pro Phe Gln Leu Tyr Ser
            260                 265                 270
Asp Leu Ala His Ser Gln Arg Gly Val Ala Ile Thr Leu Asp Leu Pro
            275                 280                 285
Gly Gly Ser His Leu Ser Glu Gly Arg Thr Pro Leu Ile Tyr Gln Gly
            290                 295                 300
Leu Gln Val Gly Thr Leu Thr Lys Met Thr Leu Gln Pro Asp Gln Lys
305                 310                 315                 320
Val Thr Gly Glu Leu Thr Ile Asp Pro Ser Val Val Asn Leu Met Arg
                    325                 330                 335
Ser Gly Thr Arg Ile Glu Met Asn Ser Pro Arg Ile Ser Leu Ser Asn
            340                 345                 350
Ala Asn Val Ser Glu Leu Leu Thr Gly Asn Thr Leu Glu Leu Ile Pro
            355                 360                 365
Gly Asp Gly Glu Pro Gln Gln His Phe Thr Val Leu Pro Ser Ser Lys
            370                 375                 380
Ser Leu Leu Gln Gln Pro Asn Val Leu Glu Leu Gln Leu Thr Ala Pro
385                 390                 395                 400
Gln Ser Tyr Gly Ile Asp Val Gly Gln Pro Ile Ser Leu Arg Gly Ile
                    405                 410                 415
Lys Ile Gly Gln Val Leu Thr Arg Glu Leu Ser Ala Asp Gly Val Thr
                    420                 425                 430
Phe Thr Ala Ala Ile Glu Ala Lys Tyr Arg His Leu Val His Lys Asp
            435                 440                 445
Ser Lys Phe Val Ala Asn Ser Arg Leu Asp Val Asn Val Gly Ile Asp
            450                 455                 460
Gly Val Asn Val Gln Gly Ala Ser Ala Gln Glu Trp Ile Asp Gly Gly
465                 470                 475                 480
Ile Leu Leu Leu Ser Gly Ser Lys Gly Glu Ala Leu Lys Gln Tyr Pro
                    485                 490                 495
Leu Tyr Ser Ser Val Ala Lys Ala Thr Asp Gly Ile Leu Gly Ser Ser
                    500                 505                 510
Pro Ala Thr Thr Leu Thr Leu Thr Ala Ser Ser Leu Pro Asp Ile Gln
            515                 520                 525
Ala Gly Ser Val Val Leu Tyr Arg Lys Phe Gln Val Gly Glu Ile Thr
            530                 535                 540
His Val Arg Pro Lys Ala Asn Ala Phe Glu Val Asp Val Tyr Ile Gln
545                 550                 555                 560
Pro Glu Tyr Arg Asn Leu Leu Thr Glu Lys Ser Ile Phe Trp Ser Glu
                    565                 570                 575
Gly Gly Ala Lys Val Gln Leu Ser Gly Ser Gly Leu Thr Val Gln Ala
            580                 585                 590
Ser Pro Leu Asn Arg Ala Leu Lys Gly Ala Ile Ser Phe Asp Asn Leu
            595                 600                 605
Glu Gly Val Thr Leu Asp Lys Gly Ala Lys Arg Thr Leu Tyr Ser Asn
            610                 615                 620
```

Glu Thr Ala Ala Arg Ala Val Gly Ser Gln Ile Ile Leu Arg Thr Phe
625                 630                 635                 640

Asp Ala Ser Lys Leu Ser Ala Gly Met Pro Ile Arg Tyr Leu Gly Ile
            645                 650                 655

Asp Ile Gly Gln Val Glu Ser Leu Lys Leu Ala Pro Glu Arg Asn Glu
        660                 665                 670

Val Leu Ala Lys Ala Val Leu Tyr Pro Glu Tyr Val Gln Asn Phe Thr
    675                 680                 685

Arg Ala Gly Thr Arg Phe Ser Ile Val Ser Pro Glu Ile Ser Ala Ala
690                 695                 700

Gly Val Asn Asn Leu Glu Thr Leu Phe Gln Pro Tyr Ile Asn Val Glu
705                 710                 715                 720

Pro Gly Lys Gly Gly Pro Leu Arg Asn Phe Glu Leu Gln Thr Ala Thr
            725                 730                 735

Ile Thr Asp Ser Arg Tyr Leu Asp Gly Leu Ser Ile Ile Leu Asp Thr
        740                 745                 750

Ala Glu Ala Gly Ser Leu Gln Val Gly Thr Pro Val Leu Phe Arg Gly
    755                 760                 765

Leu Glu Val Gly Thr Val Thr Gly Phe Asn Leu Gly Ala Met Ser Asp
770                 775                 780

Arg Val Gln Val Ser Leu Arg Ile Ser Gln Lys Phe Gln His Leu Val
785                 790                 795                 800

Arg Gln Asn Thr Val Phe Trp Leu Ala Ser Gly Tyr Asn Phe Glu Phe
            805                 810                 815

Gly Leu Ile Gly Gly Val Val Lys Ser Gly Thr Phe Gln Gln Phe Ile
        820                 825                 830

Arg Gly Gly Ile Ala Phe Ala Thr Pro Pro Thr Ile Pro Leu Ala Pro
    835                 840                 845

Arg Ala Asn Val Asn Gln His Phe Leu Leu Ala Pro Glu Glu Pro Lys
850                 855                 860

Asp Trp Arg Lys Trp Gly Thr Ala Ile Pro Arg Ser
865                 870                 875

<210> SEQ ID NO 4
<211> LENGTH: 877
<212> TYPE: PRT
<213> ORGANISM: Escherichia coli

<400> SEQUENCE: 4

Met Ser Gln Glu Thr Pro Ala Ser Thr Thr Glu Ala Gln Ile Lys Asn
1               5                   10                  15

Lys Arg Arg Ile Ser Pro Phe Trp Leu Leu Pro Phe Ile Ala Leu Met
            20                  25                  30

Ile Ala Gly Trp Leu Ile Trp Asp Ser Tyr Gln Asp Arg Gly Asn Thr
        35                  40                  45

Val Thr Ile Asp Phe Met Ser Ala Asp Gly Ile Val Pro Gly Arg Thr
    50                  55                  60

Pro Val Arg Tyr Gln Gly Val Glu Val Gly Thr Val Gln Asp Ile Ser
65                  70                  75                  80

Leu Ser Asp Asp Leu Arg Lys Ile Glu Val Lys Val Ser Ile Lys Ser
            85                  90                  95

Asp Met Lys Asp Ala Leu Arg Glu Glu Thr Gln Phe Trp Leu Val Thr
            100                 105                 110

Pro Lys Ala Ser Leu Ala Gly Val Ser Gly Leu Asp Ala Leu Val Gly

-continued

```
                115                 120                 125
Gly Asn Tyr Ile Gly Met Met Pro Gly Lys Gly Lys Glu Gln Asp His
            130                 135                 140
Phe Val Ala Leu Asp Thr Gln Pro Lys Tyr Arg Leu Asp Asn Gly Asp
145                 150                 155                 160
Leu Met Ile His Leu Gln Ala Pro Asp Leu Gly Ser Leu Ser Ser Gly
                165                 170                 175
Ser Leu Val Tyr Phe Arg Lys Ile Pro Val Gly Lys Val Tyr Asp Tyr
            180                 185                 190
Ala Ile Asn Pro Asn Lys Gln Gly Val Val Asp Val Leu Ile Glu
            195                 200                 205
Arg Arg Phe Thr Asp Leu Val Lys Lys Gly Ser Arg Phe Trp Asn Val
            210                 215                 220
Ser Gly Val Asp Ala Asn Val Ser Ile Ser Gly Ala Lys Val Lys Leu
225                 230                 235                 240
Glu Ser Leu Ala Ala Leu Val Asn Gly Ala Ile Ala Phe Asp Ser Pro
                245                 250                 255
Glu Glu Ser Lys Pro Ala Glu Ala Glu Asp Thr Phe Gly Leu Tyr Glu
            260                 265                 270
Asp Leu Ala His Ser Gln Arg Gly Val Ile Ile Lys Leu Glu Leu Pro
            275                 280                 285
Gly Gly Ala Gly Leu Thr Ala Asp Ser Thr Pro Leu Met Tyr Gln Gly
            290                 295                 300
Leu Glu Val Gly Gln Leu Thr Lys Leu Asp Leu Asn Pro Gly Gly Asn
305                 310                 315                 320
Val Thr Gly Glu Met Thr Val Asp Pro Ser Val Val Thr Leu Leu Arg
                325                 330                 335
Glu Asn Thr Arg Ile Glu Leu Arg Asn Pro Lys Leu Ser Leu Ser Asp
            340                 345                 350
Ala Asn Leu Ser Ala Leu Leu Thr Gly Lys Thr Phe Glu Leu Val Pro
            355                 360                 365
Gly Asp Gly Glu Pro Arg Lys Glu Phe Val Val Pro Gly Glu Lys
            370                 375                 380
Ala Leu Leu Gln Glu Pro Asp Val Leu Thr Leu Thr Leu Thr Ala Pro
385                 390                 395                 400
Glu Ser Tyr Gly Ile Asp Ala Gly Gln Pro Leu Ile Leu His Gly Val
                405                 410                 415
Gln Val Gly Gln Val Ile Asp Arg Lys Leu Thr Ser Lys Gly Val Thr
            420                 425                 430
Phe Thr Val Ala Ile Glu Pro Gln His Arg Glu Leu Val Lys Gly Asp
            435                 440                 445
Ser Lys Phe Val Val Asn Ser Arg Val Asp Val Lys Val Gly Leu Asp
            450                 455                 460
Gly Val Glu Phe Leu Gly Ala Ser Ala Ser Glu Trp Ile Asn Gly Gly
465                 470                 475                 480
Ile Arg Ile Leu Pro Gly Asp Lys Gly Glu Met Lys Ala Ser Tyr Pro
                485                 490                 495
Leu Tyr Ala Asn Leu Glu Lys Ala Leu Glu Asn Ser Leu Ser Asp Leu
            500                 505                 510
Pro Thr Thr Thr Val Ser Leu Ser Ala Glu Thr Leu Pro Asp Val Gln
            515                 520                 525
Ala Gly Ser Val Val Leu Tyr Arg Lys Phe Glu Val Gly Glu Val Ile
            530                 535                 540
```

Thr Val Arg Pro Arg Ala Asn Ala Phe Asp Ile Asp Leu His Ile Lys
545                 550                 555                 560

Pro Glu Tyr Arg Asn Leu Leu Thr Ser Asn Ser Val Phe Trp Ala Glu
            565                 570                 575

Gly Gly Ala Lys Val Gln Leu Asn Gly Ser Gly Leu Thr Val Gln Ala
            580                 585                 590

Ser Pro Leu Ser Arg Ala Leu Lys Gly Ala Ile Ser Phe Asp Asn Leu
            595                 600                 605

Ser Gly Ala Ser Ala Ser Gln Arg Lys Gly Asp Lys Arg Ile Leu Tyr
            610                 615                 620

Ala Ser Glu Thr Ala Ala Arg Ala Val Gly Gly Gln Ile Thr Leu His
625                 630                 635                 640

Ala Phe Asp Ala Gly Lys Leu Ala Val Gly Met Pro Ile Arg Tyr Leu
            645                 650                 655

Gly Ile Asp Ile Gly Gln Ile Gln Thr Leu Asp Leu Ile Thr Ala Arg
            660                 665                 670

Asn Glu Val Gln Ala Lys Ala Val Leu Tyr Pro Glu Tyr Val Gln Thr
            675                 680                 685

Phe Ala Arg Gly Gly Thr Arg Phe Ser Val Val Thr Pro Gln Ile Ser
690                 695                 700

Ala Ala Gly Val Glu His Leu Asp Thr Ile Leu Gln Pro Tyr Ile Asn
705                 710                 715                 720

Val Glu Pro Gly Arg Gly Asn Pro Arg Arg Asp Phe Glu Leu Gln Glu
            725                 730                 735

Ala Thr Ile Thr Asp Ser Arg Tyr Leu Asp Gly Leu Ser Ile Ile Val
            740                 745                 750

Glu Ala Pro Glu Ala Gly Ser Leu Gly Ile Gly Thr Pro Val Leu Phe
            755                 760                 765

Arg Gly Leu Glu Val Gly Thr Val Thr Gly Met Thr Leu Gly Thr Leu
770                 775                 780

Ser Asp Arg Val Met Ile Ala Met Arg Ile Ser Lys Arg Tyr Gln His
785                 790                 795                 800

Leu Val Arg Asn Asn Ser Val Phe Trp Leu Ala Ser Gly Tyr Ser Leu
            805                 810                 815

Asp Phe Gly Leu Thr Gly Gly Val Val Lys Thr Gly Thr Phe Asn Gln
            820                 825                 830

Phe Ile Arg Gly Gly Ile Ala Phe Ala Thr Pro Pro Gly Thr Pro Leu
            835                 840                 845

Ala Pro Lys Ala Gln Glu Gly Lys His Phe Leu Leu Gln Glu Ser Glu
            850                 855                 860

Pro Lys Glu Trp Arg Glu Trp Gly Thr Ala Leu Pro Lys
865                 870                 875

<210> SEQ ID NO 5
<211> LENGTH: 93
<212> TYPE: PRT
<213> ORGANISM: Vibrio parahaemolyticus

<400> SEQUENCE: 5

Ala Gly Gln Arg Val Gln Ile Tyr Phe Ser Asp Ala Ala Gly Leu Val
1               5                   10                  15

Ala Gly Arg Thr Thr Ile Arg Tyr Gln Gly Leu Glu Val Gly Met Val
            20                  25                  30

Arg Asp Ile Asn Leu Ser Glu Asp Leu Gly Ser Ile Tyr Val Asp Ala

```
            35                  40                  45

Asp Ile Tyr Pro Glu Ala Thr Lys Leu Leu Asn Asp Lys Thr Arg Phe
        50                  55                  60

Trp Leu Val Lys Pro Thr Ala Ser Leu Thr Gly Val Ser Gly Leu Asp
65                  70                  75                  80

Ala Leu Val Ser Gly Asn Tyr Ile Ser Ile Gln Pro Gly
                85                  90

<210> SEQ ID NO 6
<211> LENGTH: 91
<212> TYPE: PRT
<213> ORGANISM: Vibrio parahaemolyticus

<400> SEQUENCE: 6

Gln Gly Leu Asn Ile Lys Leu Lys Ser Arg Asp Leu Gly Gly Val Ser
1               5                   10                  15

Ile Gly Ser Gln Ile Val Tyr Lys Lys Ile Pro Ile Gly Ala Val Tyr
                20                  25                  30

Ser Tyr Gln Leu Asp Glu Asp Ala Lys Ser Ile Thr Ile Gln Ala Asn
            35                  40                  45

Ile Gln Glu Gln Tyr Arg His Ile Ile Asn Asp Arg Ser Arg Phe Trp
        50                  55                  60

Asn Val Ser Gly Ile Gly Ala Ser Ile Gly Phe Glu Gly Val Asp Val
65                  70                  75                  80

Arg Leu Glu Ser Met Ser Ala Leu Leu Gly Gly
                85                  90

<210> SEQ ID NO 7
<211> LENGTH: 93
<212> TYPE: PRT
<213> ORGANISM: Vibrio parahaemolyticus

<400> SEQUENCE: 7

Arg Gly Ile Ala Ile Lys Ile Ala Leu Pro Asp Asp Asn Lys Val Ser
1               5                   10                  15

Ser Glu Gly Ala Pro Ile Met Tyr Arg Gly Ile Glu Ile Gly Gln Val
                20                  25                  30

Thr Asp Leu Ser Leu Ser Glu Gly Arg Glu Val Ile Leu Ala Ser Ala
            35                  40                  45

Ala Ile Gln Pro Ala Phe Ser Asp Met Leu Thr Thr Gly Thr Arg Phe
        50                  55                  60

Val Leu Glu Glu Ala Lys Val Ser Leu Ser Gly Val Gly Asn Ile Ala
65                  70                  75                  80

Asn Leu Val Arg Gly Asn Phe Leu Thr Ile Val Pro Gly
                85                  90

<210> SEQ ID NO 8
<211> LENGTH: 86
<212> TYPE: PRT
<213> ORGANISM: Vibrio parahaemolyticus

<400> SEQUENCE: 8

Ser Ile Ala Ile Arg Leu Ile Ser Asp Asn Ser Phe Gly Leu Asp Ser
1               5                   10                  15

Gly Ala Asn Val Leu Tyr Lys Gly Ile Val Val Gly Ser Ile Ile Asn
                20                  25                  30

Val Gly Leu Val Asp Glu Lys Lys Gln Thr Lys His Glu Val Phe Met
            35                  40                  45
```

-continued

Asp Val Leu Ile Asp His Glu Tyr Lys His Leu Ile Lys Ser Asn Asn
                50                  55                  60

Arg Phe Tyr Val Thr Gly Ser Ala Ser Ala Glu Leu Thr Glu Ser Gly
 65                  70                  75                  80

Leu Ser Val Thr Val Pro
                85

<210> SEQ ID NO 9
<211> LENGTH: 89
<212> TYPE: PRT
<213> ORGANISM: Vibrio parahaemolyticus

<400> SEQUENCE: 9

Gly Ser Lys Thr Leu Met Leu Phe Ala Ser Glu Leu Pro Pro Ile Ser
 1               5                  10                  15

Lys Gly Ser Pro Leu Leu Tyr Arg Asn Leu Pro Val Gly Asn Val Ser
                20                  25                  30

Asp Phe His Leu Val Asp Gly Val Leu Ile Lys Ala Thr Ile Glu
                35                  40                  45

Asn Arg Phe Ala Tyr Leu Val Thr Pro Gln Thr Val Phe Trp Asn Arg
 50                  55                  60

Ser Gly Ile Glu Ile Asp Ala Ser Leu Ser Gly Val Ser Val Lys Ala
 65                  70                  75                  80

His Pro Leu Lys Ser Leu Ile Glu Gly
                85

<210> SEQ ID NO 10
<211> LENGTH: 92
<212> TYPE: PRT
<213> ORGANISM: Vibrio parahaemolyticus

<400> SEQUENCE: 10

Phe Gly Arg Val Ile Ser Leu Glu Thr Asp Gly Thr Gln Glu Val Leu
 1               5                  10                  15

Lys Gly Met Pro Ile Glu Tyr Gln Gly Val Lys Val Gly Glu Val Thr
                20                  25                  30

Leu Val Val Pro Asn Phe Arg Arg Asn Leu Val Glu Val Thr Ala Arg
                35                  40                  45

Ile Leu Pro Glu Tyr Val Glu Asn Ile Ala Val Glu Gly Thr His Phe
 50                  55                  60

Trp Leu Thr Glu Pro Glu Ile Gly Leu Gly Gly Val Lys Asn Leu Gly
 65                  70                  75                  80

Ala Leu Val Ser Lys Ser Ile Ser Val Glu Pro Gly
                85                  90

<210> SEQ ID NO 11
<211> LENGTH: 91
<212> TYPE: PRT
<213> ORGANISM: Vibrio parahaemolyticus

<400> SEQUENCE: 11

Glu Gly Val Met Phe Thr Leu Gln Ser Glu Gln Arg Gly Ser Val Gln
 1               5                  10                  15

Val Gly Thr Pro Val Leu Tyr Arg Gln Met Glu Val Gly Gln Val Thr
                20                  25                  30

Asp Val Arg Leu Gly Glu Phe Ala Asp Arg Val Val Ser Thr Ile Lys
                35                  40                  45

```
Ile Lys Pro Glu Tyr Ala Tyr Leu Val Arg Gln Asn Ser Val Phe Trp
 50                  55                  60
Asn Val Ser Gly Val Asp Val Ser Ile Gly Ile Thr Gly Ala Asn Ile
 65                  70                  75                  80
Lys Ala Gly Thr Ile Asp Ser Leu Val Arg Gly
                 85                  90

<210> SEQ ID NO 12
<211> LENGTH: 869
<212> TYPE: PRT
<213> ORGANISM: Shewanella oneidensis

<400> SEQUENCE: 12

Met Lys Lys Lys Leu Phe Ser Pro Ile Trp Leu Leu Pro Ile Val Ala
 1               5                  10                  15
Leu Ala Leu Gly Ala Trp Leu Gly Ile Lys Ser Ile Lys Glu Ser Gly
                 20                  25                  30
Val Glu Ile Gln Ile His Phe Pro Ser Ala Thr Gly Ile Asp Val Gly
                 35                  40                  45
Lys Thr Leu Val Lys Tyr Gln Gly Leu Thr Val Gly Lys Val Lys Asp
 50                  55                  60
Ile Gly Ile Asp Asp Leu Lys Gly Val Asn Val Lys Val Met Met
 65                  70                  75                  80
Asp Tyr Arg Ala Lys Pro Phe Leu Asn Lys Glu Thr Leu Phe Trp Leu
                 85                  90                  95
Val Thr Pro Lys Ala Ser Ile Thr Gly Val Glu Gly Leu Asp Ala Leu
                 100                 105                 110
Phe Ser Gly Asn Tyr Ile Ala Ile Gln Pro Gly Lys Gly Asn Ala Ala
                 115                 120                 125
Thr Phe Phe Glu Ala Glu Arg Gln Pro Pro Met Gln Ile Gly Ser
                 130                 135                 140
Glu Gly Val Met Ile Glu Leu Thr Ala Asp Lys Leu Gly Ser Leu Asp
145                 150                 155                 160
Val Gly Ser Pro Val Phe Phe Arg Gln Ile Pro Val Gly Ser Val Val
                 165                 170                 175
Ser Tyr Arg Leu Asp Gly Asn Ala Arg Val Ile Ile Ser Ala Phe Ile
                 180                 185                 190
Gln Glu Gln Tyr Ala Arg Leu Val Lys Lys Asn Ser His Phe Trp Asn
                 195                 200                 205
Val Ser Gly Val Lys Val Asp Ala Ser Leu Ala Gly Ile Lys Val Asn
                 210                 215                 220
Thr Glu Ser Leu Ala Ser Ile Leu Ala Gly Val Ser Phe Ser Ser
225                 230                 235                 240
Asp Glu Lys Ala Ala Ala Gln Asn Gly Asp Ser Phe Ala Leu Tyr
                 245                 250                 255
Asp Ser Glu Thr Ser Ala Leu Gly Gly Val Glu Val Ser Leu Thr Met
                 260                 265                 270
Asn Asp Gly Asn Gly Ile Asp Lys Gly Thr Arg Ile Val Tyr Arg Gly
                 275                 280                 285
Ile Ser Val Gly Ser Ile Gln Ser Lys Asn Leu Thr Thr Thr Gly Val
                 290                 295                 300
Thr Ala Ile Ala Lys Phe Glu Pro Glu Tyr Ala Asn Leu Leu Thr Ser
305                 310                 315                 320
Asp Gly Arg Phe Trp Leu Glu Gly Ala Asp Ile Ser Leu Ser Gly Ile
                 325                 330                 335
```

```
Lys Asn Pro Glu Arg Leu Leu Thr Gly Ser Val Ile Asn Phe Leu Pro
            340                 345                 350

Gly Thr Asn Ala Asn Thr Ala Leu Pro Ser Ser Phe Ala Leu Gln Ser
            355                 360                 365

Ser Ala Pro Asp Leu Leu Gln Ala Lys Lys Arg Leu Leu Thr Ile Thr
370                 375                 380

Ser Ala Glu Asn Met Gly Leu Thr Ala Gly Ala Glu Val Arg Tyr Lys
385                 390                 395                 400

Gln Leu Pro Ile Gly Gln Val Leu Ala Val Lys Leu Thr Lys Asp Leu
                405                 410                 415

Ser Ala Val Glu Tyr Gln Leu Glu Leu Gln Pro Glu Phe Ala Ser Leu
            420                 425                 430

Val Arg Ser Asp Ser Tyr Phe Ile Pro Glu Ser Ala Leu Ser Val Asp
            435                 440                 445

Ala Ser Ile Glu Gly Val Ser Val Lys Thr Arg Asp Leu Ala Thr Leu
            450                 455                 460

Thr Lys Gly Ala Val Ser Leu Ile Pro Gly Ser Asn Asn Thr Pro Val
465                 470                 475                 480

Ala Ala Asn Ala Arg Leu Ser Leu Phe Ser Ser Val Glu Glu Ala Lys
                485                 490                 495

Gln Phe Phe Glu Arg Gln Gln Arg Leu Tyr Phe Thr Leu Thr Ser Gln
            500                 505                 510

Asp Gly Ala Asp Val Ser Gln Gly Ser Pro Ile Tyr Tyr Lys Lys Met
            515                 520                 525

Gln Ile Gly Arg Val Glu Ser Val Asn Trp Gln Ser Lys Thr Glu Asp
            530                 535                 540

Phe Ala Ile Lys Ile Ala Ile Asp Lys Gln Phe Gln Pro Leu Met Gln
545                 550                 555                 560

Lys Pro Lys Val Phe Trp Arg Asn Ser Ala Leu Asp Val Ser Ala Ser
                565                 570                 575

Leu Ala Gly Ile Asp Val Ala Val Ala Pro Leu Gln Gly Ala Leu Lys
            580                 585                 590

Gly Ser Ile Ser Leu Gly Leu Leu Glu Asn Pro Leu Ala Asp Pro Thr
            595                 600                 605

Ala Ser Leu Lys Leu Tyr Glu Asn Lys Gln Leu Ala Leu Ala Gln Ala
            610                 615                 620

Gln Ala Ile Arg Leu Thr Leu Ser Ala Ser Ala Lys Leu Ala Ala Lys
625                 630                 635                 640

Ala Ala Ile Arg Tyr Gln Gly His Gln Val Gly Glu Val Thr Gln Val
                645                 650                 655

Lys Leu Asn Ala Asp Leu Asn Thr Leu Ser Ala Thr Ala Tyr Leu Tyr
            660                 665                 670

Gly Glu Tyr Ala Asp His Phe Ser Ser Ser Asp Ala Glu Tyr His Met
            675                 680                 685

Val Glu Ala Gln Ile Ser Leu Ala Gly Ile Lys Ala Pro Glu Thr Leu
            690                 695                 700

Ile Thr Gly Pro Tyr Ile Gly Val Leu Pro Gly Lys Ser Lys Gln Lys
705                 710                 715                 720

Ala Thr Gln Phe Gln Ala Lys Leu Val Glu Ser Ser Tyr Ala Asn Val
                725                 730                 735

Ala Glu Asp Ala Leu Lys Phe Thr Leu Glu Asp Ser Asn Leu Gly Ser
            740                 745                 750
```

```
Met Lys Val Gly Thr Pro Ile Phe Phe Arg Gly Leu Lys Val Gly Gln
            755                 760                 765

Ile Asp Gly Tyr Ser Leu Ser Ser Gln Gly Asn Ser Val Leu Met Gln
        770                 775                 780

Ala His Ile Glu Pro Gln Tyr Arg His Leu Val Asn Lys Thr Ser Gln
785                 790                 795                 800

Phe Trp Asp Ala Ser Gly Ile Lys Val Asp Val Gly Ile Phe Ser Gly
            805                 810                 815

Ala Gln Ile Glu Ala Gly Ser Leu Glu Thr Leu Leu Ala Gly Gly Ile
        820                 825                 830

Asn Val Ala Thr Lys Glu Thr Thr Gln Ala Asn Asn Arg Leu Ser Gln
        835                 840                 845

Gly Ala Val Ile Thr Leu Gln His Lys Ala Gln Thr Glu Trp Gln Glu
    850                 855                 860

Trp Ala Pro Ala Gln
865
```

<210> SEQ ID NO 13
<211> LENGTH: 879
<212> TYPE: PRT
<213> ORGANISM: Shewanella baltica OS155

<400> SEQUENCE: 13

```
Met Thr Gln Ile Glu Ser Pro Lys Val Val Lys Lys Leu Phe Ser
1               5                   10                  15

Pro Ile Trp Leu Leu Pro Ile Val Ala Leu Ala Leu Gly Ala Trp Leu
                20                  25                  30

Gly Ile Lys Ser Ile Lys Glu Ser Gly Val Glu Ile Gln Ile His Phe
            35                  40                  45

Pro Ser Ala Thr Gly Ile Asp Val Gly Lys Thr Leu Val Lys Tyr Gln
        50                  55                  60

Gly Leu Thr Val Gly Lys Val Lys Asp Ile Gly Ile Asp Glu Asp Leu
65                  70                  75                  80

Lys Gly Val Asn Val Lys Val Met Met Asp Tyr Arg Ala Lys Pro Phe
                85                  90                  95

Leu Asn Lys Glu Thr Leu Phe Trp Leu Val Thr Pro Lys Ala Ser Ile
            100                 105                 110

Thr Gly Val Glu Gly Leu Asp Ala Leu Phe Ser Gly Asn Tyr Ile Ala
        115                 120                 125

Ile Gln Pro Gly Lys Gly Asn Ala Ser Thr Phe Phe Glu Ala Glu Arg
130                 135                 140

Gln Pro Pro Met Gln Ile Gly Ser Glu Gly Val Met Val Glu Leu
145                 150                 155                 160

Thr Ser Asp Lys Leu Gly Ser Leu Asp Val Gly Ser Pro Ile Phe Phe
                165                 170                 175

Arg Gln Ile Pro Val Gly Ser Val Ser Tyr Arg Leu Asp Gly Asn
            180                 185                 190

Gln Arg Val Ile Ile Ser Ala Phe Ile Gln Glu Gln Tyr Ala Arg Leu
        195                 200                 205

Val Lys Lys Asn Ser His Phe Trp Asn Val Ser Gly Val Lys Ile Asp
210                 215                 220

Ala Ser Leu Thr Gly Val Lys Val Ser Ser Glu Ser Leu Ala Ser Ile
225                 230                 235                 240

Leu Ala Gly Gly Val Ser Phe Ser Ser Asp Asp Lys Ala Asp Ile Ala
                245                 250                 255
```

```
Lys Asn Gly Asp Ile Phe Ser Leu Tyr Asp Ser Glu Thr Thr Ala Leu
            260                 265                 270

Gly Gly Ile Glu Ile Asn Leu Thr Met Ala Asp Ala Asn Gly Val Asp
            275                 280                 285

Lys Gly Thr Arg Ile Val Tyr Arg Gly Ile Asn Ile Gly Ser Ile Leu
            290                 295                 300

Ser Lys Gln Leu Thr Ala Asn Gly Val Ile Ala Val Ala Lys Phe Glu
305                 310                 315                 320

Pro Gln Tyr Gly Ser Leu Leu Thr Asn Asp Gly Val Phe Trp Leu Glu
                325                 330                 335

Gly Ala Asp Ile Ser Leu Ser Gly Ile Lys Asn Pro Glu Arg Leu Leu
            340                 345                 350

Thr Gly Ser Val Ile Asn Phe Leu Pro Gly Ile Asn Thr Lys Thr Ala
            355                 360                 365

Met Pro Ser Ser Phe Ala Leu Gln Ala Lys Ala Pro Asp Leu Leu Gln
            370                 375                 380

Ser Lys Lys Arg Phe Leu Thr Leu Thr Ser Ala Glu Asn Met Gly Ile
385                 390                 395                 400

Ser Ala Gly Ala Glu Val Arg Phe Lys Gln Ile Pro Ile Gly Ser Val
                405                 410                 415

Leu Ala Val Lys Leu Thr Lys Asp Leu Ser Ala Val Glu Tyr Gln Leu
            420                 425                 430

Glu Leu Gln Pro Glu Phe Ala Ser Leu Ile Arg Ser Asp Ser Tyr Phe
            435                 440                 445

Val Pro Glu Ser Ala Leu Thr Val Lys Ala Ser Leu Glu Gly Val Ser
            450                 455                 460

Val Lys Ala Arg Asp Phe Thr Thr Leu Thr Gln Gly Ala Val Ser Leu
465                 470                 475                 480

Ile Gln Gly His Ser Asp Thr Pro Leu Ala Ala Asn Ser Ala Leu Thr
                485                 490                 495

Leu Phe Ser Ser Val Asp Ala Ala Thr Ala Phe Tyr Asp Arg Gln Gln
            500                 505                 510

Gln Val His Leu Thr Leu Ile Ser Gln Asp Gly Ala Asp Val Ser Gln
            515                 520                 525

Gly Ser Pro Ile Tyr Tyr Lys Lys Met Gln Ile Gly Thr Val Asp Ser
            530                 535                 540

Val Asn Trp Gln Ser Lys Thr Glu Asp Phe Ala Ile Lys Leu Ala Ile
545                 550                 555                 560

Asp Lys Gln Phe Gln Pro Leu Leu Lys Lys Pro Asn Val Phe Trp Arg
                565                 570                 575

Asn Ser Ala Val Asp Ile Ser Ala Ser Leu Ala Gly Ile Asp Val Ala
            580                 585                 590

Val Ala Pro Leu Gln Gly Ala Leu Lys Gly Ser Ile Ser Leu Gly Leu
            595                 600                 605

Leu Asp Ser Asn Gly Lys Ala Ser Asn Thr Ala Asn Leu Lys Leu Tyr
            610                 615                 620

Glu Ser Lys Gln Leu Ala Leu Thr Gln Ala Gln Ala Ile Arg Leu Thr
625                 630                 635                 640

Leu Pro Ala Ser Ser Lys Leu Thr Ala Lys Ala Ala Ile Arg Tyr Gln
                645                 650                 655

Gly His Gln Val Gly Glu Val Ser Gln Val Lys Leu Asn Ala Asp Leu
            660                 665                 670
```

```
Asn Thr Leu Thr Ala Thr Ala Tyr Leu Tyr Gly Glu Tyr Ala Glu His
            675                 680                 685

Phe Ser Arg Ser Asp Cys Glu Tyr His Leu Val Asp Ala Gln Ile Ser
690                 695                 700

Leu Ala Gly Ile Lys Ala Pro Glu Thr Leu Ile Thr Gly Pro Tyr Ile
705                 710                 715                 720

Gly Val Leu Pro Gly Thr Ser Ser Gln Lys Ala Thr Gln Phe Val Ala
            725                 730                 735

Asn Leu Ala Ala Ser Ser Tyr Ala Asn Val Ala Glu Asp Ala Leu Lys
            740                 745                 750

Phe Thr Leu Glu Asp Asn Asn Leu Gly Ser Met Lys Val Gly Thr Pro
            755                 760                 765

Ile Phe Phe Arg Gly Ile Lys Val Gly Gln Ile Asp Gly Tyr His Leu
770                 775                 780

Ser Thr Gln Gly Asn Ser Val Leu Met Gln Ala His Ile Glu Pro Gln
785                 790                 795                 800

Tyr Ser His Leu Val Asn Gln Ser Ser Gln Phe Trp Asp Ala Ser Gly
            805                 810                 815

Ile Lys Val Asp Val Gly Leu Phe Ser Gly Ala Gln Ile Glu Ala Gly
            820                 825                 830

Ser Leu Glu Thr Leu Leu Ala Gly Gly Ile Asn Val Ala Thr Lys Asp
            835                 840                 845

Thr Thr Gln Glu Gly Asn Arg Leu Ala Ala Gly Thr Val Leu Arg Leu
            850                 855                 860

Gln His Lys Ala Glu Asn Glu Trp Gln Glu Trp Ala Pro Ala Gln
865                 870                 875

<210> SEQ ID NO 14
<211> LENGTH: 771
<212> TYPE: PRT
<213> ORGANISM: Azotobacter vinelandii

<400> SEQUENCE: 14

Met Asn Asp Leu Pro Glu Ala Arg Thr Arg Pro Ala Ser Thr Trp Ser
1               5                   10                  15

Ala Ile Trp Val Leu Pro Leu Ile Ala Leu Leu Ile Gly Ser Trp Leu
            20                  25                  30

Ala Trp Arg Ala Tyr Asp Gln Ala Gly Ile Glu Val Gln Val Arg Phe
        35                  40                  45

Thr Ser Gly Glu Gly Ile Gln Ile Asn Lys Thr Glu Val Ile Tyr Lys
    50                  55                  60

Gly Met Pro Val Gly Lys Val Val Gly Leu Thr Leu Asp Asp Glu Gly
65                  70                  75                  80

Ser Asn Thr Gly Val Ile Ala Thr Leu Glu Met Asn Lys Asp Val Glu
            85                  90                  95

Ser Tyr Leu Arg Ser Asn Thr Arg Phe Trp Leu Val Lys Pro Arg Val
            100                 105                 110

Ser Leu Ala Gly Ile Thr Gly Leu Glu Thr Leu Val Ser Gly Asn Tyr
        115                 120                 125

Ile Ala Val Ser Pro Gly Asp Gly Glu Pro Asn Lys Lys Phe Thr Ala
    130                 135                 140

Leu Ser Glu Glu Pro Pro Leu Pro Asp Ser Thr Pro Gly Leu His Ile
145                 150                 155                 160

Thr Leu Lys Ala Glu Arg Leu Gly Ser Leu Asn Arg Asp Ser Pro Val
            165                 170                 175
```

-continued

```
Phe Tyr Lys Gln Ile Gln Val Gly Arg Val Lys Ser Tyr Gln Leu Ala
                180                 185                 190

Glu Asp Leu Ser Thr Val Glu Ile Arg Ile Phe Val Glu Pro Ala Tyr
            195                 200                 205

Ala His Leu Val Arg Lys His Thr Arg Phe Trp Asn Ala Ser Gly Ile
        210                 215                 220

Thr Val Asp Ala Gly Leu Gly Gly Val Lys Phe His Thr Glu Ser Leu
225                 230                 235                 240

Ala Ser Ile Val Ala Gly Ile Ala Phe Ala Thr Pro Glu Asn Arg
                245                 250                 255

Lys Asp Ser Pro Pro Thr Asp Pro Arg Leu Pro Phe Arg Leu Tyr Asp
                260                 265                 270

Asn Phe Asp Ala Ala Gln Thr Gly Ile Lys Val Met Leu Glu Leu Ser
            275                 280                 285

Asp Phe Glu Gly Leu Gln Ala Gly Arg Thr Pro Val Val Tyr Lys Gly
        290                 295                 300

Ile Gln Val Gly Ile Leu Lys Thr Leu Gln Ile Glu Pro Gly Leu Ser
305                 310                 315                 320

Arg Ala Met Ala Glu Leu Thr Leu Asp Pro Leu Ala Glu Asp Phe Leu
                325                 330                 335

Val Glu Gly Ala Asp Phe Trp Val Val Lys Pro Ser Ile Ser Leu Gly
            340                 345                 350

Gly Val Thr Gly Leu Glu Ala Leu Val Lys Gly Asn Tyr Ile Gly Met
        355                 360                 365

Arg Pro Gly Glu Lys Gly Ala Ser Val Arg Arg Ser Phe Val Ala Arg
    370                 375                 380

Ser Lys Ala Pro Pro Met Asp Leu Gly Ala Pro Gly Leu His Leu Val
385                 390                 395                 400

Leu Thr Ser Asp Thr Leu Gly Ser Leu Asp Ile Gly Ser Pro Val Leu
                405                 410                 415

Tyr Arg Gln Ile Lys Val Gly Ser Val Gln Ser Phe Gln Leu Ser Arg
            420                 425                 430

Asn Arg Arg Val Leu Leu Gly Val His Ile Glu Pro Glu Tyr Ala
        435                 440                 445

Ser Leu Val Asn Ser Ser Thr Arg Phe Trp Asn Ala Ser Gly Val Thr
    450                 455                 460

Leu Ser Gly Gly Leu Ser Gly Ile Glu Val Lys Ser Glu Ser Leu Gln
465                 470                 475                 480

Thr Leu Leu Ala Gly Ile Ala Phe Glu Thr Pro Asp Pro Glu Ala
                485                 490                 495

Ser Ala Asn Thr Arg Arg Ile Pro Arg Tyr Ala Leu His Ala Asp Arg
            500                 505                 510

Glu Thr Ala Leu Gln Ala Gly Leu Glu Leu Gln Ile Arg Val Asp Ser
        515                 520                 525

Gly Asp Gly Leu Lys Ala Gly Thr Pro Ile Arg Tyr Lys Gly Leu Asp
    530                 535                 540

Val Gly Lys Val Glu Gly Val Glu Leu Ser Asp Asp Leu Gln Ser Val
545                 550                 555                 560

Leu Leu Arg Ala Arg Ile Thr Gln Ala Ala Glu Arg Ile Ala Arg Val
                565                 570                 575

Gly Ser Gln Phe Trp Val Val Arg Pro Glu Leu Gly Leu Met Arg Thr
            580                 585                 590
```

```
Ala Asn Leu Asp Thr Leu Ile Ser Gly Pro Tyr Ile Glu Val Arg Pro
            595                 600                 605

Asp Ala Gly Lys Ser Ser Arg Gln Thr Ser Phe Val Ala Leu Ser Arg
610                 615                 620

Ala Pro Glu Ser Ala Ala Lys Pro Glu Pro Gly Leu Arg Leu Val Leu
625                 630                 635                 640

Ser Ser Pro Arg Arg Gly Ser Leu Lys Ala Gly Val Pro Val Thr Tyr
            645                 650                 655

Arg Glu Val Thr Val Gly Lys Val Thr Gly Phe Glu Leu Gly Pro Asn
                660                 665                 670

Ala Asp Arg Val Leu Ile Gly Ile Leu Ile Glu Pro Arg Tyr Ala Pro
            675                 680                 685

Leu Val Arg Ser Gly Ser Arg Phe Trp Asn Ala Ser Gly Phe Gly Phe
    690                 695                 700

Asp Phe Ser Leu Leu Lys Gly Ala Gln Leu Arg Thr Glu Ser Leu Glu
705                 710                 715                 720

Thr Leu Glu Gly Gly Ile Ala Phe Ala Thr Pro Asp Gly Glu Arg
                725                 730                 735

Met Gly Lys Pro Ala Leu Pro Gly Gln Thr Phe Pro Leu Phe Ser Glu
            740                 745                 750

Ala Asp Gly Glu Trp Leu Gln Trp Ala Pro Lys Ile Ala Leu Glu Lys
            755                 760                 765

Glu Arg Lys
    770

<210> SEQ ID NO 15
<211> LENGTH: 767
<212> TYPE: PRT
<213> ORGANISM: Pseudomonas aeruginosa

<400> SEQUENCE: 15

Met Ser Asp Leu Pro Ser Pro Lys Lys His Lys Thr Ser Asn Trp Ser
1               5                   10                  15

Ala Ile Trp Val Leu Pro Leu Val Ala Leu Ala Ile Gly Ala Trp Leu
                20                  25                  30

Gly Trp Arg Ala Tyr Asp Gln Ala Gly Val Leu Ile Gln Val Arg Phe
            35                  40                  45

Glu Ser Ser Asp Gly Ile Gln Ala Lys Lys Thr Glu Val Leu Tyr Lys
    50                  55                  60

Gly Ile Ala Val Gly Lys Val Val Ala Leu Asp Val Ser Glu Asp Ile
65                  70                  75                  80

Lys Gly Val Val Ala Thr Ile Glu Met Asp Lys Glu Ala Arg Gln Tyr
                85                  90                  95

Leu Ser Lys Gly Thr Arg Phe Trp Leu Val Lys Pro Arg Val Ser Leu
            100                 105                 110

Ala Gly Val Thr Gly Leu Glu Thr Leu Val Ser Gly Val Tyr Ile Ala
        115                 120                 125

Val Asp Pro Val Lys Gly Glu Lys Glu Arg Asn Phe Thr Ala Leu
130                 135                 140

Lys Gln Pro Pro Leu Ser Asp Arg Leu Pro Gly Leu His Leu Thr
145                 150                 155                 160

Leu Lys Ala Asp Arg Leu Gly Ser Leu Glu Gln Gly Ser Pro Val Phe
                165                 170                 175

Tyr Arg Gln Ile Gln Val Gly Gln Val Lys Ser Phe Gln Leu Gly Asp
            180                 185                 190
```

```
Asp Gln Arg Thr Ile Glu Ile Lys Val His Ile Glu Pro Ala Tyr Ala
        195                 200                 205

Asp Leu Val Arg Lys His Thr Arg Phe Trp Asn Ala Ser Gly Ile Ser
    210                 215                 220

Ile Ser Gly Gly Leu Ser Gly Phe Lys Val Arg Ser Glu Ser Leu Leu
225                 230                 235                 240

Thr Leu Ala Ala Gly Gly Ile Ala Phe Ala Thr Ser Asp Ser Arg Gly
                245                 250                 255

Asp Ser Pro Pro Thr Asp Pro Ser Lys Pro Phe Arg Leu Tyr Asp Asp
            260                 265                 270

Tyr Asp Ala Ala Gln Ala Gly Leu Arg Val Lys Leu Lys Met Asn Asp
        275                 280                 285

Val Ser Gly Ile Asp Pro Gly Arg Thr Pro Val Met Phe Asn Gly Val
    290                 295                 300

Gln Val Gly Leu Val Lys Ser Ile Asp Met Gly Lys Asp Tyr Ser Ser
305                 310                 315                 320

Ala Thr Ala Asp Leu Ala Met Asp Pro Arg Val Glu Asp Met Leu Leu
                325                 330                 335

Glu Gly Thr Glu Phe Trp Thr Val Lys Pro Ser Ile Ser Leu Ala Gly
            340                 345                 350

Ile Thr Gly Leu Glu Ala Leu Val Lys Gly Asn Tyr Ile Asp Val Arg
        355                 360                 365

Phe Ala Lys Ser Gly Ala Pro Ser Arg Glu Phe Thr Ile Arg Pro Lys
    370                 375                 380

Ala Pro Pro Leu Asn Thr Asp Ala Pro Gly Leu His Leu Val Leu Thr
385                 390                 395                 400

Ser Asp Lys Leu Gly Ser Ile Asp Ile Gly Ala Pro Ile Leu Tyr Arg
                405                 410                 415

Gln Val Arg Val Gly Ser Val Gln Ser Tyr Gln Leu Ser Arg Asp Arg
            420                 425                 430

Gln Arg Val Val Val Gly Val His Ile Glu Pro Glu Tyr Ala His Leu
        435                 440                 445

Val Asn Thr Ser Thr Arg Phe Trp Asn Ser Ser Gly Ile Thr Leu Thr
    450                 455                 460

Gly Asn Leu Ser Gly Val Gln Val Lys Ser Glu Ser Leu Gln Thr Leu
465                 470                 475                 480

Ile Thr Gly Gly Ile Ser Phe Asp Thr Leu Asp Pro Lys Ala Pro Thr
                485                 490                 495

Val Thr Lys Val Arg Arg Phe Thr Leu Phe Asp Ser Glu Glu Ala Ala
            500                 505                 510

Met Ala Arg Gly Val Glu Ile Gln Leu Ser Ile Asp Asn Ala Asp Gly
        515                 520                 525

Leu Arg Glu Gly Thr Pro Ile Arg Phe Lys Gly Leu Asp Ile Gly Lys
    530                 535                 540

Ile Glu Ser Val Glu Leu Asn Pro Asp Leu Ser Gly Val Leu Met Arg
545                 550                 555                 560

Ala Arg Leu Thr Ser Arg Gly Glu Arg Val Ala Arg Ser Gly Thr Arg
                565                 570                 575

Phe Trp Val Val Arg Pro Ala Leu Gly Leu Leu Arg Thr Glu Asn Leu
            580                 585                 590

Gly Thr Leu Val Ser Gly Pro Tyr Ile Glu Ala Leu Pro Ser Ser Thr
        595                 600                 605
```

```
Pro Gly Glu Arg Gln Ala Arg Phe Gln Thr Leu Ala Glu Ala Pro Asn
    610                 615                 620

Leu Leu Gly Arg Glu Asn Gly Leu Arg Leu Thr Leu Ser Ala Pro Arg
625                 630                 635                 640

Lys Gly Ser Ile Lys Pro Gly Asn Leu Val Thr Tyr Arg Gln Ile Pro
                645                 650                 655

Val Gly Lys Val Val Asp Leu Ala Leu Gly Glu Gln Ala Asp Arg Val
            660                 665                 670

Leu Ile Ser Ile Leu Ile Glu Pro Arg Tyr Val Pro Leu Val Arg Thr
        675                 680                 685

Gly Ser Arg Phe Trp Asn Ala Ser Gly Phe Gly Val Asp Ala Ser Leu
    690                 695                 700

Phe Lys Gly Leu Ser Leu Arg Thr Glu Ser Met Glu Ala Leu Met Glu
705                 710                 715                 720

Gly Gly Ile Ala Phe Ala Thr Pro Asn Asn Ala Gln Met Gly Glu Pro
                725                 730                 735

Ala Lys Pro Gly Gln Thr Phe Ala Leu Phe Asp Ser Ala Asn Asp Glu
            740                 745                 750

Trp Leu Glu Trp Ala Pro Arg Ile Ala Leu Arg Ser Gly Ala Arg
        755                 760                 765

<210> SEQ ID NO 16
<211> LENGTH: 875
<212> TYPE: PRT
<213> ORGANISM: Photobacterium profundum SS9

<400> SEQUENCE: 16

Met Asn Asn Gly Gln Asn Asp Gln Gln Pro Glu Ala Val Asp Ile Arg
1               5                   10                  15

Arg Asp Arg Gly Leu Ser Pro Leu Trp Leu Leu Pro Leu Leu Ala Leu
                20                  25                  30

Val Leu Ala Gly Trp Leu Val Phe Lys Ala Val Asn Glu Ser Gly Glu
            35                  40                  45

Arg Ile Gln Ile His Phe Asn Asp Ala Ala Gly Leu Ile Ala Gly Arg
        50                  55                  60

Thr Thr Ile Arg Tyr Gln Gly Leu Glu Val Gly Ile Val Arg Asp Val
65                  70                  75                  80

Asn Leu Ser Glu Asp Leu Lys Ser Ile Tyr Val Asp Ala Asp Ile Tyr
                85                  90                  95

Pro Lys Ala Val Gln Thr Leu Lys Ala Asn Thr Arg Phe Trp Leu Val
            100                 105                 110

Lys Pro Lys Ala Ser Ile Thr Gly Ile Ser Gly Leu Asp Ala Leu Val
        115                 120                 125

Ser Gly Asn Tyr Ile Ala Leu Gln Pro Gly Glu Gly Lys Thr Thr Lys
    130                 135                 140

Lys Phe Thr Ala Leu Asp Thr Gln Pro Ala Asp Thr Pro Leu Gly Glu
145                 150                 155                 160

Gly Leu Thr Leu Gln Leu Arg Ser Pro Asp Leu Ala Ser Val Ser Ile
                165                 170                 175

Gly Ser Gln Val Phe Tyr Lys Lys Ile Pro Val Gly Glu Val Tyr Asn
            180                 185                 190

Tyr Thr Leu Ser Gln Asn Arg Lys Gln Val Leu Ile Asp Val Thr Ile
        195                 200                 205

Lys Pro Lys Tyr Ser Glu Leu Ile Thr Asn Lys Ser Arg Phe Trp Asn
    210                 215                 220
```

```
Val Ser Gly Met Ser Ala Asn Ile Gly Phe Asn Gly Ile Asp Val Gln
225                 230                 235                 240

Phe Glu Ser Leu Ser Ala Met Ile Ala Gly Ala Ile Ala Phe Asp Ser
            245                 250                 255

Pro Asp Glu Gly Val Ala Ile Asp Pro Asn His Leu Phe Arg Leu Tyr
        260                 265                 270

Pro Asp Leu Asn Thr Ala Gly Arg Gly Ile Ala Ile Lys Val Glu Leu
        275                 280                 285

Pro Asp Gly Asn Asn Ile Ser Thr Ser Gly Ala Pro Ile Ile Tyr Arg
        290                 295                 300

Gly Leu Glu Ile Gly Gln Ile Ser Ser Leu Arg Leu Asp Lys Glu Thr
305                 310                 315                 320

Asn Lys Ile Ile Ala Asn Ala Ala Ile Glu Pro Ser Met Ser Asp Leu
                325                 330                 335

Leu Asn Thr Gly Ser Arg Leu Leu Glu Glu Ala Glu Val Ser Leu
                340                 345                 350

Asn Gly Val Lys Asn Ile Gly Asn Leu Ile Arg Gly Asn Phe Leu Thr
                355                 360                 365

Leu Ile Pro Gly Glu Gly Glu Lys Val Arg Met Phe Lys Ala Ile Thr
370                 375                 380

Gln Asp Gln Leu Gln Glu Gln Pro Gly Thr Val Ser Phe Ala Leu
385                 390                 395                 400

Tyr Ala Asn Asn Ser Phe Gly Ile Lys Arg Gly Ser Lys Leu Arg His
                405                 410                 415

Arg Gly Leu Asp Val Gly Arg Val Lys Lys Val Ser Phe Glu Gly Asn
                420                 425                 430

Ser Val Arg Phe Asp Val Ile Val Arg Pro Gln Tyr Thr Ser Leu Val
                435                 440                 445

Arg Ser Asn Ser Arg Phe Phe Ile Asp Gly Gly Ile Gln Ala Ser Ile
450                 455                 460

Ser Ala Lys Gly Ile Asp Val Ser Met Pro Pro Ala Asp Gln Leu Ile
465                 470                 475                 480

Ser Asn Gly Ile Ser Phe Thr Ser Ser Gly Ser Lys Asn Ile Gln Lys
                485                 490                 495

Asn Tyr Pro Leu Tyr Glu Asn Lys Arg Leu Ser Thr Leu Ala Ala Asp
            500                 505                 510

Asn Gln Arg Gly Phe Ala Lys Tyr Ser Leu Phe Ala Asp Glu Leu Pro
            515                 520                 525

Pro Val Ser Glu Gly Ser Pro Ile Leu Tyr Arg Asn Leu Gln Val Gly
            530                 535                 540

Glu Val Thr Gly Tyr Ala Leu Val Arg Asp Gly Val Thr Val Ser Phe
545                 550                 555                 560

Lys Ile Glu Asn Lys Tyr Arg His Leu Ile Ser Pro Ser Thr Val Phe
                565                 570                 575

Trp Asn Arg Ser Gly Val Glu Ile Glu Ala Gly Phe Asp Gly Ile Lys
            580                 585                 590

Val Lys Ala Asp Pro Ile Ser Thr Leu Ile Ile Gly Gly Ile Ala Phe
            595                 600                 605

Asp Asp Ile Val Gly Val Thr Asn Lys Ala Gly Ser Lys Phe Lys Leu
            610                 615                 620

Tyr Pro Ser Leu Ser Asp Ala Gln Asn Phe Gly Leu Leu Val Thr Leu
625                 630                 635                 640
```

Thr Ala Pro Asn Ala Arg Ser Val Ser Lys Asn Ser Asp Ile Arg Tyr
            645                 650                 655

Gln Gly Val Asn Val Gly Lys Val Val Ser Ile Glu Pro Asn Phe Asn
        660                 665                 670

Ala Gly Asn Val Gln Ile Lys Ala Arg Leu Phe Pro Lys Tyr Ala Asn
        675                 680                 685

Ile Leu Ala Lys Ser Asp Ser Tyr Phe Trp Thr Val Thr Pro Lys Leu
    690                 695                 700

Ser Leu Thr Gly Ala Lys Asn Leu Asp Ser Leu Leu Asn Ser Tyr Ile
705                 710                 715                 720

Ala Val Gln Pro Gly Asp Gly Thr Tyr Ser Gln Thr Phe Lys Leu Gly
                725                 730                 735

Thr Ala Glu Leu Ile Ser Ser Gly Leu Thr Leu Ile Leu Glu Ser Glu
                740                 745                 750

Asp Arg Gly Ser Val Ser Glu Gly Thr Pro Leu Leu Tyr Arg Asp Ile
            755                 760                 765

Gln Val Gly Gln Val Ile Glu Val Ala Leu Gly Asp Leu Ser Asp Arg
        770                 775                 780

Val Leu Ile Lys Ile Gln Ile Glu Lys Glu Tyr Ser His Leu Ile Arg
785                 790                 795                 800

Thr Asp Thr Val Phe Trp Asn Ala Ser Gly Val Asp Phe Thr Ile Gly
                805                 810                 815

Leu Thr Gly Ala Lys Ile Gln Thr Gly Thr Val Asp Ser Leu Leu Arg
                820                 825                 830

Gly Gly Ile Ser Phe Ala Thr Pro Glu Glu Gln Pro Leu Ser Pro Leu
            835                 840                 845

Ala Lys Gln Glu Glu His Phe Leu Leu His Lys Glu Ala Asp Asp Lys
        850                 855                 860

Trp Arg Thr Trp Arg Thr Ala Ile Pro Arg Asp
865                 870                 875

<210> SEQ ID NO 17
<211> LENGTH: 880
<212> TYPE: PRT
<213> ORGANISM: Aliivibrio salmonicida LFI1238

<400> SEQUENCE: 17

Met Asn Ala Pro Lys Thr Val Asp Ser Ser Ile Glu Lys Val Asn Ile
1               5                   10                  15

Lys Thr Glu Arg Gly Ile Ser Pro Leu Trp Ile Leu Pro Leu Leu Ala
            20                  25                  30

Leu Cys Leu Gly Gly Trp Leu Val Tyr Ser Ala Phe Val Glu Ala Gly
        35                  40                  45

Gln Arg Ile Gln Ile Tyr Phe Asp Asp Ala Gln Gly Leu Thr Ala Gly
    50                  55                  60

Arg Thr Thr Ile Arg Tyr Gln Gly Leu Glu Val Gly Met Val Lys Asn
65                  70                  75                  80

Ile Thr Leu Ser Lys Asp Leu Ser Asn Ile Tyr Val Asp Ala Asp Ile
                85                  90                  95

Tyr Pro Glu Ala Ser Glu Leu Leu Lys Asp Asn Thr Gln Phe Trp Leu
            100                 105                 110

Val Lys Pro Gln Ala Ser Leu Thr Gly Ile Ser Gly Leu Asp Ala Leu
        115                 120                 125

Val Ser Gly Asn Tyr Ile Ala Ile Leu Pro Gly Ser Gly Glu Ala Lys
    130                 135                 140

```
Thr Gln Phe Asn Ala Leu Ala Asn Ser Pro Val Ile Gln Pro Asn Ser
145                 150                 155                 160

Thr Gly Leu Asn Ile Thr Leu Arg Ser Ser Asp Leu Gly Ser Ile Ser
            165                 170                 175

Val Gly Ser Lys Ile Tyr Tyr Lys Lys Ile Pro Ile Gly Glu Val Tyr
        180                 185                 190

Asn Phe Lys Leu Asp Glu Lys Thr Asp Lys Ile Lys Ile Lys Ala Leu
    195                 200                 205

Ile Asp Glu Glu Tyr Ala His Leu Ile Thr Ser Lys Ser Arg Phe Trp
210                 215                 220

Asn Ala Ser Gly Ile Gly Ala Ser Ile Gly Phe Asp Gly Val Asp Val
225                 230                 235                 240

Gln Phe Glu Ser Leu Ser Ala Leu Ile Gly Gly Ala Ile Ala Val Asp
                245                 250                 255

Ser Pro Asp Asp Gly Lys Ala Ile Asp Asn Gly Glu Glu Phe Arg Leu
            260                 265                 270

Tyr Ser Asn Ile Lys Thr Ala Arg Gly Ile Ser Ile Lys Ile Thr
        275                 280                 285

Leu Pro Asp Asn Gln Ile Ser Pro Asn Gly Ser Ser Ile Met Tyr
290                 295                 300

Arg Gly Leu Glu Ile Gly Gln Ile Asn Ser Leu Lys Leu Ser Asp Asp
305                 310                 315                 320

Lys Lys Asp Ile Ile Ala Ser Ala Thr Val Glu Pro Ala Phe Ala Asp
                325                 330                 335

Tyr Leu Asn Asp Gly Ser Arg Phe Val Leu Glu Ala Lys Val Gly
            340                 345                 350

Leu Ser Gly Val Glu Asn Ile Gly Asn Leu Val Arg Gly Asn Phe Leu
        355                 360                 365

Thr Leu Val Pro Gly Glu Gly Asp Lys Ser Arg Thr Phe Ser Ala Ile
    370                 375                 380

Arg Lys Pro Glu Leu Ile Lys Gln Asp Ala Lys Ala Ile Thr Phe Ser
385                 390                 395                 400

Leu Tyr Ala Asp Arg Ser Phe Gly Leu Thr Ala Asp Thr Lys Ile Leu
                405                 410                 415

Tyr Lys Gly Ile Lys Val Gly Ser Ile Thr His Val Ala Leu Val Gly
            420                 425                 430

Asp Arg Val Lys Phe Glu Ala Met Ile Phe Glu Gln Tyr Lys Arg Leu
        435                 440                 445

Ile Lys Ser His Ser Lys Phe Val Ser Gly Ser Val Ser Ala Glu
    450                 455                 460

Leu Thr Asp Ser Gly Leu Ser Ile Asp Val Pro Pro Ala Gln Glu Leu
465                 470                 475                 480

Ile Ser Gly Ser Ile Ser Phe Thr Ser Glu Gly Lys Gly Tyr Lys Gln
            485                 490                 495

Lys Asn Tyr Thr Leu Phe Lys Asn Ser Ser Leu Ala Glu Leu Ala Gln
        500                 505                 510

Phe Lys Thr Glu Lys Ser Thr Glu Leu Thr Leu Phe Ser Ala Glu Leu
    515                 520                 525

Pro Pro Ile Thr Lys Asn Ser Pro Ile Leu Tyr Arg Asn Leu Val Val
    530                 535                 540

Gly Lys Val Thr Asp Phe Ser Leu Gly Asn Asp Gly Val Asn Ile Lys
545                 550                 555                 560
```

```
Val Asn Ile Glu Lys Gln Tyr Ala His Leu Ile His Ser Asp Thr Val
            565                 570                 575

Phe Trp Asn Tyr Ser Gly Val Asn Val Glu Ala Ser Leu Ser Gly Val
        580                 585                 590

Asn Ile Gln Ala Ala Pro Leu Leu Ser Met Ile Arg Gly Gly Ile Gly
            595                 600                 605

Phe Asp Asn Ile Gln Gly Val Glu Asn Lys Leu Gly Gln Lys Trp Lys
        610                 615                 620

Leu Tyr Ser Thr Leu Ser Glu Ala Gln Ala Phe Gly Lys Ile Ile Ala
625                 630                 635                 640

Phe Thr Ala Lys Asp Ser Ser Ile Ser Lys Gly Thr Leu Ile Lys
            645                 650                 655

Tyr Gln Gly Val Thr Val Gly Glu Ile Ser Lys Val Thr Pro Asn Phe
        660                 665                 670

Lys Gln Ser Asn Val Tyr Ile Gln Ala Arg Ile Phe Pro Glu Tyr Val
            675                 680                 685

Asn Gln Ile Ala Ile Pro Gly Ser His Phe Trp Val Val Lys Pro Thr
        690                 695                 700

Ile Ser Leu Thr Lys Thr Glu Asn Leu Asp Thr Leu Leu Gly Ser Tyr
705                 710                 715                 720

Ile Gln Val Thr Pro Gly Lys Gly Lys Gly Lys Val Gln Thr Gln Phe
            725                 730                 735

Ser Leu Thr Asp Gln Pro Gln Ala Ala Leu Ile Ser Tyr Thr Leu
        740                 745                 750

Glu Ser Ser Thr Arg Gly Ser Val Lys Val Gly Thr Pro Leu Leu Phe
        755                 760                 765

Arg Glu Ile Glu Val Gly Glu Val Val Asp Val Arg Leu Gly Asp Leu
770                 775                 780

Ser Asp Arg Ile Ile Ile Thr Ile Gly Val Gln Pro Asn Tyr Ala Tyr
785                 790                 795                 800

Leu Ile Arg Glu Asn Ser Val Phe Trp Asn Val Ser Gly Val Asn Met
            805                 810                 815

Ser Ile Gly Ile Ser Gly Ala Lys Val Arg Ala Gly Thr Val Asp Ser
        820                 825                 830

Ile Leu Arg Gly Gly Ile Ala Phe Ser Thr Pro Asp Asp Glu Ser Leu
835                 840                 845

Ala Pro Gln Ala Lys Glu Asn Lys Ser Tyr Leu Leu Tyr Lys Thr Ser
        850                 855                 860

Glu Asp Asp Trp Pro Leu Trp Asn Ala Ala Ile Pro Asn Pro Asn Lys
865                 870                 875                 880

<210> SEQ ID NO 18
<211> LENGTH: 879
<212> TYPE: PRT
<213> ORGANISM: Vibrio cholerae

<400> SEQUENCE: 18

Met Ser Gln Glu Asn Thr Thr Gln Thr Ser Tyr Thr Pro Glu Ile Arg
1               5                   10                  15

Lys Arg Arg Gly Ile Ser Pro Leu Trp Ile Leu Pro Ile Val Thr Met
            20                  25                  30

Ile Leu Ala Gly Trp Leu Val Phe Lys Ala Val His Asp Ala Gly Val
        35                  40                  45

Arg Ile Gln Ile His Phe Glu Asn Ala Gln Gly Leu Ile Ala Gly Arg
    50                  55                  60
```

```
Thr Thr Ile Arg Tyr Gln Gly Leu Glu Val Gly Met Val Arg Asp Ile
 65                  70                  75                  80
Lys Leu Ser Glu Gly Leu Asp Ser Ile Tyr Val Glu Ala Asp Ile Tyr
                 85                  90                  95
Pro Glu Ala Thr Lys Leu Leu Ser Asn Gln Thr Arg Phe Trp Met Val
            100                 105                 110
Lys Pro Thr Ala Ser Leu Ser Gly Val Ser Gly Leu Asp Ala Leu Val
        115                 120                 125
Ser Gly Asn Tyr Ile Ala Ile Gln Pro Gly Ser Thr His Gln Glu Asp
    130                 135                 140
Tyr Pro Thr Gln Tyr Gln Ala Leu Asp Ser Ala Pro Ser Asp Leu Leu
145                 150                 155                 160
Ala Gln Arg Gly Leu Thr Ile Ser Leu Lys Ala Arg Asp Leu Gly Gly
                165                 170                 175
Ile Ser Val Gly Ser Gln Ile Val Tyr Lys Lys Ile Pro Ile Gly Glu
            180                 185                 190
Val Phe Ser Tyr Gln Leu Asp Asp Ala Gln Ser Val Ile Ile Gln
        195                 200                 205
Ala Ser Ile Lys Glu Glu Tyr Gln His Ile Ile Asn Thr Glu Ser Arg
    210                 215                 220
Phe Trp Asn Val Ser Gly Ile Gly Ala Ser Ile Gly Phe Glu Gly Val
225                 230                 235                 240
Asp Val Arg Leu Glu Ser Leu Ser Ala Leu Ile Gly Gly Ser Ile Ala
                245                 250                 255
Val Asp Ser Pro Asp Glu Gly Lys Pro Val Gln Asn Ala Gln Phe
            260                 265                 270
Arg Leu Tyr Arg Asp Leu Lys Thr Ala Arg Gly Ile Ala Val Ser
        275                 280                 285
Ile Thr Leu Pro Asp Asp Asn Asn Ile Ser Ala Ser Gly Ala Pro Ile
    290                 295                 300
Met Tyr Arg Gly Ile Glu Ile Gly Gln Ile Thr Asp Leu Gln Leu Thr
305                 310                 315                 320
Glu Asn Arg Lys Ser Ile Val Ala Ser Ala Ile Gln Pro Ala Phe
                325                 330                 335
Ser Asp Met Leu Asn Gln Gly Ser Gln Phe Val Leu Glu Glu Ala Gln
            340                 345                 350
Val Ser Leu Thr Gly Val Glu Asn Leu Thr Asn Leu Val Lys Gly Asn
        355                 360                 365
Tyr Leu Thr Leu Ile Pro Gly Ala Gly Glu Arg Thr Arg Asn Phe Gln
    370                 375                 380
Ala Val Arg Lys Asn Glu Phe Lys Tyr Ala Arg Ser Asn Ser Ile Ser
385                 390                 395                 400
Phe Asn Leu Val Ala Asp Asn Ser Phe Gly Leu Glu Ala Gly Thr Pro
                405                 410                 415
Ile Leu Tyr Arg Gly Val Ala Val Gly Ser Val Thr Ala Val Asn Leu
            420                 425                 430
Lys Leu Asp Tyr Val Glu Phe Asn Val Leu Ile Asp Glu Gln Tyr Gly
        435                 440                 445
Ala Leu Ile Arg Ser Gln Asn Arg Phe Tyr Val Thr Gly Ser Ala Ala
    450                 455                 460
Ala Glu Leu Thr Glu Ser Gly Leu Ser Val Ser Ile Pro Pro Ala Lys
465                 470                 475                 480
```

```
Gln Leu Leu Leu Gly Ser Ile Ser Phe Ala Ser Glu Gly Ser Ser Thr
                485                 490                 495

Pro Leu Glu Gln Tyr Arg Leu Tyr Ser Ser Gln Ser Leu Ala Glu Leu
            500                 505                 510

Ala Lys Tyr Asn Gln Ser Gly Ser Arg Ser Leu Thr Leu Phe Ala His
        515                 520                 525

Glu Leu Pro Ser Ile Asn Ala Gly Ser Pro Leu Leu Tyr Arg Asn Leu
    530                 535                 540

Lys Val Gly Ser Ile Ser Gly Phe Thr Leu Thr Pro Lys Gly Val Gln
545                 550                 555                 560

Ile Glu Ala Thr Ile Glu Lys Gln Tyr Gln His Leu Leu Thr Pro Asp
                565                 570                 575

Thr Val Phe Trp Asn Arg Ser Gly Val Glu Ile Lys Ala Ser Met Asp
            580                 585                 590

Gly Val Asp Val Lys Ala Ala Pro Leu Gln Thr Leu Ile Arg Gly Gly
        595                 600                 605

Ile Ala Phe Asp Asn Leu Pro Gly Ile Glu Asn Lys Val Gly Ser Met
    610                 615                 620

Trp Lys Leu Tyr Ser Asp Tyr Asp His Ala Arg Arg Tyr Gly Glu Lys
625                 630                 635                 640

Ile Thr Leu Thr Ala Leu Gly Thr Leu Gly Val Lys Val Gly Thr Pro
                645                 650                 655

Val Gln Tyr Gln Gly Val Gln Ile Gly Glu Val Phe Glu Ile Ile Pro
            660                 665                 670

Asp Phe Glu Ser Asp Phe Val Lys Leu Ala Ala Arg Ile Glu Pro Gln
        675                 680                 685

Tyr Ala Pro Lys Ile Ala Lys Gln Asn Ser Gln Phe Trp Leu Ser Gln
    690                 695                 700

Ala Lys Ile Gly Leu Ser Gly Ile Glu Asn Val Gln Asn Leu Leu Gly
705                 710                 715                 720

Gln Ser Ile Glu Val Gln Pro Gly Asn Gly Ser Arg Phe Glu Phe
                725                 730                 735

Glu Leu His Lys Glu Ala Arg His Gly Gly Ala Gly Asn Thr Tyr Thr
            740                 745                 750

Leu Gln Ser Glu Lys Arg Gly Ser Val Ser Val Gly Thr Pro Ile Leu
        755                 760                 765

Tyr Arg Asp Ile Glu Val Gly Lys Val Ile Asp Val Arg Leu Gly Glu
    770                 775                 780

Phe Ala Asp Arg Val Ile Thr Thr Ile Arg Ile Ala Pro Gln Tyr Thr
785                 790                 795                 800

Tyr Leu Leu Arg Gln Asn Ser Val Phe Trp Asn Val Ser Gly Leu Asp
                805                 810                 815

Met Ser Ile Gly Ile Thr Gly Ala Asn Val Lys Ala Gly Thr Phe Asp
            820                 825                 830

Ser Met Leu Arg Gly Gly Ile Thr Phe Ala Thr Pro Glu Gln Lys Gln
        835                 840                 845

Leu Thr Pro Ala Ala Pro Glu Gly His Thr Phe Tyr Leu Tyr Pro Gln
    850                 855                 860

Ala Gln Glu Glu Trp Thr Lys Trp Arg Thr Pro Ile Pro Lys Pro
865                 870                 875

<210> SEQ ID NO 19
<211> LENGTH: 877
<212> TYPE: PRT
```

<213> ORGANISM: Citrobacter koseri

<400> SEQUENCE: 19

```
Met Ser Gln Glu Thr Pro Ala Ser Pro Thr Glu Ala Gln Ile Lys Thr
1               5                   10                  15

Lys Arg Arg Ile Ser Pro Phe Trp Leu Leu Pro Phe Ile Ala Leu Met
            20                  25                  30

Ile Ala Gly Trp Leu Ile Trp Gly Ser Tyr Glu Asp Arg Gly Asn Thr
        35                  40                  45

Val Thr Ile Asp Phe Met Ser Ala Asp Gly Ile Val Pro Gly Arg Thr
    50                  55                  60

Pro Val Arg Tyr Gln Gly Val Glu Val Gly Thr Val Gln Asp Ile Ser
65                  70                  75                  80

Leu Ser Lys Asp Leu Arg Lys Ile Glu Val Arg Val Ser Ile Lys Ser
                85                  90                  95

Asn Met Lys Asp Ala Leu Arg Glu Glu Thr Gln Phe Trp Leu Val Thr
            100                 105                 110

Pro Lys Ala Ser Leu Ala Gly Val Ser Gly Leu Asp Ala Leu Val Gly
        115                 120                 125

Gly Asn Tyr Ile Gly Met Met Pro Gly Lys Gly Ala Glu Lys Asp His
    130                 135                 140

Phe Val Ala Leu Asp Thr Gln Pro Lys Tyr Arg Leu Asp Asn Gly Asp
145                 150                 155                 160

Leu Met Ile His Leu His Ala Pro Asp Leu Gly Ser Leu Asn Ser Gly
                165                 170                 175

Ser Leu Val Tyr Phe Arg Lys Ile Pro Val Gly Arg Val Tyr Asp Tyr
            180                 185                 190

Ala Ile Asn Pro Asn Lys Gln Gly Val Thr Ile Asp Val Leu Ile Glu
        195                 200                 205

Arg Arg Phe Thr Asn Leu Val Lys Lys Gly Ser Arg Phe Trp Asn Val
    210                 215                 220

Ser Gly Val Asn Ala Asp Val Ser Leu Ser Gly Ala Lys Val Lys Leu
225                 230                 235                 240

Glu Ser Leu Ala Ala Leu Val Asn Gly Ala Ile Ala Phe Asp Ser Pro
                245                 250                 255

Asp Asp Ser Gln Pro Ala Thr Ala Asp Asp Ala Phe Gly Leu Tyr Glu
            260                 265                 270

Asp Leu Ala His Ser Gln Arg Gly Val Ile Val Lys Leu Glu Leu Pro
        275                 280                 285

Asn Gly Asp Gly Leu Lys Ala Asp Ser Thr Pro Leu Met Tyr Gln Gly
    290                 295                 300

Leu Glu Val Gly Glu Leu Thr Lys Leu Thr Leu Asn Pro Gly Gly Lys
305                 310                 315                 320

Val Thr Gly Glu Met Thr Val Asp Pro Ser Val Val Thr Leu Leu Arg
                325                 330                 335

Asp Lys Thr Arg Ile Glu Leu Arg Ser Pro Lys Leu Ser Leu Ser Asp
            340                 345                 350

Ala Ser Ile Ser Ser Leu Leu Thr Gly Lys Thr Phe Glu Leu Val Pro
        355                 360                 365

Gly Glu Gly Glu Pro Arg Ser Glu Phe Val Val Pro Gly Glu Glu
    370                 375                 380

Ala Leu Leu His Glu Pro Asn Ala Leu Thr Leu Thr Leu Thr Ala Pro
385                 390                 395                 400
```

```
Glu Ser Tyr Gly Ile Asp Ala Gly Gln Pro Leu Val Leu His Gly Val
                405                 410                 415
Gln Val Gly Gln Val Ile Glu Arg Lys Leu Ser Ser Lys Gly Val Ala
            420                 425                 430
Phe Thr Val Ala Ile Asp Pro Gln His Arg Ala Leu Ile Gln Gly Asp
        435                 440                 445
Ser Lys Phe Val Val Asn Ser Arg Val Asp Ile Lys Val Gly Leu Asp
    450                 455                 460
Gly Val Glu Phe Leu Gly Ala Ser Ala Ser Glu Trp Val Ser Gly Gly
465                 470                 475                 480
Ile Arg Ile Leu Pro Gly Thr Lys Gly Glu Met Lys Ser Ser Tyr Pro
                485                 490                 495
Leu Tyr Ala Asn Leu Glu Lys Ala Val Glu Asn Ser Leu Ser Asp Leu
            500                 505                 510
Pro Thr Thr Thr Val Ser Leu Thr Ala Glu Thr Leu Pro Asp Val Gln
        515                 520                 525
Thr Gly Ser Val Val Leu Tyr Arg Lys Phe Glu Val Gly Glu Val Ile
    530                 535                 540
Thr Val Arg Pro Arg Ala Asn Ala Phe Asp Ile Asp Leu His Ile Lys
545                 550                 555                 560
Pro Glu Tyr Arg Asn Leu Leu Thr Ser Asn Ser Val Phe Trp Ala Glu
                565                 570                 575
Gly Gly Ala Lys Val Gln Leu Asn Gly Ser Gly Leu Thr Val Gln Ala
            580                 585                 590
Ser Pro Leu Ser Arg Ala Leu Lys Gly Ala Ile Ser Phe Asp Asn Leu
        595                 600                 605
Ser Gly Ala Ser Ala Ser Gln Arg Lys Gly Asp Lys Arg Ile Leu Tyr
    610                 615                 620
Ala Ser Glu Thr Ala Ala Arg Ala Val Gly Gly Gln Ile Thr Leu His
625                 630                 635                 640
Ala Phe Asp Ala Gly Lys Leu Ala Ala Gly Met Pro Ile Arg Tyr Leu
                645                 650                 655
Gly Ile Asp Ile Gly Gln Ile Gln Thr Leu Glu Leu Ile Thr Ala Arg
            660                 665                 670
Asn Glu Val Gln Ala Lys Ala Val Leu Tyr Pro Glu Tyr Val Gln Thr
        675                 680                 685
Phe Ala Arg Ser Gly Thr Arg Phe Ser Val Ile Thr Pro Gln Ile Ser
    690                 695                 700
Ala Ala Gly Val Glu His Leu Asp Thr Ile Leu Gln Pro Tyr Ile Asn
705                 710                 715                 720
Val Glu Pro Gly Arg Gly Asn Pro Arg Arg Asp Phe Glu Leu Gln Glu
                725                 730                 735
Ala Thr Ile Ser Asp Ser Arg Tyr Leu Asp Gly Leu Ser Ile Val Val
            740                 745                 750
Glu Ala Pro Glu Ala Gly Ser Leu Asn Ile Gly Thr Pro Val Leu Phe
        755                 760                 765
Arg Gly Ile Glu Val Gly Thr Val Thr Gly Met Thr Leu Gly Ser Leu
    770                 775                 780
Ser Asp Arg Val Met Ile Ala Met Arg Ile Ser Gln Arg Tyr Gln His
785                 790                 795                 800
Leu Val Arg Asn Asn Ser Val Phe Trp Leu Ala Ser Gly Tyr Ser Leu
                805                 810                 815
Asp Phe Gly Leu Thr Gly Gly Val Val Lys Thr Gly Thr Phe Asn Gln
```

```
                820             825             830
Phe Ile Arg Gly Gly Ile Ala Phe Ala Thr Pro Pro Gly Thr Pro Leu
            835             840             845

Ala Pro Lys Ala Gln Ala Gly Lys His Phe Leu Leu Leu Glu Ser Glu
850             855             860

Pro Lys Glu Trp Arg Glu Trp Gly Thr Ala Leu Pro Arg
865             870             875

<210> SEQ ID NO 20
<211> LENGTH: 879
<212> TYPE: PRT
<213> ORGANISM: Escherichia coli

<400> SEQUENCE: 20

Met His Met Ser Gln Glu Thr Pro Ala Ser Thr Thr Glu Ala Gln Ile
1               5                   10                  15

Lys Asn Lys Arg Arg Ile Ser Pro Phe Trp Leu Leu Pro Phe Ile Ala
                20                  25                  30

Leu Met Ile Ala Gly Trp Leu Ile Trp Asp Ser Tyr Gln Asp Arg Gly
            35                  40                  45

Asn Thr Val Thr Ile Asp Phe Met Ser Ala Asp Gly Ile Val Pro Gly
        50                  55                  60

Arg Thr Pro Val Arg Tyr Gln Gly Val Glu Val Gly Thr Val Gln Asp
65                  70                  75                  80

Ile Ser Leu Ser Asp Asp Leu Arg Lys Ile Glu Val Lys Val Ser Ile
                85                  90                  95

Lys Ser Asp Met Lys Asp Ala Leu Arg Glu Glu Thr Gln Phe Trp Leu
            100                 105                 110

Val Thr Pro Lys Ala Ser Leu Ala Gly Val Ser Gly Leu Asp Ala Leu
        115                 120                 125

Val Gly Gly Asn Tyr Ile Gly Met Met Pro Gly Lys Gly Lys Glu Gln
130                 135                 140

Asp His Phe Val Ala Leu Asp Thr Gln Pro Lys Tyr Arg Leu Asp Asn
145                 150                 155                 160

Gly Asp Leu Met Ile His Leu Gln Ala Pro Asp Leu Gly Ser Leu Asn
                165                 170                 175

Ser Gly Ser Leu Val Tyr Phe Arg Lys Ile Pro Val Gly Lys Val Tyr
            180                 185                 190

Asp Tyr Ala Ile Asn Pro Asn Lys Gln Gly Val Val Ile Asp Val Leu
        195                 200                 205

Ile Glu Arg Arg Phe Thr Asp Leu Val Lys Lys Gly Ser Arg Phe Trp
210                 215                 220

Asn Val Ser Gly Val Asp Ala Asn Val Ser Ile Ser Gly Ala Lys Val
225                 230                 235                 240

Lys Leu Glu Ser Leu Ala Ala Leu Val Asn Gly Ala Ile Ala Phe Asp
                245                 250                 255

Ser Pro Glu Glu Ser Lys Pro Ala Glu Ala Asp Thr Phe Gly Leu
            260                 265                 270

Tyr Glu Asp Leu Ala His Ser Gln Arg Gly Val Ile Ile Lys Leu Glu
        275                 280                 285

Leu Pro Ser Gly Ala Gly Leu Thr Ala Asp Ser Thr Pro Leu Met Tyr
290                 295                 300

Gln Gly Leu Glu Val Gly Gln Leu Thr Lys Leu Asp Leu Asn Pro Gly
305                 310                 315                 320
```

Gly Lys Val Thr Gly Glu Met Thr Val Asp Pro Ser Val Val Thr Leu
              325                 330                 335

Leu Arg Glu Asn Thr Arg Ile Glu Leu Arg Asn Pro Lys Leu Ser Leu
              340                 345                 350

Ser Asp Ala Asn Leu Ser Ala Leu Leu Thr Gly Lys Thr Phe Glu Leu
              355                 360                 365

Val Pro Gly Asp Gly Glu Pro Arg Lys Glu Phe Val Val Pro Gly
370                 375                 380

Glu Lys Ala Leu Leu His Glu Pro Asp Val Leu Thr Leu Thr Leu Thr
385                 390                 395                 400

Ala Pro Glu Ser Tyr Gly Ile Asp Ala Gly Gln Pro Leu Ile Leu His
              405                 410                 415

Gly Val Gln Val Gly Gln Val Ile Asp Arg Lys Leu Thr Ser Lys Gly
              420                 425                 430

Val Thr Phe Thr Val Ala Ile Glu Pro Gln His Gln Glu Leu Val Lys
              435                 440                 445

Gly Asp Ser Lys Phe Val Val Asn Ser Arg Val Asp Val Lys Val Gly
              450                 455                 460

Leu Asp Gly Val Glu Phe Leu Gly Ala Ser Ser Glu Trp Ile Asn
465                 470                 475                 480

Gly Gly Ile Arg Ile Leu Pro Gly Asp Lys Gly Glu Met Lys Ala Ser
              485                 490                 495

Tyr Pro Leu Tyr Ala Asn Leu Glu Lys Ala Leu Glu Asn Ser Leu Ser
              500                 505                 510

Asp Leu Pro Thr Thr Thr Val Ser Leu Ser Ala Glu Thr Leu Pro Asp
              515                 520                 525

Val Gln Ala Gly Ser Val Val Leu Tyr Arg Lys Phe Glu Val Gly Glu
              530                 535                 540

Val Ile Thr Val Arg Pro Arg Ala Asn Ala Phe Asp Ile Asp Leu His
545                 550                 555                 560

Ile Lys Pro Glu Tyr Arg Asn Leu Leu Thr Ser Asn Ser Val Phe Trp
              565                 570                 575

Ala Glu Gly Gly Ala Lys Val Gln Leu Asn Gly Ser Gly Leu Thr Val
              580                 585                 590

Gln Ala Ser Pro Leu Ser Arg Ala Leu Lys Gly Ala Ile Ser Phe Asp
              595                 600                 605

Asn Leu Ser Gly Ala Ser Ala Ser Gln Arg Lys Gly Asp Lys Arg Ile
              610                 615                 620

Leu Tyr Ala Ser Glu Thr Ala Arg Ala Val Gly Gly Gln Ile Thr
625                 630                 635                 640

Leu His Ala Phe Asp Ala Gly Lys Leu Ala Val Gly Met Pro Ile Arg
              645                 650                 655

Tyr Leu Gly Ile Asp Ile Gly Gln Ile Gln Thr Leu Asp Leu Ile Thr
              660                 665                 670

Ala Arg Asn Glu Val Gln Ala Lys Ala Val Leu Tyr Pro Glu Tyr Val
              675                 680                 685

Gln Thr Phe Ala Arg Gly Gly Thr Arg Phe Ser Val Val Thr Pro Gln
              690                 695                 700

Ile Ser Ala Ala Gly Val Glu His Leu Asp Thr Ile Leu Gln Pro Tyr
705                 710                 715                 720

Ile Asn Val Glu Pro Gly Arg Gly Asn Pro Arg Arg Asp Phe Glu Leu
              725                 730                 735

Gln Glu Ala Thr Ile Thr Asp Ser Arg Tyr Leu Asp Gly Leu Ser Ile

-continued

```
                        740                 745                 750
Ile Val Glu Ala Pro Glu Ala Gly Ser Leu Gly Ile Gly Thr Pro Val
                755                 760                 765

Leu Phe Arg Gly Leu Glu Val Gly Thr Val Thr Gly Met Thr Leu Gly
            770                 775                 780

Thr Leu Ser Asp Arg Val Met Ile Ala Met Arg Ile Ser Lys Arg Tyr
785                 790                 795                 800

Gln His Leu Val Arg Asn Asn Ser Val Phe Trp Leu Ala Ser Gly Tyr
                805                 810                 815

Ser Leu Asp Phe Gly Leu Thr Gly Gly Val Val Lys Thr Gly Thr Phe
                820                 825                 830

Asn Gln Phe Ile Arg Gly Gly Ile Ala Phe Ala Thr Pro Pro Gly Thr
                835                 840                 845

Pro Leu Ala Pro Lys Ala Gln Glu Gly Lys His Phe Leu Leu Gln Glu
            850                 855                 860

Ser Glu Pro Lys Glu Trp Arg Glu Trp Gly Thr Ala Leu Pro Lys
865                 870                 875

<210> SEQ ID NO 21
<211> LENGTH: 877
<212> TYPE: PRT
<213> ORGANISM: Escherichia coli

<400> SEQUENCE: 21

Met Ser Gln Glu Thr Pro Ala Ser Thr Thr Glu Ala Gln Ile Lys Asn
1               5                   10                  15

Lys Arg Arg Ile Ser Pro Phe Trp Leu Leu Pro Phe Ile Ala Leu Met
            20                  25                  30

Ile Ala Gly Trp Leu Ile Trp Asp Ser Tyr Gln Asp Arg Gly Asn Thr
        35                  40                  45

Val Thr Ile Asp Phe Met Ser Ala Asp Gly Ile Val Pro Gly Arg Thr
    50                  55                  60

Pro Val Arg Tyr Gln Gly Val Glu Val Gly Thr Val Gln Asp Ile Ser
65                  70                  75                  80

Leu Ser Asp Asp Leu Arg Lys Ile Glu Val Lys Val Ser Ile Lys Ser
                85                  90                  95

Asp Met Lys Asp Ala Leu Arg Glu Glu Thr Gln Phe Trp Leu Val Thr
            100                 105                 110

Pro Lys Ala Ser Leu Ala Gly Val Ser Gly Leu Asp Ala Leu Val Gly
        115                 120                 125

Gly Asn Tyr Ile Gly Met Met Pro Gly Lys Gly Lys Glu Gln Asp His
    130                 135                 140

Phe Val Ala Leu Asp Thr Gln Pro Lys Tyr Arg Leu Asp Asn Gly Asp
145                 150                 155                 160

Leu Met Ile His Leu Gln Ala Pro Asp Leu Gly Ser Leu Ser Ser Gly
                165                 170                 175

Ser Leu Val Tyr Phe Arg Lys Ile Pro Val Gly Lys Val Tyr Asp Tyr
            180                 185                 190

Ala Ile Asn Pro Asn Lys Gln Gly Val Val Ile Asp Val Leu Ile Glu
        195                 200                 205

Arg Arg Phe Thr Asp Leu Val Lys Lys Gly Ser Arg Phe Trp Asn Val
    210                 215                 220

Ser Gly Val Asp Ala Asn Val Ser Ile Ser Gly Ala Lys Val Lys Leu
225                 230                 235                 240
```

-continued

Glu Ser Leu Ala Ala Leu Val Asn Gly Ala Ile Ala Phe Asp Ser Pro
                245                 250                 255

Glu Glu Ser Lys Pro Ala Glu Ala Glu Asp Thr Phe Gly Leu Tyr Glu
            260                 265                 270

Asp Leu Ala His Ser Gln Arg Gly Val Ile Ile Lys Leu Glu Leu Pro
        275                 280                 285

Gly Gly Ala Gly Leu Thr Ala Asp Ser Thr Pro Leu Met Tyr Gln Gly
    290                 295                 300

Leu Glu Val Gly Gln Leu Thr Lys Leu Asp Leu Asn Pro Gly Gly Asn
305                 310                 315                 320

Val Thr Gly Glu Met Thr Val Asp Pro Ser Val Val Thr Leu Leu Arg
                325                 330                 335

Glu Asn Thr Arg Ile Glu Leu Arg Asn Pro Lys Leu Ser Leu Ser Asp
            340                 345                 350

Ala Asn Leu Ser Ala Leu Leu Thr Gly Lys Thr Phe Glu Leu Val Pro
        355                 360                 365

Gly Asp Gly Glu Pro Arg Lys Glu Phe Val Val Pro Gly Glu Lys
    370                 375                 380

Ala Leu Leu Gln Glu Pro Asp Val Leu Thr Leu Thr Leu Thr Ala Pro
385                 390                 395                 400

Glu Ser Tyr Gly Ile Asp Ala Gly Gln Pro Leu Ile Leu His Gly Val
                405                 410                 415

Gln Val Gly Gln Val Ile Asp Arg Lys Leu Thr Ser Lys Gly Val Thr
            420                 425                 430

Phe Thr Val Ala Ile Glu Pro Gln His Arg Glu Leu Val Lys Gly Asp
        435                 440                 445

Ser Lys Phe Val Val Asn Ser Arg Val Asp Val Lys Val Gly Leu Asp
    450                 455                 460

Gly Val Glu Phe Leu Gly Ala Ser Ala Ser Glu Trp Ile Asn Gly Gly
465                 470                 475                 480

Ile Arg Ile Leu Pro Gly Asp Lys Gly Glu Met Lys Ala Ser Tyr Pro
                485                 490                 495

Leu Tyr Ala Asn Leu Glu Lys Ala Leu Glu Asn Ser Leu Ser Asp Leu
            500                 505                 510

Pro Thr Thr Thr Val Ser Leu Ser Ala Glu Thr Leu Pro Asp Val Gln
        515                 520                 525

Ala Gly Ser Val Val Leu Tyr Arg Lys Phe Glu Val Gly Glu Val Ile
    530                 535                 540

Thr Val Arg Pro Arg Ala Asn Ala Phe Asp Ile Asp Leu His Ile Lys
545                 550                 555                 560

Pro Glu Tyr Arg Asn Leu Leu Thr Ser Asn Ser Val Phe Trp Ala Glu
                565                 570                 575

Gly Gly Ala Lys Val Gln Leu Asn Gly Ser Gly Leu Thr Val Gln Ala
            580                 585                 590

Ser Pro Leu Ser Arg Ala Leu Lys Gly Ala Ile Ser Phe Asp Asn Leu
        595                 600                 605

Ser Gly Ala Ser Ala Ser Gln Arg Lys Gly Asp Lys Arg Ile Leu Tyr
    610                 615                 620

Ala Ser Glu Thr Ala Ala Arg Ala Val Gly Gly Gln Ile Thr Leu His
625                 630                 635                 640

Ala Phe Asp Ala Gly Lys Leu Ala Val Gly Met Pro Ile Arg Tyr Leu
                645                 650                 655

Gly Ile Asp Ile Gly Gln Ile Gln Thr Leu Asp Leu Ile Thr Ala Arg

```
               660                 665                 670
Asn Glu Val Gln Ala Lys Ala Val Leu Tyr Pro Glu Tyr Val Gln Thr
                675                 680                 685

Phe Ala Arg Gly Gly Thr Arg Phe Ser Val Val Thr Pro Gln Ile Ser
            690                 695                 700

Ala Ala Gly Val Glu His Leu Asp Thr Ile Leu Gln Pro Tyr Ile Asn
705                 710                 715                 720

Val Glu Pro Gly Arg Gly Asn Pro Arg Arg Asp Phe Glu Leu Gln Glu
                725                 730                 735

Ala Thr Ile Thr Asp Ser Arg Tyr Leu Asp Gly Leu Ser Ile Ile Val
            740                 745                 750

Glu Ala Pro Glu Ala Gly Ser Leu Gly Ile Gly Thr Pro Val Leu Phe
            755                 760                 765

Arg Gly Leu Glu Val Gly Thr Val Thr Gly Met Thr Leu Gly Thr Leu
            770                 775                 780

Ser Asp Arg Val Met Ile Ala Met Arg Ile Ser Lys Arg Tyr Gln His
785                 790                 795                 800

Leu Val Arg Asn Asn Ser Val Phe Trp Leu Ala Ser Gly Tyr Ser Leu
                805                 810                 815

Asp Phe Gly Leu Thr Gly Gly Val Val Lys Thr Gly Thr Phe Asn Gln
            820                 825                 830

Phe Ile Arg Gly Gly Ile Ala Phe Ala Thr Pro Pro Gly Thr Pro Leu
            835                 840                 845

Ala Pro Lys Ala Gln Glu Gly Lys His Phe Leu Leu Gln Glu Ser Glu
            850                 855                 860

Pro Lys Glu Trp Arg Glu Trp Gly Thr Ala Leu Pro Lys
865                 870                 875

<210> SEQ ID NO 22
<211> LENGTH: 879
<212> TYPE: PRT
<213> ORGANISM: Salmonella paratyphi

<400> SEQUENCE: 22

Met His Met Ser Gln Glu Thr Pro Ala Ser Lys Thr Glu Ala Gln Ile
1               5                   10                  15

Lys Thr Lys Arg Arg Ile Ser Pro Phe Trp Leu Leu Pro Leu Ile Ala
                20                  25                  30

Leu Met Ile Ala Gly Trp Leu Val Trp Asp Ser Tyr Gln Asp Arg Gly
            35                  40                  45

Asn Ser Val Thr Ile Asp Phe Met Ser Ala Asp Gly Ile Val Pro Gly
50                  55                  60

Arg Thr Pro Val Arg Tyr Gln Gly Val Glu Val Gly Thr Val Glu Asp
65                  70                  75                  80

Val Ser Leu Ser Lys Asp Leu Arg Lys Ile Glu Val Arg Val Ser Ile
                85                  90                  95

Lys Ser Asp Met Glu Asp Ala Leu Arg Glu Glu Thr Gln Phe Trp Leu
            100                 105                 110

Val Thr Pro Lys Ala Ser Leu Ala Gly Val Ser Gly Leu Asp Ala Leu
            115                 120                 125

Val Gly Gly Asn Tyr Ile Gly Met Met Pro Gly Lys Gly Lys Pro Arg
        130                 135                 140

Asp His Phe Val Ala Leu Asp Thr Gln Pro Lys Tyr Arg Leu Ser Asn
145                 150                 155                 160
```

```
Gly Asp Leu Met Ile His Leu Asn Ala Pro Asp Leu Gly Ser Leu Asn
            165                 170                 175

Ser Gly Ser Leu Val Tyr Phe Arg Lys Ile Pro Val Gly Arg Val Tyr
            180                 185                 190

Asp Tyr Ser Ile Asn Pro Asn Lys Gln Gly Val Thr Ile Asp Val Leu
            195                 200                 205

Ile Glu Arg Arg Phe Thr Asp Leu Val Lys Lys Gly Ser Arg Phe Trp
210                 215                 220

Asn Val Ser Gly Ile Asp Ala Asp Leu Ser Leu Ser Gly Ala Lys Val
225                 230                 235                 240

Lys Leu Glu Ser Leu Ala Ala Leu Val Asn Gly Ala Ile Ala Phe Asp
            245                 250                 255

Ser Pro Asp Asn Ser Lys Pro Ala Ala Gln Asp Asp Thr Phe Gly Leu
            260                 265                 270

Tyr Lys Asp Leu Ala His Ser Gln Arg Gly Val Ile Val Lys Leu Glu
            275                 280                 285

Leu Pro Ser Gly Asp Gly Leu Lys Ala Glu Ser Thr Pro Leu Met Tyr
            290                 295                 300

Gln Gly Leu Glu Val Gly Glu Leu Ser Lys Leu Thr Leu Asn Pro Gly
305                 310                 315                 320

Gly Lys Val Thr Gly Glu Met Thr Val Asp Pro Ser Val Val Pro Leu
            325                 330                 335

Met Arg Glu Asn Thr Arg Ile Glu Leu Arg Asn Pro Lys Leu Ser Leu
            340                 345                 350

Ser Asp Ala Asn Ile Ser Ser Leu Leu Thr Gly Lys Thr Phe Glu Leu
            355                 360                 365

Val Pro Gly Asp Gly Glu Pro Arg Ser Glu Phe Val Val Pro Gly
            370                 375                 380

Glu Lys Ala Leu Leu His Glu Ala Asn Ala Leu Thr Leu Thr Leu Thr
385                 390                 395                 400

Ala Pro Glu Ser Tyr Gly Ile Glu Pro Gly Pro Leu Ile Leu His
            405                 410                 415

Gly Val Lys Ile Gly Gln Val Ile Glu Arg Asn Leu Ser Ser Lys Gly
            420                 425                 430

Val Ser Phe Thr Val Ala Ile Glu Pro Gln His Arg Asp Leu Val Gln
            435                 440                 445

Gly Asp Ser Lys Phe Val Val Asn Ser Arg Val Asp Val Lys Val Gly
            450                 455                 460

Leu Asp Gly Val Glu Phe Leu Gly Ala Ser Ala Ser Glu Trp Ile Asp
465                 470                 475                 480

Gly Gly Ile Arg Ile Leu Pro Gly Thr Ser Gly Lys Met Lys Ser Thr
            485                 490                 495

Tyr Pro Leu Tyr Ala Asn Leu Glu Lys Ala Leu Glu Asn Ser Leu Ser
            500                 505                 510

Asp Leu Pro Thr Thr Leu Thr Leu Thr Ala Glu Thr Leu Pro Asp
            515                 520                 525

Val Gln Ala Gly Ser Val Val Leu Tyr Arg Lys Phe Glu Val Gly Glu
            530                 535                 540

Val Ile Thr Val Arg Pro Arg Ala Asn Thr Phe Asp Ile Asp Leu His
545                 550                 555                 560

Ile Lys Pro Glu Tyr Arg His Leu Leu Thr Ser Asn Ser Val Phe Trp
            565                 570                 575

Ala Glu Gly Gly Ala Lys Val Gln Leu Asn Gly Ser Gly Leu Thr Val
```

```
                580             585             590
    Gln Ala Ser Pro Leu Ser Arg Ala Leu Lys Gly Ala Ile Ser Phe Asp
                595                 600                 605

Asn Leu Ser Gly Ala Ser Ala Ser Arg Arg Lys Gly Asp Lys Arg Ile
                610                 615                 620

Leu Tyr Ala Ser Glu Thr Ser Ala Arg Ala Val Gly Gly Gln Ile Thr
    625                 630                 635                 640

Leu His Ala Phe Asp Ala Gly Lys Leu Ala Glu Gly Met Pro Ile Arg
                    645                 650                 655

Tyr Leu Gly Ile Asp Ile Gly Gln Ile Gln Thr Leu Glu Leu Ile Thr
                    660                 665                 670

Ala Arg Asn Glu Val Gln Ala Lys Ala Val Leu Tyr Pro Glu Tyr Val
                675                 680                 685

Gln Thr Phe Ala Arg Ala Gly Thr Arg Phe Ser Val Ile Thr Pro Gln
                690                 695                 700

Ile Ser Ala Ala Gly Val Glu His Leu Asp Thr Ile Leu Gln Pro Tyr
    705                 710                 715                 720

Ile Asn Val Glu Pro Gly Arg Gly Ala Ala Arg Arg Asp Phe Glu Leu
                    725                 730                 735

Gln Glu Ala Thr Ile Thr Asp Ser Arg Tyr Leu Asp Gly Leu Ser Ile
                    740                 745                 750

Val Val Glu Ala Pro Ala Gly Ser Leu Asn Ile Gly Thr Pro Val
                755                 760                 765

Leu Phe Arg Gly Ile Glu Val Gly Thr Val Thr Gly Met Ser Leu Gly
                770                 775                 780

Ser Leu Ser Asp Arg Val Met Ile Thr Leu Arg Ile Ser Lys Arg Tyr
    785                 790                 795                 800

Gln Tyr Leu Val Arg Asn Asn Ser Val Phe Trp Leu Ala Ser Gly Tyr
                    805                 810                 815

Ser Leu Asp Phe Gly Leu Thr Gly Gly Val Val Lys Thr Gly Thr Phe
                    820                 825                 830

Asn Gln Phe Ile Arg Gly Gly Ile Ala Phe Ala Thr Pro Pro Gly Thr
                835                 840                 845

Pro Leu Ala Pro Lys Ala Gln Ala Gly Lys His Phe Leu Leu Gln Glu
                850                 855                 860

Ser Glu Pro Lys Glu Trp Arg Glu Trp Gly Thr Ala Leu Pro Arg
    865                 870                 875

<210> SEQ ID NO 23
<211> LENGTH: 879
<212> TYPE: PRT
<213> ORGANISM: Salmonella typhimurium

<400> SEQUENCE: 23

Met His Met Ser Gln Glu Thr Pro Ala Ser Lys Thr Glu Ala Gln Ile
    1               5                   10                  15

Lys Thr Lys Arg Arg Ile Ser Pro Phe Trp Leu Leu Pro Leu Ile Ala
                20                  25                  30

Leu Met Ile Ala Gly Trp Leu Val Trp Asp Ser Tyr Gln Asp Arg Gly
                35                  40                  45

Asn Ser Val Thr Ile Asp Phe Met Ser Ala Asp Gly Ile Val Pro Gly
                50                  55                  60

Arg Thr Pro Val Arg Tyr Gln Gly Val Glu Val Gly Thr Val Glu Asp
    65                  70                  75                  80
```

-continued

```
Val Ser Leu Ser Lys Asp Leu Arg Lys Ile Glu Val Arg Val Ser Ile
             85                  90                  95

Lys Ser Asp Met Glu Asp Ala Leu Arg Glu Glu Thr Gln Phe Trp Leu
            100                 105                 110

Val Thr Pro Lys Ala Ser Leu Ala Gly Val Ser Gly Leu Asp Ala Leu
            115                 120                 125

Val Gly Gly Asn Tyr Ile Gly Met Met Pro Gly Lys Gly Lys Pro Arg
            130                 135                 140

Asp His Phe Val Ala Leu Asp Thr Gln Pro Lys Tyr Arg Leu Ser Asn
145                 150                 155                 160

Gly Asp Leu Met Ile His Leu His Ala Pro Asp Leu Gly Ser Leu Asn
                165                 170                 175

Ser Gly Ser Leu Val Tyr Phe Arg Lys Ile Pro Val Gly Arg Val Tyr
            180                 185                 190

Asp Tyr Ser Ile Asn Pro Asn Lys Gln Gly Val Thr Ile Asp Val Leu
            195                 200                 205

Ile Glu Arg Arg Phe Thr Asp Leu Val Lys Lys Gly Ser Arg Phe Trp
    210                 215                 220

Asn Val Ser Gly Ile Asp Ala Asp Leu Ser Leu Ser Gly Ala Lys Val
225                 230                 235                 240

Lys Leu Glu Ser Leu Ala Ala Leu Val Asn Gly Ala Ile Ala Phe Asp
                245                 250                 255

Ser Pro Asp Asn Ser Lys Pro Ala Ala Gln Asp Asp Thr Phe Gly Leu
            260                 265                 270

Tyr Lys Asp Leu Ala His Ser Gln Arg Gly Val Ile Val Lys Leu Glu
            275                 280                 285

Leu Pro Ser Gly Asp Gly Leu Lys Ala Glu Ser Thr Pro Leu Met Tyr
    290                 295                 300

Gln Gly Leu Glu Val Gly Glu Leu Ser Lys Leu Thr Leu Asn Pro Gly
305                 310                 315                 320

Gly Lys Val Thr Gly Glu Met Thr Val Asp Pro Ser Val Val Pro Leu
                325                 330                 335

Met Arg Glu Asn Thr Arg Ile Glu Leu Arg Asn Pro Lys Leu Ser Leu
            340                 345                 350

Ser Asp Ala Asn Ile Ser Ser Leu Leu Thr Gly Lys Thr Phe Glu Leu
            355                 360                 365

Val Pro Gly Asp Gly Glu Pro Arg Ser Glu Phe Val Val Pro Gly
    370                 375                 380

Glu Lys Ala Leu Leu His Glu Ala Asn Ala Leu Thr Leu Thr Leu Thr
385                 390                 395                 400

Ala Pro Glu Ser Tyr Gly Ile Glu Pro Gly Gln Pro Leu Ile Leu His
                405                 410                 415

Gly Val Lys Ile Gly Gln Val Ile Glu Arg Asn Leu Ser Ser Lys Gly
            420                 425                 430

Val Ser Phe Ile Val Ala Ile Glu Pro Gln His Arg Asp Leu Val Gln
            435                 440                 445

Gly Asp Ser Lys Phe Val Val Asn Ser Arg Val Asp Val Lys Val Gly
            450                 455                 460

Leu Asp Gly Val Glu Phe Leu Gly Ala Ser Ser Glu Trp Ile Asp
465                 470                 475                 480

Gly Gly Ile Arg Ile Leu Pro Gly Thr Ser Gly Lys Met Lys Ser Thr
                485                 490                 495

Tyr Pro Leu Tyr Ala Asn Leu Glu Lys Ala Leu Glu Asn Ser Leu Ser
```

```
                500                 505                 510
Asp Leu Pro Thr Thr Leu Thr Leu Thr Ala Glu Thr Leu Pro Asp
            515                 520                 525

Val Gln Ala Gly Ser Val Val Leu Tyr Arg Lys Phe Glu Val Gly Glu
    530                 535                 540

Val Ile Thr Val Arg Pro Arg Ala Asn Thr Phe Asp Ile Asp Leu His
545                 550                 555                 560

Ile Lys Pro Glu Tyr Arg His Leu Leu Thr Ser Asn Ser Val Phe Trp
                565                 570                 575

Ala Glu Gly Gly Ala Lys Val Gln Leu Asn Gly Ser Gly Leu Thr Val
            580                 585                 590

Gln Ala Ser Pro Leu Ser Arg Ala Leu Lys Gly Ala Ile Ser Phe Asp
        595                 600                 605

Asn Leu Ser Gly Ala Ser Ala Ser Arg Arg Lys Gly Asp Lys Arg Ile
            610                 615                 620

Leu Tyr Ala Ser Glu Thr Ser Ala Arg Ala Val Gly Gly Gln Ile Thr
625                 630                 635                 640

Leu His Ala Phe Asp Ala Gly Lys Leu Ala Glu Gly Met Pro Ile Arg
                645                 650                 655

Tyr Leu Gly Ile Asp Ile Gly Gln Ile Gln Thr Leu Glu Leu Ile Thr
            660                 665                 670

Ala Arg Asn Glu Val Gln Ala Lys Ala Val Leu Tyr Pro Glu Tyr Val
        675                 680                 685

Gln Thr Phe Ala Arg Ala Gly Thr Arg Phe Ser Val Ile Thr Pro Gln
    690                 695                 700

Ile Ser Ala Ala Gly Val Glu His Leu Asp Thr Ile Leu Gln Pro Tyr
705                 710                 715                 720

Ile Asn Val Glu Pro Gly Arg Gly Ala Ala Arg Arg Asp Phe Glu Leu
                725                 730                 735

Gln Glu Ala Thr Ile Thr Asp Ser Arg Tyr Leu Asp Gly Leu Ser Ile
            740                 745                 750

Val Val Glu Ala Pro Glu Ala Gly Ser Leu Asn Ile Gly Thr Pro Val
        755                 760                 765

Leu Phe Arg Gly Ile Glu Val Gly Thr Val Thr Gly Met Ser Leu Gly
    770                 775                 780

Ser Leu Ser Asp Arg Val Met Ile Thr Leu Arg Ile Ser Lys Arg Tyr
785                 790                 795                 800

Gln Tyr Leu Val Arg Asn Asn Ser Val Phe Trp Leu Ala Ser Gly Tyr
                805                 810                 815

Ser Leu Asp Phe Gly Leu Thr Gly Gly Val Val Lys Thr Gly Thr Phe
            820                 825                 830

Asn Gln Phe Ile Arg Gly Gly Ile Ala Phe Ala Thr Pro Pro Gly Thr
        835                 840                 845

Pro Leu Ala Pro Lys Ala Gln Ala Gly Lys His Phe Leu Leu Gln Glu
    850                 855                 860

Ser Glu Pro Lys Glu Trp Arg Glu Trp Gly Thr Ala Leu Pro Arg
865                 870                 875
```

<210> SEQ ID NO 24
<211> LENGTH: 877
<212> TYPE: PRT
<213> ORGANISM: Klebsiella pneumoniae

<400> SEQUENCE: 24

```
Met Ser Gln Glu Thr Pro Ala Ser Gln Thr Glu Ala Arg Ile Lys Thr
1               5                   10                  15
Lys Arg Arg Ile Ser Pro Phe Trp Leu Leu Pro Val Ile Ala Leu Leu
            20                  25                  30
Ile Ala Ala Trp Leu Ile Trp Thr Ser Phe Asp Asp Arg Gly Ser Thr
        35                  40                  45
Ile Thr Ile Asp Phe Gln Ser Ala Asn Gly Ile Val Pro Gly Arg Thr
    50                  55                  60
Pro Ile Arg Tyr Gln Gly Val Glu Val Gly Thr Val Gln Asp Ile Ser
65                  70                  75                  80
Leu Ser Lys Asp Leu Ser Lys Ile Glu Val Ser Ala Ser Ile Lys Arg
                85                  90                  95
Asp Met Lys Asp Ala Leu Arg Lys Glu Thr Gln Phe Trp Leu Val Thr
            100                 105                 110
Pro Lys Ala Ser Leu Ala Gly Val Ser Gly Leu Asp Ala Leu Val Gly
        115                 120                 125
Gly Asn Tyr Ile Gly Met Met Pro Gly Lys Gly Glu Pro Glu Asp His
    130                 135                 140
Phe Val Ala Leu Asp Thr Gln Pro Lys Tyr Arg Ile Asn Asn Gly Glu
145                 150                 155                 160
Leu Met Ile His Leu Gln Ala Pro Asp Leu Gly Ser Leu Asn Ser Gly
                165                 170                 175
Ser Leu Val Tyr Phe Arg Lys Ile Pro Val Gly Arg Val Tyr Asp Tyr
            180                 185                 190
Ser Leu Asn Ala Asn Asn Gln Gly Val Thr Ile Asp Val Leu Ile Glu
        195                 200                 205
Arg Arg Phe Thr Asn Leu Val Lys Lys Gly Ser Arg Phe Trp Asn Val
    210                 215                 220
Ser Gly Val Lys Ala Asp Val Gly Leu Ser Gly Ala Lys Val Gln Leu
225                 230                 235                 240
Glu Asn Leu Ser Ala Leu Val Asn Gly Ala Ile Ala Phe Asp Ser Pro
                245                 250                 255
Ala Asp Ser His Val Ala Ser Gln Asn Asp Glu Tyr His Leu Tyr Glu
            260                 265                 270
Asp Leu Ala His Ser Gln Arg Gly Val Val Val Thr Leu Asp Leu Pro
        275                 280                 285
Asp Gly Asp Gly Leu Lys Ala Gly Ser Thr Pro Leu Met Tyr Gln Gly
    290                 295                 300
Leu Glu Val Gly Gln Leu Ser Lys Leu Asn Leu Asn Pro Gly Gly Lys
305                 310                 315                 320
Val Thr Gly Glu Met Thr Val Asp Pro Ser Val Val Thr Leu Leu Arg
                325                 330                 335
Glu Lys Thr Leu Ile Gln Met Lys Lys Pro Lys Leu Ser Leu Asp Asn
            340                 345                 350
Pro Ser Ile Ser Thr Leu Leu Thr Gly Asn Thr Phe Glu Leu Val Pro
        355                 360                 365
Gly Glu Gly Glu Pro Arg Asn His Phe Ser Val Met Pro Ala Asp Lys
    370                 375                 380
Ala Leu Leu Asp Glu Pro Asn Val Ala Thr Val Thr Leu Ser Ala Pro
385                 390                 395                 400
Glu Ser Tyr Gly Ile Asp Gly Gln Pro Leu Val Leu His Gly Val
                405                 410                 415
Lys Val Gly Gln Val Leu Glu Arg Lys Leu Thr Ala Lys Gly Val Thr
```

-continued

```
               420                 425                 430
Phe Gln Val Ala Ile Asp Pro Glu Tyr Arg Asp Leu Ile His Gly Asp
                435                 440                 445
Ser Lys Phe Val Val Asn Ser Arg Leu Asp Val Lys Val Gly Leu Asp
    450                 455                 460
Gly Val Gln Val Leu Gly Ala Ser Ala Ser Glu Trp Val Asn Gly Gly
465                 470                 475                 480
Ile Arg Val Ile Pro Gly Glu Lys Gly Lys Met Gln Ser Ser Tyr Pro
                485                 490                 495
Leu Tyr Ala Asn Leu Glu Lys Ala Gln Glu Asn Ser Leu Ser Glu Val
            500                 505                 510
Pro Thr Thr Thr Leu Ser Leu Ser Ala Glu Thr Leu Pro Asp Val Gln
        515                 520                 525
Ala Gly Ser Val Val Leu Tyr Arg Lys Phe Ala Val Gly Glu Ile Ile
    530                 535                 540
Ala Val Lys Pro Arg Lys Asp Ala Phe Asp Ile Asp Leu His Ile Lys
545                 550                 555                 560
Pro Glu Tyr Arg Tyr Leu Leu Thr Asn Asn Ser Val Phe Trp Ala Glu
                565                 570                 575
Gly Gly Ala Lys Val Lys Leu Asp Gly Asn Gly Leu Thr Val Gln Ala
            580                 585                 590
Ser Pro Leu Ala Arg Ala Ile Lys Gly Ala Ile Ser Phe Asp Asn Leu
        595                 600                 605
Asn Gly Ser Ser Ala Gly Ala Arg Leu Asn Asn Lys Arg Ile Leu Tyr
    610                 615                 620
Ala Ser Glu Thr Ala Ala Arg Ala Val Gly Gly Gln Ile Thr Leu His
625                 630                 635                 640
Ala Tyr Asp Ala Gly Lys Met Ala Ala Gly Met Pro Ile Arg Tyr Leu
                645                 650                 655
Gly Ile Asp Ile Gly Gln Ile Gln Ser Leu Glu Leu Ile Thr Ala Lys
            660                 665                 670
Asn Glu Val Gln Ala Lys Ala Val Leu Tyr Pro Glu Tyr Val Gly Thr
        675                 680                 685
Phe Ala Arg Ala Gly Thr Arg Phe Ser Val Ile Thr Pro Gln Ile Ser
    690                 695                 700
Ala Ala Gly Val Glu His Leu Asp Thr Leu Phe Gln Ala Tyr Ile Asn
705                 710                 715                 720
Val Glu Pro Gly Arg Gly Pro Ala Arg Arg Asp Phe Glu Ile Gln Asp
                725                 730                 735
Thr Thr Ile Ser Asp Ser Arg Tyr Ile Asp Gly Leu Asn Ile Val Val
            740                 745                 750
Glu Ala Pro Glu Ala Gly Ser Leu Gly Ile Gly Thr Pro Val Leu Phe
        755                 760                 765
Arg Gly Leu Glu Val Gly Thr Val Thr Gly Leu Ser Leu Gly Ser Met
    770                 775                 780
Ser Asp Arg Val Met Val Lys Leu Arg Ile Ser Lys Arg Tyr Gln Tyr
785                 790                 795                 800
Leu Val Arg Asn Asn Ser Val Phe Trp Leu Ala Ser Gly Tyr Ser Leu
                805                 810                 815
Asp Phe Gly Leu Ile Gly Gly Val Val Lys Thr Gly Thr Phe Asn Gln
            820                 825                 830
Phe Ile Arg Gly Gly Ile Ala Phe Ala Thr Pro Pro Gly Thr Pro Leu
        835                 840                 845
```

-continued

Ala Pro Lys Ala Gln Asp Gly Lys His Phe Leu Leu Gln Glu Ser Glu
        850                 855                 860

Pro Lys Glu Trp Arg Glu Trp Gly Thr Ala Leu Pro Gln
865                 870                 875

<210> SEQ ID NO 25
<211> LENGTH: 852
<212> TYPE: PRT
<213> ORGANISM: Yersinia bercovieri

<400> SEQUENCE: 25

Met Leu Pro Phe Ile Ala Leu Leu Ile Ala Gly Trp Leu Val Tyr Asn
1               5                   10                  15

Asn Trp Gln Glu Arg Gly Thr Glu Val Thr Ile Asp Phe Gln Ser Ala
            20                  25                  30

Ala Gly Ile Val Ala Gly Arg Thr Pro Ile Arg Tyr Gln Gly Val Glu
        35                  40                  45

Val Gly Met Val Gln Ser Ile Ser Leu Asp Asp Leu Arg Asn Ile
    50                  55                  60

Lys Val Thr Ala Ser Ile Lys Asn Asp Met Glu Asp Ser Leu Arg Glu
65                  70                  75                  80

Gly Thr Gln Phe Trp Leu Val Thr Pro Lys Ala Ser Leu Ala Gly Val
                85                  90                  95

Ser Gly Leu Asp Ala Leu Val Gly Gly Asn Tyr Ile Gly Met Met Pro
            100                 105                 110

Gly Glu Gly Lys Pro Gln Ser His Phe Thr Ala Leu Asp Thr Gln Pro
        115                 120                 125

Lys Phe Arg Leu Asn Thr Gly Glu Leu Met Ile His Leu His Ala Pro
    130                 135                 140

Asp Leu Gly Ser Leu Asn Asn Gly Ser Leu Val Tyr Tyr Arg Lys Ile
145                 150                 155                 160

Pro Val Gly Lys Val Tyr Asp Tyr Asn Ile Ala Pro Asn Asn Gly
                165                 170                 175

Val Val Ile Asp Val Leu Ile Asp Arg Arg Phe Ala Lys Leu Val Lys
            180                 185                 190

Asn Asp Thr Arg Phe Trp Asn Val Ser Gly Phe Lys Gly Asp Phe Ser
        195                 200                 205

Leu Ser Gly Ala Ser Val Gln Met Glu Ser Leu Ala Ala Leu Val Asn
    210                 215                 220

Gly Ala Ile Ala Phe Asp Ser Pro Asn Ser Gln His Ala Lys Pro
225                 230                 235                 240

Asp Gln Pro Phe Gln Leu Tyr Pro Asp Leu Ala His Ser Gln Arg Gly
                245                 250                 255

Val Ala Ile Thr Leu Asp Leu Pro Asn Gly Asn Ser Leu Ser Ala Gly
            260                 265                 270

Arg Thr Pro Leu Ile Tyr Gln Gly Leu Gln Val Gly Thr Leu Thr Lys
        275                 280                 285

Met Thr Leu Gln Pro Asp Ser Lys Val Thr Gly Glu Leu Thr Ile Asp
    290                 295                 300

Pro Ser Val Val Asp Leu Met Arg Thr Gly Ser Arg Ile Glu Met Asn
305                 310                 315                 320

Ser Pro Arg Ile Thr Leu Ser Asp Thr Lys Leu Ser Glu Leu Leu Thr
                325                 330                 335

Gly Asn Thr Leu Glu Leu Ile Pro Gly Glu Gly Glu Pro Gln Lys His

```
                    340                 345                 350
Phe Thr Val Leu Pro Ser Ser Lys Ser Leu Leu Gln Gln Pro Asn Val
                355                 360                 365

Leu Glu Leu Gln Leu Thr Ala Pro Gln Ser Tyr Gly Ile Asp Val Gly
    370                 375                 380

Gln Pro Ile Ser Leu His Gly Ile Lys Ile Gly Gln Ile Ile Thr Arg
385                 390                 395                 400

Glu Leu Ser Ala Thr Gly Val Asn Phe Thr Ala Ala Ile Glu Ala Lys
                405                 410                 415

Tyr Arg Asp Leu Val His Lys Asp Ser Lys Phe Val Val Asn Ser Arg
            420                 425                 430

Leu Asn Val Gln Leu Gly Ile Asp Gly Ile Asn Ile Gln Gly Ala Ser
        435                 440                 445

Ala Gln Glu Trp Ile Asp Gly Ile Leu Ile Leu Pro Gly Gly Lys
    450                 455                 460

Gly Asp Pro Leu Asn Lys Tyr Pro Leu Tyr Ser Ser Val Ala Lys Ala
465                 470                 475                 480

Ser Glu Gly Ile Leu Gly Asn Ser Pro Ala Thr Thr Leu Thr Leu Thr
                485                 490                 495

Ala Thr Ser Leu Pro Asp Val Gln Thr Gly Ser Val Val Leu Tyr Arg
            500                 505                 510

Lys Phe Gln Val Gly Glu Ile Thr Ala Ile Arg Pro Lys Thr Asn Glu
        515                 520                 525

Phe Glu Val Asp Val Tyr Ile Gln Pro Glu Tyr Arg Lys Leu Leu Thr
    530                 535                 540

Asp Lys Ser Ile Phe Trp Ala Glu Gly Gly Ala Lys Val Gln Leu Asn
545                 550                 555                 560

Gly Ser Gly Leu Thr Val Gln Ala Ala Pro Leu Ser Arg Ala Leu Lys
                565                 570                 575

Gly Ala Ile Ser Phe Asp Asn Leu Glu Gly Val Thr Leu Asp Lys Gly
            580                 585                 590

Ala Lys Arg Thr Leu Tyr Ser Asn Glu Thr Ala Ala Arg Ala Val Gly
        595                 600                 605

Ser Gln Ile Thr Leu Arg Thr Phe Asp Ala Ser Lys Leu Ala Pro Gly
    610                 615                 620

Met Pro Ile Arg Tyr Leu Gly Ile Asn Ile Gly Gln Val Glu Ser Leu
625                 630                 635                 640

Lys Leu Ile Pro Glu Arg Asn Glu Val Leu Ala Lys Ala Val Leu Tyr
                645                 650                 655

Pro Glu Tyr Val Gln Asn Phe Ala Arg Gly Gly Ser Arg Phe Ala Ile
            660                 665                 670

Val Ser Pro Glu Ile Ser Ala Ala Gly Val Asn Asn Leu Asp Thr Leu
        675                 680                 685

Phe Gln Pro Tyr Ile Asn Val Glu Pro Gly Lys Gly Asp Thr Leu Arg
    690                 695                 700

Ile Phe Glu Leu Gln Thr Ala Thr Ile Thr Asp Ser Arg Tyr Leu Asp
705                 710                 715                 720

Gly Leu Ser Ile Ile Leu Asp Thr Ala Glu Ala Gly Ser Leu Gln Val
                725                 730                 735

Gly Thr Pro Val Leu Phe Arg Gly Leu Glu Val Gly Thr Val Thr Gly
            740                 745                 750

Phe Asn Leu Gly Ala Met Ser Asp Arg Val Gln Val Ser Leu Arg Ile
        755                 760                 765
```

```
Ser Gln Lys Phe Gln Gln Leu Val Arg Gln Asn Ser Val Phe Trp Leu
    770                 775                 780

Ala Ser Gly Tyr Asn Leu Glu Phe Gly Leu Thr Gly Gly Val Val Lys
785                 790                 795                 800

Ser Gly Thr Phe Gln Gln Phe Ile Arg Gly Gly Ile Ala Phe Ala Thr
                805                 810                 815

Pro Pro Thr Thr Pro Leu Ala Pro Lys Ala Ser Val Asn Gln His Phe
            820                 825                 830

Leu Leu Asn Pro Ala Glu Pro Lys Asp Trp Arg Asn Trp Gly Thr Ala
        835                 840                 845

Ile Pro Arg Phe
    850

<210> SEQ ID NO 26
<211> LENGTH: 876
<212> TYPE: PRT
<213> ORGANISM: Yersinia pseudotuberculosis

<400> SEQUENCE: 26

Met Gln Gln Glu Thr Pro Ser Thr Pro Thr Glu Ala His Val Lys His
1               5                   10                  15

Lys Arg Arg Phe Ser Pro Phe Trp Leu Leu Pro Phe Ile Ala Leu Leu
            20                  25                  30

Ile Thr Gly Trp Leu Ile Tyr Asn Asn Trp Gln Glu Arg Gly Thr Glu
        35                  40                  45

Ile Thr Ile Asp Phe Gln Ser Thr Ala Gly Ile Val Ala Gly Arg Thr
    50                  55                  60

Pro Ile Arg Tyr Gln Gly Val Asp Val Gly Leu Val Gln Ser Ile Arg
65                  70                  75                  80

Leu Asp Asp Asn Leu Arg Asn Ile Lys Val Thr Ala Ser Ile Lys Asn
                85                  90                  95

Asp Met Glu Asp Ser Leu Arg Glu Gly Thr Gln Phe Trp Leu Val Thr
            100                 105                 110

Pro Lys Ala Ser Leu Ala Gly Val Ser Gly Leu Asp Ala Leu Val Gly
        115                 120                 125

Gly Asn Tyr Ile Gly Met Met Pro Gly Glu Gly Lys Pro Gln Ser His
    130                 135                 140

Phe Thr Ala Leu Asp Thr Gln Pro Lys Phe Arg Leu Asn Thr Gly Glu
145                 150                 155                 160

Leu Met Ile His Leu Ser Ala Pro Asp Leu Gly Ser Leu Asn Asn Gly
                165                 170                 175

Ser Leu Val Tyr Tyr Arg Lys Ile Pro Val Gly Lys Val Tyr Asp Tyr
            180                 185                 190

Thr Ile Ala Pro Asp Asn Asn Gly Val Ile Ile Asp Val Leu Ile Asp
        195                 200                 205

Arg Arg Phe Ala Asn Leu Val Lys Lys Asp Ser Arg Phe Trp Asn Val
    210                 215                 220

Ser Gly Phe Lys Ala Asp Phe Ser Leu Ser Gly Ala Ser Val Gln Met
225                 230                 235                 240

Glu Ser Leu Ala Ala Leu Val Asn Gly Ala Ile Ala Phe Asp Ser Pro
                245                 250                 255

Gln Asn Ser Gln Asp Ala Ala Pro Asp Gln Pro Phe Gln Leu Tyr Ser
            260                 265                 270

Asp Leu Ala His Ser Gln Arg Gly Val Ala Ile Thr Leu Asp Leu Pro
```

```
                    275                 280                 285
Gly Gly Ser His Leu Ser Glu Gly Arg Thr Pro Leu Ile Tyr Gln Gly
        290                 295                 300
Leu Gln Val Gly Thr Leu Thr Lys Met Thr Leu Gln Pro Asp Gln Lys
305                 310                 315                 320
Val Thr Gly Glu Leu Thr Ile Asp Pro Ser Val Asn Leu Met Arg
                325                 330                 335
Ser Gly Thr Arg Ile Glu Met Asn Ser Pro Arg Ile Ser Leu Ser Asn
            340                 345                 350
Ala Asn Val Ser Glu Leu Leu Thr Gly Asn Thr Leu Glu Leu Ile Pro
                355                 360                 365
Gly Asp Gly Glu Pro Gln Gln His Phe Thr Val Leu Pro Ser Ser Lys
        370                 375                 380
Ser Leu Leu Gln Gln Pro Asn Val Leu Glu Leu Gln Leu Thr Ala Pro
385                 390                 395                 400
Gln Ser Tyr Gly Ile Asp Val Gly Gln Pro Ile Ser Leu Arg Gly Ile
                405                 410                 415
Lys Ile Gly Gln Val Leu Thr Arg Glu Leu Ser Ala Asp Gly Val Thr
            420                 425                 430
Phe Thr Ala Ala Ile Glu Ala Lys Tyr Arg His Leu Val His Lys Asp
                435                 440                 445
Ser Lys Phe Val Ala Asn Ser Arg Leu Asp Val Asn Val Gly Ile Asp
        450                 455                 460
Gly Val Asn Val Gln Gly Ala Ser Ala Gln Glu Trp Ile Asp Gly Gly
465                 470                 475                 480
Ile Leu Leu Leu Ser Gly Ser Lys Gly Glu Ala Leu Lys Gln Tyr Pro
                485                 490                 495
Leu Tyr Ser Ser Val Ala Lys Ala Thr Asp Gly Ile Leu Gly Ser Ser
            500                 505                 510
Pro Ala Thr Thr Leu Thr Leu Thr Ala Ser Ser Leu Pro Asp Ile Gln
                515                 520                 525
Ala Gly Ser Val Val Leu Tyr Arg Lys Phe Gln Val Gly Glu Ile Thr
        530                 535                 540
His Val Arg Pro Lys Ala Asn Ala Phe Glu Val Asp Val Tyr Ile Gln
545                 550                 555                 560
Pro Glu Tyr Arg Asn Leu Leu Thr Glu Lys Ser Ile Phe Trp Ser Glu
                565                 570                 575
Gly Gly Ala Lys Val Gln Leu Ser Gly Ser Gly Leu Thr Val Gln Ala
            580                 585                 590
Ser Pro Leu Asn Arg Ala Leu Lys Gly Ala Ile Ser Phe Asp Asn Leu
        595                 600                 605
Glu Gly Val Thr Leu Asp Lys Gly Ala Lys Arg Thr Leu Tyr Ser Asn
            610                 615                 620
Glu Thr Ala Ala Arg Ala Val Gly Ser Gln Ile Ile Leu Arg Thr Phe
625                 630                 635                 640
Asp Ala Ser Lys Leu Ser Ala Gly Met Pro Ile Arg Tyr Leu Gly Ile
                645                 650                 655
Asp Ile Gly Gln Val Glu Ser Leu Lys Leu Ala Pro Glu Arg Asn Glu
            660                 665                 670
Val Leu Ala Lys Ala Val Leu Tyr Pro Glu Tyr Val Gln Asn Phe Thr
        675                 680                 685
Arg Ala Gly Thr Arg Phe Ser Ile Val Ser Pro Glu Ile Ser Ala Ala
            690                 695                 700
```

```
Gly Val Asn Asn Leu Glu Thr Leu Phe Gln Pro Tyr Ile Asn Val Glu
705                 710                 715                 720

Pro Gly Lys Gly Gly Pro Leu Arg Asn Phe Glu Leu Gln Thr Ala Thr
                725                 730                 735

Ile Thr Asp Ser Arg Tyr Leu Asp Gly Leu Ser Ile Ile Leu Asp Thr
            740                 745                 750

Ala Glu Ala Gly Ser Leu Gln Val Gly Thr Pro Val Leu Phe Arg Gly
        755                 760                 765

Leu Glu Val Gly Thr Val Thr Gly Phe Asn Leu Gly Ala Met Ser Asp
770                 775                 780

Arg Val Gln Val Ser Leu Arg Ile Ser Gln Lys Phe Gln His Leu Val
785                 790                 795                 800

Arg Gln Asn Thr Val Phe Trp Leu Ala Ser Gly Tyr Asn Phe Glu Phe
                805                 810                 815

Gly Leu Ile Gly Gly Val Val Lys Ser Gly Thr Phe Gln Gln Phe Ile
            820                 825                 830

Arg Gly Gly Ile Ala Phe Ala Thr Pro Pro Thr Ile Pro Leu Ala Pro
        835                 840                 845

Arg Ala Asn Val Asn Gln His Phe Leu Leu Ala Pro Glu Glu Pro Lys
850                 855                 860

Asp Trp Arg Lys Trp Gly Thr Ala Ile Pro Arg Ser
865                 870                 875

<210> SEQ ID NO 27
<211> LENGTH: 840
<212> TYPE: PRT
<213> ORGANISM: Serratia odorifera

<400> SEQUENCE: 27

Met Val Tyr Thr Asn Phe Gln Glu Arg Gly Ser Thr Val Thr Ile Asp
1               5                   10                  15

Phe Gln Ser Ala Ala Gly Ile Val Ala Gly Arg Thr Pro Val Arg Tyr
            20                  25                  30

Gln Gly Val Glu Val Gly Thr Val Gln Ser Ile Ser Leu Ser Lys Asp
        35                  40                  45

Leu Arg Ser Ile Val Glu Ala Ser Ile Lys Ser Asp Leu Glu Asp
50                  55                  60

Ser Leu Arg Glu Gly Thr Gln Phe Trp Leu Val Thr Pro Lys Ala Ser
65                  70                  75                  80

Leu Ala Gly Ile Ser Gly Leu Asp Ala Leu Val Gly Gly Asn Tyr Ile
                85                  90                  95

Gly Met Met Pro Gly Ser Gly Lys Glu Gln Thr His Phe Thr Ala Leu
            100                 105                 110

Asp Thr Gln Pro Lys Tyr Arg Leu Asn Thr Gly Glu Leu Met Ile His
        115                 120                 125

Leu His Ala Asp Asp Leu Gly Ser Leu Asn Thr Gly Ser Leu Val Tyr
130                 135                 140

Tyr Arg Lys Ile Pro Val Gly Lys Val Tyr Asp Tyr Thr Ile Ala Glu
145                 150                 155                 160

Gly Asn Lys Gly Val Thr Val Asp Val Leu Ile Asp Arg Arg Phe Ala
                165                 170                 175

Asn Leu Val Lys Gly Asn Ser Arg Phe Trp Asn Val Ser Gly Phe Lys
            180                 185                 190

Gly Asp Phe Ser Leu Ala Gly Ala Ser Val Gln Val Glu Ser Leu Ala
```

-continued

```
            195                 200                 205
Ala Leu Val Asn Gly Ala Ile Ala Phe Asp Ser Pro Pro Asp Gly Gln
210                 215                 220
Gln Ala Lys Ala Asp Gln Ser Tyr Asp Leu Tyr Pro Asp Leu Ala His
225                 230                 235                 240
Ser Gln Arg Gly Val Asn Ile Thr Leu Asp Leu Pro Ser Gly Asn Asn
                245                 250                 255
Leu Ser Glu Asn Arg Thr Pro Leu Ile Tyr Gln Gly Leu Gln Val Gly
            260                 265                 270
Thr Leu Thr Lys Leu Thr Leu Gln Gln Asp Ser Lys Val Thr Gly Glu
        275                 280                 285
Leu Thr Val Asp Pro Ser Val Val Asp Leu Met Arg Ser Gly Thr Arg
    290                 295                 300
Ile Val Met Arg Ser Pro Arg Leu Ser Leu Asn Asp Ala Lys Ile Ser
305                 310                 315                 320
Gln Leu Leu Thr Gly Asn Thr Leu Glu Leu Val Pro Gly Asp Gly Glu
                325                 330                 335
Pro Gln Gln His Phe Asn Val Leu Asp Ser Ser Glu Thr Leu Leu Gln
            340                 345                 350
Gln Pro Gly Val Leu Thr Val Thr Leu Asn Ala Pro Gln Ser Tyr Gly
        355                 360                 365
Ile Asp Val Gly Gln Pro Leu Ile Val His Gly Val Lys Val Gly Gln
    370                 375                 380
Val Met Ser Arg Ala Leu Thr Asp Ser Gly Val Val Phe Thr Ala Ala
385                 390                 395                 400
Val Glu Ala Gln Tyr Arg Arg Leu Leu His Lys Asp Ser Lys Phe Val
                405                 410                 415
Val Asn Ser Arg Val Asp Val Lys Leu Gly Ile Asp Gly Met Glu Val
            420                 425                 430
Leu Gly Ala Ser Ala Gln Glu Trp Leu Asp Gly Gly Val Arg Ile Ile
        435                 440                 445
Pro Gly Ser Lys Gly Glu Pro Val Gly Gln Tyr Pro Leu Tyr Ala Asn
    450                 455                 460
Ala Glu Lys Ala Glu Ala Gly Ile Ile Gly Asn Ser Pro Thr Pro Thr
465                 470                 475                 480
Leu Thr Leu Asn Ala Val Ser Leu Pro Asp Val Gln Thr Gly Ser Val
                485                 490                 495
Val Leu Tyr Arg Lys Phe Gln Val Gly Glu Ile Val Asn Val Arg Pro
            500                 505                 510
Lys Ala Asn Glu Phe Glu Val Asp Val Tyr Ile Ser Pro Glu Tyr Arg
        515                 520                 525
Lys Leu Leu Thr Ser Glu Ser Ile Phe Trp Ala Glu Gly Gly Ala Lys
    530                 535                 540
Val Gln Leu Asn Gly Ser Gly Leu Ser Val Gln Ala Ser Pro Leu Asn
545                 550                 555                 560
Arg Ala Leu Lys Gly Ala Ile Ser Phe Asp Asn Leu Gln Gly Val Thr
                565                 570                 575
Leu Asp Lys Gly Ala Lys Arg Val Leu Tyr Ala Asn Glu Thr Ala Ala
            580                 585                 590
Arg Ala Val Gly Ser Gln Ile Val Leu Arg Thr Tyr Asp Ala Ser Lys
        595                 600                 605
Leu Ser Pro Gly Met Pro Leu Arg Tyr Leu Gly Ile Asp Ile Gly Gln
    610                 615                 620
```

```
Val Asp Ser Leu Lys Leu Ala Pro Glu Arg Asn Glu Val Leu Ala Lys
625                 630                 635                 640

Ala Val Leu Tyr Pro Glu Tyr Val Gln Thr Phe Ala Arg Leu Gly Ser
            645                 650                 655

Arg Phe Ser Val Val Ser Pro Glu Ile Ser Ala Ala Gly Val Ser Asn
        660                 665                 670

Leu Asp Thr Leu Leu Gln Pro Tyr Ile Asn Val Glu Pro Gly Arg Gly
    675                 680                 685

Arg Glu Leu Arg Ser Phe Glu Leu Gln Glu Ala Ser Ile Thr Asp Ser
690                 695                 700

Arg Tyr Leu Asp Gly Leu Ser Val Ile Leu Asp Ala Ala Glu Thr Gly
705                 710                 715                 720

Ser Leu Gln Val Gly Thr Pro Val Leu Phe Arg Gly Met Glu Val Gly
            725                 730                 735

Thr Ile Thr Gly Phe Tyr Leu Gly Ala Met Ser Asp Arg Val His Val
        740                 745                 750

Ala Leu Arg Ile Ser Lys Lys Tyr Gln His Leu Val Arg Asn Asn Ser
    755                 760                 765

Val Phe Trp Leu Ala Ser Gly Tyr Asn Leu Gln Phe Gly Leu Thr Gly
770                 775                 780

Gly Val Ile Lys Ser Gly Thr Phe Gln Gln Phe Ile Arg Gly Gly Ile
785                 790                 795                 800

Ala Phe Ala Thr Pro Pro Thr Ile Pro Leu Ala Pro Lys Ser Thr Pro
            805                 810                 815

Asn Lys His Phe Met Leu Asn Ala Glu Glu Pro Lys Asp Trp Lys Glu
        820                 825                 830

Trp Gly Thr Ala Ile Pro Arg Asp
    835                 840

<210> SEQ ID NO 28
<211> LENGTH: 888
<212> TYPE: PRT
<213> ORGANISM: Mannheimia haemolytica

<400> SEQUENCE: 28

Met Thr Met Glu Glu Asn Thr His Thr Val Val Asp Ala Gln Ile Arg
1               5                   10                  15

Gln Pro Arg Lys Ile Ser Pro Phe Trp Leu Leu Pro Ile Val Ala Phe
            20                  25                  30

Ile Ile Gly Ala Leu Leu Phe Phe Gln Ile Leu Lys Glu Gln Gly Glu
        35                  40                  45

Thr Ile Thr Ile Arg Phe Ser Lys Gly Asp Gly Ile Thr Ala Gly Lys
    50                  55                  60

Thr Ala Ile Arg Tyr Gln Gly Leu Gln Ile Gly Gln Val Lys Arg Val
65                  70                  75                  80

Tyr Phe Val Asp Asn Leu Lys Glu Val Glu Val Gln Ala Glu Ile Asn
            85                  90                  95

Pro Glu Ala Lys Ser Ile Leu Arg Lys Gln Thr Lys Phe Trp Leu Val
            100                 105                 110

Gln Pro Ser Ala Ser Leu Ala Gly Val Ser Gly Leu Asp Ala Ile Val
        115                 120                 125

Ser Gly Asn Tyr Ile Thr Leu Leu Pro Gly Glu Gly Asp Phe Val Asp
    130                 135                 140

Glu Phe Ile Ala Glu Glu Asp Pro Pro Ala Ile Thr Val Ser Asp Gly
```

```
               145                 150                 155                 160
Asp Leu Leu Ile Arg Leu Ile Ser Asp Asp Ile Gly Ser Ile Thr Val
               165                 170                 175

Gly Ala Ser Val Tyr Phe Arg Lys Val Pro Val Gly Asn Ile Ala Asp
               180                 185                 190

Tyr Arg Phe Thr Lys Asp Gln Lys Ile Glu Ile Asp Val Val Ile
               195                 200                 205

Asn Gln Lys Tyr Ala His Leu Val Lys Lys Glu Ser Arg Phe Trp Asn
    210                 215                 220

Ile Ser Gly Ile Ser Ala Asp Val Asn Leu Gln Gly Ile Lys Ile Asn
225                 230                 235                 240

Met Asp Ser Leu Ala Ser Val Val Gln Gly Val Ala Phe Asp Ser
               245                 250                 255

Pro Asp Asn Met Glu Ile Ala Glu Gln Gly Gln Lys Phe Glu Leu Tyr
               260                 265                 270

Pro Asp Leu Lys Ser Ala Lys Arg Gly Ile Glu Ile Asn Val Lys Leu
               275                 280                 285

Pro Leu Thr His Asn Leu Lys Ile Asn Glu Thr Gly Val Phe His Gln
               290                 295                 300

Asn Val Gln Ile Gly Met Leu Ser Gln Leu Lys Leu Pro Gln Val Lys
305                 310                 315                 320

Asp Asn Gly Val Pro Gln Gln Glu Ser Gly Gln His Lys Gln Ile Asp
               325                 330                 335

Gly Val Leu Leu Ile Asp Pro Ser Tyr Glu Asn Leu Leu Arg Ser Gln
               340                 345                 350

Thr Lys Ile Leu Leu Lys Glu Pro Lys Phe Ser Leu Asn Thr Glu Gln
               355                 360                 365

Leu Thr Lys Val Gly Glu Leu Arg Gly Val Tyr Phe Glu Val His
               370                 375                 380

Pro Gly Glu Gly Glu Pro Gln Ser Glu Phe Val Val Gln Asn Glu Ala
385                 390                 395                 400

Asp Tyr Leu Leu Ser Leu Pro Asn Leu Leu Ser Phe Ser Leu Ile Ala
               405                 410                 415

Pro Gln Ala Tyr Gly Val Asp Thr Asn Gln Gly Ile Tyr Tyr Ser Asp
               420                 425                 430

Val Gln Ile Gly Glu Ile Val Lys Arg Ser Leu Glu Leu Asp Lys Val
               435                 440                 445

Arg Phe Asp Val Ile Ile Tyr Pro Pro Tyr Arg Asn Leu Ile Gly Ser
    450                 455                 460

Asn Ser Lys Phe Val Ala Ile Ser Asn Ile Asp Met Ser Val Gly Leu
465                 470                 475                 480

Asp Gly Leu Arg Val His Ala Gly Ser Pro Ser Glu Trp Leu Lys Gly
               485                 490                 495

Gly Val Arg Leu Ile Asn Gly Lys Asn Asp Gly Ser Pro Lys Lys Gln
               500                 505                 510

Tyr Ala Leu Tyr Lys Asp Ile Glu Ser Ala Glu Ser Gly Met Ala Thr
               515                 520                 525

Leu Asp Lys Lys Ala Thr Thr Thr Leu Ser Ala Asp Ser Leu Ser Gly
               530                 535                 540

Ile Ser Glu Gly Ser Leu Val Leu Tyr Arg Asp Phe Gln Val Gly Glu
545                 550                 555                 560

Val Leu Lys Ile Thr Pro Lys Gln Gln Lys Phe Glu Val Glu Leu Phe
               565                 570                 575
```

```
Ile Gln Pro Asn Tyr Arg His Leu Leu Thr Glu Lys Ser Arg Phe Trp
            580                 585                 590

Ile Glu Pro Ala Thr Ser Val Asp Val Ser Leu Lys Gly Val Asn Ile
        595                 600                 605

Thr Thr Ala Pro Leu Met Arg Thr Leu Lys Gly Ala Ile Ser Phe Asp
    610                 615                 620

Asp Gly Gly Ser Lys Gly Asn Lys Thr Leu Tyr Ala Ser Lys Glu Lys
625                 630                 635                 640

Ala Thr Ser Gly Asn Thr Tyr Leu Thr Leu Ile Ala Lys Asp Ala Ser
                645                 650                 655

Lys Leu Ser Glu Gly Met Asp Ile Lys Tyr Met Gly Leu Thr Val Gly
            660                 665                 670

Gln Ile Glu Lys Leu Glu Leu Gln Asn Ala Lys Lys Gln Ile Lys Ala
        675                 680                 685

Thr Ala Tyr Ile Gln Arg Lys Tyr Tyr Pro Leu Ile Ala Lys Ala Gly
    690                 695                 700

Ser Lys Phe Asn Val Ile Ser Pro Glu Ile Ser Thr Ser Gly Phe Lys
705                 710                 715                 720

Asn Leu Asp Ala Ala Leu Gln Asn Tyr Ile Thr Val Asp Val Gly Ser
                725                 730                 735

Gly Gln Ala Gln Asn Gln Phe Val Leu Ala Asp Thr Asp Thr Val Lys
            740                 745                 750

Thr Thr Tyr Ala Asn Gly Phe Pro Ile Ile Val Glu Thr Thr Asn Ala
        755                 760                 765

Asn Gly Ile Gln Pro Glu Ala Pro Val Leu Tyr Arg Gly Met Gln Val
    770                 775                 780

Gly Ile Val Ser Arg Leu Gly Leu Ser Glu Leu Gly Asp Arg Val Leu
785                 790                 795                 800

Ile Tyr Val Asn Ile Gln Asp Lys Tyr Lys His Leu Val Arg Thr Asn
                805                 810                 815

Thr Gln Phe Trp Gln Ala Ser Gly Tyr Thr Met Asp Val Ser Leu Gln
            820                 825                 830

Gly Val Ser Met Asn Ser Gly Thr Met Ser Gln Leu Leu Asn Gly Gly
        835                 840                 845

Ile Glu Phe Ser Thr Pro Tyr Thr Lys Val Val Lys Pro Gln Ala Gln
    850                 855                 860

Pro Asn Arg Arg Phe Phe Leu Gln Arg Lys Leu Pro Asp Glu Ala Pro
865                 870                 875                 880

Ala Trp Asp Gln Gly Ile Ala Glu
                885

<210> SEQ ID NO 29
<211> LENGTH: 884
<212> TYPE: PRT
<213> ORGANISM: Pasteurella multocida

<400> SEQUENCE: 29

Met Thr Asn Lys Gln His Asp Asn Thr Gln Ala Gln Thr His Ser Thr
1               5                   10                  15

Ile Pro Ala His Leu Lys Gln Val Arg Arg Ile Ser Pro Phe Trp Leu
                20                  25                  30

Leu Pro Phe Val Ala Leu Cys Ile Gly Ala Ile Leu Phe Phe Gln Ile
            35                  40                  45

Ile Gln Glu Gln Gly His Thr Ile Arg Ile Thr Phe Ala Asn Gly Glu
```

```
                50                  55                  60
Gly Leu Val Ala Gly Lys Thr Gln Val Arg Tyr Gln Gly Leu Gln Ile
 65                  70                  75                  80

Gly Val Val Lys Lys Val Asn Phe Thr Lys Asp Leu Lys Gln Val Glu
                 85                  90                  95

Val Val Ala Asn Ile Tyr Pro Glu Ala Lys Thr Val Leu Arg Lys Asn
                100                 105                 110

Thr Lys Phe Trp Leu Val Lys Pro Ser Ala Ser Leu Ala Gly Ile Ser
                115                 120                 125

Gly Ile Asp Ala Leu Val Ser Gly Asn Tyr Ile Thr Leu Gln Pro Gly
                130                 135                 140

Asp Gly Glu Asn Glu Asp Glu Phe Ile Ala Glu Thr Glu Gly Pro Ile
145                 150                 155                 160

Ala Gln Val Asp Asp Gly Asp Leu Leu Val His Leu Leu Ala Asp Asp
                165                 170                 175

Leu Gly Ser Ile Ser Ile Gly Ala Ser Val Tyr Phe Lys Lys Leu Pro
                180                 185                 190

Val Gly Lys Val Tyr Asp Tyr Arg Phe Val Glu Asp Gly Lys Lys Val
                195                 200                 205

Ser Ile Asn Ile Val Val Asp Lys Ala Tyr Ala His Phe Val Lys Lys
210                 215                 220

Asp Ser His Phe Trp Asn Ile Ser Gly Ile Asp Ala Gln Ile Gly Leu
225                 230                 235                 240

Ser Gly Ile Asn Ile Asn Val Asp Ser Leu Asn Ala Ile Val Gln Gly
                245                 250                 255

Ala Val Ala Phe Asp Ser Pro Ala Asn Ser Glu Gln Ala Glu Ser His
                260                 265                 270

Asp Lys Phe Thr Leu Tyr Ala Asn Phe Asn Ala Ala Lys Arg Gly Ile
                275                 280                 285

Val Ile Asp Val Asn Ile Pro His Thr Thr Gly Leu Gln Thr Gly Gln
                290                 295                 300

Thr Gly Val Tyr His Gln Asn Lys Gln Ile Gly Val Leu Ser Glu Leu
305                 310                 315                 320

Thr Ser Val Glu Asp Gln Pro Ala Leu Leu Gln Gly Lys Leu Leu Ile
                325                 330                 335

Asp Pro Met Leu Ser Glu Leu Phe Thr Ser Lys Thr His Ile Val Leu
                340                 345                 350

Arg Asn Lys Lys Pro Gly Leu Ala Asn Leu Thr Asn Leu Pro Gln Leu
                355                 360                 365

Leu Arg Gly Glu Tyr Phe Glu Ile Leu Ala Ala Gly Glu Pro Gln
                370                 375                 380

Thr Ala Phe Thr Val Ile Lys Glu Asn Glu Leu Leu Gln Gln Pro
385                 390                 395                 400

Asn Thr Leu Val Leu Thr Leu Ser Ala Pro Glu Thr Tyr Gly Val Ser
                405                 410                 415

Glu Gly Gln Ala Val Tyr Tyr Asn Asp Val Thr Ile Gly Glu Ile Ile
                420                 425                 430

Gln Gln Asp Leu Asn Val Asp Gly Val Asn Phe Lys Val Ala Ile Ala
                435                 440                 445

Glu Lys Tyr Arg His Leu Ile His Gln Asp Ser Gln Phe Ile Ala Ala
                450                 455                 460

Ser Gln Leu Asp Ile Asn Ile Asp Ala Asn Gly Leu Arg Phe Glu Ala
465                 470                 475                 480
```

-continued

```
Ala Ser Pro Glu Lys Trp Leu Gln Gly Gly Val Arg Val Leu Ala Gly
            485                 490                 495

Lys Gln Lys Glu Gly Gln Pro Leu Thr His Tyr Pro Leu Tyr Lys Asp
            500                 505                 510

Ile Ser His Ala Gln Val Gly Ile Thr Asp Ala Asn Leu Thr Pro Thr
            515                 520                 525

Leu Thr Leu Ser Ser Glu Arg Leu Pro Asn Ile Asn Ala Gly Ser Val
            530                 535                 540

Val Leu Tyr Arg Gln Tyr Glu Val Gly Lys Ile Leu Asp Val Arg Pro
545                 550                 555                 560

Lys Ala Asn Thr Phe Glu Val Asp Val Phe Ile Tyr Pro Lys Tyr Gln
                565                 570                 575

Thr Leu Leu Thr His Lys Ser Val Phe Trp Val Glu Ser Ala Ala Lys
                580                 585                 590

Val Asp Ile Ser Thr Gln Gly Val Ser Ile Gln Ala Thr Pro Ile Ser
            595                 600                 605

Arg Ala Leu Lys Gly Ala Ile Ser Phe Asp Asn Ile Gly His Thr Gly
            610                 615                 620

Ser Lys Thr Leu Tyr Pro Asn Glu Leu Arg Ala Lys Ser Ala Gly Gln
625                 630                 635                 640

Gln Leu Thr Phe Ile Thr Glu Asp Ala Thr Asn Leu Ser Gln Gly Met
                645                 650                 655

Pro Leu Arg Tyr Leu Gly Leu Asn Ile Gly Glu Ile Ala Thr Val Asn
            660                 665                 670

Leu Asp Thr Lys Ser Asn Lys Val Ile Ala Lys Ala Leu Ile Asn Pro
            675                 680                 685

Gln Tyr Met Ser Leu Ile Ala Lys Glu Gly Ser Arg Phe Thr Leu Ile
            690                 695                 700

Ser Pro Gln Ile Ser Ala Ala Ser Ile Glu Asn Leu Glu Ser Leu Leu
705                 710                 715                 720

Gln Pro Tyr Ile Asp Val Glu Ile Gly Gln Gly Lys Gly Lys Thr Gln
                725                 730                 735

Phe Thr Leu Val Gln Ser Ala Pro Arg Ser Asn Asn Lys Tyr Thr Gln
            740                 745                 750

Gly Leu Pro Leu Val Leu Glu Thr His Asp Ala Leu Asn Ile Thr Val
            755                 760                 765

Gly Ser Pro Ile Leu Tyr Arg Gly Val Glu Val Gly Lys Ile Asn His
            770                 775                 780

Ile Thr Leu Asn Glu Leu Gly Asp Arg Val Phe Val His Ile Ile Ile
785                 790                 795                 800

Ala Arg Lys Tyr Gln His Leu Val Arg Gln Asn Ser Glu Phe Trp Ile
                805                 810                 815

Ala Ala Gly Tyr Asp Phe Asn Phe Ser Leu Arg Gly Ala Glu Val Asn
            820                 825                 830

Thr Gly Ser Val Gln Gln Leu Leu Lys Gly Gly Ile Ala Phe Ser Thr
            835                 840                 845

Pro Ala Ser Thr Val Ile Gln Pro Val Ala Lys Ala Asn Gln His Phe
850                 855                 860

Leu Leu Gln Val Lys Arg Pro Gln Asp Ala Gln Gln Trp Asn Ser Gly
865                 870                 875                 880

Ala Leu Pro Lys
```

<210> SEQ ID NO 30
<211> LENGTH: 908
<212> TYPE: PRT
<213> ORGANISM: Haemophilus parasuis

<400> SEQUENCE: 30

```
Met Arg Phe Arg Lys Pro Phe Ala Lys Ser Arg Arg Leu Leu Val Phe
1               5                   10                  15

Lys Ser Asp Lys Met Met Ser Glu Asn Met Pro Asn Ser Ile Pro Ala
            20                  25                  30

Lys Ile Arg Gln Pro Arg Lys Ile Ser Pro Phe Trp Leu Leu Pro Ile
        35                  40                  45

Val Ala Phe Val Ile Gly Cys Leu Leu Phe Phe Gln Ile Leu Gln Glu
    50                  55                  60

Gln Gly Gln Lys Ile Thr Ile Arg Phe Ser Lys Gly Asp Gly Ile Thr
65                  70                  75                  80

Ala Gly Lys Thr Ala Ile Arg Tyr Gln Gly Leu Gln Ile Gly Gln Val
                85                  90                  95

Lys Lys Val Tyr Phe Ile Asn Glu Leu Lys Glu Val Glu Val Glu Ala
            100                 105                 110

Glu Val Asn Pro Glu Ala Lys Ser Val Leu Lys Glu Gly Thr Lys Phe
        115                 120                 125

Trp Leu Val Lys Pro Ser Ala Ser Leu Ala Gly Val Ser Gly Leu Asp
    130                 135                 140

Ala Leu Val Ser Gly Asn Tyr Ile Thr Leu Leu Pro Asn Asp Asp Glu
145                 150                 155                 160

Asp Ala Ser Ser Glu Asp Glu Phe Val Ala Glu Asp Glu Pro Pro Ala
                165                 170                 175

Val Thr Val Ala Asp Gly Asp Leu Leu Val Lys Leu Val Ala Ser Asp
            180                 185                 190

Leu Gly Ser Met Thr Val Gly Ala Ser Val Tyr Tyr Arg Lys Val Pro
        195                 200                 205

Val Gly Ser Ile Ala Asp Tyr Arg Phe Thr Pro Asp Gln Lys Asn Val
    210                 215                 220

Glu Ile Asp Val Val Ile Asp Lys Lys Tyr Ala Asn Leu Val Lys Lys
225                 230                 235                 240

Glu Ser Arg Phe Trp Asn Ile Ser Gly Ile Gln Phe Asn Ala Asn Leu
                245                 250                 255

Thr Gly Val Asn Leu Asn Val Asp Ser Leu Ala Ser Met Val Gln Gly
            260                 265                 270

Ala Val Ala Phe Asp Ser Pro Glu Met Ala Thr Asn Ala Lys Gln Gly
        275                 280                 285

Glu Arg Phe Gln Leu Phe Asp Asn Leu Lys Leu Ala Gln Arg Gly Thr
    290                 295                 300

Glu Val Asn Ile Thr Leu Pro Ile Met Pro Asn Leu Lys Val Asn Glu
305                 310                 315                 320

Thr Pro Val Tyr Phe Gln Asn Leu Gln Val Gly Val Leu Ser His Leu
                325                 330                 335

Glu Leu Asn Glu Thr Glu Gln Asp Tyr Phe Glu Thr Lys Pro Thr Lys
            340                 345                 350

Ala Thr Ile Gln Gly Lys Leu Leu Ile Asp Pro Ala His Thr Asp Leu
        355                 360                 365

Leu Arg Ser Gly Ser Gln Ile Leu Leu Lys Glu Pro Lys Phe Ala Leu
    370                 375                 380
```

```
Asn Lys Glu Gln Leu Ser Lys Val Gly Glu Leu Leu Arg Gly Ala Tyr
385                 390                 395                 400

Phe Glu Ile Glu Lys Gly Asp Gly Glu Pro Lys Leu Thr Phe Asn Val
            405                 410                 415

Gln Lys Glu Ala Asp Tyr Leu Leu Thr Arg Pro Asn Val Leu Ala Ile
        420                 425                 430

Thr Leu Ser Ser Pro Gln Ser Tyr Gly Val Ser Glu Gly Gln Gly Ile
    435                 440                 445

Tyr Tyr Asn Asp Ile Gln Ile Gly Glu Ile Val Lys Arg Gln Leu Ser
450                 455                 460

Leu Asn Gly Val Glu Phe Gln Gly Ile Ile Tyr Pro Pro Tyr Arg Thr
465                 470                 475                 480

Leu Val Ala Gly Asn Ser Lys Phe Val Ala Ile Ser His Leu Asp Ile
                485                 490                 495

Ala Val Gly Leu Asp Gly Leu Arg Val Gln Ser Ala Ser Pro Ser Glu
            500                 505                 510

Trp Leu Ala Gly Gly Ile Arg Ile Leu Ser Asp Lys Ala Gln Gly Glu
        515                 520                 525

Ala Lys Lys Gln Tyr Pro Leu Tyr Lys Asp Leu Glu Ser Ala Glu Ala
    530                 535                 540

Gly Ile Val Ser Gly Glu Lys Lys Ala Thr Leu Ser Leu Ser Ala Thr
545                 550                 555                 560

Glu Leu Ser Gly Ile Asp Lys Gly Ser Gln Val Leu Tyr Arg Asn Phe
                565                 570                 575

Pro Ile Gly Glu Val Leu Asn Ile Arg Pro Gln Lys Thr Lys Phe Glu
            580                 585                 590

Val Asp Leu Phe Ile Glu Pro Lys Tyr Arg His Leu Leu Thr Glu Thr
        595                 600                 605

Ser Arg Phe Trp Val Glu Pro Ala Val Asp Val Asn Val Ser Thr Asn
    610                 615                 620

Gly Val Asn Leu Lys Met Gly Ser Leu Met Arg Thr Leu Lys Gly Ala
625                 630                 635                 640

Ile Ser Phe Asp Asn Gln Gly Thr Lys Gly Asn Lys Thr Leu Tyr Ser
                645                 650                 655

Ser Tyr Thr Lys Ala Thr Ser Gly Asn Thr Tyr Ile Thr Leu Ile Ala
            660                 665                 670

Gln Asp Ala Ser Lys Leu Ser Lys Gly Met Pro Ile Lys Tyr Met Gly
        675                 680                 685

Leu Thr Ile Gly Asn Val Glu Thr Leu Gln Leu Asp Asn Ala Lys Lys
    690                 695                 700

Gln Val Lys Ala Thr Ala Tyr Ile Glu Gly Gln Tyr Tyr Ala Ile Val
705                 710                 715                 720

Ala Lys Ala Gly Ser Lys Phe Asn Ala Val Ser Pro Glu Ile Asp Thr
                725                 730                 735

Thr Gly Phe Lys Asn Leu Asp Ala Val Ile Gln Asn Tyr Ile Ser Val
            740                 745                 750

Glu Ala Gly Asn Gly Lys Arg Lys Thr Gln Phe Lys Leu Gly Ala Thr
        755                 760                 765

Asp Thr Ala Asp Thr Gln Tyr Gly Asn Gly Phe Pro Ile Ile Val Glu
    770                 775                 780

Thr Thr Asp Ala Asn Gly Ile Thr Pro Gln Ala Pro Val Met Tyr Arg
785                 790                 795                 800

Gly Met Gln Val Gly Met Val Gln Gln Leu Ser Leu Ser Glu Leu Gly
```

-continued

```
                805                 810                 815
Asp Arg Val Leu Ile His Leu Arg Ile Ala Asn Gln Tyr Lys His Leu
            820                 825                 830

Val Arg Lys Asn Ser Glu Phe Trp Ala Ser Ser Gly Tyr Thr Met Asp
            835                 840                 845

Ile Ser Leu Asn Gly Val Ser Ile Asn Ser Gly Thr Met Ser Gln Leu
            850                 855                 860

Phe Asn Gly Gly Ile Ser Phe Ser Thr Pro Ser Ser Lys Val Val Gln
865                 870                 875                 880

Pro Gln Ala Glu Ala Asn Arg Arg Phe Leu Leu Gln Arg Lys Leu Pro
                885                 890                 895

Glu Glu Ala Leu Glu Trp Asp Gln Gly Leu Ala Glu
            900                 905

<210> SEQ ID NO 31
<211> LENGTH: 888
<212> TYPE: PRT
<213> ORGANISM: Actinobacillus pleuropneumoniae

<400> SEQUENCE: 31

Met Thr Asp Asn Ile Ser Gln Pro Val Glu Ala Lys Val Arg Gln Pro
1               5                   10                  15

Arg Lys Ile Ser Pro Phe Trp Leu Leu Pro Ile Val Ala Phe Val Ile
            20                  25                  30

Gly Gly Leu Leu Phe Phe Gln Ile Leu Lys Glu Gln Gly Glu Met Ile
        35                  40                  45

Thr Ile Arg Phe Asn Glu Gly Asp Gly Ile Thr Ala Gly Lys Thr Val
    50                  55                  60

Ile Arg Tyr Gln Gly Leu Gln Ile Gly Gln Val Lys Lys Val Tyr Phe
65                  70                  75                  80

Val Glu Asp Leu Lys Lys Val Glu Val Gln Ala Glu Val Asn Pro Glu
                85                  90                  95

Ala Lys Ser Val Leu Arg Glu Gln Thr Lys Phe Trp Leu Val Lys Pro
            100                 105                 110

Ser Ala Ser Ile Ala Gly Val Ser Gly Leu Asp Ala Leu Val Ser Gly
        115                 120                 125

Asn Tyr Ile Thr Leu Leu Pro Gly Glu Gly Lys Ser Ser Asn Glu Phe
    130                 135                 140

Ile Ala Glu Glu Pro Pro Thr Val Ala Val Thr Asp Gly Asp Leu
145                 150                 155                 160

Leu Ile Arg Leu Ile Ser Asp Asp Leu Gly Ser Ile Thr Val Gly Ala
                165                 170                 175

Ser Val Tyr Phe Arg Lys Val Pro Val Gly Ser Ile Ala Asp Tyr Arg
            180                 185                 190

Phe Thr Ala Asp Gln Lys Lys Val Glu Ile Asp Val Ile Asp Lys
        195                 200                 205

Lys Tyr Ala Asn Leu Val Lys Gln Asp Ser His Phe Trp Asn Ile Ser
    210                 215                 220

Gly Ile Asn Ala Asn Ile Gly Leu Ser Gly Val Ser Val Asn Val Asp
225                 230                 235                 240

Ser Ile Ala Ser Val Val Gln Gly Ala Val Ala Phe Asp Ser Pro Asp
                245                 250                 255

Glu Ser Lys Ile Ala Glu Gln Gly Gln Lys Phe Thr Leu Tyr Glu Ser
            260                 265                 270
```

```
Leu Lys Ser Ala Gln Arg Gly Lys Glu Ile His Val Met Pro Ile
        275                 280                 285

Met Pro Asn Leu Lys Val Asn Glu Thr Pro Val Phe Tyr Gln Asn Ile
    290                 295                 300

Gln Val Gly Val Leu Ser Gly Leu Ala Leu Ser Ala Pro Ser Asp Glu
305                 310                 315                 320

Lys Asp Ala Lys Thr Glu Ser Gln Pro Leu Ala Lys Gly Met Ala Arg
                325                 330                 335

Gly Thr Leu Leu Ile Asp Pro Asn His Val Asp Leu Phe Lys Ser Gly
                340                 345                 350

Thr Gln Ile Leu Leu Lys Glu Pro Lys Phe Ala Leu Asn Lys Glu Gln
    355                 360                 365

Ile Ser Lys Val Gly Glu Leu Leu Arg Gly Ile Tyr Phe Asp Ile Ser
    370                 375                 380

Ala Gly Lys Gly Glu Pro Lys Leu Glu Phe Glu Val Gln Lys Glu Ala
385                 390                 395                 400

Asp Tyr Leu Leu Ser Arg Pro Asn Leu Leu Ala Leu Thr Phe Ser Ala
                405                 410                 415

Pro Gln Ser Tyr Ser Val Asp Gln Gly Gln Gly Ile Tyr Tyr Asn Asp
                420                 425                 430

Val Gln Ile Gly Glu Leu Leu Lys Arg Lys Leu Thr Leu Asp Gly Val
    435                 440                 445

Thr Phe Gln Gly Ile Ile Tyr Pro Pro Tyr Arg His Leu Val Ala Ala
    450                 455                 460

Asn Ser Lys Phe Val Ala Ile Ser Asn Leu Asp Val Ser Val Gly Leu
465                 470                 475                 480

Asp Gly Met Arg Val Gln Ala Gly Ser Pro Ser Asp Trp Leu Lys Gly
                485                 490                 495

Gly Ile Arg Leu Leu Thr Asn Lys Ala Gln Gly Glu Ala Lys Lys Gln
                500                 505                 510

Tyr Pro Leu Tyr Lys Asp Val Glu Ser Ala Glu Ala Gly Ile Ile Asp
                515                 520                 525

Asp Glu Lys Lys Thr Thr Leu Thr Leu Ser Ala Asn Asp Leu Ser Gly
    530                 535                 540

Ile Asp Lys Gly Ser Val Val Leu Tyr Arg Asn Phe Gln Ile Gly Glu
545                 550                 555                 560

Val Leu Lys Val Arg Pro Gln Lys Asn Lys Phe Asp Val Asp Leu Phe
                565                 570                 575

Val Glu Pro Ala Tyr Arg His Leu Leu Ser Asp Lys Ser Arg Phe Trp
                580                 585                 590

Ile Glu Pro Ala Val Ser Ala Glu Leu Ser Met Lys Gly Leu Asn Val
                595                 600                 605

Gln Ala Ala Pro Leu Met Arg Thr Leu Lys Gly Ala Ile Ser Phe Asp
    610                 615                 620

Asn Gly Gly Thr Lys Gly Asp Lys Thr Leu Tyr Ala Ser Gln Ala Lys
625                 630                 635                 640

Ala Thr Ser Gly Asn Thr Arg Ile Thr Leu Ile Ala Lys Asp Ala Ser
                645                 650                 655

Lys Leu Ser Lys Gly Met Asp Ile Lys Tyr Met Gly Leu Thr Ile Gly
                660                 665                 670

Gln Ile Glu Ser Leu Glu Leu Gln Asn Ala Lys Lys Gln Ile Lys Ala
    675                 680                 685

Thr Ala Tyr Ile Asp Ser Gln Tyr Tyr Ala Leu Val Ala Lys Glu Gly
```

-continued

```
                690                 695                 700
Ser Arg Phe Ser Ala Ile Ser Pro Glu Ile Thr Thr Ser Gly Val Lys
705                 710                 715                 720

Asn Ile Asp Ala Ala Leu Gln Asn Tyr Ile Asn Val Asp Ala Gly Ser
                725                 730                 735

Gly Asn Arg Lys Thr Gln Phe Ser Leu Ser Asp Thr Asp Thr Asn Lys
                740                 745                 750

Thr Ile Tyr Ala Asn Gly Phe Pro Val Ile Val Glu Thr Ser Asp Ala
                755                 760                 765

Arg Gly Ile Glu Val Asp Ala Pro Val Leu Tyr Arg Gly Met Gln Val
        770                 775                 780

Gly Ile Val Lys Arg Leu Asn Leu Ser Glu Leu Gly Asp Arg Val Met
785                 790                 795                 800

Ile His Leu Ser Ile Glu Ser Lys Tyr Gln His Leu Val Arg Asn Asn
                805                 810                 815

Thr Glu Phe Trp Ala Ala Ser Gly Tyr Thr Met Asp Ile Ser Leu Gln
                820                 825                 830

Gly Val Ser Met Asn Ser Gly Thr Met Ser Gln Leu Leu Lys Gly Gly
            835                 840                 845

Ile Glu Phe Ser Thr Pro Ser Gly Arg Val Val Gln Pro Gln Ala Lys
        850                 855                 860

Ser Asn Arg His Phe Leu Leu Gln Arg Lys Ile Pro Gln Glu Ala Pro
865                 870                 875                 880

Glu Trp Asp Gln Gly Ile Ala Glu
                885
```